US012692315B2

(12) United States Patent
Song

(10) Patent No.: US 12,692,315 B2
(45) Date of Patent: Jul. 28, 2026

(54) BISPECIFIC ANTIBODIES COMPRISING AN NRP1 BINDING DOMAIN AND METHODS OF USE THEREOF

(71) Applicant: Pinetree Therapeutics, Inc., Cambridge, MA (US)

(72) Inventor: Ho-Juhn Song, Cambridge, MA (US)

(73) Assignee: Pinetree Therapeutics, Inc., Cambridge, MA (US)

( * ) Notice: Subject to any disclaimer, the term of this patent is extended or adjusted under 35 U.S.C. 154(b) by 633 days.

(21) Appl. No.: 18/128,928

(22) Filed: Mar. 30, 2023

(65) Prior Publication Data

US 2024/0101682 A1 Mar. 28, 2024

Related U.S. Application Data

(60) Provisional application No. 63/325,317, filed on Mar. 30, 2022, provisional application No. 63/325,312, filed on Mar. 30, 2022.

(51) Int. Cl.
*C07K 16/28* (2006.01)
*A61K 39/00* (2006.01)
*A61P 35/00* (2006.01)

(52) U.S. Cl.
CPC .......... *C07K 16/2863* (2013.01); *A61P 35/00* (2018.01); *C07K 16/28* (2013.01); *A61K 2039/505* (2013.01); *C07K 2317/31* (2013.01); *C07K 2317/622* (2013.01); *C07K 2317/73* (2013.01); *C07K 2317/76* (2013.01); *C07K 2317/77* (2013.01); *C07K 2317/92* (2013.01)

(58) Field of Classification Search
CPC ............... C07K 16/2863; C07K 16/28; C07K 2317/31; C07K 2317/622; C07K 2317/73; C07K 2317/76; C07K 2317/77; C07K 2317/92; A61P 35/00; A61K 2039/505
See application file for complete search history.

(56) References Cited

U.S. PATENT DOCUMENTS

| | | | |
|---|---|---|---|
| 5,580,859 | A | 12/1996 | Felgner et al. |
| 5,676,646 | A | 10/1997 | Hofmann et al. |
| 5,679,647 | A | 10/1997 | Carson et al. |
| 5,702,359 | A | 12/1997 | Hofmann et al. |
| 5,703,055 | A | 12/1997 | Felgner et al. |
| 6,068,650 | A | 5/2000 | Hofmann et al. |
| 6,096,020 | A | 8/2000 | Hofmann |
| 6,120,493 | A | 9/2000 | Hofmann |
| 6,150,148 | A | 11/2000 | Nanda et al. |
| 6,181,964 | B1 | 1/2001 | Hofmann et al. |
| 6,192,270 | B1 | 2/2001 | Hofmann et al. |
| 6,208,893 | B1 | 3/2001 | Hofmann |
| 6,216,034 | B1 | 4/2001 | Hofmann et al. |
| 6,233,482 | B1 | 5/2001 | Hofmann et al. |
| 6,235,883 | B1 | 5/2001 | Jakobovits et al. |
| 6,241,701 | B1 | 6/2001 | Hofmann |

| | | | |
|---|---|---|---|
| 6,302,874 | B1 | 10/2001 | Zhang et al. |
| 7,476,724 | B2 | 1/2009 | Dennis et al. |
| 7,664,545 | B2 | 2/2010 | Westersten et al. |
| 7,807,798 | B2 | 10/2010 | Jakobovits et al. |
| 7,994,286 | B2 | 8/2011 | Watts et al. |
| 8,211,429 | B2 | 7/2012 | Watts et al. |
| 8,378,080 | B2 | 2/2013 | Watts et al. |
| 8,628,773 | B2 | 1/2014 | Guo |
| 8,673,302 | B2 | 3/2014 | Goetsch et al. |
| 8,795,660 | B2 | 8/2014 | Watts et al. |
| 9,068,011 | B2 | 6/2015 | Neijssen et al. |
| 9,975,933 | B2 | 5/2018 | Kim et al. |
| 10,106,614 | B2 | 10/2018 | Stanimirovic et al. |
| 10,112,998 | B2 | 10/2018 | Stanimirovic et al. |
| 10,227,413 | B2 | 3/2019 | Hicklin et al. |
| 10,377,825 | B2 | 8/2019 | Mathieu et al. |
| 10,400,022 | B2 | 9/2019 | Kim et al. |
| 10,519,245 | B2 | 12/2019 | Gastwirt et al. |
| 11,186,644 | B2 | 11/2021 | Hicklin et al. |
| 11,548,915 | B2 | 1/2023 | Kim et al. |
| 2008/0213268 | A1 * | 9/2008 | Watts .................... A61K 45/06 |
| | | | 530/387.5 |
| 2009/0226466 | A1 | 9/2009 | Fong et al. |
| 2010/0047230 | A1 | 2/2010 | Mamalaki et al. |
| 2010/0143340 | A1 | 6/2010 | Kolhe et al. |
| 2011/0313137 | A1 | 12/2011 | Zha |

(Continued)

FOREIGN PATENT DOCUMENTS

| | | |
|---|---|---|
| EP | 979246 B1 | 7/2007 |
| EP | 1951758 A2 | 8/2008 |

(Continued)

OTHER PUBLICATIONS

Almagro JC et al, Progress and Challenges in the Design and Clinical Development of Antibodies for Cancer Therapy (2018), Front. Immunol, 8(1751): 1-19 (Year: 2018).*
Almagro JC and Fransson J, Humanization of antibodies (2008), Frontiers in Bioscience, 13:1619-33 (Year: 2008).*
Chiu ML et al, Antibody Structure and Function: The Basis for Engineering Therapeutics (2019), Antibodies, 8(4):55, pp. 1-80 (Year: 2019).*
Hasegawa H et al, Single amino acid substitution in LC-CDR1 induces Russell body phenotype that attenuates cellular protein synthesis through eIF2a phosphorylation and thereby downregulates IgG secretion despite operational secretory pathway traffic (2017) mAbs, 9(5): 854-873) (Year: 2017).*

(Continued)

*Primary Examiner* — Julie Wu
*Assistant Examiner* — Jieun Ham
(74) *Attorney, Agent, or Firm* — Nelson Mullins Riley & Scarborough LLP; Jane E. Remillard, Esq.

(57) ABSTRACT

The present disclosure provides bispecific antibodies, and compositions and methods of treating cancer incorporating said bispecific antibodies. The bispecific antibodies include a polypeptide comprising an EGFR-binding domain and a neuropilin (NRP1)-specific binding domain at the C-terminal end. Monoclonal antibodies that specifically bind NRP1 are also provided.

13 Claims, 20 Drawing Sheets

Specification includes a Sequence Listing.

(56) References Cited

U.S. PATENT DOCUMENTS

| | | | |
|---|---|---|---|
| 2012/0309942 A1 | 12/2012 | Li et al. | |
| 2013/0216527 A1 | 8/2013 | Goetsch et al. | |
| 2014/0079665 A1 | 3/2014 | Goetsch et al. | |
| 2015/0322162 A1 | 11/2015 | Cho et al. | |
| 2017/0066829 A1 | 3/2017 | Shokri et al. | |
| 2018/0201692 A1 | 7/2018 | Lowman et al. | |
| 2019/0062375 A1 | 2/2019 | Kim et al. | |
| 2019/0248907 A1 | 8/2019 | Doerner et al. | |
| 2020/0095319 A1* | 3/2020 | Kufer | C07K 16/2809 |
| 2021/0087278 A1 | 3/2021 | Goetsch et al. | |
| 2022/0073626 A1 | 3/2022 | Hermine et al. | |
| 2022/0098312 A1 | 3/2022 | Hicklin et al. | |
| 2022/0098329 A1 | 3/2022 | Santich et al. | |
| 2023/0257422 A1 | 8/2023 | Kim et al. | |
| 2023/0312684 A1 | 10/2023 | Song et al. | |

FOREIGN PATENT DOCUMENTS

| | | |
|---|---|---|
| EP | 2570434 A2 | 3/2013 |
| EP | 2694552 B1 | 10/2017 |
| EP | 3275895 A1 | 1/2018 |
| EP | 3558365 A1 | 10/2019 |
| EP | 3680250 A1 | 7/2020 |
| EP | 3902834 A1 | 11/2021 |
| EP | 3978519 A1 | 4/2022 |
| KR | 20190046489 A | 5/2019 |
| WO | 2007056470 A3 | 5/2007 |
| WO | 2010/064089 A1 | 6/2010 |
| WO | 2011/057064 A1 | 5/2011 |
| WO | 2011/143408 A1 | 11/2011 |
| WO | 2012138997 A1 | 10/2012 |
| WO | 2013/075382 A1 | 5/2013 |
| WO | 2017/171373 A2 | 10/2017 |
| WO | 2017/209351 A1 | 12/2017 |
| WO | 2018119171 A1 | 6/2018 |
| WO | 2018/197502 A1 | 11/2018 |
| WO | 2019050326 A1 | 3/2019 |
| WO | 2020/027224 A1 | 2/2020 |
| WO | 2020/079280 A1 | 4/2020 |
| WO | 2020113164 A1 | 6/2020 |
| WO | 2022026943 A2 | 2/2022 |
| WO | 2023/192514 A1 | 10/2023 |
| WO | 2024/102187 A1 | 5/2024 |
| WO | 2025/029618 A1 | 2/2025 |

OTHER PUBLICATIONS

Brinkmann, U and Kontermann, RE, The making of bispecific antibodies (2017), mAbs, 9(2): 182-212 (Year: 2017).*
Altschul, S. et al., "Basic local alignment search tool," J Mol Biol., vol. 215:403-410 (1990).
Altschul, S. et al., "Gapped BLAST and PSI-BLAST: a new generation of protein database search programs," Nucleic Acids Res., vol. 25(17):3389-3402 (1997).
Behr et al., "Differential adhesion pattern of B cell chronic lymphocytic leukemia cells," Leukemia, vol. 12: 71-77 (1998).
Berge, S. et al., "Pharmaceutical Salts", Journal of Pharmaceutical Science, vol. 66: 1-19 (1977).
Beyer , I. et al. "Epithelial Junction Opener JO-1 Improves Monoclonal Antibody Therapy of Cancer," Cancer Res., vol. 71(22):7080-7090 (2011).
Chou, T.C. and Talalay, P., "Quantitative analysis of dose-effect relationships: the combined effects of multiple drugs or enzyme inhibitors," Adv. Enzyme Regul., vol. 22: 27-55 (1984).
Chuckran, C. et al., "Neuropilin-1: a checkpoint target with unique implications for cancer immunology and Immunotherapy," Journal for Immuno Therapy of Cancer, vol. 8:e000967. doi: 10.1136/jitc-2020-000967, 12 pages (2020).
Davies, D. et al. "Antibody—Antigen Complexes," Annual Rev Biochem, vol. 59:439-473 (1990).
Garcia-Foncillas, J. et al., "Distinguishing Features of Cetuximab and Panitumumab in Colorectal Cancer and Other Solid Tumors," Front. Oncol. vol. 9(849) 16 pages (2019).

Graziani G and Lacal PM, "Neuropilin-1 as therapeutic target for malignant melanoma," Front. Oncol., vol. 5:125. doi: 10.3389/fonc.2015.00125 (2015).
International Search Report and Written Opinion, PCT/US2023/016963, dated Jul. 11, 2023, 14 pages.
Jain and Stylianopoulos, "Delivering nanomedicine to solid tumors," Nat. Rev. Clin. Oncol., vol. 7:653-664 (2010).
Kamba and McDonald, "Mechanisms of adverse effects of anti-VEGF therapy for cancer," British Journal of Cancer, vol. 96: 1788-1795 (2007).
Kim, Y. et al., "Co-targeting of EGF receptor and neuropilin-1 overcomes cetuximab resistance in pancreatic ductal adenocarcinoma with integrin ?1-driven Src-Akt bypass signaling," Oncogene, vol. 36(18): 2543-2552 (2017).
Kim, Y. et al., "Dual-targeting of EGFR and Neuropilin-1 attenuates resistance to EGFR-targeted antibody therapy in KRAS-mutant non-small cell lung cancer," Cancer Lett., vol. 466: 23-34 (2019).
Malmqvist, M., "Biospecific interaction analysis using biosensor technology," Nature, vol. 361:186-87 (1993).
Marcucci, F. et al., "Improving drug uptake and penetration into tumors: current and forthcoming opportunities," Drug Frontiers in Oncology, vol. 3 (161): 3 pages (2013).
Milosevic et al., "The relationship between elevated interstitial fluid pressure and blood flow in tumors: a bioengineering analysis," Int J Radiat Oncol Biol Phys., vol. 43:1111-1123 (1999).
Needleman and Wunsch, "A general method applicable to the search for similarities in the amino acid sequence of two proteins," J. Mol. Biol., vol. 48:443-453 (1970).
Nicolaou, K. et al. "Calicheamicin 0: A Rationally Designed Molecule with Extremely Potent and Selective DNA Cleaving Properties and Apoptosis Inducing Activity," Agnew, Chem. Intl. Ed. Engl., 33: 183-186 (1994).
Pan Q et al., "Blocking Neuropilin-1 Function Has an Additive Effect with Anti-VEGF to Inhibit Tumor Growth," Cancer Cell, vol. 11(1):53-67. doi: 10.1016/j.ccr.2006.10.018 (2007).
Parker, M. et al., "Mechanism of selective VEGF-A binding by neuropilin-1 reveals a basis for specific ligand inhibition," PLoS One, vol. 7(11) e49177: 7 pages (2012).
Patnaik, A. et al., "A Phase Ib study evaluating MNRP1685A, a fully human anti?NRP1 monoclonal antibody, in combination with bevacizumab and paclitaxel in patients with advanced solid tumors," Cancer Chemother Pharmacol., vol. 73:951-960 (2014).
Pyzik, M. et al., "The Neonatal Fc Receptor (FcRn): A Misnomer?," Front. Immunol., vol. 10(10):1540: 24 pages (2019).
Rizzolio, S. et al . . . "Downregulating Neuropilin-2 Triggers a Novel Mechanism Enabling EGFR-Dependent Resistance to Oncogene-Targeted Therapies," Cancer Res., vol. 78(4): 1058-1068 (2017).
Schneider-Merck, T. et al., "Human IgG2 antibodies against epidermal growth factor receptor effectively trigger antibody-dependent cellular cytotoxicity but, in contrast to IgG1, only by cells of myeloid lineage," J. Immunol., vol. 184(Issue 1):512-520 (2010).
Shin, T. et al., "Enhancement of the Tumor Penetration of Monoclonal Antibody by Fusion of a Neuropilin-Targeting Peptide Improves the Antitumor Ef?cacy," Mol Cancer Ther; vol. 13(3):651-61 (2014).
Sugahara, K. et al., "Coadministration of a Tumor-Penetrating Peptide Enhances the Efficacy of Cancer Drugs," Science, vol. 328, 1030-1035 (2010).
Tashima, T., "Delivery of Orally Administered Digestible Antibodies Using Nanoparticles," Int. J. Mol. Sci., vol. 22(3349) 20 pages (2021).
Teesalu, T. et al., "C-end rule peptides mediate neuropilin-1-dependent cell, vascular, and tissue penetration," Proc. Natl. Acad. Sci. USA, vol. 106(38): 16157-16162 (2009).
Thurber, G. et al., "Factors determining antibody distribution in tumors," Trends Pharmacol. Sci., vol. 29(2):57-61 (2008).
Weekes, C. et al., "A phase I study of the human monoclonal anti-NRP1 antibody MNRP1685A in patients with advanced solid tumors," Invest New Drugs, vol. 32:653-660 (2014).
Zanuy, D. et al., "Sequence dependence of C-end rule peptides in binding and activation of neuropilin-1 receptor," J. Struct. Biol., vol. 182(2): 78-86 (2013).

(56) References Cited

OTHER PUBLICATIONS

Atzori, F. et al., "A phase I pharmacokinetic and pharmacodynamic study of dalotuzumab (MK-0646), an anti-insulin-like growth factor-1 receptor monoclonal antibody, in patients with advanced solid tumors," Clin. Cancer Res., vol. 17(19):6304-6312 (2011).

Baselga, J. et al., "Phase II trial of pertuzumab and trastuzumab in patients with human epidermal growth factor receptor 2-positive metastatic breast cancer that progressed during prior trastuzumab therapy," J. Clin. Oncol., vol. 28(7):1138-1144 (2010).

Camidge, D. et al., "A Phase 1b Study of Telisotuzumab Vedotin in Combination With Nivolumab in Patients With NSCLC," JTO Clin. Res. Rep., vol. 3(1):100262 (2022).

Camidge, R. et al., "1383PD—An open-label, multicenter, phase I study of ABBV-399 (telisotuzumab vedotin, teliso-V) as monotherapy (T) and in combination with erlotinib (T+E) in non-small cell lung cancer (NSCLC)," Annals Oncol. 29(8):496-497 (2018).

Donnelly, J. et al., "DNA Vaccines," Ann. Rev. Immunol., vol. 15: 617-648 (1997).

Harman, J. et al., "Emerging Roles for Neuropilin-2 in cardiovascular disease," Int. J. Mol. Sci., vol. 21 (5154): 18 pages (2020).

Hudis, C., "Trastuzumab-mechanism of action and use in clinical practice," New Engl. J. Med., vol. 357(1):39-51 (2007).

International Search Report and Written Opinion, PCT/US2024/039715, dated Nov. 15, 2024, 11 pages.

Issitt, T. et al., "Neuropilin-1 Controls Endothelial Homeostasis by Regulating Mitochondrial Function and Iron-Dependent Oxidative Stress," iScience, vol. 11: 205-223 (2019).

Jain, N. et al., "Current ADC Linker Chemistry," (2015) Pharm. Res. 32:3526-3540.

Kofler, N. et al., "The expanding role of Neuropilin: regulation of vascular TGFβ and PDGF signaling," Curr Opin Hematol., vol. 23(3): 260-267 (2016).

Langer, C. et al., "Randomized, phase III trial of first-line figitumumab in combination with paclitaxel and carboplatin versus paclitaxel and carboplatin alone in patients with advanced non-small-cell lung cancer," J. Clin. Oncol., vol. 32(19):2059-2066 (2014).

Mehta, V. et al., "VEGF (Vascular Endothelial Growth Factor) Induces NRP1 (Neuropilin-1) Cleavage via ADAMs (a Disintegrin and Metalloproteinase) 9 and 10 to Generate Novel Carboxy-Terminal NRP1 Fragments That Regulate Angiogenic Signaling," Arterioscler Thromb Vasc Biol., vol. 38(8):1845-1858 (2018).

Merchant, M. et al., "Monovalent antibody design and mechanism of action of onartuzumab, a MET antagonist with anti-tumor activity as a therapeutic agent," PNAS, vol. 110 (32):e2987-e2996 (2013).

Molife, L. et al., "The insulin-like growth factor-I receptor inhibitor figitumumab (CP-751,871) in combination with docetaxel in patients with advanced solid tumours: results of a phase Ib dose-escalation, open-label study," Brit. J. Cancer, vol. 103(3):332-339 (2010).

Moody, G. et al., "IGF1R blockade with ganitumab results in systemic effects on the GH-IGF axis in mice," J. Endocrinol., vol. 221(1):145-155 (2014).

Nareshkumar J. et al., "Current ADC Linker Chemistry," Pharm Res, vol. 32:3526-3540 (2015).

Newa, H. et al., "Antibody-mediated "universal" osteoclast targeting platform using calcitonin as a model drug," Pharm. Res., vol. 28:1131-1143 (2011).

Niland, S. et al., "Neuropilins in the Context of Tumor Vasculature," Int. J. Mol. Sci., vol. 20(639): 44 pages (2019).

Pellet-Many, C. et al., "Neuropilin-1 mediates PDGF stimulation migration and signalling via p130Cas," Biochem. J., vol. 435: 609-618 (Printed in Great Britain) (2011) doi:10.1042/BJ2010058.

Pellet-Many, C. et al., "Neuropilins: structure, function and role in disease," Biochem. J. vol. 411: 211-226 (2008).

Rathkopf, D. et al., "Anti-insulin-like growth factor-1 receptor (IGF-1R) monoclonal antibody cixutumumab (cix) plus mTOR inhibitor temsirolimus (tem) in metastatic castration-resistant prostate cancer (mCRPC): Results of a phase I pilot study," J. Clin. Oncol., vol. 29(15):e15081 (2011).

Romond, E. et al., "Trastuzumab plus adjuvant chemotherapy for operable HER2-positive breast cancer," New Engl. J. Med., vol. 353 (16):1673-1684 (2005).

Rosen, L. et al., "A First-in-Human Phase I Study of a Bivalent MET Antibody, Emibetuzumab (LY2875358), as Monotherapy and in Combination with Erlotinib in Advanced Cancer," Clin. Cancer Res., vol. 23(8):1910-1919 (2017).

Rossgnol, M. et al, "Genomic Organization of Human Neuropilin-1 and Neuropilin-2 Genes: Identification and Distribution of Splice Variants and Soluble Isoforms," Genomics, vol. 70: 211-222 (2000).

Roy, S. et al., "Multifaceted Role of Neuropilins in the Immune System: Potential Targets for Immunotherapy," Front Immunol., vol. 8 (1228): 27 pages (2017).

Scartozzi, M. et al., "Dalotuzumab, a recombinant humanized mAb targeted against IGFR1 for the treatment of cancer," Curr. Opin. Mol. Therap., vol. 12(3):361-371 (2010).

Schwartz, G. et al., "Cixutumumab and temsirolimus for patients with bone and soft-tissue sarcoma: a multicentre, open-label, phase 2 trial," Lancet, vol. 14(4):371-382 (2013).

Schwarz, Q. et al., "Neuropilin, you gotta let me know Should I stay or should I go?," Cell Adhesion & Migration, vol. 4(1): 61-66 (2010).

Spigel, D. et al., "Results From the Phase III Randomized Trial of Onartuzumab Plus Erlotinib Versus Erlotinib in Previously Treated Stage IIIB or IV Non-Small-Cell Lung Cancer: METLung," J. Clin. Oncol., vol. 35(4):412-420 (2017).

Swain, S. et al., "Pertuzumab, trastuzumab, and docetaxel in HER2-positive metastatic breast cancer," New Engl. J. Med., vol. 372(8):724-734 (2015).

Tap, W. et al., "Phase II study of ganitumab, a fully human anti-type-1 insulin-like growth factor receptor antibody, in patients with metastatic Ewing family tumors or desmoplastic small round cell tumors," J. Clin. Oncol., vol. 30 (15):1849-1856 (2012).

Tumey, L. et al., "An Overview of the Current ADC Discovery Landscape," Methods Mol. Biol., vol. 2078:1-22 (2020).

Werneberg, S. et al., "Polysialylation and Lipopolysaccharide-Induced Shedding of E-Selectin Ligand-1 and Neuropilin-2 by Microglia and THP-1 Macrophages," GLIA vol. 64:1314-1330 (2016).

Yan, S. et al., "MET-targeting antibody (emibetuzumab) and kinase inhibitor (merestinib) as single agent or in combination in a cancer model bearing MET exon 14 skipping," Invest. New Drug, vol. 36(4):536-544 (2018).

Zhou, Q., "Site-Specific Antibody Conjugation for ADC and Beyond," Biomedicines, vol. 5:64 (2017).

U.S. Appl. No. 18/785,315, filed Jul. 26, 2024, Yong Sung Kim.

International Search Report and Written Opinion, PCT/US2023/028967, dated Nov. 24, 2023, 16 pages.

International Search Report and Written Opinion, PCT/US2023/031268, dated Dec. 12, 2023, 15 pages.

Majeed, U. et al., "Targeted therapy in advanced non-small cell lung cancer: current advances and future trends," Journal of Hematology & Oncology, vol. 14 (1): 20 pages (2021).

Napolitano et al., "Neuropilins Controlling Cancer Therapy Responsiveness," International Journal of Molecular Sciences, vol. 20 (8):2049, 14 pages (2019).

Rizzolio S. et al, "Neuropilin-1 upregulation elicits adaptive resistance to oncogene-targeted therapies," The Journal of Climical Investigation, vol. 128 (9): 3976-3990 (2018).

U.S. Appl. No. 14/893,317, filed Nov. 23, 2015, Yong Sung Kim.

U.S. Appl. No. 15/560,232, filed Sep. 21, 2017, Yong Sung Kim.

U.S. Appl. No. 18/506,356, filed Nov. 10, 2023, Yong Sung Kim.

U.S. Appl. No. 16/081,342, filed Aug. 30, 2018, Yong Sung Kim.

U.S. Appl. No. 18/079,858, filed Dec. 12, 2022, Yong Sung Kim.

U.S. Appl. No. 18/040,083, filed Jan. 31, 2023, Ho-Juhn Song.

Holford et al, "Understanding the Dose-Effect Relationship-Clinical Application of Pharmacokinetic-Pharmacodynamic Models," Clin. Pharmacokin., 6: 429-453 (1981)—The Back Story, The AAPS Journal, vol. 13(4): 662-664 (2011).

Loewe, S. and Muischnek, H., Arch. Exp. Pathol Pharmacol. 114: 313-326 (1926) with translation 24 pages.

* cited by examiner

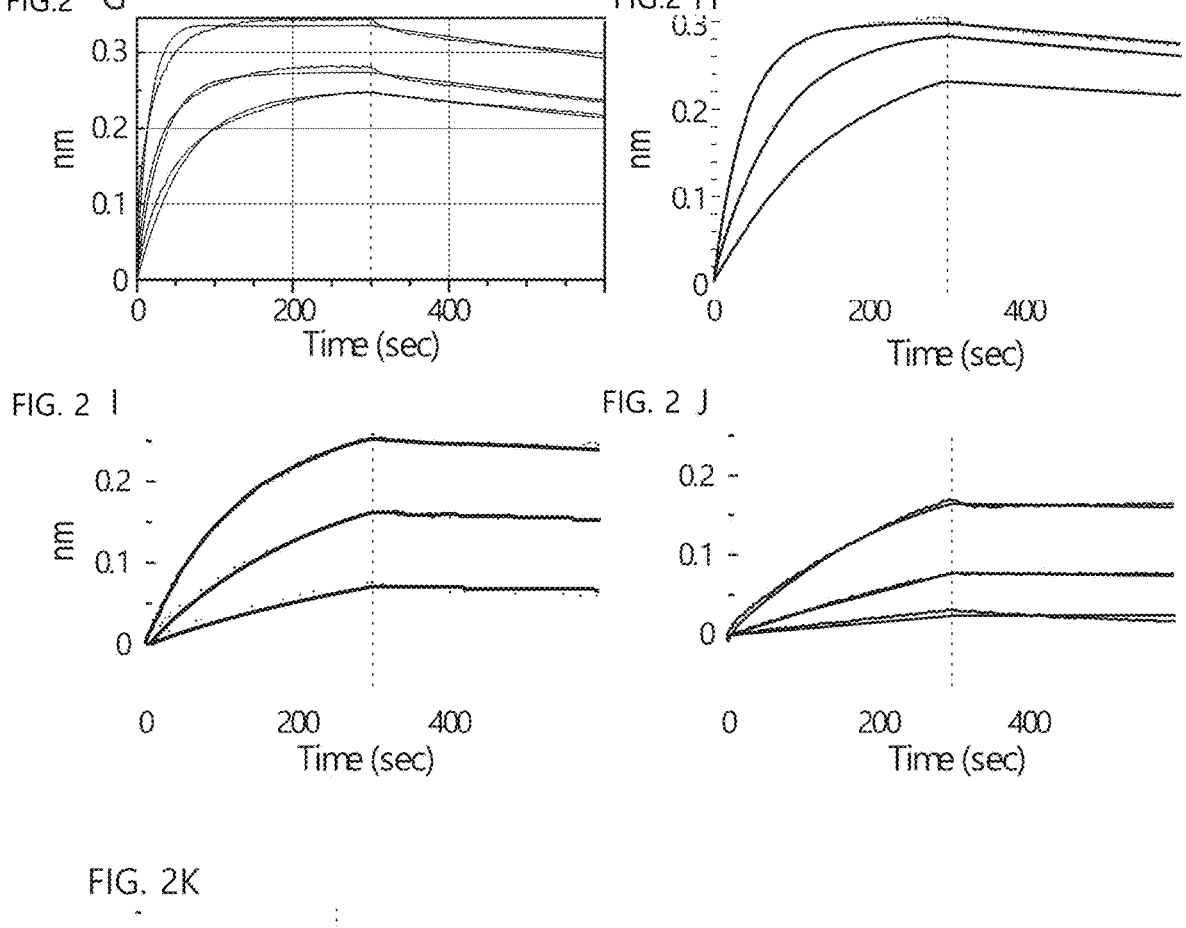

EGFR Binding
$K_D$: < 0.1 nM

NRP1 Binding
$K_D$: 24.5 nM

BISPECIFIC ANTIBODIES COMPRISING AN NRP1 BINDING DOMAIN AND METHODS OF USE THEREOF

RELATED APPLICATIONS

This application claims priority to U.S. Provisional Application No. 63/325,312, filed Mar. 30, 2022, and U.S. Provisional Application No. 63/325,317, filed Mar. 30, 2022, the entire contents of both of which are hereby incorporated by reference.

SEQUENCE LISTING

This application contains a Sequence Listing which has been submitted electronically in XML format and is hereby incorporated by reference in its entirety. Said XML copy, created on Jul. 24, 2023, is named Sequence-Listing PTJ-002.xml and is 164,154 bytes in size.

BACKGROUND

Solid tumors and blood cancers, such as leukemia and lymphoma are treated with therapeutic antibodies. Treatment of antibodies for solid tumors and blood cancers show different response rates. For instance, response rate for antibody treatment in blood cancers reaches 30 to 51%, whereas the response rate for solid tumors is only 8 to 15%. This is because cancer cells in blood are accessible to antibody targeting, whereas solid tumor efficacy depends on extravasation and tumor penetration.

An antibody has reduced tumor penetration for several reasons, including: 1) intrinsic property of the antibody size ~150 kDa prevents penetration through endothelial barrier, 2) high tumor interstitial fluid pressure; and 3) abnormal microstructural/physiological properties of tumor tissue, including reduced perfusion and abnormal angiogenesis, low lymphatic vessel formation, high cellular density, and high extracellular density (Jain and Stylianopoulos, 2010). For these reasons, the amount of antibody that accumulates in the tumor tissues is very small (0.01 to 0.0001% of injected dose per gram tumor tissue), resulting in a low response rate (Thurber et al. 2008). Accordingly, the development of antibody technology that enables an antibody to accumulate selectively in tumor tissue and to have a high ability to penetrate tumor tissue would reduce toxicity and increase the therapeutic effect.

Efforts are being made to improve tumor penetration by engineering smaller antibodies, regulating antigen binding specificity, and combining the administration an antibody with a molecule that promotes the tumor tissue penetration. For instance, antibody fragments, such as an antigen-binding fragment (Fab) (50 kDa), a single-chain variable fragment (scFv) (30 kDa), and a heavy-chain variable domain (VH) (14 kDa), have reduced sizes that overcome the endothelial barrier. However, the antibody fragment has no Fc fragment and due to its small size, the kidneys quickly filter the fragment from the serum after in vivo administration, reducing the circulation half-life and therapeutic effect (Behr et al. 1998). Antibodies could be equipped with features that improve tumor penetration.

SUMMARY

The present disclosure provides a bispecific antibody comprising a neuropilin –1 receptor (NRP1) binding domain and a second binding domain binding a second target, such as a receptor tyrosine kinase (RTK) binding domain, e.g., an epidermal growth factor receptor (EGFR) binding domain. Accordingly, in one aspect, the disclosure provides a bispecific antibody comprising a first binding domain that binds to human neuropilin-1 receptor (NRP1) and a second binding domain that binds to human epidermal growth factor receptor (EGFR).

The disclosure provides NRP1 binding domains from anti-NRP1 monoclonal antibodies that form bispecific antibodies with beneficial properties. For example, NRP1 x EGFR bispecific antibodies of the disclosure exhibit an enhanced ability for both internalization and degradation of NRP1 and EGFR receptors as compared to anti-EGFR mAb or anti-NRP1 mAb alone or in combination. The disclosure provides EGFR x NRP1 bispecific antibodies having high affinity to EGFR to provide high homing capacity to tumors expressing EGFR. The bispecific antibody has asymmetric binding affinities to EGFR and NRP1, with affinity to EGFR at least 10 times higher than the affinity to NRP1. The NRP1 targeting portion of the antibody contains a NRP1 binding domain that decreases NRP1 occupancy time to reduce toxicity in healthy tissues. The combination of these features in a bispecific antibody significantly increases the potential to deliver high therapeutic potency for cancer treatment, while decreasing toxic side effects.

In one aspect, the disclosure pertains to a bispecific antibody comprising a first binding domain that binds to human neuropilin-1 receptor (NRP1) and a second binding domain that binds to a target other than NRP1, wherein the first binding domain comprises:

i. an antibody heavy chain variable (VH) domain comprising CDR1, CDR2 and CDR3 regions (HCDR1, HCDR2 and HCDR3, respectively), wherein HCDR1 consists of the sequence shown in SEQ ID NO: 79, HCDR2 consists of the sequence shown in SEQ ID NO: 80, and HCDR3 consists of the sequence shown in any one of SEQ ID NOs: 81-84; and ii. an antibody light chain variable (VL) domain comprising CDR1, CDR2 and CDR3 regions (LCDR1, LCDR2 and LCDR3, respectively), wherein LCDR1 consists of the sequence shown in any one of SEQ ID NOs: 85-87, LCDR2 consists of the sequence shown in SEQ ID NO: 88, and LCDR3 consists the sequence shown in SEQ ID NO: 89.

In certain embodiments, (i) HCDR1 consists of the sequence shown in SEQ ID NO: 79, HCDR2 consists of the sequence shown in SEQ ID NO: 80, and HCDR3 consists of the sequence shown in any one of SEQ ID NO: 84; and (ii) LCDR1 consists of the sequence shown in SEQ ID NO: 85, LCDR2 consists of the sequence shown in SEQ ID NO: 88, and LCDR3 consists of the sequence shown in SEQ ID NO: 89.

In certain embodiments, the first binding domain comprises: (i) an antibody heavy chain variable (VH) domain comprising CDR1, CDR2 and CDR3 regions (HCDR1, HCDR2 and HCDR3, respectively), wherein HCDR1 comprises the sequence shown in SEQ ID NO: 79, HCDR2 comprises the sequence shown in SEQ ID NO: 80, and HCDR3 comprises the sequence shown in any one of SEQ ID NOs: 81-84; and (ii) an antibody light chain variable (VL) domain comprising CDR1, CDR2 and CDR3 regions (LCDR1, LCDR2 and LCDR3, respectively), wherein LCDR1 comprises the sequence shown in any one of SEQ ID NOs: 85-87, LCDR2 comprises the sequence shown in SEQ ID NO: 88, and LCDR3 comprises the sequence shown in SEQ ID NO: 89.

In certain embodiments, the second binding domain targets EGFR. For example, in an embodiment, the second binding domain is comprised of an N-terminal EGFR-binding heavy chain variable domain (VH) and a heavy chain constant 1 domain (CH1), and the first binding domain is comprised of a C-terminal NRP1-binding single chain variable fragment (scFv), wherein the N-terminal variable heavy chain (VH) and the C-terminal scFv binding domains are at opposite ends of a contiguous sequence. In an embodiment, the second binding domain further comprises a heavy chain constant 2 domain (CH2) and a heavy chain constant 3 domain (CH3). In an embodiment, the C-terminal NRP1-binding scFv comprises a light chain variable domain (VL) connected to a heavy chain variable domain (VH) by a flexible linker peptide. In an embodiment, the bispecific antibody further comprises a corresponding EGFR binding light chain variable domain (VL) and light chain constant domain (CL), wherein the bispecific antibody is comprised of two polypeptides.

In certain embodiments, the second binding domain that targets EGFR comprises: (i) an antibody heavy chain variable (VH) domain comprising CDR1, CDR2 and CDR3 regions (HCDR1, HCDR2 and HCDR3, respectively), wherein HCDR1 consists of the sequence shown in SEQ ID NO: 71, HCDR2 consists of the sequence shown in SEQ ID NO: 72, and HCDR3 consists of the sequence shown in SEQ ID NO: 73; and (ii) an antibody light chain variable (VL) domain comprising CDR1, CDR2 and CDR3 regions (LCDR1, LCDR2 and LCDR3, respectively), wherein LCDR1 consists of the sequence shown in SEQ ID NO: 74, LCDR2 consists of the sequence shown in SEQ ID NO: 75, and LCDR3 consists of the sequence shown in SEQ ID NO: 76.

In certain embodiments, the bispecific antibody comprises a first binding domain (i.e., NRP1 binding domain) comprising a VH domain comprising the sequence shown in SEQ ID NO: 77 and a VL domain comprising the sequence shown in SEQ ID NO: 78.

In certain embodiments, the bispecific antibody comprises a first binding domain (i.e., NRP1 binding domain) comprising a VH domain comprising the sequence shown in SEQ ID NO: 77 and a VL domain comprising the sequence shown in SEQ ID NO: 78; and a second binding domain (i.e., EGFR binding domain) comprising a VH domain comprising the sequence shown in SEQ ID NO: 69 and a VL domain comprising the sequence shown in SEQ ID NO: 70.

In certain embodiments of the bispecific antibody, the first binding domain and second binding domain comprise a bispecific antibody heavy chain comprising an amino acid sequence selected from SEQ ID NO: 2, 3, 4, 5, 6, 7, 8, 9, 10, 11 or 39. In certain embodiments, the bispecific antibody heavy chain pairs with an antibody light chain comprising an amino acid sequence shown SEQ ID NO: 12. In certain embodiments, the bispecific antibody heavy chain comprises the amino acid sequence shown in SEQ ID NO: 11 or 39 and the bispecific antibody light chain comprises the amino acid sequence shown in SEQ ID NO: 12.

In certain embodiments of the bispecific antibody, the binding affinity ($K_D$) of the EGFR binding domain is <0.1 nM. In certain embodiments, the binding affinity ($K_D$) of the NRP1 binding domain ranges between 0.1 nM and 100 nM. In certain embodiments, the EGFR binding domain comprises a $K_D$ for EGFR at least 2, at least 10, at least 20, at least 30, at least 40, at least 50, at least 60, at least 70, at least 80, at least 100, or more than 100 times greater than a $K_D$ for NRP1 by the NRP1-binding domain.

In another aspect, the disclosure pertains to a pharmaceutical composition comprising a bispecific antibody of the disclosure.

In another aspect, the disclosure pertains to polynucleotide encoding a bispecific antibody of the disclosure. In an embodiment, the bispecific antibody comprises a heavy chain polypeptide encoded by the polynucleotide sequence set forth in any one of SEQ ID NOs: 15, 16, 17, 18, 19, 20, 21, 22, 23, 24 and 40. In an embodiment, the polynucleotide sequence is inserted into a vector for protein expression.

In another aspect, the disclosure pertains to a method of internalizing neuropilin-1 (NRP1) receptor by a cell, the method comprising contacting the cell with a bispecific antibody of the disclosure such that NRP1 is internalized by the cell. In another embodiment, the disclosure provides a method of internalizing epidermal growth factor receptor (EGFR) by a cell, the method comprising contacting the cell with an NRP1 x EGFR bispecific antibody of the disclosure such that EGFR is internalized by the cell.

In another aspect, the disclosure pertains to a method of treating cancer associated with aberrant NRP1 expression in a subject comprising administering to the subject a bispecific antibody of the disclosure, or a pharmaceutical composition thereof. In another embodiment, the disclosure provides a method of treating cancer associated with aberrant EGFR expression in a subject comprising administering to the subject an NRP1 x EGFR bispecific antibody of the disclosure, or a pharmaceutical composition thereof. In an embodiment, the cancer is non-small cell lung cancer. In an embodiment, the method further comprises administering to the subject at least one additional chemotherapeutic agent(s) for combination therapy.

In another aspect, the disclosure pertains to use of a bispecific antibody of the disclosure in the manufacture of a medicament for use in therapy, e.g., in cancer treatment as described herein. In an embodiment, the disclosure pertains to use of an NRP1 x EGFR bispecific antibody of the disclosure in the manufacture of a medicament for treating cancer associated with aberrant EGFR expression.

BRIEF DESCRIPTION OF FIGURES

The following figures are provided by way of example and are not intended to limit the scope of the invention.

FIG. 2C Binding of bsAb with heavy chain polypeptide SEQ ID NO: 3 to recombinant NRP1 measured by Octet® Red 96 sensorgrams depicting the dose dependent binding of tumor associated receptor targeting antibody. Each line on the graph represents binding kinetics at a specific bsAb concentration (going left to right 10, 5, and 2.5 nM).

FIG. 2D Binding of bsAb with heavy chain polypeptide SEQ ID NO: 4 to recombinant NRP1 measured by Octet® Red 96 sensorgrams depicting the dose dependent binding of tumor associated receptor targeting antibody. Each line on the graph represents binding kinetics at a specific bsAb concentration (going left to right 10, 5, and 2.5 nM).

FIG. 2E Binding of bsAb with heavy chain polypeptide SEQ ID NO: 5 to recombinant NRP1 measured by Octet® Red 96 sensorgrams depicting the dose dependent binding of tumor associated receptor targeting antibody. Each line on the graph represents binding kinetics at a specific bsAb concentration (going left to right 10, 5, and 2.5 nM).

FIG. 2F Binding of bsAb with heavy chain polypeptide SEQ ID NO: 6 to recombinant NRP1 measured by Octet® Red 96 sensorgrams depicting the dose dependent binding of tumor associated receptor targeting antibody. Each line on the graph represents binding kinetics at a specific bsAb concentration (going left to right 10, 5, and 2.5 nM).

FIG. 2G Binding of bsAb with heavy chain polypeptide SEQ ID NO: 7 to recombinant NRP1 measured by Octet® Red 96 sensorgrams depicting the dose dependent binding of T tumor associated receptor targeting antibody. Each line on the graph represents binding kinetics at a specific bsAb concentration (going left to right 10, 5, and 2.5 nM).

FIG. 2H Binding of bsAb with heavy chain polypeptide SEQ ID NO: 8 to recombinant NRP1 measured by Octet® Red 96 sensorgrams depicting the dose dependent binding of tumor associated receptor targeting antibody. Each line on the graph represents binding kinetics at a specific bsAb concentration (going left to right 10, 5, and 2.5 nM).

FIG. 2I Binding of bsAb with heavy chain polypeptide SEQ ID NO: 9 to recombinant NRP1 measured by Octet® Red 96 sensorgrams depicting the dose dependent binding of tumor associated receptor targeting antibody. Each line on the graph represents binding kinetics at a specific bsAb concentration (going left to right 10, 5, and 2.5 nM).

FIG. 2J Binding of bsAb with heavy chain polypeptide SEQ ID NO: 10 to recombinant NRP1 measured by Octet® Red 96 sensorgrams depicting the dose dependent binding of tumor associated receptor targeting antibody. Each line on the graph represents binding kinetics at a specific bsAb concentration (going left to right 10, 5, and 2.5 nM).

FIG. 2K Binding of bsAb with heavy chain polypeptide SEQ ID NO: 11 to recombinant NRP1 measured by Octet® Red 96 sensorgrams depicting the dose dependent binding of tumor associated receptor targeting antibody. Each line on the graph represents binding kinetics at a specific bsAb concentration (going left to right 10, 5, and 2.5 nM).

DETAILED DESCRIPTION

Definitions

Figures 1, 1A, 1B, 1C, 1D, 1F:
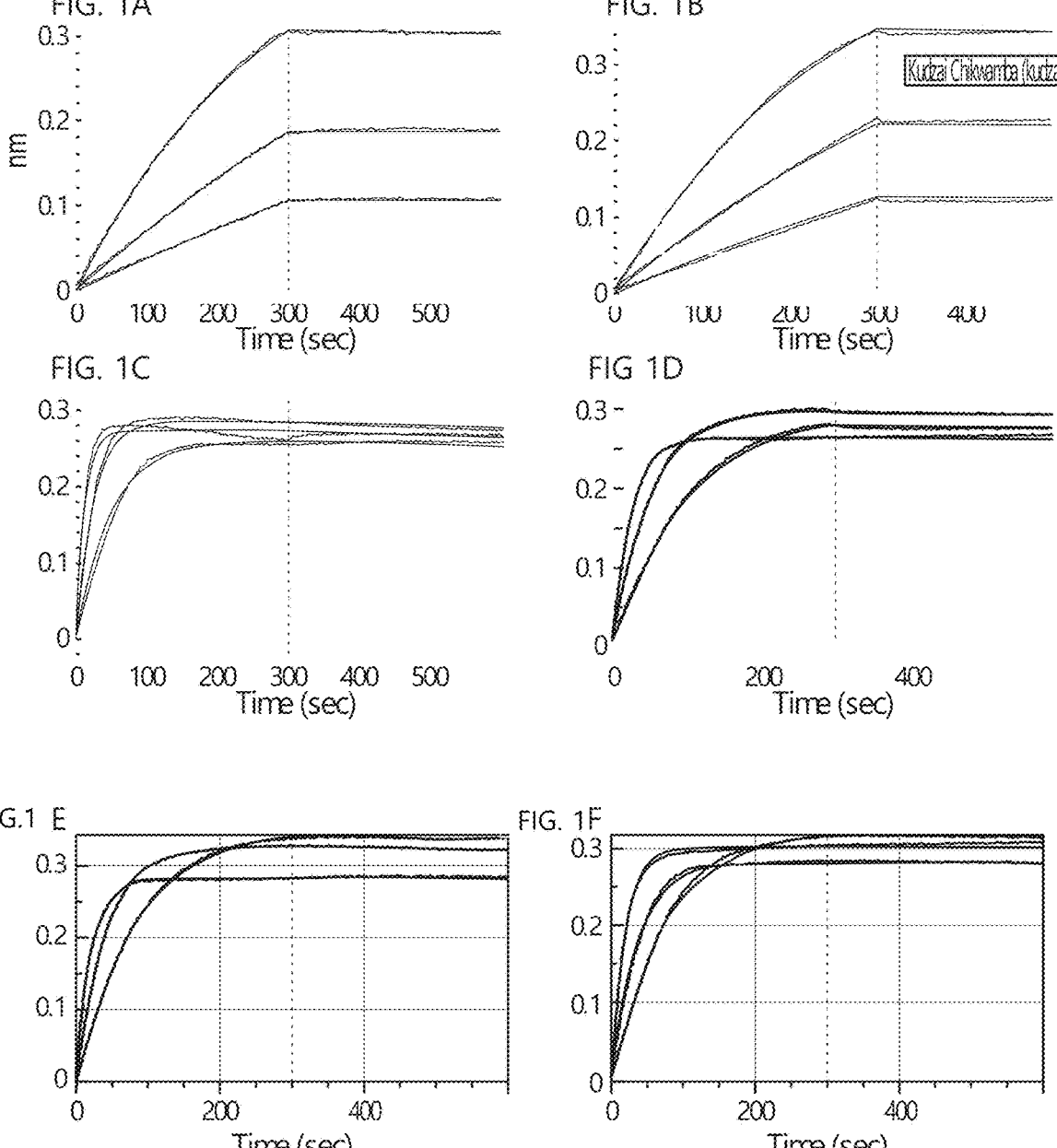
FIG. 1A Binding of bsAb with heavy chain polypeptide SEQ ID NO: 1 to recombinant human EGFR measured by Octet® Red 96 sensorgrams depicts the dose dependent binding of tumor associated receptor targeting antibody. Each line on the graph represents binding kinetics at a specific bsAb concentration (going left to right 10, 5, and 2.5 nM).
FIG. 1B Binding of bsAb with heavy chain polypeptide SEQ ID NO: 2 to recombinant human EGFR measured by Octet® Red 96 sensorgrams depicts the dose dependent binding of tumor associated receptor targeting antibody. Each line on the graph represents binding kinetics at a specific bsAb concentration (going left to right 10, 5, and 2.5 nM).
FIG. 1C Binding of bsAb with heavy chain polypeptide SEQ ID NO: 3 to recombinant human EGFR measured by Octet® Red 96 sensorgrams depicts the dose dependent binding of tumor associated receptor targeting antibody. Each line on the graph represents binding kinetics at a specific bsAb concentration (going left to right 10, 5, and 2.5 nM).
FIG. 1D Binding of bsAb with heavy chain polypeptide SEQ ID NO: 4 to recombinant human EGFR measured by Octet® Red 96 sensorgrams depicts the dose dependent binding of tumor associated receptor targeting antibody. Each line on the graph represents binding kinetics at a specific bsAb concentration (going left to right 10, 5, and 2.5 nM).
FIG. 1F Binding of bsAb with heavy chain polypeptide SEQ ID NO: 6 to recombinant human EGFR measured by Octet® Red 96 sensorgrams depicts the dose dependent binding of tumor associated receptor targeting antibody. Each line on the graph represents binding kinetics at a specific bsAb concentration (going left to right 10, 5, and 2.5 nM).
Figure 1G:
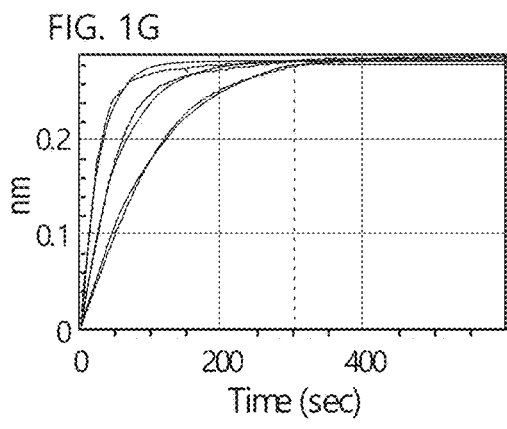
FIG. 1G Binding of bsAb with heavy chain polypeptide SEQ ID NO: 7 to recombinant human EGFR measured by Octet® Red 96 sensorgrams depicts the dose dependent binding of tumor associated receptor targeting antibody. Each line on the graph represents binding kinetics at a specific bsAb concentration (going left to right 10, 5, and 2.5 nM).
Figure 1H:
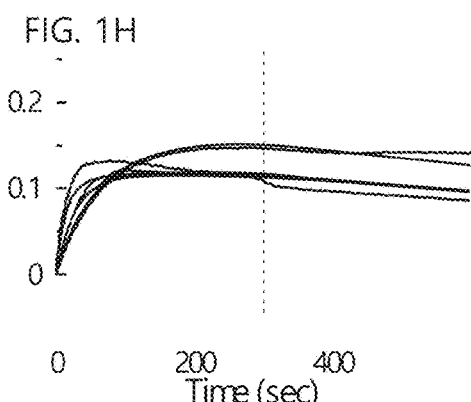
FIG. 1H Binding of bsAb with heavy chain polypeptide SEQ ID NO: 8 to recombinant human EGFR measured by Octet® Red 96 sensorgrams depicts the dose dependent binding of tumor associated receptor targeting antibody. Each line on the graph represents binding kinetics at a specific bsAb concentration (going left to right 10, 5, and 2.5 nM).
Figure 1I:
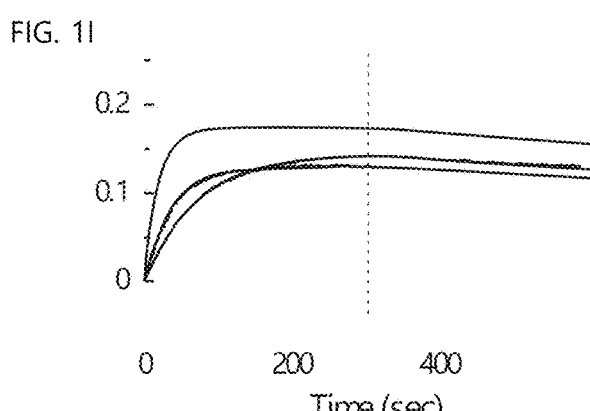
FIG. 1I Binding of bsAb with heavy chain polypeptide SEQ ID NO: 9 to recombinant human EGFR measured by Octet® Red 96 sensorgrams depicts the dose dependent binding of tumor associated receptor targeting antibody. Each line on the graph represents binding kinetics at a specific bsAb concentration (going left to right 10, 5, and 2.5 nM).
Figure 1:
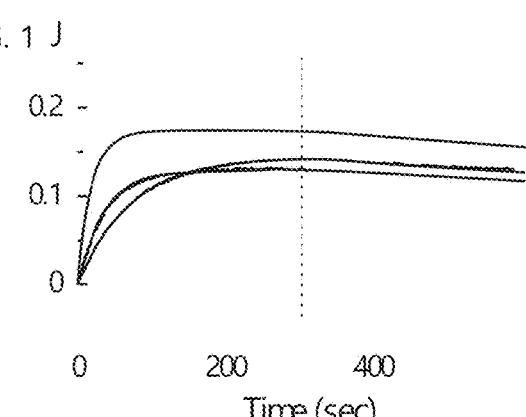
FIG. 1E Binding of bsAb with heavy chain polypeptide SEQ ID NO: 5 to recombinant human EGFR measured by Octet® Red 96 sensorgrams depicts the dose dependent binding of tumor associated receptor targeting antibody. Each line on the graph represents binding kinetics at a specific bsAb concentration (going left to right 10, 5, and 2.5 nM).
FIG. 1J Binding of bsAb with heavy chain polypeptide SEQ ID NO: 10 to recombinant human EGFR measured by Octet® Red 96 sensorgrams depicts the dose dependent binding of tumor associated receptor targeting antibody. Each line on the graph represents binding kinetics at a specific bsAb concentration (going left to right 10, 5, and 2.5 nM).
FIG. 1K Binding of bsAb with heavy chain polypeptide SEQ ID NO: 11 to recombinant human EGFR measured by Octet® Red 96 sensorgrams depicts the dose dependent binding of tumor associated receptor targeting antibody. Each line on the graph represents binding kinetics at a specific bsAb concentration (going left to right 10, 5, and 2.5 nM).
Figure 1K:
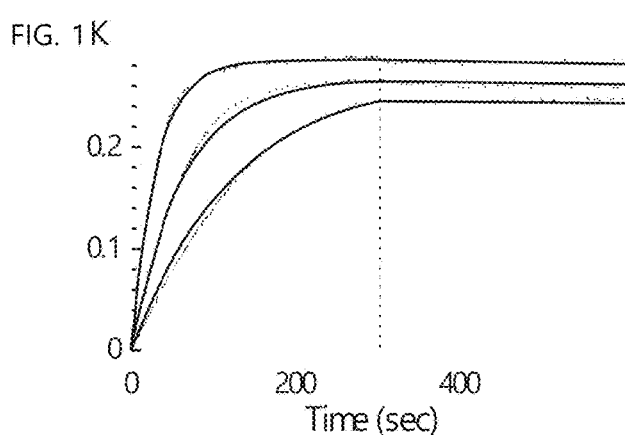
Figures 2, 2A, 2B:
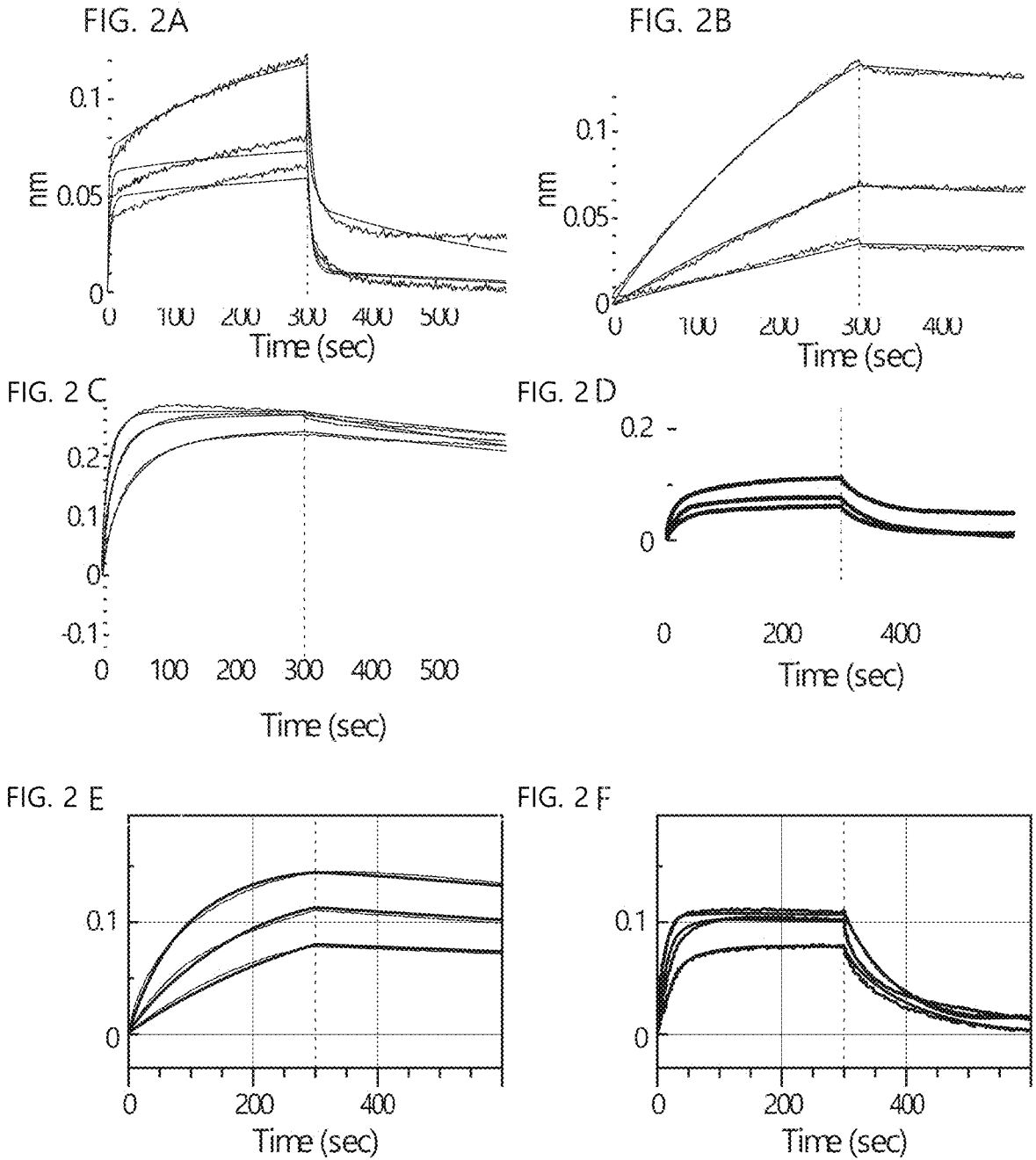
FIG. 2A Binding of bsAb with heavy chain polypeptide SEQ ID NO: 1 to recombinant NRP1 measured by Octet® Red 96 sensorgrams depicting the dose dependent binding of tumor associated receptor targeting antibody. Each line on the graph represents binding kinetics at a specific bsAb concentration (going left to right 10, 5, and 2.5 nM).
FIG. 2B Binding of bsAb with heavy chain polypeptide SEQ ID NO: 2 to recombinant NRP1 measured by Octet® Red 96 sensorgrams depicting the dose dependent binding of tumor associated receptor targeting antibody. Each line on the graph represents binding kinetics at a specific bsAb concentration (going left to right 10, 5, and 2.5 nM).

Unless defined otherwise, all technical and scientific terms used herein have the same meaning as commonly understood by one of ordinary skill in the art to which this disclosure belongs. Accordingly, the following terms are intended to have the following meanings:

As used in the specification and claims, the singular form "a", "an" and "the" includes plural references unless the context clearly dictates otherwise.

As used herein, "administration" of a disclosed polypeptide encompasses the delivery to a subject of a polypeptide or composition of the present invention, as described herein, or a prodrug or other pharmaceutically acceptable derivative thereof, using any suitable formulation or route of administration, e.g., as described herein.

As used herein, the term "and/or," when used in a list of two or more items, means that any one of the listed items can be employed by itself, or any combination of two or more of the listed items can be employed.

As used herein, the term "bispecific antibody" refers to an antibody comprising two binding sites that bind two different target antigens or target epitopes.

As used herein, "treatment", "treat", or "treating", are used interchangeably herein, and refer to an approach for obtaining a therapeutic benefit. A therapeutic benefit is determined by whether the tumor shrinks, stays the same size, or increase progression free survival compared to placebo.

A "subject," as used herein, can refer to any animal with a cancer, e.g., a mammal, such as an experimental animal, a farm animal, pet, or the like. In some embodiments, the animal is a primate, preferably a human. As used herein, the terms "subject" and "subjects" are used interchangeably. The terms "subject" and "subjects" refer to an animal (e.g., a bird such as a chicken, quail or turkey, or a mammal), specifically a "mammal" including a non-primate (e.g., a cow, pig, horse, sheep, rabbit, guinea pig, rat, cat, dog, and mouse) and a primate (e.g., a monkey, chimpanzee and a human), and more specifically a human. In one embodiment, the subject is a non-human animal such as a farm animal (e.g., a horse, cow, pig or sheep), or a pet (e.g., a dog, cat, guinea pig or rabbit). In a preferred embodiment, the subject is a "human".

As used herein, the term "fusion" refers to unifying two molecules having the same or different function or structure, and the methods of fusing may include any physical, chemical or biological method capable of binding the peptide to the protein, the small-molecule drug, the nanoparticle or the liposome. Preferably, the fusion may be mediated by a linker peptide, and for example, the linker peptide may be fused to the C-terminus of a fragment of an antibody light-chain variable region (Fc). Alternatively, two molecules are fused by the integration of multiple domains within the polypeptide sequence.

The term "linker" as used herein is a molecule or peptide that links two polypeptides subunits together. A linker peptide sequence may include the amino acid sequence (GGGGS)n (SEQ ID NO: 13), wherein n defines the number of repeats. The number of subunit repeats defines linker peptide flexibility. A flexible peptide linker allows more flexibility between two binding domains.

As used herein, an "effective amount" refers to an amount sufficient to elicit the desired anti-cancer response. In the present invention, the desired biological response is to inhibit cell proliferation. The precise amount of bispecific antibody administered to a subject will depend on the mode of administration, the type and severity of the cancer and on the characteristics of the subject, such as general health, age, sex, body weight and tolerance to drugs. The skilled artisan will be able to determine appropriate dosages depending on these and other factors. When co-administered with other anti-cancer agents, e.g., when co-administered with a chemotherapy, an "effective amount" of the second agent will depend on the type of drug used. Suitable dosages are known for approved agents and can be adjusted by the skilled artisan according to the condition of the subject, the type of cancer being treated and the amount of a polypeptide herein administered. In cases where no amount is expressly noted, an effective amount should be assumed. For example, bispecific antibodies described herein can be administered to a subject in a dosage range between approximately 0.01 to 100 mg/kg body weight/day at weekly or biweekly intervals.

The terms "polypeptide," "peptide" and "protein" are used interchangeably herein to refer to a polymer of amino acid residues.

The term "variant" as used herein describes a sequence with changes from the wildtype, conventional, or primary sequence. The changes may take the form of deletions, substitutions, or insertions of amino acids or nucleotides. The variant may contain one or more, including a combination of sequence changes.

The term "reduce" or other forms of the word, such as "reducing" or "reduction," generally refers to the lowering of an event or characteristic (e.g., one or more symptoms, or the binding of one protein to another). It is understood that this is typically in relation to some standard or expected value, in other words it is relative, but that it is not always necessary for the standard or relative value to be referred to.

The term "affinity" as used in the context of "binding affinity" refers to a decrease in the affinity of one molecule to another molecule. For example, in some embodiments, a protein, domain, or motif can specifically bind to a particular target, e.g., a peptide, polypeptide, protein, carbohydrate, saccharide, polysaccharide, glycosaminoglycan, or any epitope thereof, with a given affinity. The term "affinity"

refers to the strength of the sum total of non-covalent interactions between a single binding site of a molecule and its binding target or partner (e.g., an antigen). The affinity of a molecule for its target can be represented by the dissociation constant ($K_D$), which is the ratio of dissociation and association rate constants ($k_{off}$ and $k_{on}$, respectively). The strength, or affinity of binding interactions can be expressed in terms of the dissociation constant ($K_D$) of the interaction, wherein a smaller $K_D$ represents a greater affinity. The binding properties (affinity) of selected polypeptides can be quantified using methods well known in the art. One such method entails measuring the rates of antigen-binding site/ antigen complex formation and dissociation, wherein those rates depend on the concentrations of the complex partners, the affinity of the interaction, and geometric parameters that equally influence the rate in both directions. Thus, both the "on rate constant" ($K_{on}$) and the "off rate constant" ($K_{off}$) can be determined by calculation of the concentrations and the actual rates of association and dissociation, (See Malmqvist (1993) *Nature* 361:186-187).

The ratio of $K_{off}/K_{on}$, enables the cancellation of all parameters not related to affinity, and is equal to the dissociation constant $K_D$. (See, generally, Davies et al. (1990) Annual Rev Biochem 59:439-473). In some embodiments, a recombinant polypeptide of the present invention can specifically bind to an epitope when the equilibrium binding constant ($K_D$) is 1 μM. In some embodiments, a recombinant polypeptide of the present invention can specifically bind to an epitope when the equilibrium binding constant ($K_D$) is <100 nM. In some embodiments, a recombinant polypeptide of the present invention can specifically bind to an epitope when the equilibrium binding constant ($K_D$) is <10 nM. In some embodiments, a recombinant polypeptide of the present invention can specifically bind to an epitope when the equilibrium binding constant ($K_D$) is <100 μM to about 1 μM, as measured by assays such as Surface Plasmon Resonance (SPR), Octet® assays, or similar assays known to those skilled in the art. In some embodiments, a $K_D$ can be $10^{-5}$ M or less (e.g., $10^{-6}$ M or less, $10^{-7}$ M or less, $10^{-8}$ M or less, $10^{-8}$ M or less, $10^{11}$ M or less, $10^{-11}$ M or less, $10^{-12}$ M or less, $10^{-13}$ M or less, $10^{-14}$ M or less, $10^{-15}$ M or less, or $10^{-16}$M or less).

Thus, equivalent affinities may comprise different rate constants, as long as the ratio of the rate constants remains the same. Thus, in some embodiments, "reduced binding" refers to a decrease in affinity for the respective interaction. Conversely, "increased binding" refers to an increase in binding affinity for the respective interaction.

The term "heavy chain" as used herein may be interpreted to include a full-length heavy chain including heavy chain variable region domain (VH), which includes an amino acid sequence having a variable region sequence sufficient to confer antigen-specificity, and three heavy chain constant region domains CH1, CH2 and CH3, or a fragment thereof. Also, the term "light chain" as used herein may be interpreted to include a full-length light chain including a light chain variable region domain (VL), which includes an amino acid sequence having a variable region sequence sufficient to confer antigen-specificity and a light chain constant region domain (CL), a fragment thereof. The term "FAB" as used herein refers to the region that binds the antigen. The FAB consists of one variable heavy and light chain and one constant heavy and light chain.

As used herein, the term "percent identity" between two sequences (e.g., amino acid or nucleotide sequences) refers to the percentage of positions (out of a possible 100%) that when optimally aligned and compared, are identical (with appropriate insertions or deletions for optimal alignment). The percent identity between two sequences is a function of the number of identical positions shared by the sequences (i.e., % identity=# of identical positions/total # of positions ×100), taking into account the number of gaps, and the length of each gap, which need to be introduced for optimal alignment of the two sequences. The comparison of sequences and determination of percent identity between two sequences can be accomplished using mathematical algorithm, as described in the non-limiting examples below. Methods and algorithms for determining the % homology between two protein sequences are well established in the art.

For example, the percent identity between two amino acid sequences can be determined using the Needleman and Wunsch ((1970) *J. Mol. Biol.* (48):444-453) algorithm which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6. Furthermore, a protein amino acid sequence can be used as a "query sequence" to perform a search against public databases to, for example, identify related sequences. Such searches can be performed using the XBLAST programs (version 2.0) of Altschul, et al. (1990) *J. Mol. Biol.* 215:403-10. BLAST protein searches can be performed with the XBLAST program, score=50, word-length=3 to obtain amino acid sequences homologous to the protein molecules of the invention. To obtain gapped alignments for comparison purposes, Gapped BLAST can be utilized as described in Altschul et al. (1997) *Nucleic Acids Res.* 25(17):3389-3402. When utilizing BLAST and Gapped BLAST programs, the default parameters of the respective programs (e.g., XBLAST and NBLAST) can be used.

As used herein, the terms "in combination" or "co-administration" can be used interchangeably to refer to the use of more than one therapy (e.g., one or more prophylactic and/or therapeutic agents). The use of the terms does not restrict the order in which therapies (e.g., prophylactic and/or therapeutic agents) are administered to a subject.

As used herein, the term "synergistic" refers to a combination of a polypeptide of the invention and another therapy (e.g., a prophylactic or therapeutic agent), which is more effective than the additive effects of the therapies.

The term "pharmaceutically acceptable salts" is meant to include salts of the active bispecific antibodies that are prepared with relatively nontoxic acids or bases, depending on the particular substituents found on the bispecific antibodies described herein.

The term "parenteral" as used herein includes, but is not limited to, subcutaneous, intravenous, intramuscular, intra-articular, intra-synovial, intrasternal, intrathecal, intrahepatic, intralesional and intracranial injection or infusion techniques.

The term "carrier" refers to the vehicle used in the formulation of a composition and can be composed of multiple excipients.

The term "excipient" as used herein refers to any pharmacologically inactive, natural, or synthetic, component or substance that is formulated alongside (e.g., concomitantly), or subsequent to, the active ingredient of the present invention. In some embodiments, an excipient can be any additive, adjuvant, binder, bulking agent, carrier, coating, diluent, disintegrant, filler, glidant, lubricant, preservative, vehicle, or combination thereof, with which a recombinant polypeptide of the present invention can be administered, and or which is useful in preparing a composition of the present invention. Excipients, include any such materials known in the art that are nontoxic and do not interact with other components of a composition. In some embodiments, excipients can be formulated alongside a recombinant polypeptide when preparing a composition for the purpose of bulking up compositions (thus often referred to as bulking agents, fillers or diluents). In other embodiments, an excipient can be used to confer an enhancement on the active ingredient in the final dosage form, such as facilitating absorption and/or solubility. In yet other embodiments, an excipient can be used to provide stability, or prevent contamination (e.g., microbial contamination). In other embodiments, an excipient can be used to confer a physical property to a composition (e.g., a composition that is a dry granular, or dry flowable powder physical form). Reference to an excipient includes both one and more than one such excipients. Suitable pharmaceutical excipients are described in Remington's Pharmaceutical Sciences, by E. W. Martin, the disclosure of which is incorporated herein by reference in its entirety.

Throughout this specification, unless the context requires otherwise, the word "comprise," or variations such as "comprises" or "comprising," will be understood to imply the inclusion of a stated step, element, or integer, or a group of steps, elements, or integers but not the exclusion of any other step, element, or integer or group of elements, steps, or integers.

All patent applications, patents, and printed publications referred to herein are incorporated by reference in their entirety to the same extent as if each individual publication, patent, or patent application was specifically and individually indicated to be incorporated by reference in its entirety. And, all patent applications, patents, and printed publications cited herein are incorporated herein by reference in their entireties, except for any definitions, subject matter disclaimers, or disavowals, and except to the extent that the incorporated material is inconsistent with the express disclosure herein, in which case the language in this disclosure controls.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims. It is further to be understood that all values are approximate, and are provided for description.

Bispecific Antibodies with an EGFR Binding Domain and a NRP1 Binding Domain

Bispecific antibodies have many advantages over monoclonal antibodies. First, it is more efficient to manufacture one molecule with two efficacious targets. For example, a bispecific antibody can target multiple immune cell receptors (CD3, CD16, or CD47) or immune checkpoint proteins (PD1, LAG-3, or CTLA-4) or both. For example, bispecific antibodies can target a cancer cell antigen, such as EGFR, and an immune cell receptor or immune checkpoint regulator, such as neuropilin 1 (NRP1). Bispecific antibodies for anticancer therapy are designed to increase anticancer potency.

EGFR Binding Domain

The epidermal growth factor receptor (EGFR) is one of the most frequently altered oncogenes in solid tumors. Increased EGFR signaling drives proliferation and cell survival in many cancer types, including breast, prostrate, non-small cell lung cancer (NSCLC), esophagogastric, liver, glioblastoma, cervix, ovary, bladder, kidney, pancreas, colon, and rectum. Increased EGFR signaling can occur from EGFR overexpression, mutations in EGFR or transduction factors within the EGFR signaling pathway resulting in constitutive activation, and/or increased levels of EGFR cognate ligands, such as EGF, tumor necrosis factor-α (TGF-α), amphiregulin (AREG), epigen, β-cellulin, heparin-binding EGF (HB-EGF), and epiregulin. EGFR signaling activates downstream signaling cascades including RAS-RAF-MEK-ERK and PI3K-Akt-mTOR axes that lead to proliferation and cancer cell survival. Unfortunately, anti-EGFR agents, including tyrosine kinase inhibitors, monoclonal antibodies, and radiotherapy, are only effective in a few cancer types, such as metastatic colorectal cancer, non-small cell lung cancer (NSCLC), and advanced head and neck cancers. Moreover, treatment only improves survival in some individuals and the initial response usually ends with drug resistance. Thus, new rational designs are necessary to improve therapeutic efficacy.

An antibody is a protein that binds to an antigen with high specificity and high affinity, and can neutralize the antigen activity. Anti-EGFR antibodies block ligand activated EGFR signaling and induce receptor endocytosis, leading to EGFR degradation in proteasomes. Subjects can acquire anti-EGFR antibody resistance during the course of treatment when mutations occur at the antibody's EGFR binding site. Cetuximab, a chimeric mouse/human monoclonal, and panitumumab, a fully humanized monoclonal antibody, have different binding sites on EGFR, and therefore panitumumab is still effective after resistance to cetuximab develops, and vice versa. Thus, subjects who acquire resistance to one anti-EGFR antibody can be administered another anti-EGFR antibody targeting a different EGFR binding site.

Panitumumab is an IgG2 anti-EGFR humanized monoclonal antibody that binds EGFR with an approximately 8-fold greater affinity than cetuximab, an IgG1 anti-EGFR chimeric human/mouse monoclonal antibody (Garcia-Foncillas et al. 2019). Before inducing endocytosis, antibody binding can induce an immune response. Panitumumab binding induces antibody-dependent cell-mediated cytotoxicity (ADCC) and initiates antibody-dependent cellular phagocytosis (ADCP) through activation of neutrophils and monocytes (Schneider-Merk et al. 2010). The IgG1 Fc domain of cetuximab binds to the FcγRIIIA (CD16) receptor on natural killer (NK) cells to induce ADCC. Activated NK cells secrete perforins and granzymes resulting in lysis of the cancer cell and release immunostimulatory molecules, such as interferon-γ (IFN-7), TNF-α, chemokines, and granulocyte macrophage colony-stimulating factor (GM-CSF). The secretion of cytokines by NK cells stimulates dendritic cells maturation, NK cell cross-talk, and coexpression of CD137. CD137 expression recruits anti-EGFR CD8+ T cells leading to increased killing of EGFR expressing cancer cells. Mature dendritic cells further activate NK cells and present tumor antigen to cytotoxic CD8+ T cells. The IgG1 Fc region also binds to Fc receptors on macrophage or plasmacytoid dendritic effector cells or to the first subunit of C1 complement complex (C1q) to initiate antibody-dependent cellular phagocytosis (ADCP) by cells or complement-dependent cytotoxicity (CDC), respectively. Like cetuximab, the anti-EGFR antibodies cetuximab, necitumumab, and nimotuzumab also have an IgG1 Fc region for ADCC induction.

NRP1 Binding Domain

Cancer cells overexpress pro-angiogenic factors that promote the rapid growth of new blood vessels. The blood vessels surrounding the tumor are abnormal, with capillary constriction that reduces overall blood flow to the tumor. A reduced blood flow rate increases the tumor interstitial fluid pressure and decreases drug flow from blood vessels to the tumor (Milosevic et al., 1999). The paucity of lymphatic vessels in tumor tissue, unlike in normal tissue, also contributes to abnormal angiogenesis and high tumor interstitial pressure. The inhibition of angiogenesis by targeting the vascular endothelial cell growth factor-A ($VEGF_{165}$) could normalize blood vessel formation, blood vessel fluid pressure, and increase therapeutic drug accumulation at the tumor site (Marcucci et al. 2013). However, anti-VEGF antibodies, such as bevacizumab, can have adverse side effects and are only effective in a narrow range of exposure (Kamba and McDonald, 2007).

Neuropilin-1 (NRP1) and neuropilin-2 (NRP2) receptors are multifunctional single pass transmembrane glycoproteins with important roles in angiogenesis and lymphangiogenesis, respectively. The C-terminal region of each of the VEGF ligand family and Sema3 ligands, which bind to NRP1 and NRP2, binds to the arginine-binding pocket in the bl domain of NRP1 and NRP2 (Parker et al., 2012). Binding to the arginine-binding pocket occurs by a motif of R/K-x-x-R/K (R=arginine, K=lysine, and x=any amino acids), which is present commonly in the C-terminal region of NRP binding ligands and is known as the "C-end rule" (CendR) (Teesalu et al. 2009). A protein or peptide containing a C-end rule sequence is capable of binding to NRP by the C-terminal arginine (Arg) or lysine (Lys) residue (Zanuy et al, 2013).

Selective targeting of NRP1 is critical for anti-EGFR cancer therapy because silencing NRP2 significantly increases EGFR expression in lung and gastric cancer cells (Rizzolio et al., 2017). Moreover, NRP1 is overexpressed in many cancer cells, including colon carcinoma, melanoma, astrocytoma, lung, prostrate, and pancreatic ductal adenocarcinoma, and plays a critical role in cancer progression (Graziani and Lacal, 2015). In addition to NRP1 being overexpressed in a variety of cancers, NRP1 is also overexpressed in tumor-associated endothelial cells. NRP1 functions as a co-receptor for ligands involved in angiogenesis, such as vascular endothelial growth factor ($VEGFi_{65}$), class 3 semaphorin ligands, integrin 81, TGF-P, HGF, FGF, PDGF, and galectin-1. NRP1 interacts with receptor tyrosine kinases (RTKs) such as VEGFR1 and VEGFR2 and thereby contributes to VEGFR signal transduction leading to increased angiogenesis. NRP1 also binds the secreted class-3 semaphorin ligands (Sema3A, Sema3B, Sema3C, Sema3D, Sema3E, Sema3F, Sema3G), to function as a co-receptor to the plexin family receptors, which also regulate angiogenesis.

Blocking NRP1 ligand binding with the anti-NPR1-specific binding domain reduces the expression of endothelial adhesion molecule VE-cadherin, resulting in increased extravasation of an anti-EGFR antibody from blood vessels. Increased extravasation also reduces tumor interstitial pressure allowing drug to flow more freely from blood vessels to the tumor environment.

The epithelial barrier around solid tumors consists of intercellular space densely filled with interstitial epithelial cells connected by intercellular adhesion factors, and prevents a therapeutic agent from penetrating the tumor. E-cadherin overexpression contributes to intercellular adhesion. Since a substance that reduces E-cadherin was found in a virus (adenovirus-3), a case has been reported in which only a portion (JO-1) having an activity of reducing cellular E-cadherin in tight junctions, among proteins constituting the virus, was co-administered with an antibody, thereby increasing the anti-cancer effect of the antibody (Beyer et al.

2011). Targeting NRP1 reduces the expression of the epithelial barrier adhesion molecule E-cadherin and the integrin BI subunit, which are overexpressed in many solid tumors and increases extracellular matrix connectivity, resulting in decreased drug penetration. Moreover, the integrin BI subunit is involved in activating growth factor receptor mediated cell proliferation.

To summarize, targeting NRP1 can reduce $VEGF_{165}$ binding, and VE-cadherin, E-cadherin, and integrin BI expression, which altogether serves to reduce angiogenesis, tumor interstitial pressure, and increase extravasation and tumor penetration of anti-EGFR antibodies.

Cancer cells produce immune checkpoint molecules that inhibit an immune response. NRP1 is an immune checkpoint molecule and its expression is increased in tumor associated endothelial cells and cancer cells. NRP1 expression induces immunosuppression by increasing Treg activity and decreasing tumor specific CD8+ T cell response (Chuckran et al. 2020). Thus, besides increasing drug extravasation and penetration, the NRP1 binding domain functions as an immune checkpoint inhibitor. In yet another aspect, the disclosure provides a bispecific antibody, which targets NRP1 to reduce cancer-mediated checkpoint molecule immunosuppression, permitting natural immunity at the tumor site, and increasing the likelihood of a tumor response.

The anti-NRP1 antibody MNRP1685A, also known as vesencumab, binds competitively with $VEGF_{165}$ on NRP1, and functions to inhibit VEGF signaling through VEGFR2, thereby affecting angiogenesis, cell survival, migration, adhesion, and invasion (Pan Q et al. 2007). However, subjects treated with vesencumab in phase I trials for advanced solid tumors endured intolerable side effects, including gastrointestinal bleeding, fungemia, duodenal obstruction, thrombocytopenia, proteinuria, alopecia, dysphonia, fatigue, and nausea, which led to aborting further trials (Weekes et al., 2014, Patnaik et al., 2014).

NRP1 is active as a homodimer or heterodimer, and monomeric peptides, such as the cleaved penetrating peptide iRGD, have only a weak ability to regulate NRP1 biological activity (Sugahara et al. 2010). Accordingly, a peptide that selectively binds NRP1 as a homodimer to regulate the biological activity is preferred. Unfortunately, while the Fc heavy-chain fused NRP binding peptide A22p is presented as dual peptides (homodimer), A22p binds to both NRP1 and NRP2 (Shin et al. 2014). Thus, identifying an effective and non-toxic NRP1 selective targeting molecule is important.

In an aspect, the disclosure pertains to monoclonal antibodies that bind NRP1 (anti-NRP1 mAbs), which can be used in the bispecific antibodies of the disclosure. In embodiments, the disclosure provides monoclonal antibodies with heavy chain polypeptide sequences set forth in SEQ ID NOs: 41-47, which includes an N-terminal NPR1 binding domain. In some embodiments, the monoclonal antibody heavy chain polypeptide comprises the N-terminal NRP1 binding domain including a variable heavy chain (VH) and a constant heavy chain 1 (CH1), and Fc domain comprising a constant heavy chain 2 (CH2) and constant heavy chain 3 (CH3). In some embodiments, the monoclonal antibody comprises a light chain polypeptide sequence as set forth in any of SEQ ID NOs: 48-54. Thus, the heavy chains of SEQ ID NOs: 41-47 can pair with the light chains of SEQ ID NOs: 48-54. The polynucleotide sequences that encode the heavy and light chain polypeptides set are forth in SEQ ID NOs: 55-61 and 62-68, respectively. Example 8 describes a method of monoclonal antibody production.

In some embodiments, the NRP1 binding domain of the monoclonal antibody has NRP1 affinity ($K_D$) ranging from 70 nM to subnanomolar ranges for monoclonal antibodies with heavy chain polypeptide sequences set forth in SEQ ID NOs: 41-47, and their corresponding light chain polypeptide sequences set forth in SEQ ID NOs: 48-54.

Blocking VEGF binding to NRP1 with the NRP1 binding domain of a monoclonal antibody may inhibit the activation of VEGFR2, as measured by VEGFR2 phosphorylation.

In some embodiments, the monoclonal antibodies inhibit cancer cell growth. In some embodiments, the monoclonal antibody Fc domain, comprising constant heavy chains 2 and 3 (CH2 and CH3), are of the IgG1 or IgG2 subclass. In some embodiments, the disclosure provides a monoclonal antibody NRP1 binding domain that robustly inhibit cell proliferation in the cancer cell line H1975.

Bispecific Antibodies with Binding Affinity to EGFR and NRP1

The present disclosure provides bispecific antibodies with heavy chain polypeptide sequence, which includes an N-terminal EGFR binding domain and a C-terminal NRP1 binding domain. The bispecific antibody heavy chain polypeptide comprises an N-terminal EGFR binding domain including a variable heavy chain (VH) and a constant heavy chain 1 (CH1), and Fc domain comprising a constant heavy chain 2 (CH2) and constant heavy chain 3 (CH3), and a C-terminal short chain variable fragment (scFv) NRP1 binding domain.

Figure 15:
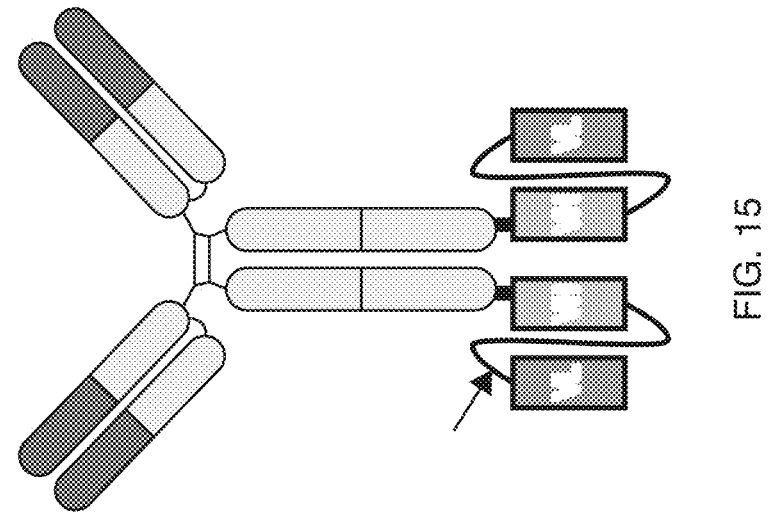
FIG. 15 Schematic diagram of a bispecific antibody of the disclosure.

A schematic diagram of a representative bispecific antibody structure of the disclosure is shown in FIG. 15.

The ScFv NRP1 binding domain consist of a variable heavy chain and a variable light chain connected by a flexible peptide linker. In some aspects, the flexible peptide linker is a repeat of the subunit sequence of SEQ ID NO: 13. In some aspects, a peptide linker connects the ScFv to CH3. In some aspects, the peptide linker is consist of one or more peptide linker subunits of the SEQ ID NO: 13, wherein GGGGS is one subunit.

The bsAb heavy chain polypeptide sequences are set forth is SEQ ID NO: 2, 3, 4, 5, 6, 7, 8, 9, 10, 11, and 39, and the polynucleotide sequences encoding the bispecific antibody's heavy chain antibody polypeptide sequence are set forth in SEQ ID NO: 15, 16, 17, 18, 19, 20, 21, 22, 23, 24, and 40. In some aspects, the bispecific antibody further comprises a light chain polypeptide sequence comprising a variable light chain and a constant light chain, that pairs with the heavy chain polypeptide and is set forth in SEQ ID NO: 12. The polynucleotide sequence that encodes the light chain polypeptide of SEQ ID NO: 12 is set forth in SEQ ID NO: 25. In some aspects, the disclosure provides the polynucleotide sequence used to encode the GGGGS (SEQ ID NO: 13) subunit, representative examples of which polynucleotide sequences are set forth in SEQ ID NOS: 26-38. Example 1 describes the method of bispecific antibody production.

In some aspects, the bispecific antibody comprises an anti-EGFR binding arm comprising (or consisting of) a VH amino acid sequence as shown in SEQ ID NO: 69 and a VL amino acid sequence as shown in SEQ ID NO: 70. In some aspects, the bispecific antibody comprises an anti-EGFR binding arm comprising heavy chain CDR1, CDR2 and CDR3 regions comprising (or consisting of) the amino acid sequences shown in SEQ ID NOs: 71, 72 and 73, respectively. In some aspects, the bispecific antibody comprises an anti-EGFR binding arm comprising a heavy chain CDR3 region comprising (or consisting of) the amino acid sequences shown in SEQ ID NO: 73. In some aspects, the bispecific antibody comprises an anti-EGFR binding arm comprising light chain CDR1, CDR2 and CDR3 regions comprising (or consisting of) the amino acid sequences shown in SEQ ID NOs: 74, 75 and 76, respectively. In some aspects, the bispecific antibody comprises an anti-EGFR binding arm comprising a light chain CDR3 region comprising (or consisting of) the amino acid sequences shown in SEQ ID NO: 76. In some embodiments, an anti-EGFR binding arm comprises (or consists of) one or more sequences at least 90%, 91%, 92%, 93%, 94%, 95%, 96%, 97%, 98%, 99%, 99.5% or 99.8% identical to any of the aforementioned VH, VL, HCDR or LCDR sequences.

In some aspects, the bispecific antibody comprises an anti-NRP1 binding arm comprising (or consisting of) a VH amino acid sequence as shown in SEQ ID NO: 77 and a VL amino acid sequence as shown in SEQ ID NO: 78. In some aspects, the bispecific antibody comprises an anti-NRP1 binding arm comprising heavy chain CDR1, CDR2 and CDR3 regions (HCDR1, HCDR2 and HCDR3, respectively), wherein HCDR1 comprises (or consists of) the sequence shown in SEQ ID NO: 79, HCDR2 comprises (or consists of) the sequence shown in SEQ ID NO: 80 and HCDR3 comprises (or consists of) the sequence shown in any one of SEQ ID NOs: 81-84. In some aspects, the bispecific antibody comprises an anti-NRP1 binding arm comprising light chain CDR1, CDR2 and CDR3 regions (LCDR1, LCDR2 and LCDR3, respectively), wherein LCDR1 comprises (or consists of) the sequence shown in any one of SEQ ID NOs: 85-87, LCDR2 comprises (or consists of) the sequence shown in SEQ ID NO: 88 and LCDR3 comprises (or consists of) the sequence shown in SEQ ID NO: 89. In some aspects, the bispecific antibody comprises an anti-NRP1 binding arm comprising a heavy chain CDR3 region comprising (or consisting of) the amino acid sequences shown in any one of SEQ ID NOs: 81-84. In some aspects, the bispecific antibody comprises an anti-NRP1 binding arm comprising heavy chain CDR1, CDR2 and CDR3 regions comprising (or consisting of) the amino acid sequences shown in SEQ ID NOs: 79, 80 and 84, respectively and light chain CDR1, CDR2 and CDR3 regions comprising (or consisting of) the amino acid sequences shown in SEQ ID NOs: 85, 88 and 89, respectively. In some embodiments, an anti-NRP1 binding arm comprises (or consists of) one or more sequences at least 90%, 91%, 92%, 93%, 94%, 95%, 96%, 97%, 98%, 99%, 99.5% or 99.8% identical to any of the aforementioned VH, VL, HCDR or LCDR sequences.

In some embodiments, the EGFR binding domain of the bispecific antibody has EGFR affinity ($K_D$) in the subnanomolar range (<0.1 nM). In some embodiments, the NRP1 binding domain of the bispecific antibody has NRP1 affinity ($K_D$) ranging from 70 nM for the bispecific antibody construct with the control polypeptide sequence with SEQ ID NO: 1 to subnanomolar ranges for bispecific antibodies with polypeptide sequences set forth in SEQ ID NO: 2, 3, 5, 7,10, and 11. Thus, in one aspect, the disclosure provides bispecific antibodies having an EGFR binding domain with affinity for EGFR in the subnanomolar range and an NRP1 binding domain with affinity for NRP1 in the subnanomolar range, as shown in Table 1 of Example 2. FIGS. 1A-1K show bispecific antibody binding affinity curves to immobilized huEGFR. FIGS. 2A-2K show bispecific antibody binding affinity curves to immobilized huNRPL.

One aspect of the disclosure provides bispecific antibodies with asymmetric binding affinity for EGFR and NRP1, see Examples. In some embodiments, the $K_D$ of EGFR binding domain for EGFR is at least 2, at least 10, at least 20, at least 30, at least 40, at least 50, at least 60, at least 70, at least 80, at least 100, or more than 100 times greater than the NRP1 binding domain $K_D$ for NRP1. The asymmetric affinities provide for better homing to EGFR expressing cancer cells while reducing NRP1-targeting cytotoxicity.

Figure 3:
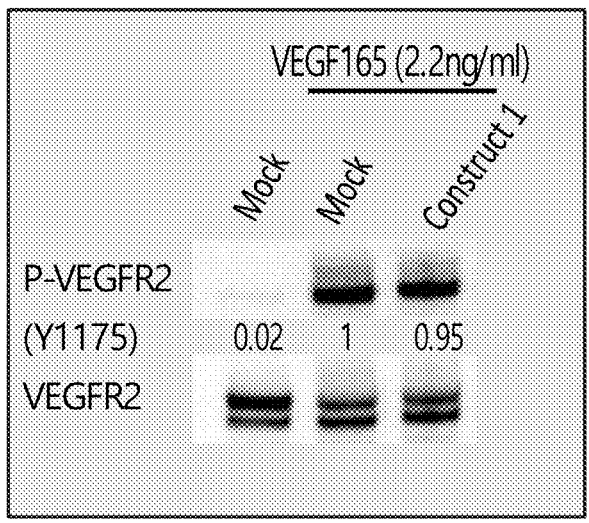
FIG. 3 A Western blot showing that incubating HUVEC cells with bsAb having heavy chain polypeptide SEQ ID NO: 1 fails to prevent VEGF-mediated VEGFR2 signal activation as by detecting phosphorylated VEGFR2 using anti-phospho-VEGFR2 (Y1175).
Figure 4A:
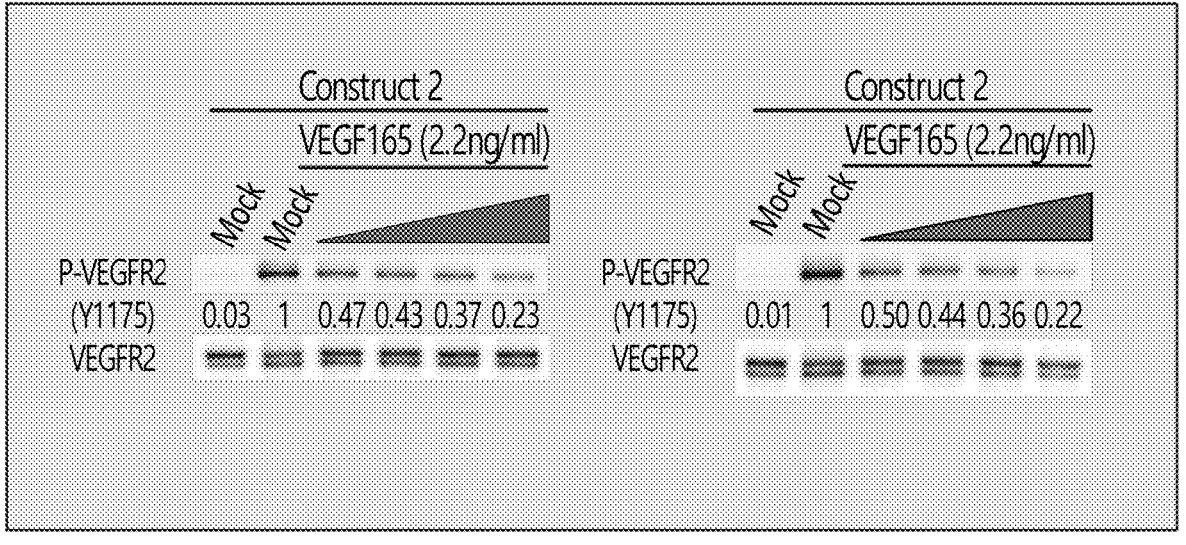
FIG. 4A Western blot density shows dose response of bsAb with heavy chain polypeptide SEQ ID NO: 2 for inhibiting VEGFR2 signaling. HUVEC cells were preincubated with the bsAb having the heavy chain polypeptide SEQ ID NO: 2 (6-fold serially diluted concentration from 1 μM) for 30 min and treated with VEGF165 (2.2 ng/ml) for additional 10 min to induce VEGFR2 activation. VEGFR2 signaling activation was detected by western blotting of lysate using anti-phospho-VEGFR2 (Y1175). Inhibitory effect of bsAb with heavy chain polypeptide SEQ ID NO: 2 was calculated by comparing band strength to VEGF165 control lysate using Image J software densitometry analysis (Numbers shown below P-VEGFR2 (Y1175) blot).
Figure 4B:
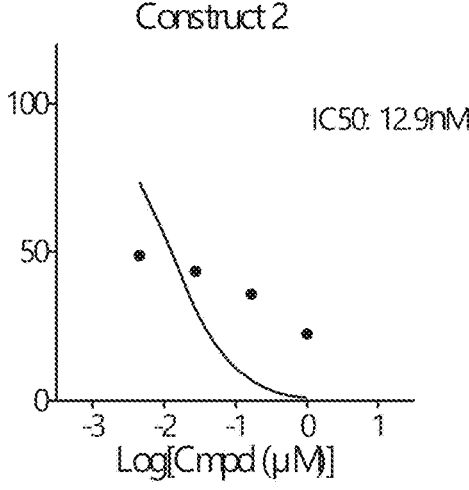
FIG. 4B The IC50 of bsAb with heavy chain polypeptide SEQ ID NO: 2 (n=2) in VEGFR2 phosphorylation was calculated using GraphPad Prism® 9.
Figure 5A:
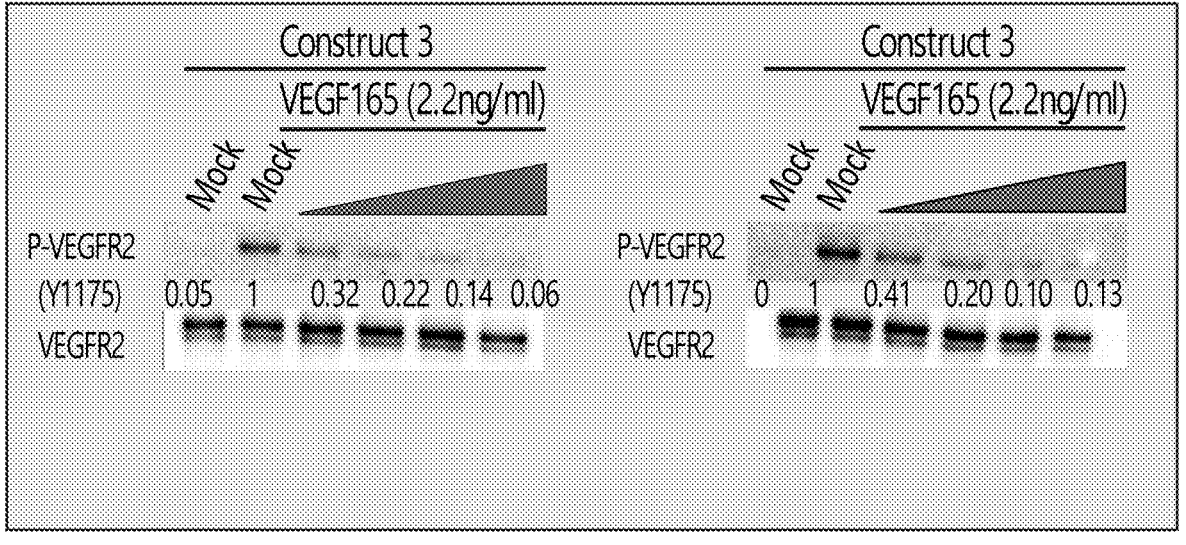
FIG. 5A Western blot density shows dose response of bsAb with heavy chain polypeptide SEQ ID NO: 3 for inhibiting VEGFR2 signaling. HUVEC cells were preincubated with bsAb having heavy chain polypeptide SEQ ID NO: 3 (6-fold serially diluted concentration from 1 μM) for 30 min and treated with VEGF165 (2.2 ng/ml) for additional 10 min to induce VEGFR2 activation. VEGFR2 signaling activation was detected by western blotting of lysate using anti-phospho-VEGFR2 (Y1175). Inhibitory effect of bsAb with heavy chain polypeptide SEQ ID NO: 3 was calculated by comparing band strength to VEGF165 control lysate using Image J software densitometry analysis (Numbers shown below P-VEGFR2 (Y1175) blot).
Figure 5B:
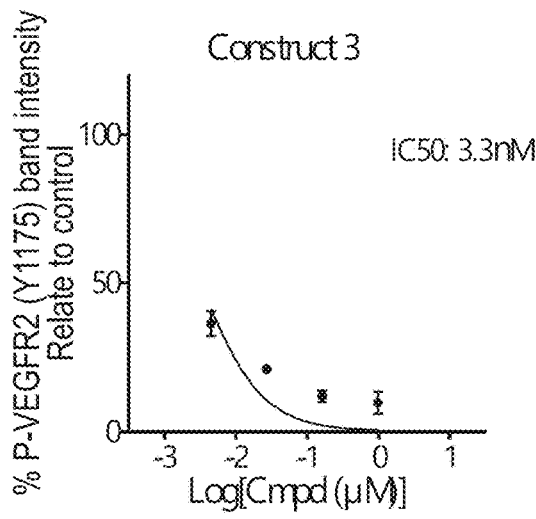
FIG. 5B An IC50 graph of bsAb with heavy chain polypeptide SEQ ID NO: 3 (n=2) VEGFR2 phosphorylation inhibition. IC50 was calculated using GraphPad Prism® 9.
Figure 6A:
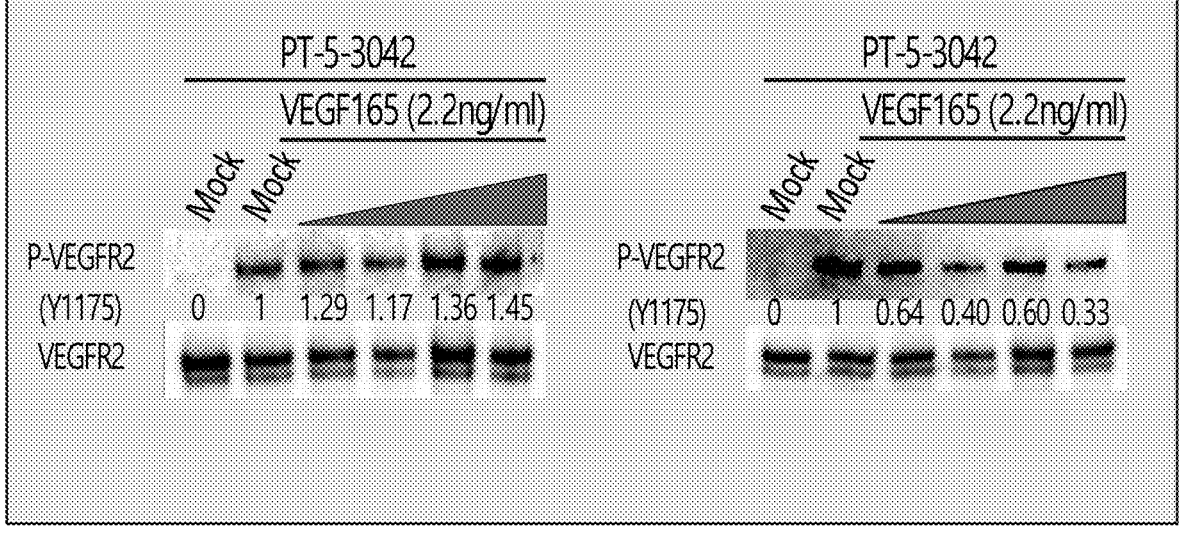
FIG. 6A Western blot density shows dose response of bsAb with heavy chain polypeptide SEQ ID NO: 4-mediated VEGFR2 signaling inhibition. HUVEC cells were preincubated with bsAb having heavy chain polypeptide SEQ ID NO: 4 (6-fold serially diluted concentration from 1 μM) for 30 min and treated with VEGF165 (2.2 ng/ml) for additional 10 min to induce VEGFR2 activation. VEGFR2 signaling activation was detected by western blotting of lysate using anti-phospho-VEGFR2 (Y1175). Inhibitory effect of bsAb with heavy chain polypeptide SEQ ID NO: 4 was calculated by comparing band strength to VEGF165 control lysate using Image J software densitometry analysis (Numbers shown below P-VEGFR2 (Y1175) blot).
Figure 6B:
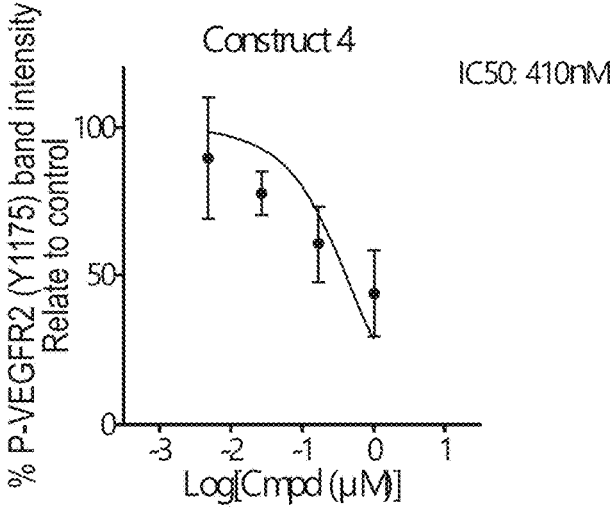
FIG. 6B An IC50 graph of bsAb with heavy chain polypeptide SEQ ID NO: 4 (n=2) VEGFR2 phosphorylation inhibition. IC50 was calculated using GraphPad Prism® 9.
Figure 7A:
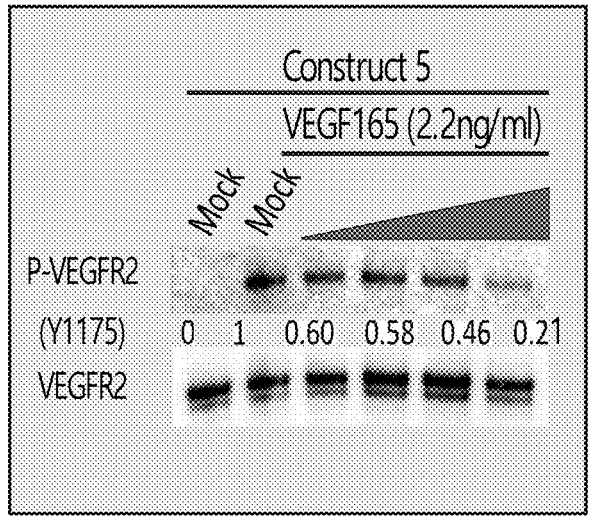
FIG. 7A Western blot density shows dose response of bsAb with heavy chain polypeptide SEQ ID NO: 5 inhibiting VEGFR2 signaling. HUVEC cells were preincubated with bsAb with heavy chain polypeptide SEQ ID NO: 5 (6-fold serially diluted concentration from 1 μM) for 30 min and treated with VEGF165 (2.2 ng/ml) for an additional 10 min to induce VEGFR2 activation. VEGFR2 signaling activation was detected by western blotting of lysate using anti-phospho-VEGFR2 (Y1175). Inhibitory effect of bsAb with heavy chain polypeptide SEQ ID NO: 5 was calculated by comparing band strength to VEGF165 control lysate using Image J software densitometry analysis (Numbers shown below P-VEGFR2 (Y1175) blot).
Figure 7B:
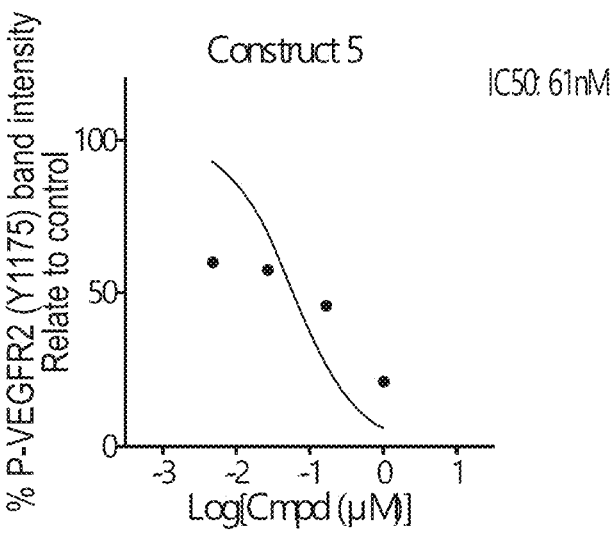
FIG. 7B An IC50 graph of bsAb with heavy chain polypeptide SEQ ID NO: 5 (n=1) in VEGFR2 phosphorylation inhibition. IC50 was calculated using GraphPad Prism® 9.
Figure 8A:
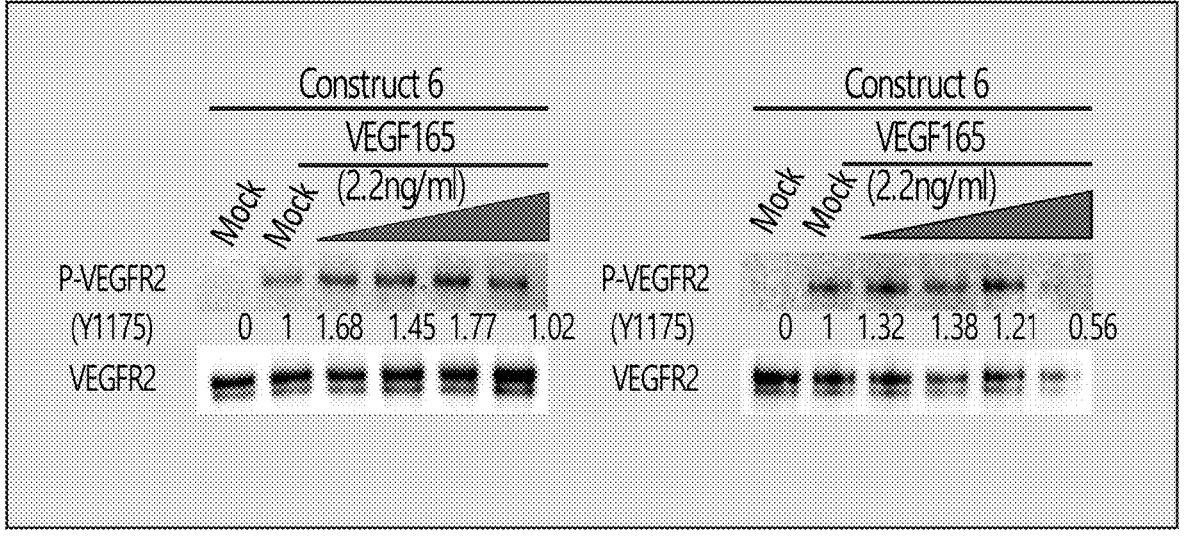
FIG. 8A Western blot density shows dose response of bsAb with heavy chain polypeptide SEQ ID NO: 6 inhibiting VEGFR2 signaling. HUVEC cells were preincubated with bsAb having heavy chain polypeptide SEQ ID NO: 6 (6-fold serially diluted concentration from 1 μM) for 30 min and treated with VEGF165 (2.2 ng/ml) for an additional 10 min to induce VEGFR2 activation. VEGFR2 signaling activation was detected by western blotting of lysate using anti-phospho-VEGFR2 (Y1175). Inhibitory effect of bsAb with heavy chain polypeptide SEQ ID NO: 6 was calculated by comparing band strength to VEGF165 control lysate using Image J software densitometry analysis (Numbers shown below P-VEGFR2 (Y1175) blot).
Figure 8B:
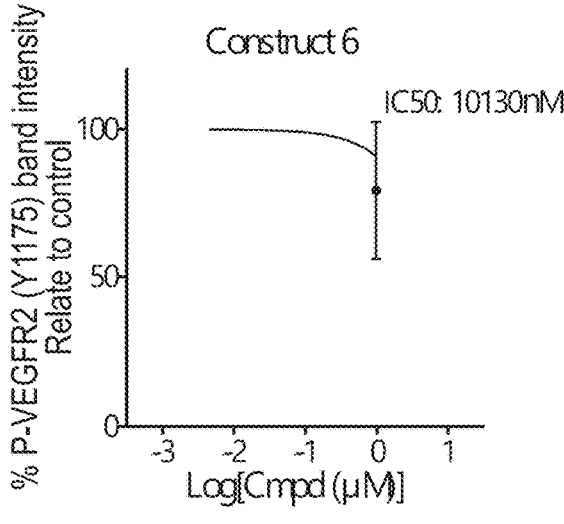
FIG. 8B An IC50 graph of bsAb with heavy chain polypeptide SEQ ID NO: 6 (n=2) in VEGFR2 phosphorylation inhibition. IC50 was calculated using GraphPad Prism® 9.
Figure 9A:
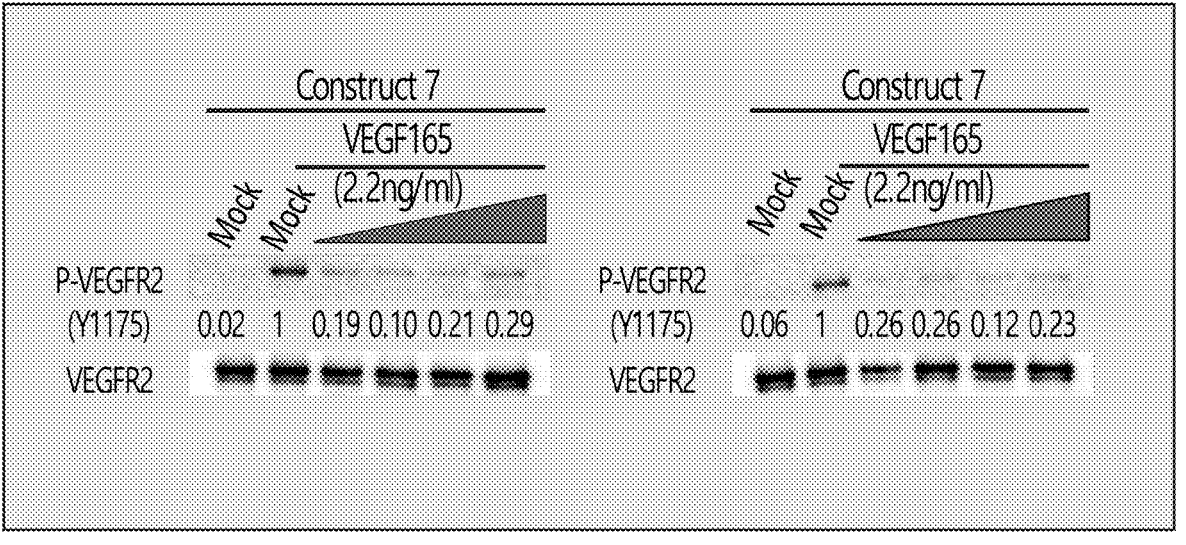
FIG. 9A Western blot density shows dose response of bsAb with heavy chain polypeptide SEQ ID NO: 7 inhibiting VEGFR2 signaling. HUVEC cells were preincubated with bsAb having heavy chain polypeptide SEQ ID NO: 7 (6-fold serially diluted concentration from 1 μM) for 30 min and treated with VEGF165 (2.2 ng/ml) for additional 10 min to induce VEGFR2 activation. VEGFR2 signaling activation was detected by western blotting of lysate using anti-phospho-VEGFR2 (Y1175). Inhibitory effect of bsAb with heavy chain polypeptide SEQ ID NO: 7 was calculated by comparing band strength to VEGF165 control lysate using Image J software densitometry analysis (Numbers shown below P-VEGFR2 (Y1175) blot).
Figure 9B:
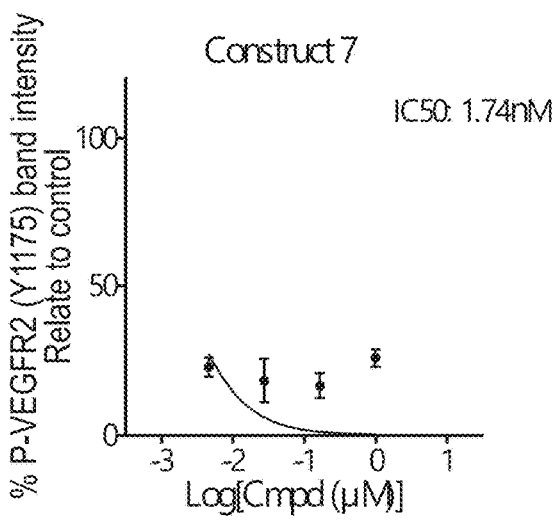
FIG. 9B An IC50 graph of bsAb with heavy chain polypeptide SEQ ID NO: 7 (n=2) in VEGFR2 phosphorylation inhibition. IC50 was calculated using GraphPad Prism® 9.
Figure 10A:
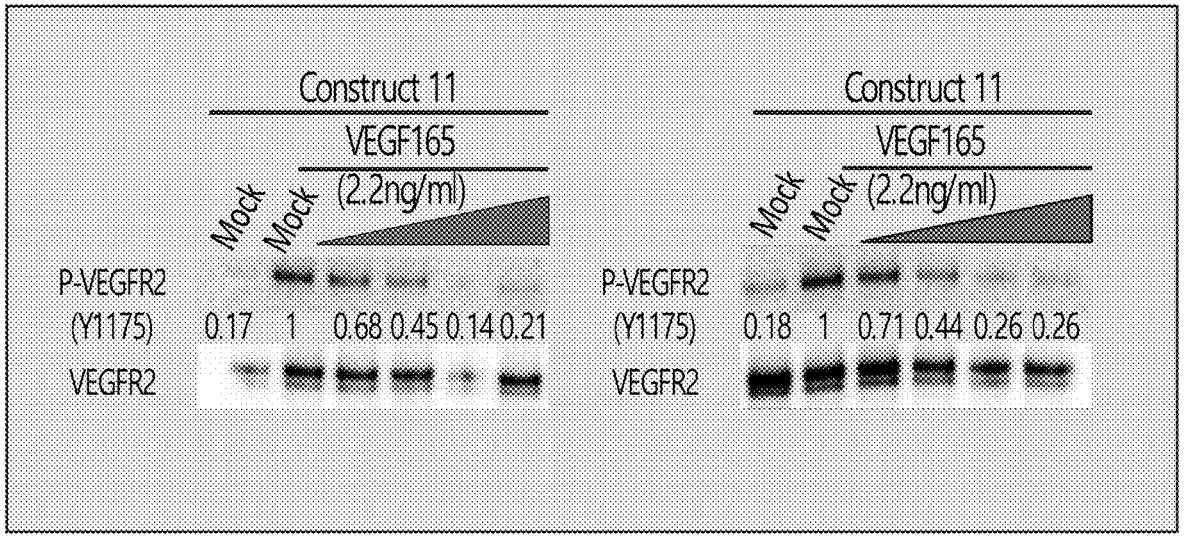
FIG. 10A Western blot density shows dose response of bsAb with heavy chain polypeptide SEQ ID NO: 11 inhibiting VEGFR2 signaling. HUVEC cells were preincubated with bsAb with heavy chain polypeptide SEQ ID NO: 11 (6-fold serially diluted concentration from 1 μM) for 30 min and treated with VEGF165 (2.2 ng/ml) for additional 10 min to induce VEGFR2 activation. VEGFR2 signaling activation was detected by western blotting of lysate using anti-phospho-VEGFR2 (Y1175). Inhibitory effect of bsAb with heavy chain polypeptide SEQ ID NO: 11 was calculated by comparing band strength to VEGF165 control lysate using Image J software densitometry analysis (Numbers shown below P-VEGFR2 (Y1175) blot).
Figure 10B:
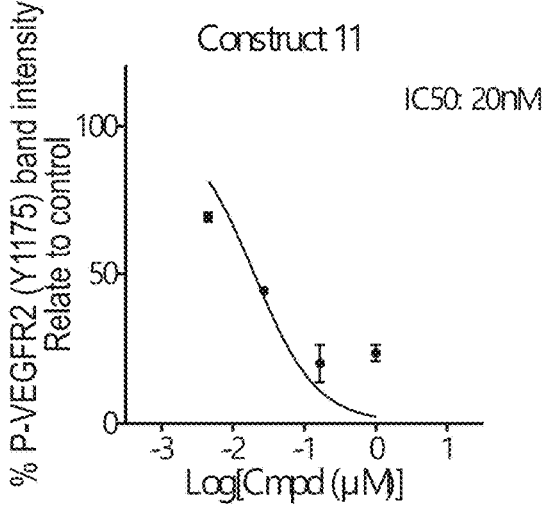
FIG. 10B An IC50 graph of the bsAb with heavy chain polypeptide SEQ ID NO: 11 (n=2) in VEGFR2 phosphorylation inhibition. IC50 was calculated using GraphPad Prism® 9.

Blocking VEGF binding to NRP1 with the NRP1 binding domain of a bispecific antibody may inhibit the activation of VEGFR2, as measured by VEGFR2 phosphorylation. However, the bispecific antibody with heavy chain of SEQ ID NO: 1 has an NRP1 $K_D$ of 69.7 nM, does not inhibit VEGFR phosphorylation (FIG. 3). In some embodiments, the bispecific antibody inhibits VEGFR2 phosphorylation to prevent angiogenesis, see Table 2 and FIGS. 4A, 4B-10A, 10B. In some embodiments, the inventors discovered that the dissociation constants ($K_D$) of the NRP1 binding domain does not reflect the bispecific antibody's ability to inhibit VEGFR2 phosphorylation. For example, the bispecific antibody with heavy chain SEQ ID NO: 6 inhibits 50% VEGFR2 phosphorylation is 10130 nM (IC50) but the NRP1 $K_D$ is 3.76 nM, whereas the bispecific antibody with heavy chain SEQ ID NO: 4 inhibits 50% VEGFR2 phosphorylation at 410 nM (IC50), but the NRP1 $K_D$ is 8.8 nM. Thus, in some aspects the disclosure provides bispecific antibodies wherein the NRP1 binding domain affinity and biological function are disproportionate in regards to inhibiting VEGFR2 phosphorylation.

In some aspects, the bispecific antibodies inhibit cancer cell growth. In some embodiments, the bispecific antibody Fc domain, comprising constant heavy chains 2 and 3 (CH2 and CH3), are of the IgG1 or IgG2 subclass. In some aspects, the disclosure provides a bispecific antibody with an EGFR binding domain and NRP1 scFv binding domain that robustly inhibit cell proliferation in the cancer cell line H1975, Table 3 and FIGS. 11A and 11B. Example 4 describes methods used to measure the bispecific antibody IC50 for cell growth inhibition in the H1975 cancer cell line.

Additional Binding Arms for Bispecific Antibodies

In other embodiments, an anti-NRP1 binding arm (as described herein) can be paired in a bispecific antibody with a second binding arm that binds a second target protein. Antibodies are known in the art that bind these second target protein, which can be used in a bispecific antibody of the disclosure as described herein.

In some embodiments, the second target protein comprises a receptor tyrosine kinase (RTK). In some embodiments, the tyrosine kinase comprises platelet-derived growth factor receptors (PDGFRs), fibroblast growth factor receptors (FGFRs), receptors tyrosine kinase Met (METs), and receptors vascular endothelial growth factors (VEGFRs). In some embodiments, the receptor tyrosine kinase comprises EGFR/HER1/Erb1, HER2/ErbB2, HER3/ErbB3, HER4/ErbB4, FGFR1, FGFR2, FGFR3, FGFR4, MET, RON, PDGFR, PDGFRα, PDGFRβ, CSF-1R, Kit, FLT-3, VEGFR1, VEGFR2, and VEGFR3.

In some embodiments, the target protein comprises the EGFRs. In some embodiments, the EGFR is selected from the group of consisting of EGFR/HER1/Erb1, HER2/ErbB2, HER3/ErbB3, and HER4/ErbB4. In some embodiments, the target protein is EGFR.

In some embodiments, the target protein comprises the FGFRs. In some embodiments, the FGFR1 is selected from the group of consisting of FGFR1, FGFR2, FGFR3, and FGFR4.

In some embodiments, the target protein comprises receptors tyrosine kinase MET. In some embodiments, the receptor tyrosine kinase MET is MET or macrophage-stimulating protein receptor (MST1R/RON).

In some embodiments, the target protein comprises the PDGFRs. In some embodiments, the PDGFR is selected from the group of consisting of PDGFR, PDGFRα, PDGFRβ, CSF-1R, Kit, and FLT-3.

In some embodiments, the target protein comprises the VEGFRs. In some embodiments, the VEGFR is selected from the group of consisting of VEGFR1, VEGFR2, and VEGFR3.

In some embodiments, the receptor tyrosine kinase is selected from the group of consisting of EGFR/HER1/Erb1, HER2/ErbB2, HER3/ErbB3, HER4/ErbB4 VEGFR1, VEGFR2, and VEGFR3.

In some embodiments, the target protein comprises receptors serine/threonine kinase (RSTKs), G-protein coupled receptors (GPCRs), immune checkpoint receptors, and ion channel receptors.

In some embodiments, the target protein comprises receptors serine/threonine kinase (RSTKs). In some embodiments, the RSTK comprises ACVRL1, ACVR1, ACVR1B, ACVR1C, BMPR1A, BMPR1B, TGFBR1, ACVR2A, ACVR2B, AMHR2, BMPR2, TGFBR2.

In some embodiments, the target protein comprises G-protein coupled receptors (GPCRs). In some embodiments, the GPCR is selected from the group of consisting of CXCR4, CCR5, FFAR2, GLP2R, 5-HT1A receptor, 5-HT2A receptor, 5-HT4 receptor, 5-HT5A receptor, M1 receptor, M2 receptor, A1 receptor, A2A receptor, α1A-adrenoceptor, a2A-adrenoceptor, β1-adrenoceptor, β3-adrenoceptor, AT1 receptor, BB1 receptor, B1 receptor, CB1 receptor, CB2 receptor, chemerin receptor 1, CCR1, CX3CR1, ACKR3, CCK1 receptor, GPR3, GPR12, GPR17, GPR32, GPR35.

In some embodiments, the target protein comprises immune checkpoint receptors. In some embodiments, the immune checkpoint receptor is selected from the group of consisting of CD27, CD28, CD40, CD122, CD 137, OX40, GITR, ICOS, A2AR, B7-H3, B7-H4, BTLA, CTLA-4, IDO, KIR, ILAG3, NOX2, PD-1, TIM-3, VISTA, SIGEC7 and PD-L1.

In some embodiments, the target protein comprises ion channel receptors. In some embodiments, the ion channel receptor is selected from the group of consisting of KCa1.1, KCa2.1, CatSper1, TPC1, CNGA1, HCN1, Kir1.1, Kir3.2, RyR1, TRPA1, TRPC3, TRPM1, TRPP1, TRPV1, K2P1.1, K2P10.1, Cav1.1, Cav2.1, Kv1.1, Kv1.8, Kv11.2, Hv1, Nav1.1, and Nav1.2.

In some embodiments, the target protein comprises a membrane associated target protein, which the target protein binding domain of a bispecific binding molecule binds to a cell surface receptor. In some embodiments, the target protein binding domain of a bispecific binding molecule binds to the extracellular epitope of a membrane-associated target protein. In some embodiments, the target cell comprises a neoplastic cell. In some embodiments, the target cell is a cancer cell. In some embodiments, the cancer cell is selected from the group consisting of lung cancer, breast cancer, colon and rectum cancer, head and neck cancer, esophagogastric cancer, liver cancer, glioblastoma, prostate cancer, cervical cancer, ovarian cancer, bladder cancer, kidney cancer, and pancreatic cancer. In some embodiments, the target cell comprises an immune cell.

Bispecific Antibody Tumor Growth Inhibition in Tumor Mouse Model

In some aspects of the disclosure, treatment with the bispecific antibodies decreases tumor growth. In some aspects, the bispecific antibody with heavy chain SEQ ID NO: 11 and light chain SEQ ID NO: 12 (also referred to herein as Construct 11) significantly decreases tumor growth. In some aspects, the bispecific antibody with heavy chain SEQ ID NO: 39 and light chain SEQ ID NO: 12 (also referred to herein as Construct 12) significantly decreases tumor growth. In some aspects, the addition of the scFv NRP1 binding domain significantly increases efficacy of tumor growth inhibition. Example 5 describes the methods and results of treating H1975 xenograph mouse models with bispecific antibodies for tumor growth inhibition. Table 4 shows the percent tumor growth inhibited and FIGS. 12A-12F and FIG. 17 show the tumor growth over days post-implantation.

Summary of Bispecific Antibody Biological Effects

In summary, the disclosure provides bispecific antibodies comprising an NRP1 binding domain, such as bispecific antibodies that combine an EGFR binding domain with an NRP1 binding domain to facilitate homing to high EGFR expression tumors by increased EGFR affinity. The bispecific antibody will have multiple biological effects that combine to reduce cancer cell proliferation and survival, including reducing abnormal angiogenesis, increasing extravasation and penetration by reducing VE-cadherin, E-cadherin, and integrin B1 expression. NRP1 targeting further decreases EGFR surface pooling to enhance EGFR downregulation and inhibit NRP1 checkpoint immunosuppression. The combination of these features provides for a bispecific antibody with potent ability to reduce EGFR-mediated cancer cell proliferation and survival.

FcRn Binding for Transcytosis Recycling

The antibody size of ~150 kDa ensures a long serum half-life and therefore a long-lasting therapeutic effect. In addition, antibody IgG Fc portions consisting of heavy chain constant regions 2 and 3 (CH2 and CH3) binds to the neonatal Fc receptor (FcRn) and Fc gamma receptors (Fc-TRs) at the cell surface is endocytosed and recycled back to the serum through transcytosis, which further increases antibody serum half-life. Cancers with low FcRn or FcTR expression are associated with poor prognosis (Pyzik et al., 2019) and thus, the FcRn- or FcTR-mediated recycling plays an important role in sustaining antibody serum concentrations. IgG1 antibodies have a more efficient FcRn and FcTR recycling process than IgG2 antibodies. Thus, having an IgG1 Fc domain in therapeutic antibodies helps maintain drug therapeutic levels and reduce the frequency of administration, while half-life reduction would be ideal for diagnostic tests or toxicity control.

In some embodiments, the polypeptides of the present invention comprise an immunoglobulin domain, which includes a polypeptide comprising an immunoglobulin domain that comprises an Fc domain selected from the IgG1 subclass.

Expression Construct

The term "vector" as used herein refers to means for expressing a target gene in a host cell. For example, the vector may include plasmid vector, cosmid vector, bacteriophage vector, and virus vectors such as adenovirus vector, retrovirus vector, and adeno-associated virus vector. The recombinant vector may be produced by operating plasmid (for example, pSC101, pGV1106, pACYC177, ColEl, pKT230, pME290, pBR322, pUC8/9, pUC6, pBD9, pHC79, pIJ61, pLAFRI, pHV14, pGEX series, pET series and pUC19, etc.), phages (for example, Agt4AB, A-Charon, AAz1 and M13, etc.), or virus (for example, CMV, SV40, etc.) commonly used in the pertinent art.

In another aspect, the disclosure provides isolated polynucleotides encoding the bispecific antibody heavy and light chain amino acid sequence. A polynucleotide encoding an in the recombinant vector may be operatively linked to a promoter. The term "operatively linked" as used herein refers a functional linkage between a nucleotide expression control sequence (such as a promoter sequence) and a second nucleotide sequence. Accordingly, the regulation sequence may control the transcription and/or translation of the second nucleotide sequence. The recombinant vector may be generally constructed as a vector for cloning or a vector for expression. As the vector for expression, vectors generally used for expressing foreign protein from plants, animals or microorganisms in the pertinent art may be used. The recombinant vector may be constructed by various methods known in the pertinent art. The recombinant vector may be constructed using an eukaryotic cell as a host with an f1 replication origin, an SV40 replication origin, a pMB1 replication origin, an adeno replication origin, an AAV replication origin, a CMV replication origin and a BBV replication origin, etc., but is not limited thereto.

In addition, a promoter derived from a genome of a mammal cell (for example, a metalthionine promoter) or a promoter derived from a virus of a mammal cell (for example, an adenovirus anaphase promoter, a vaccinia virus 7.5K promoter, a SV40 promoter, a cytomegalo virus (CMV) promoter, or a tk promoter of HSV) may be used, and the promoter generally has a polyadenylated sequence as a transcription termination sequence. The vector may express not only the peptide domain that binds specifically to NRP1 according to the present disclosure, but also an antibody having the peptide fused thereto, as well as a linker peptide. In the case of an antibody having the peptide fused thereto, the vector may use both a vector system that expresses a peptide and an antibody or a fragment thereof in one vector, and a vector system that expresses the peptide and the antibody or the fragment thereof in separate vectors. For the latter, the two vectors may be introduced into the host cell through co-transformation and targeted transformation. Thus, in another aspect, the disclosure includes a vector containing the nucleic acids disclosed in any of SEQ ID NOs: 14-38 and 40. Example 1 describes vector properties that may be utilized for the production of the bispecific antibodies.

Another aspect of the present disclosure provides a host cell transformed with the recombinant vector. Any kind of host cell known in the pertinent art may be used as a host cell. Examples of a prokaryotic cell comprise strains such as E. coli JM109, E. coli BL21, E. coli RR1, E. coli LE392, E. coli B, E. coli X 1776, E. coli W3110, or strains belonging to the genus Bacillus such as Bascillus subtilus and Bascillus thuringiensis, Salmonella typhimurium, Serratia marcescens and intestinal flora and strains such as various Pseudomonas Spp., etc. Prokaryote cell transformation is useful for cloning plasmids at high scale. Prokaryote host cells may be deficient in the required post-translational modifications required for antibody assembly and structure, and thus, a preferred embodiment is vector transformation in eukaryotic host cells, such as yeast (Saccharomyces cerevisiae), an insect cell, a plant cell, a mammalian cell, for example, SP2/0, CHO (Chinese hamster ovary) K1, CHO DG44, PER.C6, W138, BHK, COS-7, 293, HepG2, Huh7, 3T3, RN, and MDCK cell line, etc.

Another aspect of the present disclosure provides a method for preparing a peptide that binds specifically to NRP1, comprising culturing the above-described host cell. The polynucleotide and a recombinant vector including the polynucleotide the may be inserted into a host cell using an insertion method well known in the pertinent art. For example, when a host cell is a prokaryotic cell, the transfer may be carried out according to Cacl2 method or an electroporation method, etc., and when a host cell is an eukaryotic cell, the vector may be transferred into a host cell by various methods including a microscope injection, calcium phosphate precipitation, electroporation, a liposome-mediated transformation, and a gene bombardment, etc., but the transferring method is not limited thereto. The method for selecting the transformed host cell may be readily carried out according to a method well known in the pertinent art using a phenotype expressed by a selected label. For example, when the selected label is a specific antibiotic resistance gene, the transformant may be readily selected by culturing the transformant in a medium containing the antibiotic.

Pharmaceutical Compositions

The polypeptides described herein (bsAbs and mAbs) can be formulated into pharmaceutical compositions that further comprise a pharmaceutically acceptable carrier, diluent, adjuvant or vehicle. In one embodiment, the present invention relates to a pharmaceutical composition comprising the disclosed polypeptide, and a pharmaceutically acceptable carrier, diluent, adjuvant or vehicle. In one embodiment, the present invention is a pharmaceutical composition comprising an effective amount of a polypeptide of the present invention or a pharmaceutically acceptable salt thereof and a pharmaceutically acceptable carrier, diluent, adjuvant or vehicle. Pharmaceutically acceptable carriers include, for example, pharmaceutical diluents, excipients or carriers suitably selected with respect to the intended form of administration, and consistent with conventional pharmaceutical practices.

A pharmaceutically acceptable carrier or excipient may contain inert ingredients that do not unduly inhibit the biological activity of the polypeptides. The pharmaceutically acceptable carriers should be biocompatible, e.g., non-toxic, non-inflammatory, non-immunogenic or devoid of other undesired reactions or side-effects upon the administration to a subject. Standard pharmaceutical formulation techniques can be employed.

The pharmaceutically acceptable carrier, adjuvant, or vehicle, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the polypeptides described herein, such as by producing any undesirable biological effect or otherwise interacting in a deleterious manner with any other component(s) of the pharmaceutically acceptable composition, its use is contemplated to be within the scope of this invention. As used herein, the phrase "side effects" encompasses unwanted and adverse effects of a therapy.

Materials which can serve as pharmaceutically acceptable carriers for antibodies increase conformation stability, reduce protein dynamics, inhibit aggregation, and protect protein adsorbing to liquid air interface, and include but are not limited to cyclodextrin hydrogels, ion exchangers, alumina, aluminum stearate, lecithin, serum proteins (such as human serum albumin), buffer substances (such as twin 80, phosphates, glycine, sorbic acid, or potassium sorbate), partial glyceride mixtures of saturated vegetable fatty acids, water, salts or electrolytes (such as protamine sulfate, disodium hydrogen phosphate, potassium hydrogen phosphate, sodium chloride, or zinc salts), colloidal silica, magnesium trisilicate, polyvinyl pyrrolidone, polyacrylates, waxes, polyethylene-polyoxypropylene-block polymers, methylcellulose, hydroxypropyl methylcellulose, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

In some embodiments, a composition of the present invention comprises a pharmaceutically acceptable salt. When polypeptides of the present invention contain relatively acidic functionalities, base addition salts can be obtained by contacting the neutral form of such polypeptides with a sufficient amount of the desired base, either neat or in a suitable inert solvent. Examples of pharmaceutically acceptable base addition salts include sodium, potassium, calcium, ammonium, organic amino, or magnesium salt, or a similar salt. When polypeptides of the present invention contain relatively basic functionalities, acid addition salts can be obtained by contacting the neutral form of such polypeptides with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science,* 1977, 66, 1-19). Certain specific polypeptides of the disclosure contain both basic and acidic functionalities that allow the polypeptides to be converted into either base or acid addition salts.

Thus, the disclosed polypeptides may exist as salts, such as with pharmaceutically acceptable acids. The present invention includes such salts. Non-limiting examples of such salts include hydrochlorides, hydrobromides, phosphates, sulfates, methanesulfonates, nitrates, maleates, acetates, citrates, fumarates, proprionates, tartrates (e.g., (+)-tartrates, (−)-tartrates, or mixtures thereof including racemic mixtures), succinates, benzoates, and salts with amino acids such as glutamic acid, and quaternary ammonium salts (e.g. methyl iodide, ethyl iodide, and the like). These salts may be prepared by methods known to those skilled in the art.

The neutral forms of the polypeptides are preferably regenerated by contacting the salt with a base or acid and isolating the parent polypeptides in the conventional manner. The parent form of the polypeptides may differ from the various salt forms in certain physical properties, such as solubility in polar solvents.

Certain polypeptides of the present invention can exist in unsolvated forms as well as solvated forms, including hydrated forms. In general, the solvated forms are equivalent to unsolvated forms and are encompassed within the scope of the present invention. Certain polypeptides of the present invention may exist in multiple crystalline or amorphous forms. In general, all physical forms are equivalent for the uses contemplated by the present invention and are intended to be within the scope of the present invention.

In some embodiments, subcutaneous formulations may contain recombinant human PH20 hyaluronidase (rH-uPH20) to facilitate dispersion of the antibody from the injection site.

Administration Methods

The compositions of the present invention may be administered to a subject in need of cancer treatment. The terms "administration" or "administering" refer to the act of providing a composition of the present invention, e.g., a polypeptide or pharmaceutically acceptable salt thereof, to a subject in need of cancer treatment.

As used herein, "intermittent administration" includes the administration of an agent for a period of time (which can be considered a "first period of administration"), followed by a time during which the composition is not taken or is taken at a lower maintenance dose (which can be considered "off-period") followed by a period during which the composition is administered again (which can be considered a "second period of administration"). Generally, during the second phase of administration, the dosage level of the agent will match that administered during the first period of administration but can be increased or decreased as medically necessary.

In some embodiments, the compositions of the present invention can be administered by oral administration, as a suppository, topical contact, intravenous, parenteral, intraperitoneal, intramuscular, intralesional, intrathecal, intranasal or subcutaneous administration, or the implantation of a slow-release device, e.g., a mini-osmotic pump, to a subject. Accordingly, administration can be by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and. Other modes of delivery include, but are not limited to, the use of liposomal formulations, intravenous infusion, or via an implanted reservoir, etc. Specifically, the compositions are administered orally, intraperitoneally or intravenously.

In some embodiments, the composition (e.g., bispecific antibody composition) is administered by systemic intravenous (IV) or by oral route for intestinal cancers, such as gastric or intestinal cancer (Tashima et al., 2021). Formulations for delivery can be optimized by routine, conventional methods that are well-known in the art. Liquid dosage forms for oral administration include, but are not limited to, pharmaceutically acceptable emulsions, microemulsions, solutions, suspensions, syrups and elixirs. In addition to the active polypeptides, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

In some embodiments, the composition (e.g., bispecific antibody composition) is administered by subcutaneous injection. Injectable bispecific antibody formulations can be sterilized, for example, by filtration through a bacterial-retaining filter, or by incorporating sterilizing agents dispersed in sterile water or other sterile injectable medium prior to use. In order to prolong the effect of a polypeptide described herein, it is often desirable to slow the absorption of the polypeptide from subcutaneous or intramuscular injection. This may be accomplished by the use of a liquid suspension of crystalline or amorphous material with poor water solubility. The rate of absorption of the polypeptide then depends upon its rate of dissolution that, in turn, may depend upon crystal size and crystalline form. Alternatively, delayed absorption of a parenterally administered polypeptide form is accomplished by dissolving or suspending the polypeptide in an oil vehicle. Injectable depot forms are made by forming microencapsule matrices of the polypeptide in biodegradable polymers such as polylactide-polyglycolide. Depending upon the ratio of polypeptide to polymer and the nature of the particular polymer employed, the rate of polypeptide release can be controlled. Examples of other biodegradable polymers include poly(orthoesters) and poly (anhydrides). Depot injectable formulations are also prepared by entrapping the polypeptide in liposomes or microemulsions that are compatible with body tissues.

Sterile injectable forms of the compositions described herein may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tween®s, Span®s and other emulsifying agents or bioavailability enhancers which are commonly used in the manufacture of pharmaceutically acceptable dosage forms may also be used for the purposes of formulation.

In some embodiments, the formulation can include agents, such as an excipient, a buffer, an isotonicity agent, a preservative, a surfactant, and preferably zinc. The formulation can also include an excipient or agent for polypeptide stabilization, such as a buffer, a reducing agent, a bulk protein, or a carbohydrate. Bulk proteins useful in formulating at least one polypeptide compositions include albumin, protamine, or the like. Typical carbohydrates useful in formulating at least one polypeptide include sucrose, mannitol, lactose, trehalose, glucose, or the like. The bispecific antibody formulation can also include a surfactant, which can reduce or prevent surface-induced aggregation of the at least one polypeptide caused by atomization of the solution in forming an aerosol. Various conventional surfactants can be employed, such as polyoxyethylene fatty acid esters and alcohols, and polyoxyethylene sorbital fatty acid esters. Amounts will generally range between about 0.001 and 4% by weight of the formulation. Especially preferred surfactants for purposes of this invention are polyoxyethylene sorbitan mono-oleate, polysorbate 80, polysorbate 20, or the like. Additional agents known in the art for formulation of a polypeptide, such as antibody protein, can also be included in the formulation.

Cellular Treatment Methods

In another aspect, the disclosure provides methods of treating cells with a bispecific antibody of the disclosure, for example for receptor internalization or receptor degradation purposes. As demonstrated herein, a bsAb of the disclosure can mediate the internalization and degradation of a receptor to which the bsAb binds (e.g., NRP1, EGFR).

Accordingly, in an embodiment, the disclosure provides a method of internalizing one or more receptors by a cell, the method comprising contacting the cell with a bispecific antibody of the disclosure that binds to the receptor(s) on the cell such that the receptor(s) is internalized. In one embodiment, the bsAb mediates internalization of the receptors NRP1 and EGFR.

In another embodiment, the disclosure provides a method of degrading one or more receptors by a cell, the method comprising contacting the cell with a bispecific antibody of the disclosure that binds to the receptor(s) on the cell such that the receptor(s) is degraded. In one embodiment, the bsAb mediates degradation of the receptor NRP1 and EGFR.

Tumor Growth Inhibition

In another aspect, the disclosure provides methods of inhibiting the growth of tumor cells using a bispecific antibody of the disclosure. As demonstrated herein, a bsAb of the disclosure exhibits tumor growth inhibitory ability. Accordingly, a bsAb of the disclosure can be used to inhibit the growth of tumor cells, such as in the treatment of cancer. In one aspect, provided herein is a method of treating cancer comprising administering to a subject in need thereof a bsAb of the disclosure in an effective amount so that the growth of a cancerous tumor is inhibited or reduced and/or that regression and/or that prolonged survival is achieved. In some embodiments, the bsAb described herein may be administered in combination with additional cytotoxic or therapeutic agent(s) as described herein.

Cancers whose growth may be inhibited using the bsAb described herein include, but are not limited to, carcinoma, lymphoma, blastoma, sarcoma, and leukemia. In an embodiment, the cancer is associated with aberrant EGFR expression and/or function (e.g., overexpression of EGFR, expression of mutant EGFR), non-limiting examples of which include lung cancer (e.g., non-small cell lung cancer), kidney cancer, breast cancer (e.g., invasive ductal breast carcinoma), gliobastoma, head and neck cancer, prostate cancer and ovarian cancer. In one embodiment, the cancer is a non-small cell lung cancer (NSCLC). In an embodiment, the cancer is selected from the group consisting of lung (e.g., NSCLC), colon and head and neck cancers.

In another embodiment, the cancer is associated with aberrant NRP1 expression and/or function (e.g., overexpression of NRP1, expression of mutant NRP1), non-limiting examples of which include lung cancer, breast cancer, leukemia, malignant melanoma, glioma, osteosarcoma, gastic cancer, esophageal cancer and colon cancer.

In another embodiment, the cancer associated with aberrant expression of both EGFR and NRP1, e.g., overexpression of both EGFR and NRP1. Non-limiting examples of cancers associated with overexpression of both EGFR and NRP1 include pancreatic, lung, head and neck, cervical, kidney, ovarian, and colon cancers. Gene expression profile analysis of the Cancer Genome Atlas database of patients' samples showed that pancreatic, lung, head and neck, cervical, kidney, ovarian, and colon cancer had 75%, 70%, 65%, 65%, 60%, 55%, and 40%, respectively, of patient tumor population overexpressing both EGFR and NRP1.

In an embodiment, a bsAb of the disclosure is used in the treatment of metastatic squamous non-small cell lung cancer, optionally in combination with gemcitabine and/or cisplatin. In certain embodiments, use of the bsAb is not indicated for treatment of non-squamous non-small cell lung cancer.

In an embodiment, a bsAb of the disclosure is used in the treatment of wild-type RAS metastatic colorectal cancer (defined as wild-type in both KRAS and NRAS as determined by an FDA-approved test for this use), optionally in combination with FOLFOX (folinic acid, fluorouracil and oxaliplatin) or FOLFIRI (folinic acid, fluorouracil and irinotecan), e.g., for first line therapy. In an embodiment, a bsAb of the disclosure is used in the treatment of wild-type RAS metastatic colorectal cancer (defined as wild-type in both KRAS and NRAS as determined by an FDA-approved test for this use) as monotherapy following disease progression after prior chemotherapy treatment, e.g., with fluoropyrimidine, oxaliplatin and/or irinotecan-containing chemotherapy. In certain embodiments, use of the bsAb is not indicated for treatment of patients with RAS-mutant metastatic colorectal cancer or for whom RAS mutation status is unknown.

In an embodiment, a bsAb of the disclosure is used in the treatment of locally or regionally advanced squamous cell carcinoma of the head and neck, optionally in combination with radiation therapy. In an embodiment, a bsAb of the disclosure is used in the treatment of recurrent locoregional disease or metastatic squamous cell carcinoma of the head and neck, optionally in combination with platinum-based therapy with fluorouracil. In an embodiment, a bsAb of the disclosure is used in the treatment of recurrent or metastatic squamous cell carcinoma of the head and neck progressing after platinum-based therapy.

Additional non-limiting examples of suitable cancers include, but are not limited to, basal cell carcinoma, biliary tract cancer; bladder cancer; bone cancer; brain and CNS cancer; breast cancer (e.g. estrogen-receptor positive breast cancer HER2-positive breast cancer; triple negative breast cancer); cancer of the peritoneum; cervical cancer; cholangiocarcinoma; choriocarcinoma; colon and rectum cancer; connective tissue cancer; cancer of the digestive system; endometrial cancer; esophageal cancer; eye cancer; cancer of the head and neck; gastric cancer (including gastrointestinal cancer); glioblastoma; liver cancer (e.g., hepatocellular carcinoma; hepatoma); intra-epithelial neoplasm; kidney or renal cancer; larynx cancer; leukemia; lung cancer (e.g., small-cell lung cancer, adenocarcinoma of the lung, and squamous carcinoma of the lung); lymphoma including Hodgkin's and non-Hodgkin's lymphoma; melanoma;

myeloma; neuroblastoma; oral cavity cancer (e.g., lip, tongue, mouth, and pharynx); ovarian cancer; pancreatic cancer; prostate cancer; retinoblastoma; rhabdomyosarcoma; rectal cancer; cancer of the respiratory system; salivary gland carcinoma; sarcoma; skin cancer; squamous cell cancer; teratocarcinoma; testicular cancer; thyroid cancer; uterine or endometrial cancer; cancer of the urinary system; vulval cancer; as well as other carcinomas and sarcomas; as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblasts leukemia; and post-transplant lymphoproliferative disorder (PTLD), as well as abnormal vascular proliferation associated with phakomatoses, edema (such as that associated with brain tumors), tumors of primitive origins and Meigs' syndrome.

Additional cancers which can be treated using the bsAb described herein include metastatic pancreatic cancer, metastatic adenocarcinoma of the pancreas, stomach cancer, fibrotic cancer, glioma, malignant glioma, diffuse intrinsic pontine glioma, recurrent childhood brain neoplasm renal cell carcinoma, clear-cell metastatic renal cell carcinoma, metastatic castration resistant prostate cancer, stage IV prostate cancer, metastatic melanoma, malignant melanoma, recurrent melanoma of the skin, melanoma brain metastases, malignant melanoma of head and neck, squamous cell non-small cell lung cancer, metastatic breast cancer, follicular lymphoma, advanced B-cell NHL, HL including diffuse large B-cell lymphoma (DLBCL), multiple myeloma, chronic myeloid leukemia, adult acute myeloid leukemia in remission, adult acute myeloid leukemia with Inv(16) (p13.1q22), CBFB-MYH11, adult acute myeloid leukemia with t(16:16) (p13.1:q22), CBFB-MYH11, adult acute myeloid leukemia with t(8:21)(d22:q22), RUNX1-RUNX1T1, adult acute myeloid leukemia with t(9:11)(p22: q23), MLLT3-MLL, adult acute promyelocytic leukemia with tO15:17)(q22:q12), PML-RARA, alkylating agent-related acute myeloid leukemia, Richter's syndrome, adult glioblastoma, adult gliosarcoma, recurrent glioblastoma, recurrent childhood rhabdomyosarcoma, recurrent Ewing sarcoma/peripheral primitive neuroectodermal tumor, recurrent neuroblastoma, recurrent osteosarcoma, colorectal cancer, MSI positive colorectal cancer, MSI negative colorectal cancer, nasopharyngeal nonkeratinizing carcinoma, recurrent nasopharyngeal undifferentiated carcinoma, cervical adenocarcinoma, cervical adenosquamous carcinoma; cervical squamous cell carcinoma, recurrent cervical carcinoma, anal canal squamous cell carcinoma, metastatic anal canal carcinoma, recurrent anal canal carcinoma, recurrent head and neck cancer, squamous cell of head and neck, head and neck squamous cell carcinoma (HNSCC), ovarian carcinoma, colon cancer, advanced GI cancer, gastric adenocarcinoma, gastroesophageal junction adenocarcinoma, bone neoplasms, soft tissue sarcoma, bone sarcoma, thymic carcinoma, urothelial carcinoma, Merkel cell carcinoma, recurrent Merkel cell carcinoma, mycosis fungoides, Sezary syndrome, neuroendocrine cancer, nasopharyngeal cancer, basal cell skin cancer, squamous cell skin cancer, dermato-fibrosarcoma trotuberans, glioma, mesothelioma, myelodysplastic syndromes (MDS), myelofibrosis (MF), myeloproliferative neoplasms, and acute myeloid leukemia (AML).

Cancers may be, e.g., metastatic or primary cancers; desmoplastic or non-desmoplastic cancers; or recurrent cancers.

The ability of the bsAb described herein to inhibit cancer growth can be evaluated in suitable animal models or human xenograft models predictive of efficacy in human tumors, as described in the Examples. In one embodiment, the xenograft model is an H1975 model, as described in the Examples. Alternatively, this property of a composition can be evaluated by examining the ability of the compound to inhibit using in vitro assays known to the skilled practitioner. Therapeutically effective amounts of one or more therapeutic agents can decrease tumor size, or otherwise ameliorate symptoms in a subject. One of ordinary skill in the art would be able to determine such amounts based on such factors as the subject's size, the severity of the subject's symptoms, and the particular composition or route of administration selected.

In an embodiment, a cancer patient to be treated with a bsAb of the disclosure is selected prior to treatment based on expression of one or more biomarkers indicative of a likelihood that the bsAb treatment will be effective. For example, for an NRP1 x EGFR bispecific antibody, a cancer patient to be treated may be selected based on overexpression of EGFR, NRP1, or both, on tumor cells of the patient. Methods of testing for surface expression of a biomarker(s) of interest on a patient's tumor cells (e.g., expression of NRP1 and/or EGFR) prior to bsAb treatment are well-established in the art (e.g., FACS analysis by flow cytometry and the like).

Combination Therapy

In some embodiments, an effective amount of a composition of the disclosure (e.g., bispecific antibodies) can be achieved in the method or pharmaceutical composition of the invention employing the polypeptide or a pharmaceutically acceptable salt or solvate (e.g., hydrate) thereof alone or in combination with an additional suitable chemotherapeutic agent, for example, oxaliplatin, irinotecan, or FOLFOX. When "combination therapy" is employed, an effective amount can be achieved using a first amount of the polypeptide, or a pharmaceutically acceptable salt or solvate (e.g., hydrate) thereof, and a second amount of an additional suitable therapeutic agent, e.g., chemotherapeutic agent.

Suitable anti-cancer agents for use in combination therapy with a bsAb described herein include, but are not limited to, surgery, chemotherapeutic agents, growth inhibitory agents, cytotoxic agents, radiotherapy and agents used in radiation therapy, anti-angiogenesis agents, apoptotic agents, anti-tubulin agents, and other agents to treat cancer, such as anti-HER-2 antibodies (e.g., HERCEPTIN®), anti-CD20 antibodies, an epidermal growth factor receptor (EGFR) antagonist (e.g., a tyrosine kinase inhibitor), HER1/EGFR inhibitor (e.g., erlotinib (TARCEVA®)), platelet derived growth factor inhibitors (e.g., GLEEVEC® (Imatinib Mesylate)), COX-2 inhibitors (e.g., celecoxib), interferons, and cytokines; antagonists (e.g., neutralizing antibodies) that bind to and/or neutralize the activity of one or more of the following targets: PD 1, PDL1, PDL2 (e.g., pembrolizumab; nivolumab; MK-3475; AMP-224; MPDL3280A; MEDIO680; MSB0010718C; and/or MEDI4736); CTLA4 (e.g., tremelimumab (PFIZER) and ipilimumab); LAG3 (e.g., BMS-986016); CD 103; TIM-3 and/or other TIM family members; CEACAM1, CEACAM6, and/or other CEACAM family members; ErbB2, ErbB3, ErbB4, PDGFR-beta, BlyS, APRIL, BCMA or VEGF receptor(s), TRAIL/Apo2, PARP inhibitors (e.g., AZD-2281, Lynparza OCEACAM5arib, Rubraca Rucaparib; (Zejula) niraparib), DNA damage repair inhibitors (e.g., ATMi, ATRi, DNAPKi), and other bioactive and organic chemical agents, including those described in section VII. Combinations thereof are also specifically contemplated for the methods described herein.

Suitable chemotherapeutic agents for use in combination therapy with a bsAb described herein include, but are not limited to, alkylating agents such as thiotepa and CYTOXAN® cyclosphosphamide; temozolomide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); irinotecan (Camptosar, CPT-11) (including the treatment regimen of irinotecan with 5-FU and leucovorin); topoisomerase inhibitor RFS 2000; bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB 1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma 1I and calicheamicin omega 11 (see, e.g., Agnew, Chem. Intl. Ed. Engl., 33: 183-186 (1994)); dynemicin, including dynemicin A; bisphosphonates, such as clodronate; an esperamicin; as well as neocarzinostatin chromophore and related chromoprotein enediyne antibiotic chromophores), aclacinomycins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites, such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as folinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE® Cremophor-free, albumin-engineered nanoparticle formulation of paclitaxel (American Pharmaceutical Partners, Schaumberg, 111.), and TAXOTERE® doxetaxel (Rhone-Poulenc Rorer, Antony, France); chloranbucil; GEMZAR® gemcitabine; 6-thioguanine; mercaptopurine; platinum analogs such as cisplatin, oxaliplatin and carboplatin, vinblastine; platinum; etoposide (VP-16); ifosfamide; mitoxantrone; vincristine; NAVELBINE®, vinorelbine; novantrone; teniposide; edatrexate; daunomycin; aminopterin; xeloda; ibandronate; difluoromethylornithine (DMFO); retinoids such as retinoic acid; capecitabine; combretastatin; leucovorin (LV); oxaliplatin, including the oxaliplatin treatment regimen (FOLFOX); CEACAM5atinib (TYKERB®); inhibitors of PKC-alpha, Raf, H-Ras, EGFR (e.g., erlotinib (TARCEVA®)) and VEGF-A that reduce cell proliferation and pharmaceutically acceptable salts, acids or derivatives of any of the above.

In some embodiments, the additional therapeutic agent is an immune checkpoint inhibitor. In some embodiments, the additional therapeutic agent is selected from the group consisting of an anti-PD-I antibody or an antigen binding fragment thereof, an anti-LAG3 antibody or an antigen biding portion thereof, an anti-VISTA antibody or an antigen binding fragment thereof, an anti-BTLA antibody or an antigen binding fragment thereof, an anti-TIM3 antibody or an antigen binding fragment thereof, an anti-CTLA4 antibody or an antigen binding fragment thereof, an anti-HVEM antibody or an antigen binding fragment thereof, an anti-CD27 antibody or an antigen binding fragment thereof, an anti-CD137 antibody or an antigen binding fragment thereof, an anti-OX40 antibody or an antigen binding fragment thereof, an anti-CD28 antibody or an antigen binding fragment thereof, an anti-PDL1 antibody or an antigen binding fragment thereof, an anti-PDL2 antibody or an antigen binding fragment thereof, an anti-GITR antibody or an antigen binding fragment thereof, an anti-ICOS antibody or an antigen binding fragment thereof, an anti-SIRPα antibody or an antigen binding fragment thereof, an anti-ILT2 antibody or an antigen binding fragment thereof, an anti-ILT3 antibody or an antigen binding fragment thereof, an anti-ILT4 antibody or an antigen binding fragment thereof, an anti-ILT5 antibody or an antigen binding fragment thereof, and an anti-4-1BB antibody or an antigen binding fragment thereof. In some embodiments, anti-PD1 antibody or antigen binding fragment thereof is pembrolizumab or an antigen biding fragment thereof.

Co-administration encompasses administration of the first and second amounts of the polypeptides and chemotherapeutic agent in an essentially simultaneous manner, such as in a single pharmaceutical composition, for example, a capsule having a fixed ratio of first and second amounts, or in multiple, separate capsules for each. In addition, such co-administration also encompasses use of each polypeptide in a sequential manner in either order.

When co-administration involves the separate administration of the first amount of the polypeptide and a second amount of an additional therapeutic agent, the polypeptides are administered sufficiently close in time to have the desired therapeutic effect. For example, the period of time between each administration which can result in the desired therapeutic effect, can range from minutes to hours and can be determined taking into account the properties of each agent such as potency, solubility, bioavailability, plasma half-life and kinetic profile. For example, the polypeptide and the second therapeutic agent can be administered in any order within about 24 hours of each other, within about 16 hours of each other, within about 8 hours of each other, within about 4 hours of each other, within about 1 hour of each other or within about 30 minutes of each other.

More, specifically bispecific antibody of the invention can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second anticancer agent to a subject.

It is understood that the method of co-administration of a first amount of the bispecific antibody and a second amount of an additional therapeutic agent can result in an enhanced or synergistic therapeutic effect, wherein the combined effect is greater than the additive effect that would result from separate administration of the first amount of the polypeptide and the second amount of the additional therapeutic agent.

A synergistic effect of a combination of therapies (e.g., a combination of prophylactic or therapeutic agents) can permit the use of lower dosages of one or more of the therapies and/or less frequent administration of said therapies to a subject. The ability to utilize lower dosages of a therapy (e.g., a prophylactic or therapeutic agent) and/or to administer said therapy less frequently can reduce the toxicity associated with the administration of said therapy to a subject without reducing the efficacy of said therapy in the treatment of cancer. In addition, a synergistic effect can result in improved efficacy of agents in the prevention, management or treatment of a disorder. Finally, a synergistic effect of a combination of therapies (e.g., a combination of prophylactic or therapeutic agents) may avoid or reduce adverse or unwanted side effects associated with the use of either therapy alone.

When the combination therapy using the bispecific antibody of the present invention is in combination with another anti-cancer agent, both therapeutic agents can be administered so that the period of time between each administration can be longer (e.g. days, weeks or months).

The presence of a synergistic effect can be determined using suitable methods for assessing drug interaction. Suitable methods include, for example, the Sigmoid-Emax equation (Holford, N. H. G. and Scheiner, L. B., Clin. Pharmacokinet. 6: 429-453 (1981)), the equation of Loewe additivity (Loewe, S. and Muischnek, H., Arch. Exp. Pathol Pharmacol. 114: 313-326 (1926)) and the median-effect equation (Chou, T. C. and Talalay, P., Adv. Enzyme Regul. 22: 27-55 (1984)). Each equation referred to above can be applied with experimental data to generate a corresponding graph to aid in assessing the effects of the drug combination. The corresponding graphs associated with the equations referred to above are the concentration-effect curve, isobologram curve and combination index curve, respectively.

EXEMPLARY EMBODIMENTS

The Examples in this specification are not intended to, and should not be used to, limit the invention; they are provided only to illustrate the invention.

Example 1. Production of Bispecific Antibodies

The designed proteins were generated by codon-optimized gene synthesis and inserted into pcDNA3.4 as expression vector using Not I and Hind III restriction enzyme. Examples of amino acid sequences of the bispecific antibody heavy chain polypeptide are shown in SEQ ID NO: 2, 3, 4, 5, 6, 7, 8, 9, 10, 11, and 39, which combine with the light chain polypeptide sequence set forth in SEQ ID NO: 12. SEQ ID NO: 1 (encoded by SEQ ID NO: 14) shows a control heavy chain that comprises an NRP1 binding peptide. Examples of polynucleotide sequences encoding the heavy chain polypeptide of the bispecific antibodies are shown in SEQ ID NO: 15, 16, 17, 18, 19, 20, 21, 22, 23, 24, and 40 (encoding the heavy chain polypeptides of SEQ ID NOs: 2-11 and 39, respectively). The polynucleotide sequence encoding the light chain polynucleotide that combines with the heavy chains of the bispecific antibodies is set forth in SEQ ID NO: 25 (encoding the light chain polypeptide of SEQ ID NO: 12). Sequences set forth in SEQ ID NO: 26-38 disclose the polynucleotide sequence used to encode the GGGGS peptide linker subunit (the amino acid sequence of which is shown in SEQ ID NO: 13). The constructed expression vectors include signal peptides and for optimized transcription a Kozak sequence may be included in the 5' untranslated region.

To obtain the amount of the plasmid constructs for transfection, the plasmid construct were transformed into One Shot™ Top10 *E. coli* competent cells followed by culturing overnight. The construct plasmids were obtained by PureLink™ HiPure Expi plasmid Megaprep kit.

Fusion proteins were transiently expressed in the CHO-S system (Thermo Fisher Scientific Inc.). The proteins were expressed individually as per the manufacturer's instructions. Briefly, a total of 0.8 g of plasmid DNA at a ratio of 1:1 light to heavy chain per mL of CHO-S culture was prepared with OPTIPRO™ SFM and ExpiFectamine™. The mixture was added to CHO-S cells at a viable cell density of 6×106 cells/mL and greater than 98% viability. The cell culture was incubated overnight at 37° C., 80% humidity, 8% CO2 in a Nalgene™ Single-Use PETG Erlenmeyer Flasks shaking at 125 RPM with a 19-mm orbit. The next day the culture was enhanced (ExpiCHO™ enhancer; Thermo Fisher Scientific Inc.) and fed (ExpiCHO™ feed; Thermo Fisher Scientific Inc.) and transferred to 32° C., 80% humidity, 5% CO2 shaking at 125 RPM with a 19-mm orbit. The second feed was performed on day 5 and the culture returned to 32° C. until harvest on day 12. Harvesting was accomplished via centrifugation at 4000×g for 20 minutes. The clarified supernatant was sterilized using an asymmetrical polyethersulfone (PES) 0.22-µM filter assembly (Nalgene). The filtrate was stored at 4° C. until purification the next day.

All of the antibody sterilized supernatants were purified using MabSelect prismA™ resin (GE Healthcare Life Sciences) on an AKTA pure (GE Healthcare Life Sciences). A 50 mM sodium phosphate, 150 mM NaCl, pH 7.0 buffer is used to equilibrate the resin. The antibody supernatant was then loaded into the column. The resin was washed with 50 mM sodium phosphate, 150 mM NaCl, pH 7.0 buffer until the chromatographic baseline returned to column equilibration levels. Elution was then performed using 100 mM sodium acetate, 20% glycerol, pH 3.0, and fractions are collected. The fractions were immediately neutralized with 1 M Tris, pH 9. The fractions containing predominant absorbance at wavelength 280 nm were pooled into an Amicon® 10-kDa ultrafiltration device for buffer exchange. The storage buffer (Phosphate Buffered Saline) was used to remove the elution buffer by centrifugation with half dilution, seven times in the Amicon® concentrator. The material was submitted for SEC and then stored at 4° C.

Cationic exchange chromatography was used to purify the antibodies. The cationic exchange chromatography column (Capto® S ImpAct) was sanitized with 1 M NaOH and rinsed with molecular grade water. Equilibration was done with 50 mM NaAc pH 5.5 (starting buffer) and 50 mM NaAc pH5.5, 1M NaCl (elution buffer). The protein A purified antibody was loaded with a concentration of 1-2 g antibody/mL resin. The column was then washed with 50 mM NaAc pH 5.5. The antibody product was then eluted using a gradient of 5-60% elution buffer in 25 column volumes. Each peak in CEX purification was collected separately and concentrated via centrifugation at 4000×g using Amicon® Ultra-15 Centrifugal Filter Units followed by buffer change into PBS.

Size exclusion chromatography (SEC) analysis was performed on a Agilent® Infinity 1260 II Quaternary Pump high performance liquid chromatographic (HPLC) system with diode array UV detector WR. Twenty (20) ag of antibody material was injected on an XBridge® Protein BEH SEC Column, 200 Å, 2.5 µm, 4.6 mm×150 mm column. The mobile phase was 100 mM Phosphate, 300 mM Sodium Chloride pH7.0 at 50° C. and, and the flowrate was 0.3 mL/min. The antibody material was detected at wavelength 220, 280 and 330 nm at 1 Hz sampling rate during a 10-minute acquisition.

Example 2. Bispecific Antibody Binding Affinity to EGFR and NRP1

BLI binding studies using the Octet® Red 96 system were conducted to assess the binding of the bispecific antibody to recombinant huEGFR and huNRP1. Briefly, commercially sourced biotinylated huEGFR and huNRP1 were immobilized on Streptavidin (Sa) biosensors and interrogated with the produced constructs for binding and characterization. Using BLI technology, the binding to the constructs was evaluated for both kinetics and binding affinity (equilibrium binding constant, $K_D$) and were assessed in the bivalent format. These studies were performed to determine if tumor associated essential receptor targeting antibodies (TARE-TAB) bind cancer targets (EGFR and NRP1) with and to assess their affinity for the targets. The constructs binding huEGFR and huNRP1 as well as the $K_D$ determination were performed using the Octet® Red 96 system.

huEGFR and huNRP1 (in their respective immobilization columns) were immobilized at a concentration of 0.2 µg/ml (load signal range if 0.2-0.4 nanometers) in 2×Kinetic buffer onto Sa biosensors with a loading time of 180 seconds for each. Baseline post-loading was performed for 60 seconds. Association of the constructs starting at 100 nM (10 nM for high affinity binding) followed by 2 1:1 serial dilution and then a fourth well with only buffer (blank). Dissociation of the constructs followed in the baseline wells. Reference sensors were generated by applying the constructs over a blank AMC biosensors or streptavidin biosensors surface. The association and dissociation steps were 600 seconds each. The data were analyzed using the Octet® analysis software with 1:1 and 2:1 model fit applied which reports a dissociation constant $K_D$ (M).

All the constructs, including SEQ ID NO: 1 (control) and SEQ ID NO: 11, bind EGFR with double digit picomolar affinity, see Table 1. For NRP-1 binding, bsAb with heavy chain SEQ ID NO: 7 exhibited sub-nanomolar affinity while SEQ ID NO: 1 binds NRP-1 with double digit nanomolar affinity. FIGS. 1A-1K show binding affinity curves to immobilized huEGFR for bispecific antibodies. FIGS. 2A-2K show binding affinity curves to immobilized huNRP1 for bispecific antibodies.

TABLE 1

| EGFR and NRP1 Binding Affinity of Bispecific Antibodies | | |
|---|---|---|
| Bispecific binding antibody | Binding affinity ($K_D$) | |
| (heavy and light chain) | EGFR (nM) | NRP1 (nM) |
| SEQ ID NO: 1, 12 | <0.1 | 69.7 |
| SEQ ID NO: 2, 12 | <0.1 | 0.19 |
| SEQ ID NO: 3, 12 | <0.1 | 0.53 |
| SEQ ID NO: 4, 12 | <0.1 | 8.8 |
| SEQ ID NO: 5, 12 | <0.1 | 0.72 |
| SEQ ID NO: 6, 12 | <0.1 | 3.76 |
| SEQ ID NO: 7, 12 | <0.1 | 0.28 |
| SEQ ID NO: 8, 12 | <0.1 | 2 |
| SEQ ID NO: 9, 12 | <0.1 | 0.88 |
| SEQ ID NO: 10, 12 | <0.1 | 0.25 |
| SEQ ID NO: 11, 12 | <0.1 | 0.25 |

Example 3. VEGFR2 Signaling Inhibition in HUVEC Cells

Bispecific antibody inhibition of VEGFR2 signaling was tested in HUVEC cells by probing electrophoresed cell lysates with anti-phospho-VEGFR2 on Western blots. The HUVEC cells were grown in 6 well plates in EBM-2 medium supplemented with EGM-2 SingleQuots overnight. Next day, cells were incubated with 2 ml of F-12K medium with 0.1 mg/ml heparin, endothelial cell growth supplement and 10% FBS for 4 hours. To see the dose dependent response to antibodies, cells were treated with bsAb serially diluted by six fold from the highest concentration of 1 µM to lowest concentration 0.005 µM with serum free media for 30 minutes, followed by 2.2 ng/ml of VEGF165 or control for 10 minutes. Cell lysates were prepared by collecting cells with a cell scraper and incubating with 100 µl of NP-40 lysis buffer with protease/phosphatase inhibitors for 20 minutes on ice. Supernatant lysate was collected after centrifugation at 13,000 rpm for 10 minutes into a new tube, measured for protein quantification using BCA protein assay, and denatured at 70° C. for 10 minutes after mixing with NuPAGE® LDS sample buffer and LDS sample reducing buffer.

The cell lysates equal to 10 µg were loaded with 4 µl of PageRuler Plus prestained protein ladder into 4-12% Bis-Tris Gel and run at 200V for 45 minutes. Gels were washed with distilled water and transferred to membranes using iBlot™ 2 Drying Blotting System. Membranes were blocked with 5% milk in 1×TBST at room temperature for an hour and incubated with Anti-phospho-VEGFR2 (Y1175) in 5% milk in 1×TBST at 4° C. overnight. Next day, membranes were washed with TBST for 10 minutes three times and incubated with a secondary antibody in 5% milk at room temperature for an hour. Membranes were washed with 1×TBST for 10 minutes three times. Then, membranes were incubated with SuperSignal® Femto Chemilumines-cent substrate for 1-2 minutes and imaged with Amersham®

ImageQuant® 800. Blots were then stripped with Restore Plus® Western Blot stripping buffer for 15 minutes on rocker at room temperature followed by 1×TBST washing three times and the procedure was repeated from milk blocking followed by incubation of primary Anti-VEGFR2 antibody.

Figure 11A:
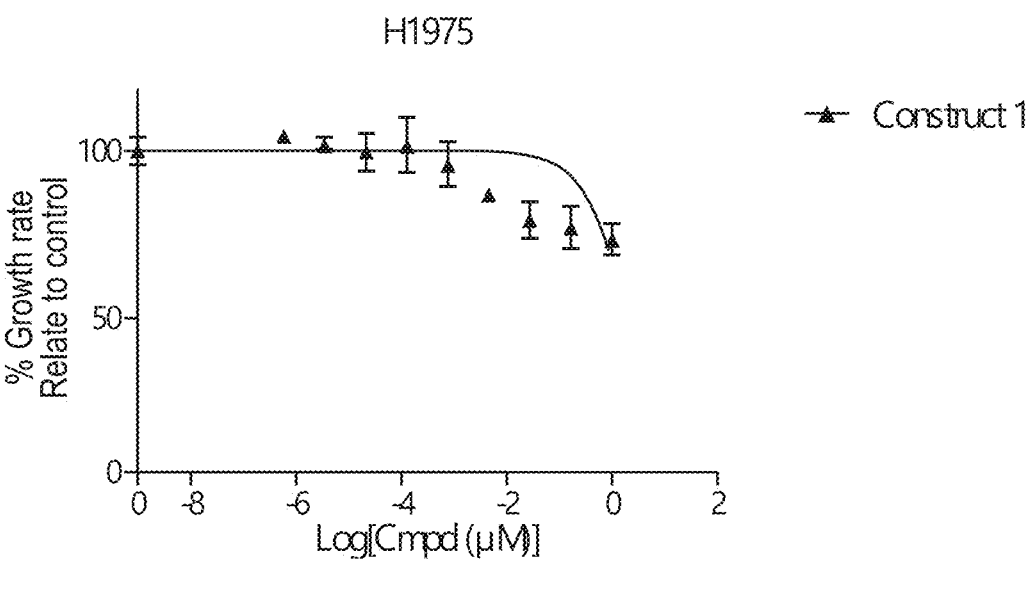
FIG. 11A Percent growth rate of H1975 cells relative to control in the presence of bsAb with heavy chain polypeptide SEQ ID NO: 1.
Figure 11B:
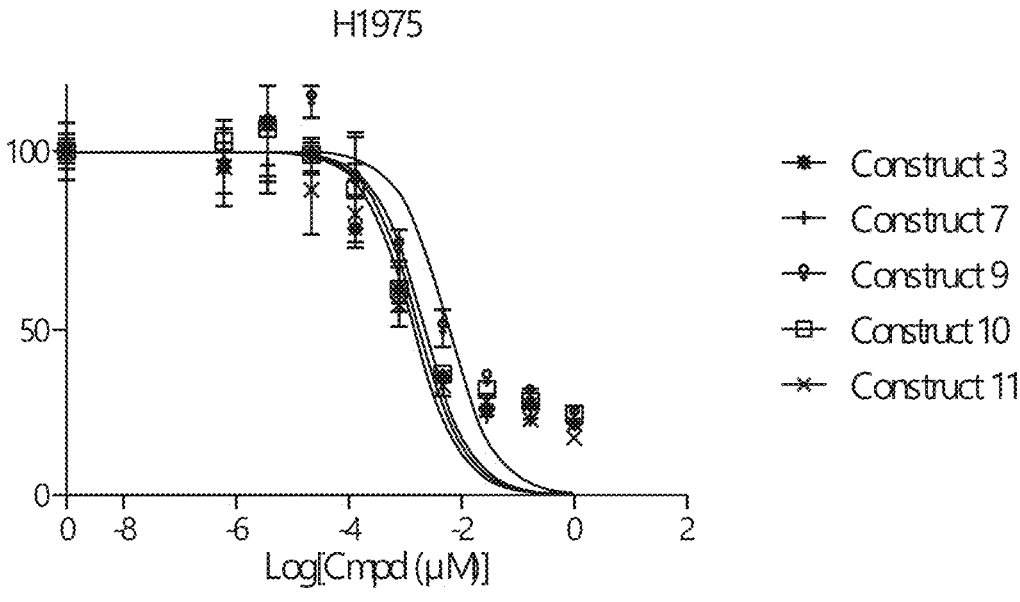
FIG. 11B Percent growth rate of H1975 cells relative to control in the presence of bsAb with heavy chain polypeptide SEQ ID NOs: 3, 7, 9, 10 and 11.
Figure 12A:
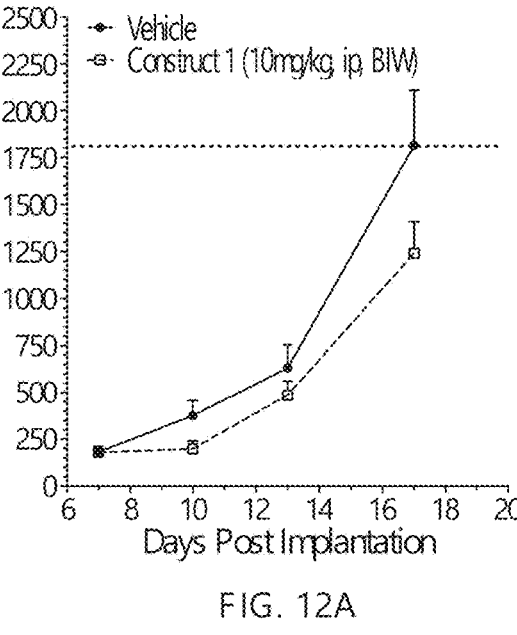
FIG. 12A Mean tumor growth inhibition in H1975 xenograft mouse model treated with PBS (control) and bsAb with heavy chain polypeptide SEQ ID NO: 1 (10 mg/kg, ip, BIW).
Figure 12B:
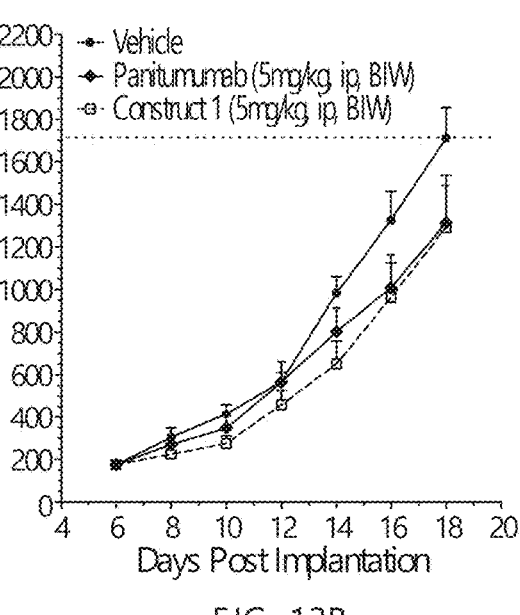
FIG. 12B Mean tumor growth inhibition in H1975 xenograft mouse model treated with PBS (control), panitumumab (5 mg/kg, ip, BIW), or bsAb with heavy chain polypeptide SEQ ID NO: 1 (5 mg/kg, ip, BIW).
Figure 12C:
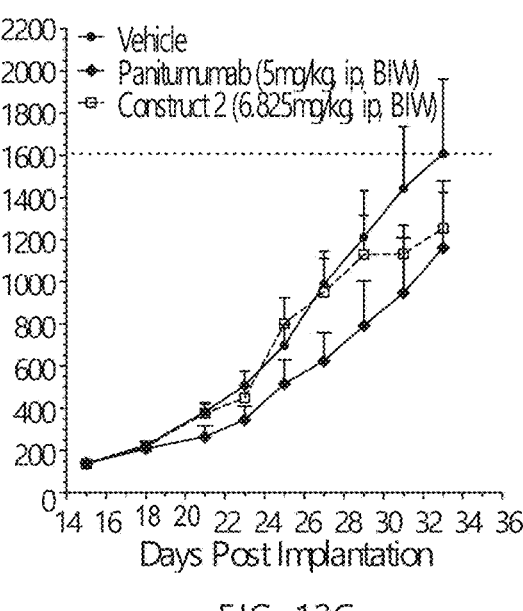
FIG. 12C Mean tumor growth inhibition in H1975 xenograft mouse model treated with PBS (control), panitumumab (5 mg/kg, ip, BIW), or bsAb with heavy chain polypeptide SEQ ID NO: 2 (6.825 mg/kg, ip, BIW).
Figure 12D:
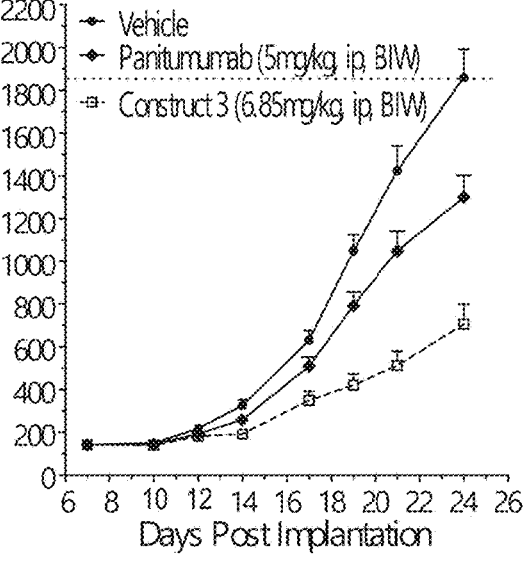
FIG. 12D Mean tumor growth inhibition in H1975 xenograft mouse model treated with PBS (control), panitumumab (5 mg/kg, ip, BIW), or bsAb with heavy chain polypeptide SEQ ID NO: 3 (6.85 mg/kg, ip, BIW).
Figure 12E:
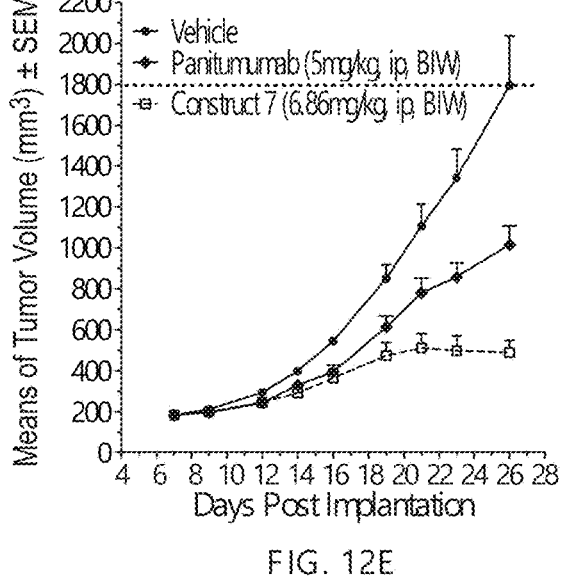
FIG. 12E Mean tumor growth inhibition in H1975 xenograft mouse model treated with PBS (control), panitumumab (5 mg/kg, ip, BIW), or bsAb with heavy chain polypeptide SEQ ID NO: 7 (6.85 mg/kg, ip, BIW).
Figure 12F:
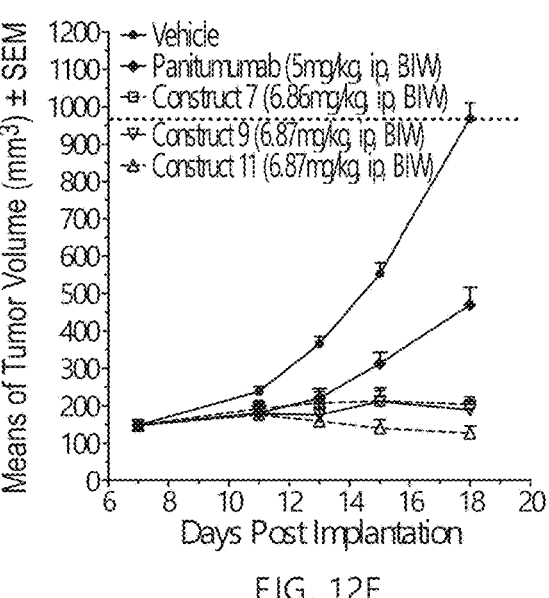
FIG. 12F Mean tumor growth inhibition in H1975 xenograft mouse model treated with PBS (control), panitumumab (5 mg/kg, ip, BIW), or bsAbs with heavy chain polypeptides SEQ ID NO: 7, 9, and 11 (6.86 mg/kg, ip, BIW).

Intensity of western blot band of phosphorylated-VEGFR2 (Y1175) and VEGFR2 was analysed using ImageJ Table 3 shows the IC50s for the bispecific antibodies. The bispecific antibody with heavy chain SEQ ID NO: 1 (control) has a high IC50 (1.96 μM) as shown in FIG. 11A compared to the other bispecific antibodies FIG. 11B. The IC50 for cell growth inhibition is much lower in bispecific antibodies with a NRP1 short chain variable fragment (scFv) binding domain, improving cell growth inhibition.

TABLE 3

| | IC50(μM) of Cell growth inhibition | | | | | |
| | IC50 (μM) | | | | | |
| Cell line | SEQ ID NO: 1 | SEQ ID NO: 11 | SEQ ID NO: 9 | SEQ ID NO: 10 | SEQ ID NO: 7 | SEQ ID NO: 3 |
| H1975 | 1.96 | 0.001362 | 0.005693 | 0.002074 | 0.001652 | 0.001727 | software. Obtained band density of phosphorylated-VEGFR2 (Y1175) were normalized by the VEGFR2 and inhibition of VEGFR2 phosphorylation by bsAb were calculated by ratio against VEGF165 control cell lysate (positive control). IC50 of VEGFR2 phosphorylation by bsAb was determined using GraphPad Prism® 9 software. The Western blot in FIG. 3 shows that incubating HUVEC cells with the bispecific antibody of SEQ ID NO: 1 did not inhibit VEGF165-mediated VEGFR phosphorylation. FIGS. 4-10 show Western blots and IC50 plots of VEGFR2 phosphorylation inhibition after incubation with bispecific antibodies. The IC50 of bispecific antibodies are shown in Table 2.

TABLE 2

Bispecific antibody IC50 for VEGFR signaling inhibition

| Bispecific antibodies (Heavy and light chain) | FIG. | VEGF inhibition (nM) |
| SEQ ID NO: 1, 12 | 3 | n/a (below 5% inhibition in the 1 μM) |
| SEQ ID NO: 2, 12 | 4 | 12.9 |
| SEQ ID NO: 3, 12 | 5 | 3.3 |
| SEQ ID NO: 4, 12 | 6 | 410 |
| SEQ ID NO: 5, 12 | 7 | 61 |
| SEQ ID NO: 6, 12 | 8 | 10130 |
| SEQ ID NO: 7, 12 | 9 | 1.74 |
| SEQ ID NO: 11, 12 | 10 | 20 |

Example 4: Bispecific Antibody Effect on Cell Viability

The inhibition of cell viability by bispecific antibodies was tested in the H1975 lung cancer cell line. Briefly, H1975 lung cancer cells were grown in RPMI1640 supplemented with 1% Penicillin/Streptomycin, and 10% FBS. Cells were trypsinized and plated into 96 well 3D culture plate with round bottom (3,000 cells/120 μl/well) and incubated for 3-4 hours until they aggregated to form 3D spheroids. A stock master plate of 6-fold serially diluted bsAb was prepared from 5 μM to 0.6 μM. H1975 cells were treated with 30 ul of bsAb and incubated for 72 hours (duplicate). Subsequently, CellTiter-Glo® 3D reagent plus 25 μl of serum-free media was added into each well, wrapped with foil, and incubated on a rocker for 7 minutes. Plates were read with Varioskan® Lux Multimode Plate Reader and analyzed with GraphPad Prism® 9 software.

Example 5: Tumor Growth Inhibition in H1975 Xenouraft Mouse Model Cell Line

The ability of bsAbs to inhibit tumor growth was tested in a H1975 cell line xenograph mouse model. All cell lines were acquired from the American Type Culture Collection (Manassas, VA, USA). The cells were maintained at 37° C. in a 5% C02 incubator in RPMI 1640 (Gibco, Carlsbad, CA, USA) containing 10% fetal bovine serum (HyClone®, Logan, UT, USA) and 2 mmol/L Glutamine (HyClone®, Logan, UT, USA).
Xenograft Models The experiments and procedures involving mice were performed according to the U.S. Department of Agriculture, Department of Health and Human Services, and NIH policies regarding the humane care and use of laboratory animals. Six- to eight-week-old female athymic (nu/nu) mice from Charles River Laboratories (Wilmington, MA, USA) were housed under pathogen-free conditions with laboratory chow and water ad libitum. Prior to tumor cell line implantation, all cell lines were screened for infectious agents (*mycoplasma*, etc.). Xenografts were established by injecting 100p subcutaneous into the right flanks containing $1\times10^7$ (NCI-H1975) cells per mouse mixed 1:1 in Matrigel (Corning, Corning, NY, USA). For efficacy studies, tumors were allowed to reach 150 to 300 mm$^3$ (7 to 10 mice per group) prior to randomization and start of treatment.
Treatments and Tumor Measurements Antibodies were diluted in sterile phosphate-buffered saline (Corning, Corning, NY, USA) and administered via injecting i.p. with a total volume of 100 μl per mouse per treatment at indicated dose levels on the day of randomization, and then twice weekly. Digital caliper measurements were used to measure tumor sizes and tumor volumes were calculated using the formula $V=(W^2\times L)/2$, where W is tumor width, and L is tumor length.
Statistical Analysis The GraphPad Prism 7 software (La Jolla, CA, USA) was used for statistical analysis. Results are shown as mean. The data between control and experimental groups at individual time points or at end point were compared using Student t test. For growth curve analysis, involving longitudinal data with repeated measures, a type II ANOVA was used. Statistical differences at $p < 0.05$ were considered significant. TGI % was calculated according to the formula, TGI (%)= $(Vc_1-Vt_1)/(Vc_0-Vt_0)\times100$, where $Vc_1$ and $Vt_i$ is the mean tumor volume in the control and treatment group at the study end point and $Vc_0$ and $Vt_0$ are the mean tumor volumes in the control and treatment group at the beginning of the experiment, respectively.

Table 4 shows bsAbs tumor growth inhibition and treatment-to-control percent tumor volume in the xenograph mouse model. The curves in FIGS. 12A-12F show the mean tumor volume over days post implantation in mice treated with bsAbs. The bsAbs with the scFv NRP1 binding domain have the highest tumor growth inhibition, e.g., treatment with the bsAb having heavy chain SEQ ID NO: 11 resulted in 100% tumor growth inhibition.

TABLE 4

| Tumor growth inhibition and treatment-to-control percent tumor volume | | |
| --- | --- | --- |
| Bispecific antibody polypeptides | TGI % mean ± SEM | T/C % |
| SEQ ID NO: 1; 12 | 39.94 | 74.58% |
| SEQ ID NO: 2; 12 | 23.94 | 81.91% |
| SEQ ID NO: 3; 12 | 71.13 | 37.15% |
| SEQ ID NO: 7; 12 | 81.09% | 28.08% |
| SEQ ID NO: 9; 12 | 94.96% | 18.86% |
| SEQ ID NO: 11; 12 | 102.56% | 12.54% |

Example 6: Functional Activity of Additional Bispecific Antibody

Figure 13B:
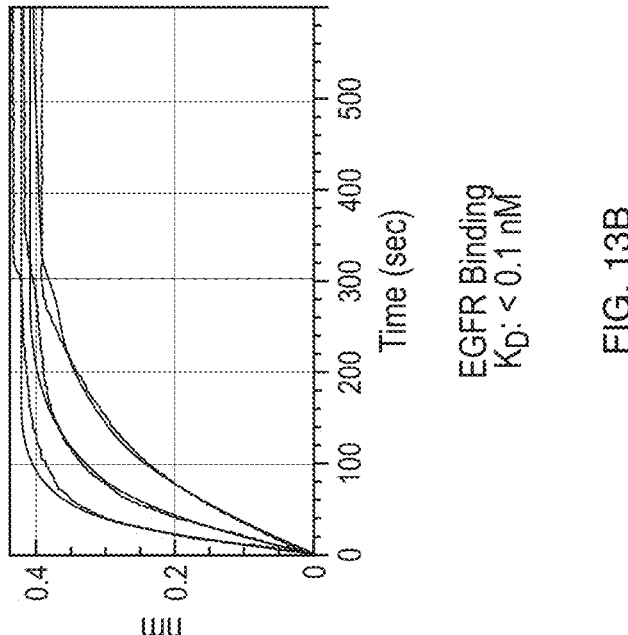
FIG. 13A-FIG. 13B Binding kinetics of Construct 12 for binding to NRP1 (FIG. 13A) or EGFR (FIG. 13B), with $K_D$s indicated.
Figure 13A:
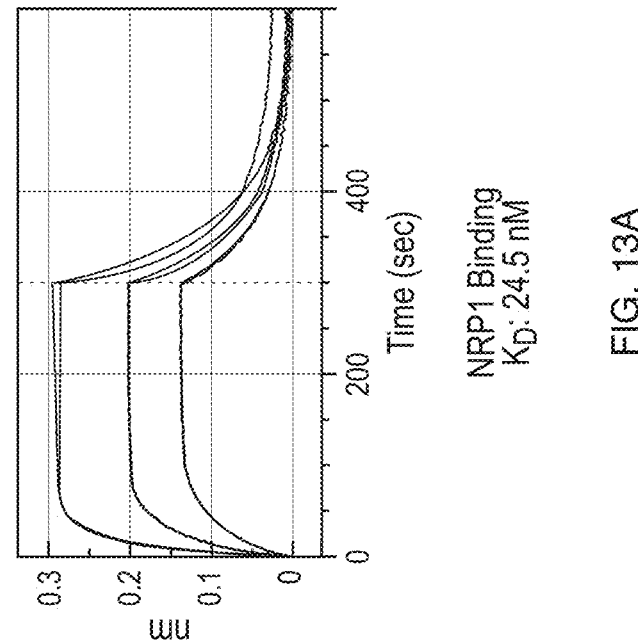

An additional bispecific antibody was prepared composed of a heavy chain comprising the amino acid sequence shown as SEQ ID NO: 39 and a light chain comprising the amino acid sequence of SEQ ID NO: 12. This bispecific antibody is referred to herein as Construct 12. The binding kinetics of Construct 12 for binding to NRP1 and EGFR are shown in FIG. 13A and FIG. 13B, respectively. Construct 12 has a $K_D$ for binding to NRP1 of 24.5 nM and a $K_D$ for binding to EGFR of <0.1 nM.

Figure 14:
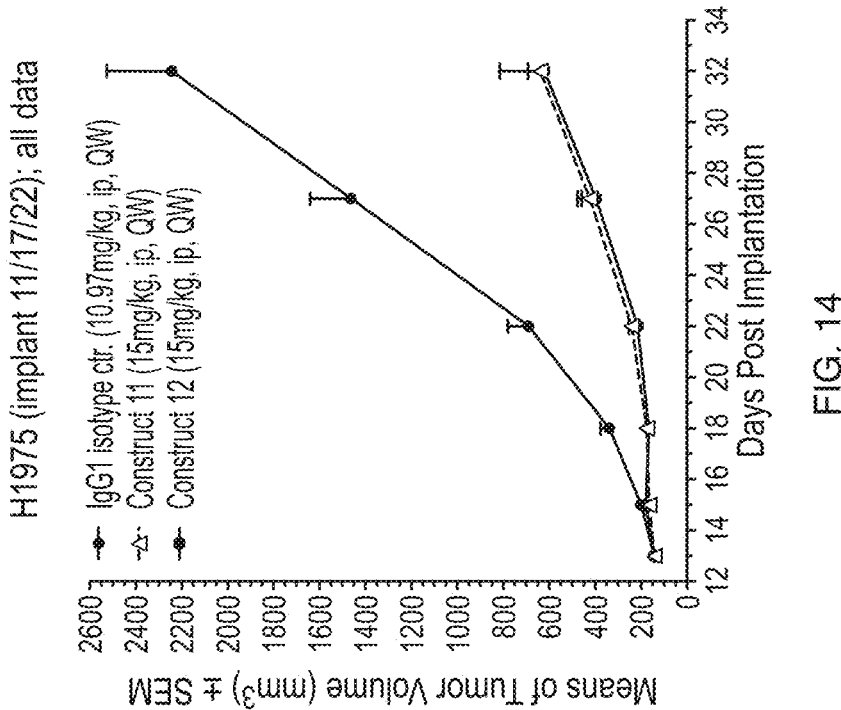
FIG. 14 Mean tumor growth inhibition in H1975 xenograft mouse model treated with IgG1 isotype control, Construct 11 bsAb (heavy chain polypeptide of SEQ ID NO: 11) or Construct 12 bsAb (heavy chain polypeptide of SEQ ID NO: 12).

The anti-tumor activity of Construct 12 was tested in the H1975 xenograft mouse model (described in Example 5), as compared to Construct 11 and an isotype control. Mice were treated with either the bsAb (15 mg/kg, i.p., QW) or isotype control (10.97 mg/kg, i.p., QW) and mean tumor volume measured over time. The results are shown in FIG. 14, which demonstrates that Construct 12 is as effective as Construct 11 in reducing tumor growth in the xenograft model.

Example 7: Receptor Internalization and Degradation Activity of Construct 11

In this example, the ability of Construct 11 bsAb to internalize NRP1 or EGFR, as well as mediate receptor degradation, was tested as compared to anti-NRP1 or anti-EGFR alone or the two mAbs in combination.

Figures 16A, 16B, 16C, 16D:
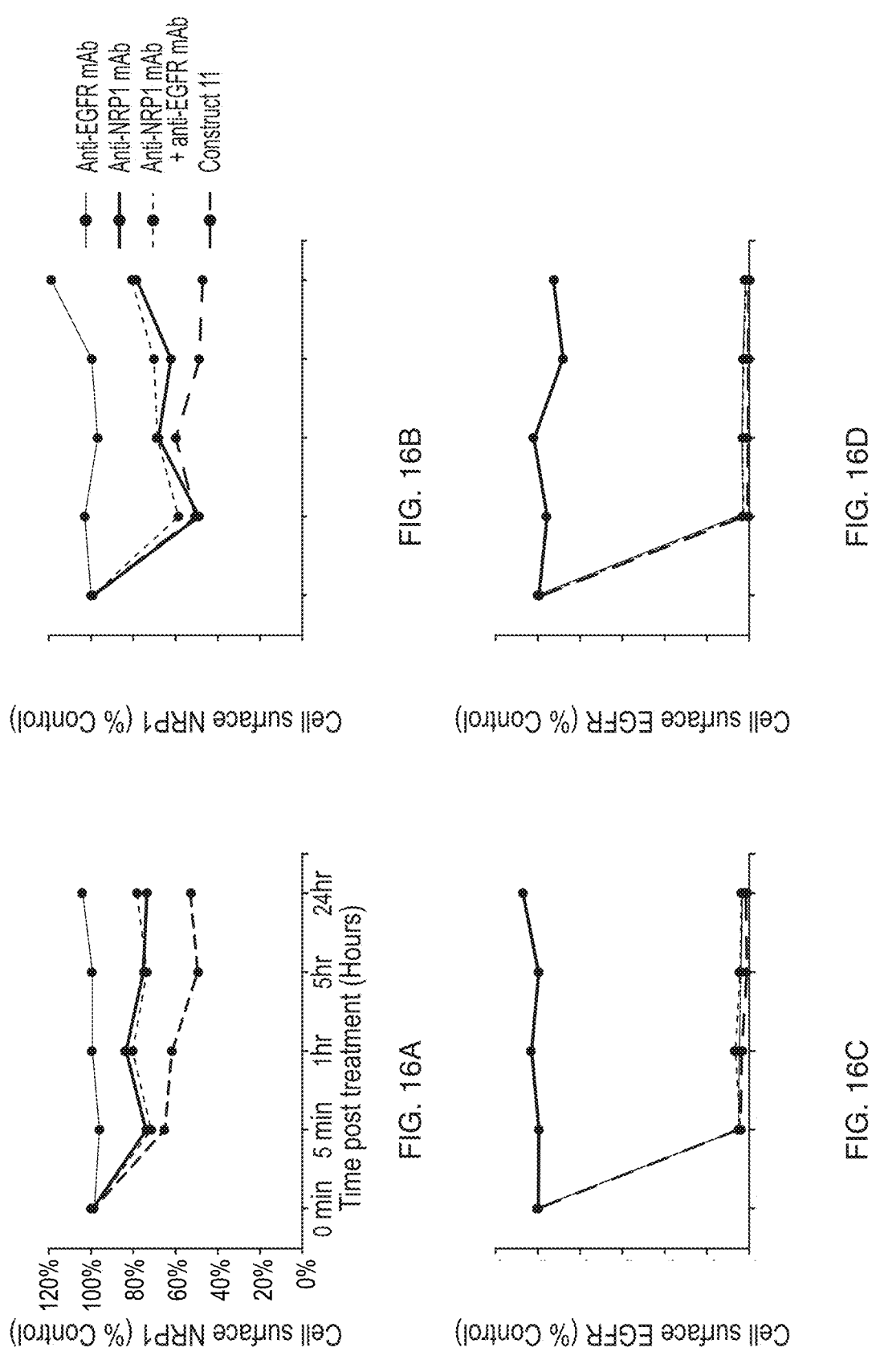
FIG. 16A-FIG. 16D Receptor internalization of NRP1 receptor (FIG. 16A, FIG. 16B) or EGFR receptor (FIG. 16C, FIG. 16D) in H1975 cells (FIG. 16A, FIG. 16C) or H1975-NRP1 OE cells (FIG. 16B, FIG. 16D) by Construct 11 bsAb (heavy chain polypeptide of SEQ ID NO: 11) as compared to anti-NRP1 alone, anti-EGFR alone, or anti-NRP1+anti-EGFR in combination.

For the receptor internalization studies, H1975 or H1975-NRP1 OE cells (which overexpress NRP1) were treated with either Construct 11, anti-NRP1 mAb alone, anti-EGFR mAb alone, or anti-NRP1+anti-EGFR in combination. For each sample, 200,000 cells were treated with 150 nM bsAb or mAb. Cell surface levels of NRP1 or EGFR (as a % of control) was determined at 5 minutes, 1 hour, 5 hours and 24 hours after treatment. The results for NRP1 expression are shown in FIG. 16A and FIG. 16B. The results for EGFR expression are shown in FIG. 16C and FIG. 16D. The results for H1975 cells are shown in FIG. 16A and FIG. 16C. The results for H1975-NRP1 OE cells are shown in FIG. 16B and FIG. 16D. For EGFR, the results showed that the anti-NRP1 antibody alone did not internalize EGFR (as expected), whereas the anti-EGFR mAb (alone or in combination with anti-NRP1) and Construct 11 were both able to fully internalize EGFR within 5 minutes of treatment. For NRP1, the results showed that the anti-EGFR antibody alone did not internalize NRP1 (as expected), the NRP1 mAb alone or in combination with anti-EGFR mAb was able to partially internalize NRP1, whereas Construct 11 was able to internalize NRP1 more effectively over time than anti-NRP1 mAb (alone or in combination with anti-EGFR).

Figure 17:
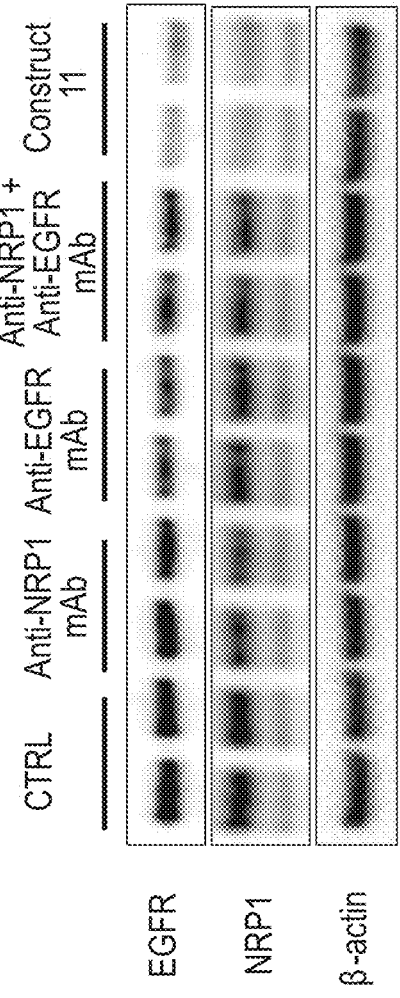
FIG. 17 Receptor degradation of NRP1 receptor or EGFR receptor mediated by Construct 11 bsAb (heavy chain polypeptide of SEQ ID NO: 11) as compared to anti-NRP1 alone, anti-EGFR alone, or anti-NRP1+anti-EGFR in combination.

For receptor degradation studies, cells were treated with either Construct 11, anti-NRP1 mAb alone, anti-EGFR mAb alone, or anti-NRP1+anti-EGFR in combination, and degradation of NRP1 and EGFR was assayed. In brief, H1975 cells (300,000 cells/sample) were cultured overnight in 6-well plates and then treated with bsAb or mAb (150 nM), followed by incubation for 6 hours. Cells lysates were prepared and analyzed by standard western blotting to detect the protein level of EGFR, NRP1 and beta-actin (used as a loading control). The results are shown in FIG. 17. The results showed that Construct 11 was more effective in degrading both NRP1 and EGFR than either the single mAb treatments or the combination treatment with anti-EGFR+ anti-NRP1 in combination.

Example 8: Production of Anti-NRP1 Monoclonal Antibodies

The designed anti-NRP1 proteins were generated by codon-optimized gene synthesis and inserted into pcDNA3.4 as expression vector using Not I and Hind III restriction enzyme. Examples of monoclonal antibody heavy chain polypeptide amino acid sequences are shown in SEQ ID NO: 41, 42, 43, 44, 45, 46 and 47, which combine with the light chain polypeptide sequences set forth in SEQ ID NO: 48, 49, 50, 51, 52, 53 and 54, respectively.

The polynucleotide sequences encoding the heavy chain polypeptides of the monoclonal antibodies are set forth in SEQ ID NO: 55, 56, 57, 58, 59, 60 and 61 (which encode SEQ ID NOs: 41-47, respectively). The polynucleotide sequences encoding the light chain polypeptides that combine with the heavy chains of the monoclonal antibodies are set forth in SEQ ID NO: 62, 63, 64, 65, 66, 67 and 68, respectively (which encode SEQ ID NOs: 48-54, respectively). The constructed expression vectors include signal peptides and for optimized transcription a Kozak sequence may be included in the 5' untranslated region.

To obtain the amount of the plasmid constructs for transfection, the plasmid construct were transformed into One Shot™ Top10 *E. coli* competent cells followed by culturing overnight. The construct plasmids were obtained by Pure-Link™ HiPure Expi plasmid Megaprep kit.

Fusion proteins were transiently expressed in the CHO-S system (Thermo Fisher Scientific Inc.). The proteins were expressed individually as per the manufacturer's instructions. Briefly, a total of 0.8 g of plasmid DNA at a ratio of 1:1 light to heavy chain per mL of CHO-S culture was prepared with OPTIPRO™ SFM and ExpiFectamine™. The mixture was added to CHO-S cells at a cell density of 6×106 cells/mL and greater than 98% viability. The cell culture was incubated overnight at 37° C., 80% humidity, 8% CO2 in a Nalgene™ Single-Use PETG Erlenmeyer Flasks shaking at 125 RPM with a 19-mm orbit. The next day the culture was enhanced (ExpiCHO™ enhancer; Thermo Fisher Scientific Inc.) and fed (ExpiCHO™ feed; Thermo Fisher Scientific Inc.) and transferred to 32° C., 80% humidity, 5% CO2 shaking at 125 RPM with a 19-mm orbit. The second feed was performed on day 5 and the culture returned to 32° C.

until harvest on day 12. Harvesting was accomplished via centrifugation at 4000×g for 20 minutes. The clarified supernatant was sterilized using an asymmetrical polyethersulfone (PES) 0.22-μM filter assembly (Nalgene). The filtrate was stored at 4° C. until purification the next day.

All of the antibody sterilized supernatants was purified using MabSelect prismA™ resin (GE Healthcare Life Sciences) on an AKTApure (GE Healthcare Life Sciences). A 50 mM sodium phosphate, 150 mM NaCl, pH 7.0 buffer was used to equilibrate the resin. The antibody supernatant was then loaded into the column. The resin was washed with 50 mM sodium phosphate, 150 mM NaCl, pH 7.0 buffer until the chromatographic baseline returned to column equilibration levels. Elution was then performed using 100 mM sodium acetate, 20% glycerol, pH 3.0, and fractions are collected. The fractions were immediately neutralized with 1 M Tris, pH 9. The fractions containing predominant absorbance at wavelength 280 nm were pooled into an Amicon® 10-kDa ultrafiltration device for buffer exchange. The storage buffer (Phosphate Buffered Saline) was used to remove the elution buffer by centrifugation with half dilution, seven times in the Amicon® concentrator. The material was submitted for SEC and then stored at 4° C.

Cationic exchange chromatography was used to purify the antibodies. The cationic exchange chromatography column (Capto® S ImpAct) was sanitized with 1 M NaOH and rinsed with MQ. Equilibration was done with 50 mM NaAc pH 5.5 (starting buffer) and 50 mM NaAc pH5.5, 1M NaCl (elution buffer). The protein A purified antibody was loaded with a concentration of 1-2 g antibody/mL resin. The column was then washed with 50 mM NaAc pH 5.5. The antibody product was then eluted using a gradient of 5-60% elution buffer in 25 column volumes. Each peak in CEX purification was collected separately and concentrated via centrifugation at 4000×g using Amicon® Ultra-15 Centrifugal Filter Units, with resuspension in PBS.

Size exclusion chromatography (SEC) analysis is performed on an Agilent® Infinity 1260 II Quaternary Pump high performance liquid chromatographic (HPLC) system with diode array UV detector WR. Twenty (20) g of antibody material was injected on a XBridge Protein BEH SEC Column, 200 Å, 2.5 μm, 4.6 mm×150 mm column. The mobile phase was 100 mM Phosphate, 300 mM Sodium Chloride pH7.0 at 50° C. and, and the flowrate was 0.3 mL/min. The antibody material was detected at wavelength 220, 280 and 330 nm at 1 Hz sampling rate during a 10-minute acquisition.

The activity of the anti-NRP1 monoclonal antibodies can be evaluated by methods established in the art. For example, binding affinity, VEGFR2 signaling inhibition and/or effects on cell viability in vitro or tumor growth in vivo can be evaluated as described in the Examples of U.S. Provisional Application No. 63/325,317, the entire contents of which is hereby specifically incorporated by reference.

Sequence Listing Summary

| SEQUENCE LISTING SUMMARY | |
|---|---|
| SEQ ID NO: | Sequence |
| 1 | QVQLQESGPGLVKPSETLSLTCTVSGGSVSSGDYYWTWIRQSPGKGLEWIGHIYYSGNTNYNPSLKS RLTISIDTSKTQFSLKLSSVTAADTAIYYCVRDRVTGAFDIWGQGTMVTVSSASTKGPSVFPLAPCSRS TSESTAALGCLVKDYFPEPVTVSWNSGALTSGVHTFPAVLQSSGLYSLSSVVTVPSSNFGTQTYTCNV DHKPSNTKVDKTVERKCCVECPPCPAPPVAGPSVFLFPPKPKDTLMISRTPEVTCVVVDVSHEDPEV QFNWYVDGVEVHNAKTKPREEQFNSTFRVVSVLTVVHQDWLNGKEYKCKVSNKGLPAPIEKTISKT KGQPREPQVYTLPPSREEMTKNQVSLTCLVKGFYPSDIAVEWESNGQPENNYKTTPPMLDSDGSFFL YSKLTVDKSRWQQGNVFSCSVMHEALHNHYTQKSLSLSPGKGGGGSGGGGGGGGGSHTPGNSKP TRTPRR |
| 2 | QVQLQESGPGLVKPSETLSLTCTVSGGSVSSGDYYWTWIRQSPGKGLEWIGHIYYSGNTNYNPSLKS RLTISIDTSKTQFSLKLSSVTAADTAIYYCVRDRVTGAFDIWGQGTMVTVSSASTKGPSVFPLAPCSRS TSESTAALGCLVKDYFPEPVTVSWNSGALTSGVHTFPAVLQSSGLYSLSSVVTVPSSNFGTQTYTCNV DHKPSNTKVDKTVERKCCVECPPCPAPPVAGPSVFLFPPKPKDTLMISRTPEVTCVVVDVSHEDPEV QFNWYVDGVEVHNAKTKPREEQFNSTFRVVSVLTVVHQDWLNGKEYKCKVSNKGLPAPIEKTISKT KGQPREPQVYTLPPSREEMTKNQVSLTCLVKGFYPSDIAVEWESNGQPENNYKTTPPMLDSDGSFFL YSKLTVDKSRWQQGNVFSCSVMHEALHNHYTQKSLSLSPGKGGGGSGGGGSGGGGSEVQLVESG GGLVQPGGSLRLSCAASGFTFSSYAMSWVRQAPGKGLEWVSQISPAGGYTNYADSVKGRFTISADT SKNTAYLQMNSLRAEDTAVYYCARGELPYYRMSKVMDVWGQGTLVTVSSGGGGSGGGGSGGGG SDIQMTQSPSSLSASVGDRVTITCRASQYFSSYLAWYQQKPGKAPKLLIYGASSRASGVPSRFSGSGS GTDFTLTISSLQPEDFATYYCQQYLGSPPTFGQGTKVEIK |
| 3 | QVQLQESGPGLVKPSETLSLTCTVSGGSVSSGDYYWTWIRQSPGKGLEWIGHIYYSGNTNYNPSLKS RLTISIDTSKTQFSLKLSSVTAADTAIYYCVRDRVTGAFDIWGQGTMVTVSSASTKGPSVFPLAPCSRS TSESTAALGCLVKDYFPEPVTVSWNSGALTSGVHTFPAVLQSSGLYSLSSVVTVPSSNFGTQTYTCNV DHKPSNTKVDKTVERKCCVECPPCPAPPVAGPSVFLFPPKPKDTLMISRTPEVTCVVVDVSHEDPEV QFNWYVDGVEVHNAKTKPREEQFNSTFRVVSVLTVVHQDWLNGKEYKCKVSNKGLPAPIEKTISKT KGQPREPQVYTLPPSREEMTKNQVSLTCLVKGFYPSDIAVEWESNGQPENNYKTTPPMLDSDGSFFL YSKLTVDKSRWQQGNVFSCSVMHEALHNHYTQKSLSLSPGKGGGGSGGGGSGGGGSEVQLVESG GGLVQPGGSLRLSCAASGFTFSSYAMSWVRQAPGKGLEWVSQISPAGGYTNYADSVKGRFTISADT SKNTAYLQMNSLRAEDTAVYYCARGELPYYRMSKVMDVWGQGTLVTVSSGGGGSGGGGSGGGG SDIQMTQSPSSLSASVGDRVTITCRASQFLSSYLAWYQQKPGKAPKLLIYGASARASGVPSRFSGSGS GTDFTLTISSLQPEDFATYYCQQYLASPATFGQGTKVEIK |
| 4 | QVQLQESGPGLVKPSETLSLTCTVSGGSVSSGDYYWTWIRQSPGKGLEWIGHIYYSGNTNYNPSLKS RLTISIDTSKTQFSLKLSSVTAADTAIYYCVRDRVTGAFDIWGQGTMVTVSSASTKGPSVFPLAPCSRS TSESTAALGCLVKDYFPEPVTVSWNSGALTSGVHTFPAVLQSSGLYSLSSVVTVPSSNFGTQTYTCNV DHKPSNTKVDKTVERKCCVECPPCPAPPVAGPSVFLFPPKPKDTLMISRTPEVTCVVVDVSHEDPEV QFNWYVDGVEVHNAKTKPREEQFNSTFRVVSVLTVVHQDWLNGKEYKCKVSNKGLPAPIEKTISKT |

-continued

| SEQUENCE LISTING SUMMARY |
|---|

SEQ
ID
NO:   Sequence

KGQPREPQVYTLPPSREEMTKNQVSLTCLVKGFYPSDIAVEWESNGQPENNYKTTPPMLDSDGSFFL
YSKLTVDKSRWQQGNVFSCSVMHEALHNHYTQKSLSLSPGKGGGGSGGGGSGGGGSEVQLVESG
GGLVQPGGSLRLSCAASGFTFSSYAMSWVRQAPGKGLEWVSQISPAGGYTNYADSVKGRFTISADT
SKNTAYLQMNSLRAEDTAVYYCARGELPYYQMSKVMDVWGQGTLVTVSSGGGGSGGGGSGGGGS
SDIQMTQSPSSLSASVGDRVTITCRASQYFSSYLAWYQQKPGKAPKLLIYGASARASGVPSRFSGSGS
GTDFTLTISSLQPEDFATYYCQQYLASPATFGQGTKVEIK

5      QVQLQESGPGLVKPSETLSLTCTVSGGSVSSGDYYWTWIRQSPGKGLEWIGHIYYSGNTNYNPSLKS
RLTISIDTSKTQFSLKLSSVTAADTAIYYCVRDRVTGAFDIWGQGTMVTVSSASTKGPSVFPLAPCSRS
TSESTAALGCLVKDYFPEPVTVSWNSGALTSGVHTFPAVLQSSGLYSLSSVVTVPSSNFGTQTYTCNV
DHKPSNTKVDKTVERKCCVECPPCPAPPVAGPSVFLFPPKPKDTLMISRTPEVTCVVVDVSHEDPEV
QFNWYVDGVEVHNAKTKPREEQFNSTFRVVSVLTVVHQDWLNGKEYKCKVSNKGLPAPIEKTISKT
KGQPREPQVYTLPPSREEMTKNQVSLTCLVKGFYPSDIAVEWESNGQPENNYKTTPPMLDSDGSFFL
YSKLTVDKSRWQQGNVFSCSVMHEALHNHYTQKSLSLSPGKGGGGSGGGGSGGGGSEVQLVESG
GGLVQPGGSLRLSCAASGFTFSSYAMSWVRQAPGKGLEWVSQISPAGGYTNYADSVKGRFTISADT
SKNTAYLQMNSLRAEDTAVYYCARGELPFFRMSQVMDVWGQGTLVTVSSGGGGSGGGGSGGGG
SDIQMTQSPSSLSASVGDRVTITCRASQFLSSYLAWYQQKPGKAPKLLIYGASARASGVPSRFSGSGS
GTDFTLTISSLQPEDFATYYCQQYLASPATFGQGTKVEIK

6      QVQLQESGPGLVKPSETLSLTCTVSGGSVSSGDYYWTWIRQSPGKGLEWIGHIYYSGNTNYNPSLKS
RLTISIDTSKTQFSLKLSSVTAADTAIYYCVRDRVTGAFDIWGQGTMVTVSSASTKGPSVFPLAPCSRS
TSESTAALGCLVKDYFPEPVTVSWNSGALTSGVHTFPAVLQSSGLYSLSSVVTVPSSNFGTQTYTCNV
DHKPSNTKVDKTVERKCCVECPPCPAPPVAGPSVFLFPPKPKDTLMISRTPEVTCVVVDVSHEDPEV
QFNWYVDGVEVHNAKTKPREEQFNSTFRVVSVLTVVHQDWLNGKEYKCKVSNKGLPAPIEKTISKT
KGQPREPQVYTLPPSREEMTKNQVSLTCLVKGFYPSDIAVEWESNGQPENNYKTTPPMLDSDGSFFL
YSKLTVDKSRWQQGNVFSCSVMHEALHNHYTQKSLSLSPGKGGGGSGGGGSGGGGSEVQLVESG
GGLVQPGGSLRLSCAASGFTFSSYAMSWVRQAPGKGLEWVSQISPAGGYTNYADSVKGRFTISADT
SKNTAYLQMNSLRAEDTAVYYCARGELPYFRMSKVMDVWGQGTLVTVSSGGGGSGGGGSGGGG
SDIQMTQSPSSLSASVGDRVTITCRASQFLSSFLAWYQQKPGKAPKLLIYGASARASGVPSRFSGSGS
GTDFTLTISSLQPEDFATYYCQQYLASPATFGQGTKVEIK

7      QVQLQESGPGLVKPSETLSLTCTVSGGSVSSGDYYWTWIRQSPGKGLEWIGHIYYSGNTNYNPSLKS
RLTISIDTSKTQFSLKLSSVTAADTAIYYCVRDRVTGAFDIWGQGTMVTVSSASTKGPSVFPLAPSSKST
SGGTAALGCLVKDYFPEPVTVSWNSGALTSGVHTFPAVLQSSGLYSLSSVVTVPSSSLGTQTYICNVN
HKPSNTKVDKKVEPKSCDKTHTCPPCPAPELLGGPSVFLFPPKPKDTLMISRTPEVTCVVVDVSHEDP
EVKFNWYVDGVEVHNAKTKPREEQYNSTYRVVSVLTVLHQDWLNGKEYKCKVSNKALPAPIEKTISK
AKGQPREPQVYTLPPSRDELTKNQVSLTCLVKGFYPSDIAVEWESNGQPENNYKTTPPVLDSDGSFFL
YSKLTVDKSRWQQGNVFSCSVMHEALHNHYTQKSLSLSPGKGGGGSGGGGSGGGGSEVQLVESG
GGLVQPGGSLRLSCAASGFTFSSYAMSWVRQAPGKGLEWVSQISPAGGYTNYADSVKGRFTISADT
SKNTAYLQMNSLRAEDTAVYYCARGELPYFRMSKVMDVWGQGTLVTVSSGGGGSGGGGSGGGG
SDIQMTQSPSSLSASVGDRVTITCRASQFLSSYLAWYQQKPGKAPKLLIYGASARASGVPSRFSGSGS
GTDFTLTISSLQPEDFATYYCQQYLASPATFGQGTKVEIK

8      QVQLQESGPGLVKPSETLSLTCTVSGGSVSSGDYYWTWIRQSPGKGLEWIGHIYYSGNTNYNPSLKS
RLTISIDTSKTQFSLKLSSVTAADTAIYYCVRDRVTGAFDIWGQGTMVTVSSASTKGPSVFPLAPSSKST
SGGTAALGCLVKDYFPEPVTVSWNSGALTSGVHTFPAVLQSSGLYSLSSVVTVPSSSLGTQTYICNVN
HKPSNTKVDKKVEPKSCDKTHTCPPCPAPELLGGPSVFLFPPKPKDTLMISRTPEVTCVVVDVSHEDP
EVKFNWYVDGVEVHNAKTKPREEQYNSTYRVVSVLTVLHQDWLNGKEYKCKVSNKALPAPIEKTISK
AKGQPREPQVYTLPPSRDELTKNQVSLTCLVKGFYPSDIAVEWESNGQPENNYKTTPPVLDSDGSFFL
YSKLTVDKSRWQQGNVFSCSVMHEALHNHYTQKSLSLSPGKGGGGSGGGGSGGGGSEVQLVESG
GGLVQPGGSLRLSCAASGFTFSSYAMSWVRQAPGKGLEWVSQISPAGGYTNYADSVKGRFTISADT
SKNTAYLQMNSLRAEDTAVYYCARGELPYFRMSKVMDVWGQGTLVTVSSGDGSSGGGGASDIQM
TQSPSSLSASVGDRVTITCRASQFLSSYLAWYQQKPGKAPKLLIYGASARASGVPSRFSGSGSGTDFTL
TISSLQPEDFATYYCQQYLASPATFGQGTKVEIK

9      QVQLQESGPGLVKPSETLSLTCTVSGGSVSSGDYYWTWIRQSPGKGLEWIGHIYYSGNTNYNPSLKS
RLTISIDTSKTQFSLKLSSVTAADTAIYYCVRDRVTGAFDIWGQGTMVTVSSASTKGPSVFPLAPSSKST
SGGTAALGCLVKDYFPEPVTVSWNSGALTSGVHTFPAVLQSSGLYSLSSVVTVPSSSLGTQTYICNVN
HKPSNTKVDKKVEPKSCDKTHTCPPCPAPELLGGPSVFLFPPKPKDTLMISRTPEVTCVVVDVSHEDP
EVKFNWYVDGVEVHNAKTKPREEQYNSTYRVVSVLTVLHQDWLNGKEYKCKVSNKALPAPIEKTISK
AKGQPREPQVYTLPPSRDELTKNQVSLTCLVKGFYPSDIAVEWESNGQPENNYKTTPPVLDSDGSFFL
YSKLTVDKSRWQQGNVFSCSVMHEALHNHYTQKSLSLSPGKGGGGSGGGGSGGGGSEVQLVESG
GGLVQPGGSLRLSCAASGFTFSSYAMSWVRQAPGKGLEWVSQISPAGGYTNYADSVKGRFTISADT
SKNTAYLQMNSLRAEDTAVYYCARGELPYFRMSKVMDVWGQGTLVTVSSGGGGSGGGGSGGGG
SGGGGSDIQMTQSPSSLSASVGDRVTITCRASQFLSSYLAWYQQKPGKAPKLLIYGASARASGVPSRF
SGSGSGTDFTLTISSLQPEDFATYYCQQYLASPATFGQGTKVEIK

10     QVQLQESGPGLVKPSETLSLTCTVSGGSVSSGDYYWTWIRQSPGKGLEWIGHIYYSGNTNYNPSLKS
RLTISIDTSKTQFSLKLSSVTAADTAIYYCVRDRVTGAFDIWGQGTMVTVSSASTKGPSVFPLAPSSKST
SGGTAALGCLVKDYFPEPVTVSWNSGALTSGVHTFPAVLQSSGLYSLSSVVTVPSSSLGTQTYICNVN
HKPSNTKVDKKVEPKSCDKTHTCPPCPAPELLGGPSVFLFPPKPKDTLMISRTPEVTCVVVDVSHEDP
EVKFNWYVDGVEVHNAKTKPREEQYNSTYRVVSVLTVLHQDWLNGKEYKCKVSNKALPAPIEKTISK
AKGQPREPQVYTLPPSRDELTKNQVSLTCLVKGFYPSDIAVEWESNGQPENNYKTTPPVLDSDGSFFL

-continued

---

SEQUENCE LISTING SUMMARY

SEQ
ID
NO:   Sequence

---

```
     YSKLTVDKSRWQQGNVFSCSVMHEALHNHYTQKSLSLSPGKGGGGSGGGGSGGGGSDIQMTQSP
     SSLSASVGDRVTITCRASQFLSSYLAWYQQKPGKAPKLLIYGASARASGVPSRFSGSGSGTDFTLTISSL
     QPEDFATYYCQQYLASPATFGQGTKVEIKGGGGSGGGGSGGGGSEVQLVESGGGLVQPGGSLRLSC
     AASGFTFSSYAMSWVRQAPGKGLEWVSQISPAGGYTNYADSVKGRFTISADTSKNTAYLQMNSLRA
     EDTAVYYCARGELPYFRMSKVMDVWGQGTLVTVSS

11   QVQLQESGPGLVKPSETLSLTCTVSGGSVSSGDYYWTWIRQSPGKGLEWIGHIYYSGNTNYNPSLKS
     RLTISIDTSKTQFSLKLSSVTAADTAIYYCVRDRVTGAFDIWGQGTMVTVSSASTKGPSVFPLAPSSKST
     SGGTAALGCLVKDYFPEPVTVSWNSGALTSGVHTFPAVLQSSGLYSLSSVVTVPSSSLGTQTYICNVN
     HKPSNTKVDKKVEPKSCDKTHTCPPCPAPELLGGPSVFLFPPKPKDTLMISRTPEVTCVVVDVSHEDP
     EVKFNWYVDGVEVHNAKTKPREEQYNSTYRVVSVLTVLHQDWLNGKEYKCKVSNKALPAPIEKTISK
     AKGQPREPQVYTLPPSRDELTKNQVSLTCLVKGFYPSDIAVEWESNGQPENNYKTTPPVLDSDGSFFL
     YSKLTVDKSRWQQGNVFSCSVMHEALHNHYTQKSLSLSPGKGGGGSGGGGSGGGGSEVQLLESG
     GGLVQPGGSLRLSCAASGFTFSSYAMSWVRQAPGKGLEWVSQISPAGGYTNYADSVKGRFTISRDN
     SKNTLYLQMNSLRAEDTAVYYCARGELPYFRMSKVMDVWGQGTLVTVSSGGGGSGGGGSGGGGS
     EIVLTQSPGTLSLSPGERATLSCRASQFLSSYLAWYQQKPGQAPRLLIYGASARASGIPDRFSGSGSGT
     DFTLTISRLEPEDFAVYYCQQYLASPATFGQGTKVEIK

12   DIQMTQSPSSLSASVGDRVTITCQASQDISNYLNWYQQKPGKAPKLLIYDASNLETGVPSRFSGSGSG
     TDFTFTISSLQPEDIATYFCQHFDHLPLAFGGGTKVEIKRTVAAPSVFIFPPSDEQLKSGTASVVCLLNN
     FYPREAKVQWKVDNALQSGNSQESVTEQDSKDSTYSLSSTLTLSKADYEKHKVYACEVTHQGLSSPV
     TKSFNRGEC

13   GGGGS

14   CAAGTGCAGCTGCAGGAATCCGGCCCCGGGCTTGTGAAGCCTAGCGAAACACTCTCGCTCACCT
     GTACTGTCAGCGGTGGATCAGTGTCCTCCGGCGATTACTACTGGACCTGGATTCGGCAGAGCCC
     TGGGAAAGGGACTGGAGTGGATCGGACACATCTACTACTCCGGGAACACTAACTACAACCCGTCG
     TTGAAGTCCAGACTGACGATCAGTATCGATACCTCCAAGACCCAGTTCAGCCTGAAGCTGAGCTC
     AGTGACAGCCGCCGACACTGCAATCTACTACTGCGTGCGGGACAGAGTGACCGGAGCCTTCGAC
     ATCTGGGGCCAGGGAACCATGGTCACTGTGTCGTCTGCGTCAACCAAGGGTCCGTCCGTGTTTC
     CCCTGGCCCCGTGCTCGCGGAGCACCTCCGAGTCCACTGCCGCCTTGGGCTGCCTGGTCAAAGA
     CTACTTCCCTGAACCCGTGACTGTCAGCTGGAACTCCGGAGCTCTGACCTCGGGAGTGCACACCT
     TCCCGGCCGTGCTGCAATGAGCGGCCTCTACTCCCTGTCCTCCGTCGTGACCGTGCCATCATCA
     AACTTCGGAACCCAAACTTATACGTGCAACGTCGACCACAAGCCCTCCAATACCAAAGTCGACAA
     GACCGTGGAGAGGAAATGCTGCGTGGAGTGTCCGCCTTGCCCCGCGCCGCCGGTGGCCGGACC
     TAGCGTGTTCCTGTTCCCGCCGAAGCCAAAGGACACTCTCATGATCTCCCGCACCCCTGAAGTCA
     CTTGCGTCGTGGTGGACGTTTCCCACGAGGATCCCGAAGTGCAGTTCAATTGGTACGTGGACGG
     GGTGGAAGTACATAACGCCAAGACCAAGCCCAGGGAAGAACAGTTTAACTCCACCTTCCGGGTG
     GTGTGTCGGTGCTCACTGTGGTGCATCAGGATTGGCTCAATGGAAAGGAGTACAAGTGCAAAGTG
     TCGAACAAGGGTCTGCCCGCTCCTATTGAAAAGACCATTTCCAAAACCAAGGGACAGCCCCAGAG
     AGCCTCAGGTCTACACCCTGCCTCCGAGCCGCGAGGAAATGACCAAGAACCAAGTGTCTCTGAC
     TTGCCCTCGTGAAGGGATTCTACCCCTCCGATATCGCGGTGGAGTGGGAGAGCAACGGGCAGCC
     AGAGAACAACTATAAGACCACCCCGCCTATGCTGGACTCCGATGGCTCCTTCTTCTTGTACTCGA
     AGCTGACCGTGGACAAGTCCCGCTGGCAACAGGGAAACGTGTTCAGCTGTAGCGTGATGCACG
     AAGCCCTGCACAACCACTACACCCAGAAGTCCCTGTCGCTTTCCCCCGGGAAGGGCGGTGGCGG
     ATCCGGCGGCGGGGGCAGCGGGGGCGGCGGTTCCCATACCCCGGGGAACTCAAAGCCCACCC
     GGACTCCACGGCGC

15   CAGGTTCAGCTGCAAGAGTCTGGCCCCTGGCCTGGTCAAGCCTTCCGAAACACTGTCTCTGACCTG
     CACCGTGTCTGGCGGCTCTGTGTCCTCTGGCGATTACTACTGGACCTGGATCCGGCAGTCTCCTG
     GCAAAGGCCTGGAATGGATCGGCCACATCTACTACTCCGGCAACACCAACTACAACCCCAGCCT
     GAAGTCCCGGCTGACCATCTCCATCGACACCAGCAAGACCCAGTTCTCCCTGAAGCTGTCCTCTG
     TGACCGCCGCTGATACCGCCATCTACTATTGCGTGCGGGACAGAGTGACCGGCGCCTTTGATATT
     TGGGGCCAGGGCACCATGGTCACCGTGTCCAGTGCTTCTACCAAGGGACCCAGCGTGTTCCCTC
     TGGCTCCTTGCTCCAGATCCACCTCCGAGTCTACAGCTGCTCTGGGCTGTCTGGTCAAGGACTAC
     TTCCCTGAGCCTGTGACCGTGTCCTGGAATTCTGGCGCTCTGACATCTGGCGTGCACACCTTTCC
     AGCTGTGCTGCAGTCTAGCGGCCTGTACTCTCTGTCCTCCGTCGTGACCGTGCCTTCCTCTAACTT
     TGGCACCCAGACCTACACCTGTAATGTGGACCACAAGCCATCCAACACCAAGGTGGACAAGACC
     GTGGAACGGAAGTGCTGCGTGGAATGCCCTCCTTGTCCTGCTCCTCCTGTGGCTGGCCCTTCCGT
     GTTTCTGTTCCCTCCAAAGCCTAAGGACACCCTGATGATCTCTCGGACCCCTGAAGTGACCTGCG
     TGGTGGTGGATGTGTCTCACGAGGATCCCGAGGTGCAGTTCAATTGGTACGTGGACGGCGTGGA
     AGTGCACAACGCCAAGACCAAGCCTAGAGAGGAACAGTTCAACTCCACCTTCAGAGTGGTGTC
     CGTGCTGACCGTGGTGCATCAGGATTGGCTGAACGGCAAAGAGTACAAGTGCAAGGTGTCCAA
     CAAGGGCCTGCCTGCTCCTATCGAAAAGACCATCTCTAAGACCAAGGGGCAGCCCCGGGAACCT
     CAGGTTTACACACTGCCTCCAAGCCGGGAAGAGATGACCAAGAACCAGGTGTCCCTGACCTGTC
     TCGTGAAGGGCTTCTACCCCTCCGATATCGCCGTGGAATGGGAGTCTAATGGCCAGCCTGAGAA
     CAACTACAAGACCACACCTCCTATGCTGGACTCCGACGGCTCATTCTTCCTGTACTCCAAGCTGAC
     AGTGGACAAGTCCAGATGGCAGCAGGGCAACGTGTTCTCCTGCTCCGTGATGCACGAGGCCCTG
     CACAATCACTACACCCAGAAGTCCCTGTCTCTGTCCCCTGGAAAAGGCGGCGGAGGATCTGGCG
     GAGGCGGTAGCGGTGGTGGCGGATCTGAAGTTCAGCTGGTTGAATCTGGCGGCGGACTGGTTC
     AACCAGGCGGATCTCTGAGACTGTCTTGTGCCGCCTCCGGCTTCACCTTCTCCTCTTACGCTATGT
     CCTGGGTCCGACAGGCCCCCAGGCAAAGGATTGGAGTGGGTGTCCCAGATCTCTCCCGCTGGCG
```

-continued

---

SEQUENCE LISTING SUMMARY

---

SEQ
ID
NO:  Sequence

---

GCTACACCAATTACGCCGACTCTGTGAAGGGCAGATTCACCATCTCTGCCGACACCTCCAAGAAC
    ACCGCCTACCTGCAGATGAACTCCCTGAGAGCCGAGGACACCGCCGTGTACTATTGTGCTAGAG
    GCGAGCTGCCCTACTACCGGATGTCCAAAGTGATGGACGTGTGGGGACAGGGAACCCTCGTGA
    CAGTTTCTAGCGGTGGCGGAGGTAGCGGAGGCGGTGGAAGCGGCGGAGGCGGAAGTGATATT
    CAGATGACCCAGTCTCCTTCCAGCCTGTCCGCTTCTGTGGGCGATAGAGTGACCATCACCTGTCG
    GGCCTCTCAGTACTTCTCCTCCTACCTGGCTTGGTATCAGCAGAAGCCTGGCAAGGCCCCTAAGC
    TGCTGATCTACGGCGCCTCCTCTAGAGCTAGCGGCGTGCCCTCTAGATTCTCCGGATCTGGCTCT
    GGCACCGACTTTACCCTGACAATCTCCAGCCTGCAGCCTGAGGACTTCGCCACCTACTACTGCCA
    GCAGTACCTGGGCTCTCCTCCAACCTTTGGCCAGGGAACAAAGGTCGAGATCAAGCGCTGA

16   CAGGTTCAGCTGCAAGAGTCTGGCCCTGGCCTGGTCAAGCCTTCCGAAACACTGTCTCTGACCTG
    CACCGTGTCTGGCGGCTCTGTGTCCTCTGGCGATTACTACTGGACCTGGATCCGGCAGTCTCCTG
    GCAAAGGCCTGGAATGGATCGGCCACATCTACTACTCCGGCAACACCAACTACAACCCCAGCCT
    GAAGTCCCGGCTGACCATCTCCATCGACACCAGCAAGACCCAGTTCTCCCTGAAGCTGTCCTCTG
    TGACCGCCGCTGATACCGCCATCTACTATTGCGTGCGGGACAGAGTGACCGGCGCCTTTGATATT
    TGGGGCCAGGGCACCATGGTCACCGTGTCCAGTGCTTCTACCAAGGGACCCAGCGTGTTCCCTC
    TGGCTCCTTGCTCCAGATCCACCTCCGAGTCTACAGCTGCTCTGGGCTGTCTGGTCAAGGACTAC
    TTCCCTGAGCCTGTGACCGTGTCCTGGAATTCTGGCGCTCTGACATCTGGCGTGCACACCTTTCC
    AGCTGTGCTGCAGTCTAGCGGCCTGTACTCTCTGTCCTCCGTCGTGACCGTGCCTTCCTCTAACTT
    TGGCACCCAGACCTACACCTGTAATGTGGACCACAAGCCATCCAACACCAAGGTGGACAAGACC
    GTGGAACGGAAGTGCTGCGTGAATGCCCTCCTTGTCCTGCTCCTCCTGTGGCTGGCCCTTCCGT
    GTTTCTGTTCCCTCCAAAGCCTAAGGACACCCTGATGATCTCTCGGACCCCTGAAGTGACCTGCG
    TGGTGGTGGATGTGTCTCACGAGGATCCCGAGGTGCAGTTCAATTGGTACGTGGACGGCGTGG
    AAGTGCACAACGCCAAGACCAAGCCTAGAGAGGAACAGTTCAACTCCACCTTCAGAGTGGTGTC
    CGTGCTGACCGTGGTGCATCAGGATTGGCTGAACGGCAAAGAGTACAAGTGCAAGGTGTCCAA
    CAAGGGCCTGCCTGCTCCTATCGAAAAGACCATCTCTAAGACCAAGGGGCAGCCCCGGGAACCT
    CAGGTTTACACACTGCCTCCAAGCCGGGAAGAGATGACCAAGAACCAGGTGTCCCTGACCTGTC
    TCGTGAAGGGCTTCTACCCCTCCGATATCGCCGTGGAATGGGAGTCTAATGGCCAGCCTGAGAA
    CAACTACAAGACCACACCTCCTATGCTGGACTCCGACGGCTCATTCTTCCTGTACTCCAAGCTGAC
    AGTGGACAAGTCCAGATGGCAGCAGGGCAACGTGTTCTCCTGCTCCGTGATGCACGAGGCCCTG
    CACAATCACTACACCCAGAAGTCCCTGTCTCTGTCCCCTGGAAAAGGCGGCGGAGGATCTGGCG
    GAGGCGGTAGCGGTGGTGGCGGATCTGAAGTTCAGCTGGTTGAATCTGGCGGCGGACTGGTTC
    AACCAGGCGGATCTCTGAGACTGTCTTGTGCCGCCTCCGGCTTCACCTTCTCCTCTTACGCTATGT
    CCTGGGTCCGACAGGCCCCAGGCAAAGGATTGGAGTGGGTGTCCCAGATCTCTCCCGCTGGCG
    GCTACACCAATTACGCCGACTCTGTGAAGGGCAGATTCACCATCTCTGCCGACACCTCCAAGAAC
    ACCGCCTACCTGCAGATGAACTCCCTGAGAGCCGAGGACACCGCCGTGTACTATTGTGCTAGAG
    GCGAGCTGCCCTACTTCCGGATGTCCAAAGTGATGGACGTGTGGGGACAGGGAACCCTCGTGA
    CAGTTTCTAGCGGTGGCGGAGGTAGCGGAGGCGGTGGAAGCGGCGGAGGCGGAAGTGATATT
    CAGATGACCCAGTCTCCTTCCAGCCTGTCCGCTTCTGTGGGCGATAGAGTGACCATCACCTGTCG
    GGCCTCTCAGTTCCTGTCCTCCTACCTGGCTTGGTATCAGCAGAAGCCTGGCAAGGCCCCTAAGC
    TGCTGATCTACGGCGCCTTCTGCTAGAGCTTCCGGCGTGCCCTCTAGATTTTCTGGCTCTGGATCT
    GGCACCGACTTTACCCTGACAATCTCCAGCCTGCAGCCTGAGGACTTCGCCACCTACTACTGCCA
    GCAGTACCTGGCCTCTCCTGCCACATTTGGCCAGGGAACAAAGGTCGAGATCAAGCGCTGA

17   CAGGTTCAGCTGCAAGAGTCTGGCCCTGGCCTGGTCAAGCCTTCCGAAACACTGTCTCTGACCTG
    CACCGTGTCTGGCGGCTCTGTGTCCTCTGGCGATTACTACTGGACCTGGATCCGGCAGTCTCCTG
    GCAAAGGCCTGGAATGGATCGGCCACATCTACTACTCCGGCAACACCAACTACAACCCCAGCCT
    GAAGTCCCGGCTGACCATCTCCATCGACACCAGCAAGACCCAGTTCTCCCTGAAGCTGTCCTCTG
    TGACCGCCGCTGATACCGCCATCTACTATTGCGTGCGGGACAGAGTGACCGGCGCCTTTGATATT
    TGGGGCCAGGGCACCATGGTCACCGTGTCCAGTGCTTCTACCAAGGGACCCAGCGTGTTCCCTC
    TGGCTCCTTGCTCCAGATCCACCTCCGAGTCTACAGCTGCTCTGGGCTGTCTGGTCAAGGACTAC
    TTCCCTGAGCCTGTGACCGTGTCCTGGAATTCTGGCGCTCTGACATCTGGCGTGCACACCTTTCC
    AGCTGTGCTGCAGTCTAGCGGCCTGTACTCTCTGTCCTCCGTCGTGACCGTGCCTTCCTCTAACTT
    TGGCACCCAGACCTACACCTGTAATGTGGACCACAAGCCATCCAACACCAAGGTGGACAAGACC
    GTGGAACGGAAGTGCTGCGTGAATGCCCTCCTTGTCCTGCTCCTCCTGTGGCTGGCCCTTCCGT
    GTTTCTGTTCCCTCCAAAGCCTAAGGACACCCTGATGATCTCTCGGACCCCTGAAGTGACCTGCG
    TGGTGGTGGATGTGTCTCACGAGGATCCCGAGGTGCAGTTCAATTGGTACGTGGACGGCGTGG
    AAGTGCACAACGCCAAGACCAAGCCTAGAGAGGAACAGTTCAACTCCACCTTCAGAGTGGTGTC
    CGTGCTGACCGTGGTGCATCAGGATTGGCTGAACGGCAAAGAGTACAAGTGCAAGGTGTCCAA
    CAAGGGCCTGCCTGCTCCTATCGAAAAGACCATCTCTAAGACCAAGGGGCAGCCCCGGGAACCT
    CAGGTTTACACACTGCCTCCAAGCCGGGAAGAGATGACCAAGAACCAGGTGTCCCTGACCTGTC
    TCGTGAAGGGCTTCTACCCCTCCGATATCGCCGTGGAATGGGAGTCTAATGGCCAGCCTGAGAA
    CAACTACAAGACCACACCTCCTATGCTGGACTCCGACGGCTCATTCTTCCTGTACTCCAAGCTGAC
    AGTGGACAAGTCCAGATGGCAGCAGGGCAACGTGTTCTCCTGCTCCGTGATGCACGAGGCCCTG
    CACAATCACTACACCCAGAAGTCCCTGTCTCTGTCCCCTGGAAAAGGCGGCGGAGGATCTGGCG
    GAGGCGGTAGCGGTGGTGGCGGATCTGAAGTTCAGCTGGTTGAATCTGGCGGCGGACTGGTTC
    AACCAGGCGGATCTCTGAGACTGTCTTGTGCCGCCTCCGGCTTCACCTTCTCCTCTTACGCTATGT
    CCTGGGTCCGACAGGCCCCAGGCAAAGGATTGGAGTGGGTGTCCCAGATCTCTCCCGCTGGCG
    GCTACACCAATTACGCCGACTCTGTGAAGGGCAGATTCACCATCTCTGCCGACACCTCCAAGAAC
    ACCGCCTACCTGCAGATGAACTCCCTGAGAGCCGAGGACACCGCCGTGTACTATTGTGCTAGAG
    GCGAGCTGCCCTACTACCAGATGTCCAAAGTGATGGACGTGTGGGGACAGGGAACCCTCGTGA
    CAGTTTCTAGCGGTGGCGGAGGTAGCGGAGGCGGTGGAAGCGGCGGAGGCGGAAGTGATATT
    CAGATGACCCAGTCTCCTTCCAGCCTGTCCGCTTCTGTGGGCGATAGAGTGACCATCACCTGTCG

-continued

| SEQUENCE LISTING SUMMARY | | |
| --- | --- | --- |

SEQ
ID
NO:    Sequence

GGCCTCTCAGTACTTCTCTTCCTATCTGGCATGGTATCAGCAGAAGCCTGGCAAGGCCCCTAAGC
TGCTGATCTACGGCGCTTCTGCTAGAGCTTCCGGCGTGCCCTCCAGATTTTCTGGCTCTGGATCT
GGCACCGACTTTACCCTGACAATCTCCAGCCTGCAGCCTGAGGACTTCGCCACCTACTACTGCCA
GCAGTACCTGGCCTCTCCTGCCACATTTGGCCAGGGAACAAAGGTCGAGATCAAGCGCTGA

18    CAGGTTCAGCTGCAAGAGTCTGGCCCTGGCCTGGTCAAGCCTTCCGAAACACTGTCTCTGACCTG
CACCGTGTCTGGCGGCTCTGTGTCCTCTGGCGATTACTACTGGACCTGGATCCGGCAGTCTCCTG
GCAAAGGCCTGGAATGGATCGGCCACATCTACTACTCCGGCAACACCAACTACAACCCCAGCCT
GAAGTCCCGGCTGACCATCTCCATCGACACCAGCAAGACCCAGTTCTCCCTGAAGCTGTCCTCTG
TGACCGCCGCTGATACCGCCATCTACTATTGCGTGCGGGACAGAGTGACCGGCGCCTTTGATATT
TGGGGCCAGGGCACCATGGTCACCGTGTCCAGTGCTTCTACCAAGGGACCCAGCGTGTTCCCTC
TGGCTCCTTGCTCCAGATCCACCTCCGAGTCTACAGCTGCTCTGGGCGTGTCTGGTCAAGGACTAC
TTCCCTGAGCCTGTGACCGTGTCCTGGAATTCTGGCGCTCTGACATCTGGCGTGCACACCTTTCC
AGCTGTGCTGCAGTCTAGCGGCCTGTACTCTCTGTCCTCCGTCGTGACCGTGCCTTCCTCTAACTT
TGGCACCCAGACCTACACCTGTAATGTGGACCACAAGCCATCCAACACCAAGGTGGACAAGACC
GTGGAACGGAAGTGCTGCGTGGAATGCCCTCCTTGTCCTGCTCCTCCTGTGGCTGGCCCTTCCGT
GTTTCTGTTCCCTCCAAAGCCTAAGGACACCCTGATGATCTCTCGGACCCCTGAAGTGACCTGCG
TGGTGGTGGATGTGTCTCACGAGGATCCCGAGGTGCAGTTCAATTGGTACGTGGACGGCGTGG
AAGTGCACAACGCCAAGACCAAGCCTAGAGAGGAACAGTTCAACTCCACCTTCAGAGTGGTGTC
CGTGCTGACCGTGGTGCATCAGGATTGGCTGAACGGCAAAGAGTACAAGTGCAAGGTGTCCAA
CAAGGGCCTGCCTGCTCCTATCGAAAAGACCATCTCTAAGACCAAGGGGCAGCCCCGGGAACCT
CAGGTTTACACACTGCCTCCAAGCCGGGAAGAGATGACCAAGAACCAGGTGTCCCTGACCTGTC
TCGTGAAGGGCTTCTACCCCTCCGATATCGCCGTGGAATGGGAGTCTAATGGCCAGCCTGAGAA
CAACTACAAGACCACACCTCCTATGCTGGACTCCGACGGCTCATTCTTCCTGTACTCCAAGCTGAC
AGTGGACAAGTCCAGATGGCAGCAGGGCAACGTGTTCTCCTGCTCCGTGATGCACGAGGCCCTG
CACAATCACTACACCCAGAAGTCCCTGTCTCTGTCCCCTGGAAAAGGCGGCGGAGGATCTGGCG
GAGGCGGTAGCGGTGGTGGCGGATCTGAAGTTCAGCTGGTTGAATCTGGCGGCGGACTGGTTC
AACCAGGCGGATCTCTGAGACTGTCTTGTGCCGCCTCCGGCTTCACCTTCTCCTCTTACGCTATGT
CCTGGGTCCGACAGGCCCCAGGCAAAGGATTGGAGTGGGTGTCCCAGATCTCTCCCGCTGGCG
GCTACACCAATTACGCCGACTCTGTGAAGGGCAGATTCACCATCTCTGCCGACACCTCCAAGAAC
ACCGCCTACCTGCAGATGAACTCCCTGAGAGCCGAGGACACCGCCGTGTACTATTGTGCTAGAG
GCGAGCTGCCATTCTTCCGGATGTCCCAAGTGATGGACGTGTGGGGACAGGGAACCCTCGTGAC
AGTTTCTAGCGGTGGCGGAGGTAGCGGAGGCGGTGGAAGCGGCGGAGGCGGAAGTGATATTC
AGATGACCCAGTCTCCTTCCAGCCTGTCCGCTTCTGTGGGCGATAGAGTGACCATCACCTGTCGG
GCCTCTCAGTTCCTGTCTAGTTATCTGGCATGGTATCAGCAGAAGCCCGGCAAGGCTCCCAAGCT
GTTGATCTACGGCGCCTCTGCTAGAGCTTCCGGCGTGCCCATCTAGATTCTCCGGCTCTGGCTCTG
GCACCGACTTTACCCTGACAATCTCCAGCCTGCAGCCTGAGGACTTCGCCACCTACTACTGCCAG
CAGTACCTGGCCTCTCCTGCCACATTTGGCCAGGGAACAAAGGTCGAGATCAAGCGCTGA

19    CAGGTTCAGCTGCAAGAGTCTGGCCCTGGCCTGGTCAAGCCTTCCGAAACACTGTCTCTGACCTG
CACCGTGTCTGGCGGCTCTGTGTCCTCTGGCGATTACTACTGGACCTGGATCCGGCAGTCTCCTG
GCAAAGGCCTGGAATGGATCGGCCACATCTACTACTCCGGCAACACCAACTACAACCCCAGCCT
GAAGTCCCGGCTGACCATCTCCATCGACACCAGCAAGACCCAGTTCTCCCTGAAGCTGTCCTCTG
TGACCGCCGCTGATACCGCCATCTACTATTGCGTGCGGGACAGAGTGACCGGCGCCTTTGATATT
TGGGGCCAGGGCACCATGGTCACCGTGTCCAGTGCTTCTACCAAGGGACCCAGCGTGTTCCCTC
TGGCTCCTTGCTCCAGATCCACCTCCGAGTCTACAGCTGCTCTGGGCGTGTCTGGTCAAGGACTAC
TTCCCTGAGCCTGTGACCGTGTCCTGGAATTCTGGCGCTCTGACATCTGGCGTGCACACCTTTCC
AGCTGTGCTGCAGTCTAGCGGCCTGTACTCTCTGTCCTCCGTCGTGACCGTGCCTTCCTCTAACTT
TGGCACCCAGACCTACACCTGTAATGTGGACCACAAGCCATCCAACACCAAGGTGGACAAGACC
GTGGAACGGAAGTGCTGCGTGGAATGCCCTCCTTGTCCTGCTCCTCCTGTGGCTGGCCCTTCCGT
GTTTCTGTTCCCTCCAAAGCCTAAGGACACCCTGATGATCTCTCGGACCCCTGAAGTGACCTGCG
TGGTGGTGGATGTGTCTCACGAGGATCCCGAGGTGCAGTTCAATTGGTACGTGGACGGCGTGG
AAGTGCACAACGCCAAGACCAAGCCTAGAGAGGAACAGTTCAACTCCACCTTCAGAGTGGTGTC
CGTGCTGACCGTGGTGCATCAGGATTGGCTGAACGGCAAAGAGTACAAGTGCAAGGTGTCCAA
CAAGGGCCTGCCTGCTCCTATCGAAAAGACCATCTCTAAGACCAAGGGGCAGCCCCGGGAACCT
CAGGTTTACACACTGCCTCCAAGCCGGGAAGAGATGACCAAGAACCAGGTGTCCCTGACCTGTC
TCGTGAAGGGCTTCTACCCCTCCGATATCGCCGTGGAATGGGAGTCTAATGGCCAGCCTGAGAA
CAACTACAAGACCACACCTCCTATGCTGGACTCCGACGGCTCATTCTTCCTGTACTCCAAGCTGAC
AGTGGACAAGTCCAGATGGCAGCAGGGCAACGTGTTCTCCTGCTCCGTGATGCACGAGGCCCTG
CACAATCACTACACCCAGAAGTCCCTGTCTCTGTCCCCTGGAAAAGGCGGCGGAGGATCTGGCG
GAGGCGGTAGCGGTGGTGGCGGATCTGAAGTTCAGCTGGTTGAATCTGGCGGCGGACTGGTTC
AACCAGGCGGATCTCTGAGACTGTCTTGTGCCGCCTCCGGCTTCACCTTCTCCTCTTACGCTATGT
CCTGGGTCCGACAGGCCCCAGGCAAAGGATTGGAGTGGGTGTCCCAGATCTCTCCCGCTGGCG
GCTACACCAATTACGCCGACTCTGTGAAGGGCAGATTCACCATCTCTGCCGACACCTCCAAGAAC
ACCGCCTACCTGCAGATGAACTCCCTGAGAGCCGAGGACACCGCCGTGTACTATTGTGCTAGAG
GCGAGCTGCCCTACTTCCAGATGTCCAAAGTGATGGACGTGTGGGGACAGGGAACCCTCGTGA
CAGTTTCTAGCGGTGGCGGAGGTAGCGGAGGCGGTGGAAGCGGCGGAGGCGGAAGTGATATT
CAGATGACCCAGTCTCCTTCCAGCCTGTCCGCTTCTGTGGGCGATAGAGTGACCATCACCTGTCG
GGCCTCTCAGTACTTCTACTCCTATCTGGCTTGGTATCAGCAGAAGCCTGGCAAGGCCCCTAAGC
TGCTGATCTACGGCGCGCTTCTGCTAGAGCTTCCGGCGTGCCCTCCAGATTTTCTGGCTCTGGATCT
GGCACCGACTTTACCCTGACAATCTCCAGCCTGCAGCCTGAGGACTTCGCCACCTACTACTGCCA
GCAGTACCTGGCCTCTCCTGCCACATTTGGCCAGGGAACAAAGGTCGAGATCAAGCGCTGA

-continued

---

SEQUENCE LISTING SUMMARY

---

SEQ
ID
NO:  Sequence

20   CAGGTTCAGCTGCAAGAGTCTGGCCCTGGCCTGGTCAAGCCTTCCGAAACACTGTCTCTGACCTG
     CACCGTGTCTGGCGGCTCTGTGTCCTCTGGCGATTACTACTGGACCTGGATCCGGCAGTCTCCTG
     GCAAAGGCCTGGAATGGATCGGCCACATCTACTACTCCGGCAACACCAACTACAACCCCAGCCT
     GAAGTCCCGGCTGACCATCTCCATCGACACCAGCAAGACCCAGTTCTCCCTGAAGCTGTCCTCTG
     TGACCGCCGCTGATACCGCCATCTACTATTGCGTGCGGGACAGAGTGACCGGCGCCTTTGATATT
     TGGGGCCAGGGCACCATGGTCACCGTGTCCAGTGCTTCTACCAAGGGACCCAGCGTGTTCCCTC
     TGGCTCCTTCCAGCAAGTCTACCTCTGGCGGAACAGCTGCTCTGGGCTGTCTGGTCAAGGACTAC
     TTCCCTGAGCCTGTGACCGTGTCCTGGAATTCTGGCGCTCTGACATCTGGCGTGCACACCTTTCC
     AGCTGTGCTGCAGTCTAGCGGCCTGTACTCTCTGTCCTCCGTCGTGACCGTGCCTTCTAGCTCTCT
     GGGCACCCAGACCTACATCTGCAATGTGAACCACAAGCCATCCAACACCAAGGTGGACAAGAAG
     GTGGAACCCAAGTCCTGCGACAAGACCCACACCTGTCCTCCATGTCCTGCTCCAGAACTGCTCGG
     CGGACCTTCCGTGTTCCTGTTTCCTCCAAAGCCTAAGGACACCCTGATGATCTCTCGGACCCCTGA
     AGTGACCTGCGTGGTGGTGGATGTGTCTCACGAGGATCCCGAAGTGAAGTTCAATTGGTACGTG
     GACGGCGTGGAAGTGCACAACGCCAAGACCAAGCCTAGAGAGGAACAGTACAACTCCACCTAC
     AGAGTGGTGTCCGTGCTGACCGTGCTGCACCAGGATTGGCTGAACGGCAAAGAGTACAAGTGC
     AAGGTGTCCAACAAGGCCCTGCCTGCTCCTATCGAAAAGACCATCAGCAAGGCTAAGGGCCAGC
     CTCGGGAACCCCAGGTTTACACATTGCCTCCATCTCGGGACGAGCTGACCAAGAACCAGGTGTC
     CCTGACCTGTCTCGTGAAGGGCTTCTACCCCTCCGATATCGCCGTGGAATGGGAGTCCAATGGCC
     AGCCTGAGAACAACTACAAGACAACCCCTCCTGTGCTGGACTCCGACGGCTCATTCTTCCTGTAC
     TCCAAGCTGACAGTGGACAAGTCCAGATGGCAGCAGGGCAACGTGTTCTCCTGCTCCGTGATGC
     ACGAGGCCCTGCACAATCACTACACCCAGAAGTCCCTGTCTCTGTCCCCTGGAAAAGGCGGCGG
     AGGATCTGGCGGAGGTGGAAGCGGAGGCGGTGGATCTGAAGTGCAGCTGGTTGAAAGTGGCG
     GCGGATTGGTTCAGCCTGGCGGATCTCTGAGACTGTCTTGTGCCGCCTCCGGCTTTACCTTCTCC
     TCCTACGCTATGTCCTGGGTCCGACAGGCTCCCGGAAAAGGACTTGAATGGGTGTCCCAGATCT
     CCCCTGCTGGCGGCTACACCCAATTACGCCGACTCTGTGAAGGGCAGATTCACCATCTCTGCCGAC
     ACCTCCAAGAACACCGCCTACCTGCAGATGAACTCCCTGAGAGCCGAGGACACCGCCGTGTACT
     ATTGTGCTAGAGGCGAGCTGCCCTACTTCCGGATGTCCAAAGTGATGGACGTGTGGGGACAGG
     GAACCCTCGTGACAGTTTCTAGTGGTGGCGGAGGAAGCGGCGGAGGCGGTTCTGGCGGTGGTG
     GATCTGATATCCAGATGACCCAGTCTCCTAGCAGCCTGTCTGCCTCTGTGGGCGATAGAGTGACC
     ATCACCTGTCGGGGCCTCTCAGTTCCTGTCCAGCTACCTGGCTTGGTATCAGCAGAAGCCTGGCAA
     GGCCCCTAAGCTGCTGATCTACGGCGCTTCTGCTAGAGCTTCCGGCGTGCCCTCCAGATTTTCTG
     GCTCTGGATCTGGCACCGACTTTACCCTGACAATCTCCAGCCTGCAGCCTGAGGACTTCGCCACC
     TACTACTGCCAGCAGTACCTGGCCTCTCCTGCCACATTTGGCCAGGGAACAAAGGTCGAGATCA
     AGCGCTGA

21   CAGGTTCAGCTGCAAGAGTCTGGCCCTGGCCTGGTCAAGCCTTCCGAAACACTGTCTCTGACCTG
     CACCGTGTCTGGCGGCTCTGTGTCCTCTGGCGATTACTACTGGACCTGGATCCGGCAGTCTCCTG
     GCAAAGGCCTGGAATGGATCGGCCACATCTACTACTCCGGCAACACCAACTACAACCCCAGCCT
     GAAGTCCCGGCTGACCATCTCCATCGACACCAGCAAGACCCAGTTCTCCCTGAAGCTGTCCTCTG
     TGACCGCCGCTGATACCGCCATCTACTATTGCGTGCGGGACAGAGTGACCGGCGCCTTTGATATT
     TGGGGCCAGGGCACCATGGTCACCGTGTCCAGTGCTTCTACCAAGGGACCCAGCGTGTTCCCTC
     TGGCTCCTTCCAGCAAGTCTACCTCTGGCGGAACAGCTGCTCTGGGCTGTCTGGTCAAGGACTAC
     TTCCCTGAGCCTGTGACCGTGTCCTGGAATTCTGGCGCTCTGACATCTGGCGTGCACACCTTTCC
     AGCTGTGCTGCAGTCTAGCGGCCTGTACTCTCTGTCCTCCGTCGTGACCGTGCCTTCTAGCTCTCT
     GGGCACCCAGACCTACATCTGCAATGTGAACCACAAGCCATCCAACACCAAGGTGGACAAGAAG
     GTGGAACCCAAGTCCTGCGACAAGACCCACACCTGTCCTCCATGTCCTGCTCCAGAACTGCTCGG
     CGGACCTTCCGTGTTCCTGTTTCCTCCAAAGCCTAAGGACACCCTGATGATCTCTCGGACCCCTGA
     AGTGACCTGCGTGGTGGTGGATGTGTCTCACGAGGATCCCGAAGTGAAGTTCAATTGGTACGTG
     GACGGCGTGGAAGTGCACAACGCCAAGACCAAGCCTAGAGAGGAACAGTACAACTCCACCTAC
     AGAGTGGTGTCCGTGCTGACCGTGCTGCACCAGGATTGGCTGAACGGCAAAGAGTACAAGTGC
     AAGGTGTCCAACAAGGCCCTGCCTGCTCCTATCGAAAAGACCATCAGCAAGGCTAAGGGCCAGC
     CTCGGGAACCCCAGGTTTACACATTGCCTCCATCTCGGGACGAGCTGACCAAGAACCAGGTGTC
     CCTGACCTGTCTCGTGAAGGGCTTCTACCCCTCCGATATCGCCGTGGAATGGGAGTCCAATGGCC
     AGCCTGAGAACAACTACAAGACAACCCCTCCTGTGCTGGACTCCGACGGCTCATTCTTCCTGTAC
     TCCAAGCTGACAGTGGACAAGTCCAGATGGCAGCAGGGCAACGTGTTCTCCTGCTCCGTGATGC
     ACGAGGCCCTGCACAATCACTACACCCAGAAGTCCCTGTCTCTGTCCCCTGGAAAAGGCGGCGG
     AGGATCTGGCGGAGGTGGAAGCGGAGGCGGTGGATCTGAAGTGCAGCTGGTTGAAAGTGGCG
     GCGGATTGGTTCAGCCTGGCGGATCTCTGAGACTGTCTTGTGCCGCCTCCGGCTTTACCTTCTCC
     TCCTACGCTATGTCCTGGGTCCGACAGGCTCCCGGAAAAGGACTTGAATGGGTGTCCCAGATCT
     CCCCTGCTGGCGGCTACACCCAATTACGCCGACTCTGTGAAGGGCAGATTCACCATCTCTGCCGAC
     ACCTCCAAGAACACCGCCTACCTGCAGATGAACTCCCTGAGAGCCGAGGACACCGCCGTGTACT
     ATTGTGCTAGAGGCGAGCTGCCCTACTTCCGGATGTCCAAAGTGATGGACGTGTGGGGACAGG
     GAACCCTCGTGACAGTGTCTAGCGGAGATGGATCTAGTGGTGGCGGAGGCGCTTCCGACATCC
     AGATGACACAGTCTCCCTCCAGCCTGTCTGCCTCTGTGGGCGATAGAGTGACCATCACCTGTCGG
     GCCTCTCAGTTCCTGTCCAGCTACCTGGCTTGGTATCAGCAGAAGCCTGGCAAGGCCCCTAAGCT
     GCTGATCTACGGCGCTTCTGCTAGAGCTTCCGGCGTGCCCTCCAGATTTTCTGGCTCTGGATCTG
     GCACCGACTTTACCCTGACAATCAGCAGCCTGCAGCCTGAGGACTTCGCCACCTACTACTGCCAG
     CAGTACCTGGCCTCTCCTGCCACATTTGGCCAGGGAACAAAGGTCGAGATCAAGTGA

22   CAGGTTCAGCTGCAAGAGTCTGGCCCTGGCCTGGTCAAGCCTTCCGAAACACTGTCTCTGACCTG
     CACCGTGTCTGGCGGCTCTGTGTCCTCTGGCGATTACTACTGGACCTGGATCCGGCAGTCTCCTG
     GCAAAGGCCTGGAATGGATCGGCCACATCTACTACTCCGGCAACACCAACTACAACCCCAGCCT
     GAAGTCCCGGCTGACCATCTCCATCGACACCAGCAAGACCCAGTTCTCCCTGAAGCTGTCCTCTG

SEQUENCE LISTING SUMMARY

SEQ
ID
NO:  Sequence

```
     TGACCGCCGCTGATACCGCCATCTACTATTGCGTGCGGGACAGAGTGACCGGCGCCTTTGATATT
     TGGGGCCAGGGCACCATGGTCACCGTGTCCAGTGCTTCTACCAAGGGACCCAGCGTGTTCCCTC
     TGGCTCCTTCCAGCAAGTCTACCTCTGGCGGAACAGCTGCTCTGGGCGTGTCTGGTCAAGGACTAC
     TTCCCTGAGCCTGTGACCGTGTCCTGGAATTCTGGCGCTCTGACATCTGGCGTGCACACCTTTCC
     AGCTGTGCTGCAGTCTAGCGGCCTGTACTCTCTGTCCTCCGTCGTGACCGTGCCTTCTAGCTCTCT
     GGGCACCCAGACCTACATCTGCAATGTGAACCACAAGCCATCCAACACCAAGGTGGACAAGAAG
     GTGGAACCCAAGTCCTGCGACAAGACCCACACCTGTCCTCCATGTCCTGCTCCAGAACTGCTCGG
     CGGACCTTCCGTGTTCCTGTTTCCTCCAAAGCCTAAGGACACCCTGATGATCTCTCGGACCCCTGA
     AGTGACCTGCGTGGTGGTGGATGTGTCTCACGAGGATCCCGAAGTGAAGTTCAATTGGTACGTG
     GACGGCGTGGAAGTGCACAACGCCAAGACCAAGCCTAGAGAGGAACAGTACAACTCCACCTAC
     AGAGTGGTGTCCGTGCTGACCGTGCTGCACCAGGATTGGCTGAACGGCAAAGAGTACAAGTGC
     AAGGTGTCCAACAAGGCCCTGCCTGCTCCTATCGAAAAGACCATCAGCAAGGCTAAGGGCCAGC
     CTCGGGAACCCCAGGTTTACACATTGCCTCCATCTCGGGACGAGCTGACCAAGAACCAGGTGTC
     CCTGACCTGTCTCGTGAAGGGCTTCTACCCCTCCGATATCGCCGTGGAATGGGAGTCCAATGGCC
     AGCCTGAGAACAACTACAAGACAACCCCTCCTGTGCTGGACTCCGACGGCTCATTCTTCCTGTAC
     TCCAAGCTGACAGTGGACAAGTCCAGATGGCAGCAGGGCAACGTGTTCTCCTGCTCCGTGATGC
     ACGAGGCCCTGCACAATCACTACACCCAGAAGTCCCTGTCTCTGTCCCCTGGAAAAGGCGGCGG
     AGGATCTGGCGGAGGTGGAAGCGGAGGCGGTGGATCTGAAGTGCAGCTGGTTGAAAGTGGCG
     GCGGATTGGTTCAGCCTGGCGGATCTCTGAGACTGTCTTGTGCCGCCTCCGGCTTTACCTTCTCC
     TCCTACGCTATGTCCTGGGTCCGACAGGCTCCCGGAAAAGGACTTGAATGGGTGTCCCAGATCT
     CCCCTGCTGGCGGCTACACCAATTACGCCGACTCTGTGAAGGGCCAGATTCACCATCTCTGCCGAC
     ACCTCCAAGAACACCGCCTACCTGCAGATGAACTCCCTGAGAGCCGAGGACACCGCCGTGTACT
     ATTGTGCTAGAGGCGAGCTGCCCTACTTCCGGATGTCCAAAGTGATGGACGTGTGGGGACAGG
     GAACCCTCGTGACAGTTTCTAGTGGTGGCGGAGGAAGCGGCGGAGGCGGTTCTGGCGGTGGTG
     GCTCTGGCGGTGGCGGATCTGATATCCAGATGACCCAGTCTCCTAGCAGCCTGTCTGCCTCTGTG
     GGCGATAGAGTGACCATCACCTGTCGGGCCTCTCAGTTCCTGTCCAGCTACCTGGCTTGGTATCA
     GCAGAAGCCTGGCAAGGCCCCTAAGCTGCTGATCTACGGCGCTTCTGCTAGAGCTTCCGGCGTG
     CCCTCCAGATTCTCTGGCTCTGGATCTGGCACCGACTTTACCCTGACAATCTCCAGCCTGCAGCCT
     GAGGACTTCGCCACCTACTACTGCCAGCAGTACCTGGCCTCTCCTGCCACATTTGGCCAGGGAAC
     AAAGGTCGAGATCAAGTGA
```

23  CAGGTTCAGCTGCAAGAGTCTGGCCCCTGGCCTGGTCAAGCCTTCCGAAACACTGTCTCTGACCTG
     CACCGTGTCTGGCGGCTCTGTGTCCTCTGGCGATTACTACTGGACCTGGATCCGGCAGTCTCCTG
     GCAAAGGCCTGGAATGGATCGGCCACATCTACTACTCCGGCAACACCAACTACAACCCCAGCCT
     GAAGTCCCGGCTGACCATCTCCATCGACACCAGCAAGACCCAGTTCTCCCTGAAGCTGTCCTCTG
     TGACCGCCGCTGATACCGCCATCTACTATTGCGTGCGGGACAGAGTGACCGGCGCCTTTGATATT
     TGGGGCCAGGGCACCATGGTCACCGTGTCCAGTGCTTCTACCAAGGGACCCAGCGTGTTCCCTC
     TGGCTCCTTCCAGCAAGTCTACCTCTGGCGGAACAGCTGCTCTGGGCGTGTCTGGTCAAGGACTAC
     TTCCCTGAGCCTGTGACCGTGTCCTGGAATTCTGGCGCTCTGACATCTGGCGTGCACACCTTTCC
     AGCTGTGCTGCAGTCTAGCGGCCTGTACTCTCTGTCCTCCGTCGTGACCGTGCCTTCTAGCTCTCT
     GGGCACCCAGACCTACATCTGCAATGTGAACCACAAGCCATCCAACACCAAGGTGGACAAGAAG
     GTGGAACCCAAGTCCTGCGACAAGACCCACACCTGTCCTCCATGTCCTGCTCCAGAACTGCTCGG
     CGGACCTTCCGTGTTCCTGTTTCCTCCAAAGCCTAAGGACACCCTGATGATCTCTCGGACCCCTGA
     AGTGACCTGCGTGGTGGTGGATGTGTCTCACGAGGATCCCGAAGTGAAGTTCAATTGGTACGTG
     GACGGCGTGGAAGTGCACAACGCCAAGACCAAGCCTAGAGAGGAACAGTACAACTCCACCTAC
     AGAGTGGTGTCCGTGCTGACCGTGCTGCACCAGGATTGGCTGAACGGCAAAGAGTACAAGTGC
     AAGGTGTCCAACAAGGCCCTGCCTGCTCCTATCGAAAAGACCATCAGCAAGGCTAAGGGCCAGC
     CTCGGGAACCCCAGGTTTACACATTGCCTCCATCTCGGGACGAGCTGACCAAGAACCAGGTGTC
     CCTGACCTGTCTCGTGAAGGGCTTCTACCCCTCCGATATCGCCGTGGAATGGGAGTCCAATGGCC
     AGCCTGAGAACAACTACAAGACAACCCCTCCTGTGCTGGACTCCGACGGCTCATTCTTCCTGTAC
     TCCAAGCTGACAGTGGACAAGTCCAGATGGCAGCAGGGCAACGTGTTCTCCTGCTCCGTGATGC
     ACGAGGCCCTGCACAATCACTACACCCAGAAGTCCCTGTCTCTGTCCCCTGGAAAAGGCGGCGG
     AGGATCTGGCGGAGGTGGAAGCGGAGGCGGTGGATCTGATATCCAGATGACCCAGTCTCCTAG
     CAGCCTGTCTGCCTCTGTGGGCGATAGAGTGACCATCACCTGTCGGGCCTCTCAGTTCCTGTCCA
     GCTACCTGGCTTGGTATCAGCAGAAGCCTGGCAAGGCCCCTAAGCTGCTGATCTACGGCGCTTC
     TGCTAGAGCTTCCGGCGTGCCCTCCAGATTTTCTGGCTCTGGATCTGGCACCGACTTTACCCTGA
     CAATCTCCAGCCTGCAGCCTGAGGACTTCGCCACCTACTACTGCCAGCAGTACCTGGCCTCTCCT
     GCCACATTTGGCCAGGGAACAAAGGTGGAAATCAAAGGTGGCGGCGGTAGTGGTGGCGGAGG
     AAGCGGCGGAGGCGGCTCTGAAGTTCAGCTTGTTGAATCTGGCGGCGGACTGGTTCAGCCTGG
     CGGATCTCTGAGACTGTCTTGTGCCGCCAGCGGCTTCACCTTCTCCTCTTACGCTATGTCCTGGGT
     CCGACAGGCCCCAGGCAAAGGATTGGAGTGGGTGTCCCAGATCTCTCCTGCTGGCGGCTACACC
     AATTACGCCGACTCTGTGAAGGGCAGATTCACCATCTCTGCCGACACCTCCAAGAACACCGCCTA
     CCTGCAGATGAACTCCCTGAGAGCCGAGGACACCGCCGTGTACTATTGTGCTAGAGGCGAGCTG
     CCCTACTTCCGGATGTCCAAAGTGATGGACGTGTGGGGACAGGGAACCCTCGTGACAGTGTCCT
     CTTGA

24  CAGGTTCAGCTGCAAGAGTCTGGCCCCTGGCCTGGTCAAGCCTTCCGAAACACTGTCTCTGACCTG
     CACCGTGTCTGGCGGCTCTGTGTCCTCTGGCGATTACTACTGGACCTGGATCCGGCAGTCTCCTG
     GCAAAGGCCTGGAATGGATCGGCCACATCTACTACTCCGGCAACACCAACTACAACCCCAGCCT
     GAAGTCCCGGCTGACCATCTCCATCGACACCAGCAAGACCCAGTTCTCCCTGAAGCTGTCCTCTG
     TGACCGCCGCTGATACCGCCATCTACTATTGCGTGCGGGACAGAGTGACCGGCGCCTTTGATATT
     TGGGGCCAGGGCACCATGGTCACCGTGTCCAGTGCTTCTACCAAGGGACCCAGCGTGTTCCCTC
     TGGCTCCTTCCAGCAAGTCTACCTCTGGCGGAACAGCTGCTCTGGGCGTGTCTGGTCAAGGACTAC

SEQUENCE LISTING SUMMARY

SEQ
ID
NO:  Sequence

TTCCCTGAGCCTGTGACCGTGTCCTGGAATTCTGGCGCTCTGACATCTGGCGTGCACACCTTTCC
AGCTGTGCTGCAGTCTAGCGGCCTGTACTCTCTGTCCTCCGTCGTGACCGTGCCTTCTAGCTCTCT
GGGCACCCAGACCTACATCTGCAATGTGAACCACAAGCCATCCAACACCAAGGTGGACAAGAAG
GTGGAACCCAAGTCCTGCGACAAGACCCACACCTGTCCTCCATGTCCTGCTCCAGAACTGCTCGG
CGGACCTTCCGTGTTCCTGTTTCCTCCAAAGCCTAAGGACACCCTGATGATCTCTCGGACCCCTGA
AGTGACCTGCGTGGTGGTGGATGTGTCTCACGAGGATCCCGAAGTGAAGTTCAATTGGTACGTG
GACGGCGTGGAAGTGCACAACGCCAAGACCAAGCCTAGAGAGGAACAGTACAACTCCACCTAC
AGAGTGGTGTCCGTGCTGACCGTGCTGCACCAGGATTGGCTGAACGGCAAAGAGTACAAGTGC
AAGGTGTCCAACAAGGCCCTGCCTGCTCCTATCGAAAAGACCATCAGCAAGGCTAAGGGCCAGC
CTCGGGAACCCCAGGTTTACACATTGCCTCCATCTCGGGACGAGCTGACCAAGAACCAGGTGTC
CCTGACCTGTCTCGTGAAGGGCTTCTACCCCTCCGATATCGCCGTGGAATGGGAGTCCAATGGCC
AGCCTGAGAACAACTACAAGACAACCCCTCCTGTGCTGGACTCCGACGGCTCATTCTTCCTGTAC
TCCAAGCTGACAGTGGACAAGTCCAGATGGCAGCAGGGCAACGTGTTCTCCTGCTCCGTGATGC
ACGAGGCCCTGCACAATCACTACACCCAGAAGTCCCTGTCTCTGTCCCCTGGAAAAGGCGGCGG
AGGATCTGGCGGAGGTGGAAGCGGAGGCGGTGGATCTGAAGTGCAGCTGTTGGAAAGTGGCG
GCGGATTGGTTCAGCCTGGCGGATCTCTGAGACTGTCTTGTGCCGCCTCCGGCTTTACCTTCTCC
TCCTACGCTATGTCCTGGGTCCGACAGGCTCCCGGAAAAGGACTTGAATGGGTGTCCCAGATCT
CCCCTGCTGGCGGCTACACCAATTACGCCGACTCTGTGAAGGGCAGATTCACCATCTCTCGGGAC
AACTCCAAGAACACCCTGTACCTGCAGATGAACTCCCTGAGAGCCGAGGACACCGCCGTGTACT
ATTGTGCTAGAGGCGAGCTGCCCTACTTCCGGATGTCCAAAGTGATGGACGTGTGGGGACAGG
GAACCCTCGTGACAGTTTCTAGTGGTGGCGGAGGAAGCGGCGGAGGCGGTTCTGGCGGTGGC
GGATCTGAAATTGTGCTGACCCAGTCTCCAGGCACACTCAGTTTGAGCCCTGGCGAGAGAGCTA
CCCTGAGCTGTAGAGCCTCTCAGTTCCTGTCCAGCTACCTGGCTTGGTATCAGCAGAAGCCAGGA
CAGGCCCCTCGGCTGTTGATCTATGGCGCTTCTGCTAGAGCCAGCGGCATCCCTGATAGATTCTC
CGGCTCTGGCTCTGGCACCGACTTCACCCTGACAATCTCCCGGCTGGAACCTGAGGACTTCGCTG
TGTACTACTGCCAGCAGTACCTGGCCTCTCCTGCCACATTTGGCCAGGGAACAAAGGTCGAGAT
CAAGTGA

25   GACATCCAGATGACCCAGTCTCCATCATCCCTGTCGGCCTCAGTGGGCGACAGAGTGACCATCA
CTTGTCAAGCCTCCCAAGACATTAGCAACTACCTGAACTGGTACCAGCAGAAGCCCGGAAAGGC
CCCGAAGCTGCTCATCTATGACGCTTCCAACCTTGAGACTGGAGTGCCTTCGCGCTTCTCCGGCT
CCGGGAGCGGTACCGATTTCACCTTCACCATCTCCTCCCTGCAACCCGAGGACATTGCGACTTAC
TTCTGCCAACATTTCGATCACCTCCCTCTCGCGTTCGGCGGCGGAACTAAGGTCGAGATTAAGCG
GACCGTGGCTGCCCCGTCCGTGTTCATCTTCCCGCCGTCCGATGAACAGCTGAAGTCCGGTACCG
CATCAGTCGTGTGCTTGCTGAACAACTTCTACCCCCGGGAAGCCAAGGTCCAGTGGAAAGTGGA
CAATGCGCTGCAGTCGGGAAACTCGCAGGAATCCGTGACCGAACAGGATTCGAAGGACAGCAC
ATACAGCCTGTCATCCACCCTCACGCTGTCGAAGGCCGACTACGAGAAGCACAAAGTGTACGCC
TGCGAAGTGACCCACCAAGGGCTTAGCAGCCCTGTGACCAAGTCCTTCAACCGCGGAGAGTGC

26   GGCGGTGGCGGATCC

27   GGCGGCGGGGGCAGC

28   GGCGGCGGAGGATCT

29   GGCGGAGGCGGTAGC

30   GGTGGTGGCGGATCT

31   GGCGGCGGAGGATCT

32   GGCGGAGGTGGAAGC

33   GGAGGCGGTGGATCT

34   GGTGGCGGAGGAAGC

35   GGCGGAGGCGGTTCT

36   GGCGGTGGCGGATCT

37   GGCGGTGGCGGATCC

38   GGCGGCGGGGGCAGC

39   QVQLQESGPGLVKPSETLSLTCTVSGGSVSSGDYYWTWIRQSPGKGLEWIGHIYYSGNTNYNPSLKS
RLTISIDTSKTQFSLKLSSVTAADTAIYYCVRDRVTGAFDIWGQGTMVTVSSASTKGPSVFPLAPSSKST
SGGTAALGCLVKDYFPEPVTVSWNSGALTSGVHTFPAVLQSSGLYSLSSVVTVPSSSLGTQTYICNVN
HKPSNTKVDKKVEPKSCDKTHTCPPCPAPELLGGPSVFLFPPKPKDTLMISRTPEVTCVVVDVSHEDP
EVKFNWYVDGVEVHNAKTKPREEQYNSTYRVVSVLTVLHQDWLNGKEYKCKVSNKALPAPIEKTISK
AKGQPREPQVYTLPPSRDELTKNQVSLTCLVKGFYPSDIAVEWESNGQPENNYKTTPPVLDSDGSFFL
YSKLTVDKSRWQQGNVFSCSVMHEALHNHYTQKSLSLSPGKGGGGSGGGGSGGGGSEVQLLESG
GGLVQPGGSLRLSCAASGFTFSSYAMSWVRQAPGKGLEWVSQISPAGGYTNYADSVKGRFTISRDN

| SEQUENCE LISTING SUMMARY |
| --- |

SEQ
ID
NO: Sequence

```
     SKNTLYLQMNSLRAEDTAVYYCARGELPYHRMSKVMDVWGQGTLVTVSSGGGGSGGGGSGGGG
     SEIVLTQSPGTLSLSPGERATLSCRASQFLSSYLAWYQQKPGQAPRLLIYGASARASGIPDRFSGSGSG
     TDFTLTISRLEPEDFAVYYCQQYLASPATFGQGTKVEIK

40   CAGGTTCAGCTGCAAGAGTCTGGCCCTGGCCTGGTCAAGCCTTCCGAAACACTGTCTCTGACCTG
     CACCGTGTCTGGCGGCTCTGTGTCCTCTGGCGATTACTACTGGACCTGGATCCGGCAGTCTCCTG
     GCAAAGGCCTGGAATGGATCGGCCACATCTACTACTCCGGCAACACCAACTACAACCCCAGCCT
     GAAGTCCCGGCTGACCATCTCCATCGACACCAGCAAGACCCAGTTCTCCCTGAAGCTGTCCTCTG
     TGACCGCCGCTGATACCGCCATCTACTATTGCGTGCGGGACAGAGTGACCGGCGCCTTTGATATT
     TGGGGCCAGGGCACCATGGTCACCGTGTCCAGTGCTTCTACCAAGGGACCCAGCGTGTTCCCTC
     TGGCTCCTTCCAGCAAGTCTACCTCTGGCGGAACAGCTGCTCTGGGCTGTCTGGTCAAGGACTAC
     TTCCCTGAGCCTGTGACCGTGTCCTGGAATTCTGGCGTCTCTGACATCTGGCGTGCACACCTTTCC
     AGCTGTGCTGCAGTCTAGCGGCCTGTACTCTCTGTCCTCCGTCGTGACCGTGCCTTCTAGCTCTCT
     GGGCACCCAGACCTACATCTGCAATGTGAACCACAAGCCATCCAACACCAAGGTGGACAAGAAG
     GTGGAACCCAAGTCCTGCGACAAGACCCACACCTGTCCTCCATGTCCTGCTCCAGAACTGCTCGG
     CGGACCTTCCGTGTTCCTGTTTCCTCCAAAGCCTAAGGACACCCTGATGATCTCTCGGACCCCTGA
     AGTGACCTGCGTGGTGGTGGATGTGTCTCACGAGGATCCCGAAGTGAAGTTCAATTGGTACGTG
     GACGGCGTGGAAGTGCACAACGCCAAGACCAAGCCTAGAGAGGAACAGTACAACTCCACCTAC
     AGAGTGGTGTCCGTGCTGACCGTGCTGCACCAGGATTGGCTGAACGGCAAAGAGTACAAGTGC
     AAGGTGTCCAACAAGGCCCTGCCTGCTCCTATCGAAAAGACCATCAGCAAGGCTAAGGGCCAGC
     CTCGGGAACCCCAGGTTTACACATTGCCTCCATCTCGGGACGAGCTGACCAAGAACCAGGTGTC
     CCTGACCTGTCTCGTGAAGGGCTTCTACCCCTCCGATATCGCCGTGGAATGGGAGTCCAATGGCC
     AGCCTGAGAACAACTACAAGACAACCCCTCCTGTGCTGGACTCCGACGGCTCATTCTTCCTGTAC
     TCCAAGCTGACAGTGGACAAGTCCAGATGGCAGCAGGGCAACGTGTTCTCCTGCTCCGTGATGC
     ACGAGGCCCTGCACAATCACTACACCCAGAAGTCCCTGTCTCTGTCCCCTGGAAAAGGCGGCGG
     AGGATCTGGCGGAGGTGGAAGCGGAGGCGGTGGATCTGAAGTGCAGCTGTTGGAAAGTGGCG
     GCGGATTGGTTCAGCCTGGCGGATCTCTGAGACTGTCTTGTGCCGCCTCCGGCTTTACCTTCTCC
     TCCTACGCTATGTCCTGGGTCCGACAGGCTCCCGGAAAAGGACTTGAATGGGTGTCCCAGATCT
     CCCCTGCTGGCGGCTACACCAATTACGCCGACTCTGTGAAGGGCAGATTCACCATCTCTCGGGAC
     AACTCCAAGAACACCCTGTACCTGCAGATGAACTCCCTGAGAGCCGAGGACACCGCCGTGTACT
     ATTGTGCTAGAGGCGAGCTGCCCTACCACCGGATGTCCAAAGTGATGGATGTGTGGGGACAGG
     GAACCCTCGTGACAGTCTCTAGTGGTGGCGGAGGAAGCGGCGGAGGCGGTTCTGGCGGTGGC
     GGATCTGAAATTGTGCTGACCCAGTCTCCAGGCACACTCAGTTTGAGCCCTGGCGAGAGAGCTA
     CCCTGAGCTGTAGAGCCTCTCAGTTCCTGTCCAGCTACCTGGCTTGGTATCAGCAGAAGCCAGGA
     CAGGCCCCTCGGCTGTTGATCTATGGCGCTTCTGCTAGAGCCAGCGGCATCCCTGATAGATTCTC
     CGGCTCTGGCTCTGGCACCGACTTCACCCTGACAATCTCCCGGCTGGAACCTGAGGACTTCGCTG
     TGTACTACTGCCAGCAGTACCTGGCCTCTCCTGCCACATTTGGCCAGGGAACAAAGGTCGAGAT
     CAAG

41   EVQLVESGGGLVQPGGSLRLSCAASGFTFSSYAMSWVRQAPGKGLEWVSQISPAGGYTNYADSVK
     GRFTISADTSKNTAYLQMNSLRAEDTAVYYCARGELPYFRMSKVMDVWGQGTLVTVSSASTKGPSV
     FPLAPSSKSTSGGTAALGCLVKDYFPEPVTVSWNSGALTSGVHTFPAVLQSSGLYSLSSVVTVPSSSLG
     TQTYICNVNHKPSNTKVDKKVEPKSCDKTHTCPPCPAPELLGGPSVFLFPPKPKDTLMISRTPEVTCVV
     VDVSHEDPEVKFNWYVDGVEVHN3OAKTKPREEQYNSTYRVVSVLTVLHQDWLNGKEYKCKVSNK
     ALPAPIEKTISKAKGQPREPQVYTLPPSREEMTKNQVSLTCLVKGFYPSDIAVEWESNGQPENNYKTT
     PPVLDSDGSFFLYSKLTVDKSRWQQGNVFSCSVMHEALHNHYTQKSLSLSPGK

42   EVQLVESGGGLVQPGGSLRLSCAASGFTFSSYAMSWVRQAPGKGLEWVSQISPAGGYTNYADSVK
     GRFTISADTSKNTAYLQMNSLRAEDTAVYYCARGELPYYQMSKVMDVWGQGTLVTVSSASTKGPS
     VFPLAPSSKSTSGGTAALGCLVKDYFPEPVTVSWNSGALTSGVHTFPAVLQSSGLYSLSSVVTVPSSSL
     GTQTYICNVNHKPSNTKVDKKVEPKSCDKTHTCPPCPAPELLGGPSVFLFPPKPKDTLMISRTPEVTC
     VVVDVSHEDPEVKFNWYVDGVEVHNAKTKPREEQYNSTYRVVSVLTVLHQDWLNGKEYKCKVSNK
     ALPAPIEKTISKAKGQPREPQVYTLPPSREEMTKNQVSLTCLVKGFYPSDIAVEWESNGQPENNYKTT
     PPVLDSDGSFFLYSKLTVDKSRWQQGNVFSCSVMHEALHNHYTQKSLSLSPGK

43   EVQLVESGGGLVQPGGSLRLSCAASGFTFSSYAMSWVRQAPGKGLEWVSQISPAGGYTNYADSVK
     GRFTISADTSKNTAYLQMNSLRAEDTAVYYCARGELPFFRMSQVMDVWGQGTLVTVSSASTKGPS
     VFPLAPSSKSTSGGTAALGCLVKDYFPEPVTVSWNSGALTSGVHTFPAVLQSSGLYSLSSVVTVPSSSL
     GTQTYICNVNHKPSNTKVDKKVEPKSCDKTHTCPPCPAPELLGGPSVFLFPPKPKDTLMISRTPEVTC
     VVVDVSHEDPEVKFNWYVDGVEVHNAKTKPREEQYNSTYRVVSVLTVLHQDWLNGKEYKCKVSNK
     ALPAPIEKTISKAKGQPREPQVYTLPPSREEMTKNQVSLTCLVKGFYPSDIAVEWESNGQPENNYKTT
     PPVLDSDGSFFLYSKLTVDKSRWQQGNVFSCSVMHEALHNHYTQKSLSLSPGK

44   EVQLVESGGGLVQPGGSLRLSCAASGFTFSSYAMSWVRQAPGKGLEWVSQISPAGGYTNYADSVK
     GRFTISADTSKNTAYLQMNSLRAEDTAVYYCARGELPYFRMSKVMDVWGQGTLVTVSSASTKGPSV
     FPLAPSSKSTSGGTAALGCLVKDYFPEPVTVSWNSGALTSGVHTFPAVLQSSGLYSLSSVVTVPSSSLG
     TQTYICNVNHKPSNTKVDKKVEPKSCDKTHTCPPCPAPELLGGPSVFLFPPKPKDTLMISRTPEVTCVV
     VDVSHEDPEVKFNWYVDGVEVHNAKTKPREEQYNSTYRVVSVLTVLHQDWLNGKEYKCKVSNKAL
     PAPIEKTISKAKGQPREPQVYTLPPSREEMTKNQVSLTCLVKGFYPSDIAVEWESNGQPENNYKTTPP
     VLDSDGSFFLYSKLTVDKSRWQQGNVFSCSVMHEALHNHYTQKSLSLSPGK

45   EVQLLESGGGLVQPGGSLRLSCAASGFTFSSYAMSWVRQAPGKGLEWVSQISPAGGYTNYADSVKG
     RFTISRDNSKNTLYLQMNSLRAEDTAVYYCARGELPYFRMSKVMDVWGQGTLVTVSSASTKGPSVF
```

SEQUENCE LISTING SUMMARY

SEQ
ID
NO:    Sequence

```
       PLAPSSKSTSGGTAALGCLVKDYFPEPVTVSWNSGALTSGVHTFPAVLQSSGLYSLSSVVTVPSSSLGT
       QTYICNVNHKPSNTKVDKKVEPKSCDKTHTCPPCPAPELLGGPSVFLFPPKPKDTLMISRTPEVTCVV
       VDVSHEDPEVKFNWYVDGVEVHNAKTKPREEQYNSTYRVVSVLTVLHQDWLNGKEYKCKVSNKAL
       PAPIEKTISKAKGQPREPQVYTLPPSREEMTKNQVSLTCLVKGFYPSDIAVEWESNGQPENNYKTTPP
       VLDSDGSFFLYSKLTVDKSRWQQGNVFSCSVMHEALHNHYTQKSLSLSPGK

46     EVQLLESGGGLVQPGGSLRLSCAASGFTFSSYAMSWVRQAPGKGLEWVSQISPAGGYTNYADSVKG
       RFTISRDNSKNTLYLQMNSLRAEDTAVYYCARGELPYYQMSKVMDVWGQGTLVTVSSASTKGPSVF
       PLAPSSKSTSGGTAALGCLVKDYFPEPVTVSWNSGALTSGVHTFPAVLQSSGLYSLSSVVTVPSSSLGT
       QTYICNVNHKPSNTKVDKKVEPKSCDKTHTCPPCPAPELLGGPSVFLFPPKPKDTLMISRTPEVTCVV
       VDVSHEDPEVKFNWYVDGVEVHNAKTKPREEQYNSTYRVVSVLTVLHQDWLNGKEYKCKVSNKAL
       PAPIEKTISKAKGQPREPQVYTLPPSREEMTKNQVSLTCLVKGFYPSDIAVEWESNGQPENNYKTTPP
       VLDSDGSFFLYSKLTVDKSRWQQGNVFSCSVMHEALHNHYTQKSLSLSPGK

47     EVQLLESGGGLVQPGGSLRLSCAASGFTFSSYAMSWVRQAPGKGLEWVSQISPAGGYTNYADSVKG
       RFTISRDNSKNTLYLQMNSLRAEDTAVYYCARGELPFFRMSQVMDVWGQGTLVTVSSASTKGPSVF
       PLAPSSKSTSGGTAALGCLVKDYFPEPVTVSWNSGALTSGVHTFPAVLQSSGLYSLSSVVTVPSSSLGT
       QTYICNVNHKPSNTKVDKKVEPKSCDKTHTCPPCPAPELLGGPSVFLFPPKPKDTLMISRTPEVTCVV
       VDVSHEDPEVKFNWYVDGVEVHNAKTKPREEQYNSTYRVVSVLTVLHQDWLNGKEYKCKVSNKAL
       PAPIEKTISKAKGQPREPQVYTLPPSREEMTKNQVSLTCLVKGFYPSDIAVEWESNGQPENNYKTTPP
       VLDSDGSFFLYSKLTVDKSRWQQGNVFSCSVMHEALHNHYTQKSLSLSPGK

48     DIQMTQSPSSLSASVGDRVTITCRASQFLSSYLAWYQQKPGKAPKLLIYGASARASGVPSRFSGSGSG
       TDFTLTISSLQPEDFATYYCQQYLASPATFGQGTKVEIKRTVAAPSVFIFPPSDEQLKSGTASVVCLLNN
       FYPREAKVQWKVDNALQSGNSQESVTEQDSKDSTYSLSSTLTLSKADYEKHKVYACEVTHQGLSSPV
       TKSFNRGEC

49     DIQMTQSPSSLSASVGDRVTITCRASQYFSSYLAWYQQKPGKAPKLLIYGASARASGVPSRFSGSGSG
       TDFTLTISSLQPEDFATYYCQQYLASPATFGQGTKVEIKRTVAAPSVFIFPPSDEQLKSGTASVVCLLNN
       FYPREAKVQWKVDNALQSGNSQESVTEQDSKDSTYSLSSTLTLSKADYEKHKVYACEVTHQGLSSPV
       TKSFNRGEC

50     DIQMTQSPSSLSASVGDRVTITCRASQFLSSYLAWYQQKPGKAPKLLIYGASARASGVPSRFSGSGSG
       TDFTLTISSLQPEDFATYYCQQYLASPATFGQGTKVEIKRTVAAPSVFIFPPSDEQLKSGTASVVCLLNN
       FYPREAKVQWKVDNALQSGNSQESVTEQDSKDSTYSLSSTLTLSKADYEKHKVYACEVTHQGLSSPV
       TKSFNRGEC

51     DIQMTQSPSSLSASVGDRVTITCRASQFLSSFLAWYQQKPGKAPKLLIYGASARASGVPSRFSGSGSG
       TDFTLTISSLQPEDFATYYCQQYLASPATFGQGTKVEIKRTVAAPSVFIFPPSDEQLKSGTASVVCLLNN
       FYPREAKVQWKVDNALQSGNSQESVTEQDSKDSTYSLSSTLTLSKADYEKHKVYACEVTHQGLSSPV
       TKSFNRGEC

52     EIVLTQSPGTLSLSPGERATLSCRASQFLSSYLAWYQQKPGQAPRLLIYGASARASGIPDRFSGSGSGT
       DFTLTISRLEPEDFAVYYCQQYLASPATFGQGTKVEIKRTVAAPSVFIFPPSDEQLKSGTASVVCLLNNF
       YPREAKVQWKVDNALQSGNSQESVTEQDSKDSTYSLSSTLTLSKADYEKHKVYACEVTHQGLSSPVT
       KSFNRGEC

53     EIVLTQSPGTLSLSPGERATLSCRASQFLSSYLAWYQQKPGQAPRLLIYGASARASGIPDRFSGSGSGT
       DFTLTISRLEPEDFAVYYCQQYLASPATFGQGTKVEIKRTVAAPSVFIFPPSDEQLKSGTASVVCLLNNF
       YPREAKVQWKVDNALQSGNSQESVTEQDSKDSTYSLSSTLTLSKADYEKHKVYACEVTHQGLSSPVT
       KSFNRGEC

54     EIVLTQSPGTLSLSPGERATLSCRASQFLSSYLAWYQQKPGQAPRLLIYGASARASGIPDRFSGSGSGT
       DFTLTISRLEPEDFAVYYCQQYLASPATFGQGTKVEIKRTVAAPSVFIFPPSDEQLKSGTASVVCLLNNF
       YPREAKVQWKVDNALQSGNSQESVTEQDSKDSTYSLSSTLTLSKADYEKHKVYACEVTHQGLSSPVT
       KSFNRGEC

55     GAGGTGCAGCTGGTGGAGAGCGGCGGCGGCCTGGTGCAGCCCGGCGGCAGCCTGAGGCTGAG
       CTGCGCCGCCAGCGGCTTCACCTTCAGCAGCTACGCCATGAGCTGGGTGAGGCAGGCCCCCGGC
       AAGGGCCTGGAGTGGGTGAGCCAGATCAGCCCCGCCGGCGGCTACACCAACTACGCCGACAGC
       GTGAAGGGCAGGTTCACCATCAGCGCCGACACCAGCAAGAACACCGCCTACCTGCAGATGAAC
       AGCCTGAGGGCCGAGGACACCGCCGTGTACTACTGCGCCAGGGGCGAGCTGCCCTACTTCAGG
       ATGAGCAAGGTGATGGACGTGTGGGGCCAGGGCACCCTGGTGACCGTGAGCAGCGCCAGCAC
       CAAGGGCCCCAGCGTGTTCCCCCTGGCCCCCAGCAGCAAGAGCACCAGCGGCGGCACCGCCGC
       CCTGGGCTGCCTGGTGAAGGACTACTTCCCCGAGCCCGTGACCGTGAGCTGGAACAGCGGCGC
       CCTGACCAGCGGCGTGCACACCTTCCCCGCCGTGCTGCAGAGCAGCGGCCTGTACAGCCTGAGC
       AGCGTGGTGACCGTGCCCAGCAGCAGCCTGGGCACCCAGACCTACATCTGCAACGTGAACCACA
       AGCCCAGCAACACCAAGGTGGACAAGAAGGTGGAGCCCAAGAGCTGCGACAAGACCCACACCT
       GCCCCCCCTGCCCCGCCCCCGAGCTGCTGGGCGGCCCCAGCGTGTTCCTGTTCCCCCCCAAGCCC
       AAGGACACCCTGATGATCAGCAGGACCCCCGAGGTGACCTGCGTGGTGGTGGACGTGAGCCAC
       GAGGACCCCGAGGTGAAGTTCAACTGGTACGTGGACGGCGTGGAGGTGCACAACGCCAAGACC
       AAGCCCAGGGAGGAGCAGTACAACAGCACCTACAGGGTGGTGAGCGTGCTGACCGTGCTGCAC
       CAGGACTGGCTGAACGGCAAGGAGTACAAGTGCAAGGTGAGCAACAAGGCCCTGCCCGCCCCC
```

SEQUENCE LISTING SUMMARY

SEQ
ID
NO:    Sequence

```
       ATCGAGAAGACCATCAGCAAGGCCAAGGGCCAGCCCAGGGAGCCCCAGGTGTACACCCTGCCC
       CCCAGCAGGGAGGAGATGACCAAGAACCAGGTGAGCCTGACCTGCCTGGTGAAGGGCTTCTAC
       CCCAGCGACATCGCCGTGGAGTGGGAGAGCAACGGCCAGCCCGAGAACAACTACAAGACCACC
       CCCCCCGTGCTGGACAGCGACGGCAGCTTCTTCCTGTACAGCAAGCTGACCGTGGACAAGAGCA
       GGTGGCAGCAGGGCAACGTGTTCAGCTGCAGCGTGATGCACGAGGCCCTGCACAACCACTACA
       CCCAGAAGAGCCTGAGCCTGAGCCCCGGCAAG

56     GAGGTGCAGCTGGTGGAGAGCGGCGGCGGCCTGGTGCAGCCCGGCGGCAGCCTGAGGCTGAG
       CTGCGCCGCCAGCGGCTTCACCTTCAGCAGCTACGCCATGAGCTGGGTGAGGCAGGCCCCCGGC
       AAGGGCCTGGAGTGGGTGAGCCAGATCAGCCCCGCCGGCGGCTACACCAACTACGCCGACAGC
       GTGAAGGGCAGGTTCACCATCAGCGCCGACACCAGCAAGAACACCGGCCTACCTGCAGATGAAC
       AGCCTGAGGGCCGAGGACACCGCCGTGTACTACTGCGCCAGGGGCGAGCTGCCCTACTACCAG
       ATGAGCAAGGTGATGGACGTGTGGGGCCAGGGCACCCTGGTGACCGTGAGCAGCGCCAGCAC
       CAAGGGCCCCAGCGTGTTCCCCCTGGCCCCCAGCAGCAAGAGCACCAGCGGCGGCACCGCCGC
       CCTGGGCTGCCTGGTGAAGGACTACTTCCCCGAGCCCGTGACCGTGAGCTGGAACAGCGGCGC
       CCTGACCAGCGGCGTGCACACCTTCCCCGCCGTGCTGCAGAGCAGCGGCCTGTACAGCCTGAGC
       AGCGTGGTGACCGTGCCCAGCAGCAGCCTGGGCACCCAGACCTACATCTGCAACGTGAACCACA
       AGCCCAGCAACACCAAGGTGGACAAGAAGGTGGAGCCCAAGAGCTGCGACAAGACCCACACCT
       GCCCCCCCTGCCCCGCCCCCGAGCTGCTGGGCGGCCCCAGCGTGTTCCTGTTCCCCCCCAAGCCC
       AAGGACACCCTGATGATCAGCAGGACCCCCGAGGTGACCTGCGTGGTGGTGGACGTGAGCCAC
       GAGGACCCCGAGGTGAAGTTCAACTGGTACGTGGACGGCGTGGAGGTGCACAACGCCAAGACC
       AAGCCCAGGGAGGAGCAGTACAACAGCACCTACAGGGTGGTGAGCGTGCTGACCGTGCTGCAC
       CAGGACTGGCTGAACGGCAAGGAGTACAAGTGCAAGGTGAGCAACAAGGCCCTGCCCGCCCCC
       ATCGAGAAGACCATCAGCAAGGCCAAGGGCCAGCCCAGGGAGCCCCAGGTGTACACCCTGCCC
       CCCAGCAGGGAGGAGATGACCAAGAACCAGGTGAGCCTGACCTGCCTGGTGAAGGGCTTCTAC
       CCCAGCGACATCGCCGTGGAGTGGGAGAGCAACGGCCAGCCCGAGAACAACTACAAGACCACC
       CCCCCCGTGCTGGACAGCGACGGCAGCTTCTTCCTGTACAGCAAGCTGACCGTGGACAAGAGCA
       GGTGGCAGCAGGGCAACGTGTTCAGCTGCAGCGTGATGCACGAGGCCCTGCACAACCACTACA
       CCCAGAAGAGCCTGAGCCTGAGCCCCGGCAAG

57     GAGGTGCAGCTGGTGGAGAGCGGCGGCGGCCTGGTGCAGCCCGGCGGCAGCCTGAGGCTGAG
       CTGCGCCGCCAGCGGCTTCACCTTCAGCAGCTACGCCATGAGCTGGGTGAGGCAGGCCCCCGGC
       AAGGGCCTGGAGTGGGTGAGCCAGATCAGCCCCGCCGGCGGCTACACCAACTACGCCGACAGC
       GTGAAGGGCAGGTTCACCATCAGCGCCGACACCAGCAAGAACACCGCCTACCTGCAGATGAAC
       AGCCTGAGGGCCGAGGACACCGCCGTGTACTACTGCGCCAGGGGCGAGCTGCCCTTCTTCAGG
       ATGAGCCAGGTGATGGACGTGTGGGGCCAGGGCACCCTGGTGACCGTGAGCAGCGCCAGCACC
       AAGGGCCCCAGCGTGTTCCCCCTGGCCCCCAGCAGCAAGAGCACCAGCGGCGGCACCGCCGCC
       CTGGGCTGCCTGGTGAAGGACTACTTCCCCGAGCCCGTGACCGTGAGCTGGAACAGCGGCGCC
       CTGACCAGCGGCGTGCACACCTTCCCCGCCGTGCTGCAGAGCAGCGGCCTGTACAGCCTGAGCA
       GCGTGGTGACCGTGCCCAGCAGCAGCCTGGGCACCCAGACCTACATCTGCAACGTGAACCACAA
       GCCCAGCAACACCAAGGTGGACAAGAAGGTGGAGCCCAAGAGCTGCGACAAGACCCACACCTG
       CCCCCCCTGCCCCGCCCCCGAGCTGCTGGGCGGCCCCAGCGTGTTCCTGTTCCCCCCCAAGCCCA
       AGGACACCCTGATGATCAGCAGGACCCCCGAGGTGACCTGCGTGGTGGTGGACGTGAGCCACG
       AGGACCCCGAGGTGAAGTTCAACTGGTACGTGGACGGCGTGGAGGTGCACAACGCCAAGACCA
       AGCCCAGGGAGGAGCAGTACAACAGCACCTACAGGGTGGTGAGCGTGCTGACCGTGCTGCACC
       AGGACTGGCTGAACGGCAAGGAGTACAAGTGCAAGGTGAGCAACAAGGCCCTGCCCGCCCCCA
       TCGAGAAGACCATCAGCAAGGCCAAGGGCCAGCCCAGGGAGCCCCAGGTGTACACCCTGCCCC
       CCAGCAGGGAGGAGATGACCAAGAACCAGGTGAGCCTGACCTGCCTGGTGAAGGGCTTCTACC
       CCAGCGACATCGCCGTGGAGTGGGAGAGCAACGGCCAGCCCGAGAACAACTACAAGACCACCC
       CCCCCGTGCTGGACAGCGACGGCAGCTTCTTCCTGTACAGCAAGCTGACCGTGGACAAGAGCAG
       GTGGCAGCAGGGCAACGTGTTCAGCTGCAGCGTGATGCACGAGGCCCTGCACAACCACTACAC
       CCAGAAGAGCCTGAGCCTGAGCCCCGGCAAG

58     GAGGTGCAGCTGGTGGAGAGCGGCGGCGGCCTGGTGCAGCCCGGCGGCAGCCTGAGGCTGAG
       CTGCGCCGCCAGCGGCTTCACCTTCAGCAGCTACGCCATGAGCTGGGTGAGGCAGGCCCCCGGC
       AAGGGCCTGGAGTGGGTGAGCCAGATCAGCCCCGCCGGCGGCTACACCAACTACGCCGACAGC
       GTGAAGGGCAGGTTCACCATCAGCGCCGACACCAGCAAGAACACCGCCTACCTGCAGATGAAC
       AGCCTGAGGGCCGAGGACACCGCCGTGTACTACTGCGCCAGGGGCGAGCTGCCCTACTTCAGG
       ATGAGCAAGGTGATGGACGTGTGGGGCCAGGGCACCCTGGTGACCGTGAGCAGCGCCAGCAC
       CAAGGGCCCCAGCGTGTTCCCCCTGGCCCCCAGCAGCAAGAGCACCAGCGGCGGCACCGCCGC
       CCTGGGCTGCCTGGTGAAGGACTACTTCCCCGAGCCCGTGACCGTGAGCTGGAACAGCGGCGC
       CCTGACCAGCGGCGTGCACACCTTCCCCGCCGTGCTGCAGAGCAGCGGCCTGTACAGCCTGAGC
       AGCGTGGTGACCGTGCCCAGCAGCAGCCTGGGCACCCAGACCTACATCTGCAACGTGAACCACA
       AGCCCAGCAACACCAAGGTGGACAAGAAGGTGGAGCCCAAGAGCTGCGACAAGACCCACACCT
       GCCCCCCCTGCCCCGCCCCCGAGCTGCTGGGCGGCCCCAGCGTGTTCCTGTTCCCCCCCAAGCCC
       AAGGACACCCTGATGATCAGCAGGACCCCCGAGGTGACCTGCGTGGTGGTGGACGTGAGCCAC
       GAGGACCCCGAGGTGAAGTTCAACTGGTACGTGGACGGCGTGGAGGTGCACAACGCCAAGACC
       AAGCCCAGGGAGGAGCAGTACAACAGCACCTACAGGGTGGTGAGCGTGCTGACCGTGCTGCAC
       CAGGACTGGCTGAACGGCAAGGAGTACAAGTGCAAGGTGAGCAACAAGGCCCTGCCCGCCCCC
       ATCGAGAAGACCATCAGCAAGGCCAAGGGCCAGCCCAGGGAGCCCCAGGTGTACACCCTGCCC
       CCCAGCAGGGAGGAGATGACCAAGAACCAGGTGAGCCTGACCTGCCTGGTGAAGGGCTTCTAC
       CCCAGCGACATCGCCGTGGAGTGGGAGAGCAACGGCCAGCCCGAGAACAACTACAAGACCACC
       CCCCCCGTGCTGGACAGCGACGGCAGCTTCTTCCTGTACAGCAAGCTGACCGTGGACAAGAGCA
```

-continued

---

SEQUENCE LISTING SUMMARY

---

SEQ
ID
NO: Sequence

---

GGTGGCAGCAGGGCAACGTGTTCAGCTGCAGCGTGATGCACGAGGCCCTGCACAACCACTACA
CCCAGAAGAGCCTGAGCCTGAGCCCCGGCAAG

59  GAGGTGCAGCTGCTGGAGAGCGGCGGCGGCCTGGTGCAGCCCGGCGGCAGCCTGAGGCTGAG
CTGCGCCGCCAGCGGCTTCACCTTCAGCAGCTACGCCATGAGCTGGGTGAGGCAGGCCCCCGGC
AAGGGCCTGGAGTGGGTGAGCCAGATCAGCCCCGCCGGCGGCTACACCAACTACGCCGACAGC
GTGAAGGGCAGGTTCACCATCAGCAGGGACAACAGCAAGAACACCCTGTACCTGCAGATGAAC
AGCCTGAGGGCCGAGGACACCGCCGTGTACTACTGCGCCAGGGGCGAGCTGCCCTACTTCAGG
ATGAGCAAGGTGATGGACGTGTGGGGCCAGGGCACCCTGGTGACCGTGAGCAGCGCCCAGCAC
CAAGGGCCCCAGCGTGTTCCCCCTGGCCCCCAGCAGCAAGAGCACCAGCGGCGGCACCGCCGC
CCTGGGCTGCCTGGTGAAGGACTACTTCCCCGAGCCCGTGACCGTGAGCTGGAACAGCGGCGC
CCTGACCAGCGGCGTGCACACCTTCCCCGCCGTGCTGCAGAGCAGCGGCCTGTACAGCCTGAGC
AGCGTGGTGACCGTGCCCAGCAGCAGCCTGGGCACCCAGACCTACATCTGCAACGTGAACCACA
AGCCCAGCAACACCAAGGTGGACAAGAAGGTGGAGCCCAAGAGCTGCGACAAGACCCACACCT
GCCCCCCCTGCCCCGCCCCCGAGCTGCTGGGCGGCCCCAGCGTGTTCCTGTTCCCCCCCAAGCCC
AAGGACACCCTGATGATCAGCAGGACCCCCGAGGTGACCTGCGTGGTGGTGGACGTGAGCCAC
GAGGACCCCGAGGTGAAGTTCAACTGGTACGTGGACGGCGTGGAGGTGCACAACGCCAAGACC
AAGCCCAGGGAGGAGCAGTACAACAGCACCTACAGGGTGGTGAGCGTGCTGACCGTGCTGCAC
CAGGACTGGCTGAACGGCAAGGAGTACAAGTGCAAGGTGAGCAACAAGGCCCTGCCCGCCCCC
ATCGAGAAGACCATCAGCAAGGCCAAGGGCCAGCCCAGGGAGCCCCAGGTGTACACCCTGCCC
CCCAGCAGGGAGGAGATGACCAAGAACCAGGTGAGCCTGACCTGCCTGGTGAAGGGCTTCTAC
CCCAGCGACATCGCCGTGGAGTGGGAGAGCAACGGCCAGCCCGAGAACAACTACAAGACCACC
CCCCCCGTGCTGGACAGCGACGGCAGCTTCTTCCTGTACAGCAAGCTGACCGTGGACAAGAGCA
GGTGGCAGCAGGGCAACGTGTTCAGCTGCAGCGTGATGCACGAGGCCCTGCACAACCACTACA
CCCAGAAGAGCCTGAGCCTGAGCCCCGGCAAG

60  GAGGTGCAGCTGCTGGAGAGCGGCGGCGGCCTGGTGCAGCCCGGCGGCAGCCTGAGGCTGAG
CTGCGCCGCCAGCGGCTTCACCTTCAGCAGCTACGCCATGAGCTGGGTGAGGCAGGCCCCCGGC
AAGGGCCTGGAGTGGGTGAGCCAGATCAGCCCCGCCGGCGGCTACACCAACTACGCCGACAGC
GTGAAGGGCAGGTTCACCATCAGCAGGGACAACAGCAAGAACACCCTGTACCTGCAGATGAAC
AGCCTGAGGGCCGAGGACACCGCCGTGTACTACTGCGCCAGGGGCGAGCTGCCCTACTACCAG
ATGAGCAAGGTGATGGACGTGTGGGGCCAGGGCACCCTGGTGACCGTGAGCAGCGCCCAGCAC
CAAGGGCCCCAGCGTGTTCCCCCTGGCCCCCAGCAGCAAGAGCACCAGCGGCGGCACCGCCGC
CCTGGGCTGCCTGGTGAAGGACTACTTCCCCGAGCCCGTGACCGTGAGCTGGAACAGCGGCGC
CCTGACCAGCGGCGTGCACACCTTCCCCGCCGTGCTGCAGAGCAGCGGCCTGTACAGCCTGAGC
AGCGTGGTGACCGTGCCCAGCAGCAGCCTGGGCACCCAGACCTACATCTGCAACGTGAACCACA
AGCCCAGCAACACCAAGGTGGACAAGAAGGTGGAGCCCAAGAGCTGCGACAAGACCCACACCT
GCCCCCCCTGCCCCGCCCCCGAGCTGCTGGGCGGCCCCAGCGTGTTCCTGTTCCCCCCCAAGCCC
AAGGACACCCTGATGATCAGCAGGACCCCCGAGGTGACCTGCGTGGTGGTGGACGTGAGCCAC
GAGGACCCCGAGGTGAAGTTCAACTGGTACGTGGACGGCGTGGAGGTGCACAACGCCAAGACC
AAGCCCAGGGAGGAGCAGTACAACAGCACCTACAGGGTGGTGAGCGTGCTGACCGTGCTGCAC
CAGGACTGGCTGAACGGCAAGGAGTACAAGTGCAAGGTGAGCAACAAGGCCCTGCCCGCCCCC
ATCGAGAAGACCATCAGCAAGGCCAAGGGCCAGCCCAGGGAGCCCCAGGTGTACACCCTGCCC
CCCAGCAGGGAGGAGATGACCAAGAACCAGGTGAGCCTGACCTGCCTGGTGAAGGGCTTCTAC
CCCAGCGACATCGCCGTGGAGTGGGAGAGCAACGGCCAGCCCGAGAACAACTACAAGACCACC
CCCCCCGTGCTGGACAGCGACGGCAGCTTCTTCCTGTACAGCAAGCTGACCGTGGACAAGAGCA
GGTGGCAGCAGGGCAACGTGTTCAGCTGCAGCGTGATGCACGAGGCCCTGCACAACCACTACA
CCCAGAAGAGCCTGAGCCTGAGCCCCGGCAAG

61  GAGGTGCAGCTGCTGGAGAGCGGCGGCGGCCTGGTGCAGCCCGGCGGCAGCCTGAGGCTGAG
CTGCGCCGCCAGCGGCTTCACCTTCAGCAGCTACGCCATGAGCTGGGTGAGGCAGGCCCCCGGC
AAGGGCCTGGAGTGGGTGAGCCAGATCAGCCCCGCCGGCGGCTACACCAACTACGCCGACAGC
GTGAAGGGCAGGTTCACCATCAGCAGGGACAACAGCAAGAACACCCTGTACCTGCAGATGAAC
AGCCTGAGGGCCGAGGACACCGCCGTGTACTACTGCGCCAGGGGCGAGCTGCCCTTCTTCAGG
ATGAGCCAGGTGATGGACGTGTGGGGCCAGGGCACCCTGGTGACCGTGAGCGCCAGCACC
AAGGGCCCCAGCGTGTTCCCCCTGGCCCCCAGCAGCAAGAGCACCAGCGGCGGCACCGCCGCC
CTGGGCTGCCTGGTGAAGGACTACTTCCCCGAGCCCGTGACCGTGAGCTGGAACAGCGGCGCC
CTGACCAGCGGCGTGCACACCTTCCCCGCCGTGCTGCAGAGCAGCGGCCTGTACAGCCTGAGCA
GCGTGGTGACCGTGCCCAGCAGCAGCCTGGGCACCCAGACCTACATCTGCAACGTGAACCACAA
GCCCAGCAACACCAAGGTGGACAAGAAGGTGGAGCCCAAGAGCTGCGACAAGACCCACACCTG
CCCCCCCTGCCCCGCCCCCGAGCTGCTGGGCGGCCCCAGCGTGTTCCTGTTCCCCCCCAAGCCCA
AGGACACCCTGATGATCAGCAGGACCCCCGAGGTGACCTGCGTGGTGGTGGACGTGAGCCACG
AGGACCCCGAGGTGAAGTTCAACTGGTACGTGGACGGCGTGGAGGTGCACAACGCCAAGACCA
AGCCCAGGGAGGAGCAGTACAACAGCACCTACAGGGTGGTGAGCGTGCTGACCGTGCTGCACC
AGGACTGGCTGAACGGCAAGGAGTACAAGTGCAAGGTGAGCAACAAGGCCCTGCCCGCCCCCA
TCGAGAAGACCATCAGCAAGGCCAAGGGCCAGCCCAGGGAGCCCCAGGTGTACACCCTGCCCC
CCAGCAGGGAGGAGATGACCAAGAACCAGGTGAGCCTGACCTGCCTGGTGAAGGGCTTCTACC
CCAGCGACATCGCCGTGGAGTGGGAGAGCAACGGCCAGCCCGAGAACAACTACAAGACCACCC
CCCCCGTGCTGGACAGCGACGGCAGCTTCTTCCTGTACAGCAAGCTGACCGTGGACAAGAGCAG
GTGGCAGCAGGGCAACGTGTTCAGCTGCAGCGTGATGCACGAGGCCCTGCACAACCACTACAC
CCAGAAGAGCCTGAGCCTGAGCCCCGGCAAG

-continued

---

SEQUENCE LISTING SUMMARY

---

SEQ
ID
NO:  Sequence

62    GACATCCAGATGACCCAGAGCCCCAGCAGCCTGAGCGCCAGCGTGGGCGACAGGGTGACCATC
      ACCTGCAGGGCCAGCCAGTTCCTGAGCAGCTACCTGGCCTGGTACCAGCAGAAGCCCGGCAAG
      GCCCCCAAGCTGCTGATCTACGGCGCCAGCGCCAGGGCCAGCGGCGTGCCCAGCAGGTTCAGC
      GGCAGCGGCAGCGGCACCGACTTCACCCTGACCATCAGCAGCCTGCAGCCCGAGGACTTCGCCA
      CCTACTACTGCCAGCAGTACCTGGCCAGCCCCGCCACCTTCGGCCAGGGCACCAAGGTGGAGAT
      CAAGAGGACCGTGGCCGCCCCCAGCGTGTTCATCTTCCCCCCCAGCGACGAGCAGCTGAAGAGC
      GGCACCGCCAGCGTGGTGTGCCTGCTGAACAACTTCTACCCCAGGGAGGCCAAGGTGCAGTGG
      AAGGTGGACAACGCCCTGCAGAGCGGCAACAGCCAGGAGAGCGTGACCGAGCAGGACAGCAA
      GGACAGCACCTACAGCCTGAGCAGCACCCTGACCCTGAGCAAGGCCGACTACGAGAAGCACAA
      GGTGTACGCCTGCGAGGTGACCCACCAGGGCCTGAGCAGCCCCGTGACCAAGAGCTTCAACAG
      GGGCGAGTGC

63    GACATCCAGATGACCCAGAGCCCCAGCAGCCTGAGCGCCAGCGTGGGCGACAGGGTGACCATC
      ACCTGCAGGGCCAGCCAGTACTTCAGCAGCTACCTGGCCTGGTACCAGCAGAAGCCCGGCAAG
      GCCCCCAAGCTGCTGATCTACGGCGCCAGCGCCAGGGCCAGCGGCGTGCCCAGCAGGTTCAGC
      GGCAGCGGCAGCGGCACCGACTTCACCCTGACCATCAGCAGCCTGCAGCCCGAGGACTTCGCCA
      CCTACTACTGCCAGCAGTACCTGGCCAGCCCCGCCACCTTCGGCCAGGGCACCAAGGTGGAGAT
      CAAGAGGACCGTGGCCGCCCCCAGCGTGTTCATCTTCCCCCCCAGCGACGAGCAGCTGAAGAGC
      GGCACCGCCAGCGTGGTGTGCCTGCTGAACAACTTCTACCCCAGGGAGGCCAAGGTGCAGTGG
      AAGGTGGACAACGCCCTGCAGAGCGGCAACAGCCAGGAGAGCGTGACCGAGCAGGACAGCAA
      GGACAGCACCTACAGCCTGAGCAGCACCCTGACCCTGAGCAAGGCCGACTACGAGAAGCACAA
      GGTGTACGCCTGCGAGGTGACCCACCAGGGCCTGAGCAGCCCCGTGACCAAGAGCTTCAACAG
      GGGCGAGTGC

64    GACATCCAGATGACCCAGAGCCCCAGCAGCCTGAGCGCCAGCGTGGGCGACAGGGTGACCATC
      ACCTGCAGGGCCAGCCAGTTCCTGAGCAGCTACCTGGCCTGGTACCAGCAGAAGCCCGGCAAG
      GCCCCCAAGCTGCTGATCTACGGCGCCAGCGCCAGGGCCAGCGGCGTGCCCAGCAGGTTCAGC
      GGCAGCGGCAGCGGCACCGACTTCACCCTGACCATCAGCAGCCTGCAGCCCGAGGACTTCGCCA
      CCTACTACTGCCAGCAGTACCTGGCCAGCCCCGCCACCTTCGGCCAGGGCACCAAGGTGGAGAT
      CAAGAGGACCGTGGCCGCCCCCAGCGTGTTCATCTTCCCCCCCAGCGACGAGCAGCTGAAGAGC
      GGCACCGCCAGCGTGGTGTGCCTGCTGAACAACTTCTACCCCAGGGAGGCCAAGGTGCAGTGG
      AAGGTGGACAACGCCCTGCAGAGCGGCAACAGCCAGGAGAGCGTGACCGAGCAGGACAGCAA
      GGACAGCACCTACAGCCTGAGCAGCACCCTGACCCTGAGCAAGGCCGACTACGAGAAGCACAA
      GGTGTACGCCTGCGAGGTGACCCACCAGGGCCTGAGCAGCCCCGTGACCAAGAGCTTCAACAG
      GGGCGAGTGC

65    GACATCCAGATGACCCAGAGCCCCAGCAGCCTGAGCGCCAGCGTGGGCGACAGGGTGACCATC
      ACCTGCAGGGCCAGCCAGTTCCTGAGCAGCTTCCTGGCCTGGTACCAGCAGAAGCCCGGCAAG
      GCCCCCAAGCTGCTGATCTACGGCGCCAGCGCCAGGGCCAGCGGCGTGCCCAGCAGGTTCAGC
      GGCAGCGGCAGCGGCACCGACTTCACCCTGACCATCAGCAGCCTGCAGCCCGAGGACTTCGCCA
      CCTACTACTGCCAGCAGTACCTGGCCAGCCCCGCCACCTTCGGCCAGGGCACCAAGGTGGAGAT
      CAAGAGGACCGTGGCCGCCCCCAGCGTGTTCATCTTCCCCCCCAGCGACGAGCAGCTGAAGAGC
      GGCACCGCCAGCGTGGTGTGCCTGCTGAACAACTTCTACCCCAGGGAGGCCAAGGTGCAGTGG
      AAGGTGGACAACGCCCTGCAGAGCGGCAACAGCCAGGAGAGCGTGACCGAGCAGGACAGCAA
      GGACAGCACCTACAGCCTGAGCAGCACCCTGACCCTGAGCAAGGCCGACTACGAGAAGCACAA
      GGTGTACGCCTGCGAGGTGACCCACCAGGGCCTGAGCAGCCCCGTGACCAAGAGCTTCAACAG
      GGGCGAGTGC

66    GAGATCGTGCTGACCCAGAGCCCCGGCACCCTGAGCCTGAGCCCCGGCGAGAGGGCCACCCTG
      AGCTGCAGGGCCAGCCAGTTCCTGAGCAGCTACCTGGCCTGGTACCAGCAGAAGCCCGGCCAG
      GCCCCCAGGCTGCTGATCTACGGCGCCAGCGCCAGGGCCAGCGGCATCCCCGACAGGTTCAGC
      GGCAGCGGCAGCGGCACCGACTTCACCCTGACCATCAGCAGGCTGGAGCCCGAGGACTTCGCC
      GTGTACTACTGCCAGCAGTACCTGGCCAGCCCCGCCACCTTCGGCCAGGGCACCAAGGTGGAGA
      TCAAGAGGACCGTGGCCGCCCCCAGCGTGTTCATCTTCCCCCCCAGCGACGAGCAGCTGAAGAG
      CGGCACCGCCAGCGTGGTGTGCCTGCTGAACAACTTCTACCCCAGGGAGGCCAAGGTGCAGTG
      GAAGGTGGACAACGCCCTGCAGAGCGGCAACAGCCAGGAGAGCGTGACCGAGCAGGACAGCA
      AGGACAGCACCTACAGCCTGAGCAGCACCCTGACCCTGAGCAAGGCCGACTACGAGAAGCACA
      AGGTGTACGCCTGCGAGGTGACCCACCAGGGCCTGAGCAGCCCCGTGACCAAGAGCTTCAACA
      GGGGCGAGTGC

67    GAGATCGTGCTGACCCAGAGCCCCGGCACCCTGAGCCTGAGCCCCGGCGAGAGGGCCACCCTG
      AGCTGCAGGGCCAGCCAGTTCCTGAGCAGCTACCTGGCCTGGTACCAGCAGAAGCCCGGCCAG
      GCCCCCAGGCTGCTGATCTACGGCGCCAGCGCCAGGGCCAGCGGCATCCCCGACAGGTTCAGC
      GGCAGCGGCAGCGGCACCGACTTCACCCTGACCATCAGCAGGCTGGAGCCCGAGGACTTCGCC
      GTGTACTACTGCCAGCAGTACCTGGCCAGCCCCGCCACCTTCGGCCAGGGCACCAAGGTGGAGA
      TCAAGAGGACCGTGGCCGCCCCCAGCGTGTTCATCTTCCCCCCCAGCGACGAGCAGCTGAAGAG
      CGGCACCGCCAGCGTGGTGTGCCTGCTGAACAACTTCTACCCCAGGGAGGCCAAGGTGCAGTG
      GAAGGTGGACAACGCCCTGCAGAGCGGCAACAGCCAGGAGAGCGTGACCGAGCAGGACAGCA
      AGGACAGCACCTACAGCCTGAGCAGCACCCTGACCCTGAGCAAGGCCGACTACGAGAAGCACA
      AGGTGTACGCCTGCGAGGTGACCCACCAGGGCCTGAGCAGCCCCGTGACCAAGAGCTTCAACA
      GGGGCGAGTGC

-continued

| SEQUENCE LISTING SUMMARY | |
| --- | --- |

SEQ
ID
NO:    Sequence

68    GAGATCGTGCTGACCCAGAGCCCCGGCACCCTGAGCCTGAGCCCCGGCGAGAGGGCCACCCTG
       AGCTGCAGGGCCAGCCAGTTCCTGAGCAGCTACCTGGCCTGGTACCAGCAGAAGCCCGGCCAG
       GCCCCCAGGCTGCTGATCTACGGCGCCAGCGCCAGGGCCAGCGGCATCCCCGACAGGTTCAGC
       GGCAGCGGCAGCGGCACCGACTTCACCCTGACCATCAGCAGGCTGGAGCCCGAGGACTTCGCC
       GTGTACTACTGCCAGCAGTACCTGGCCAGCCCCGCCACCTTCGGCCAGGGCACCAAGGTGGAGA
       TCAAGAGGACCGTGGCCGCCCCCAGCGTGTTCATCTTCCCCCCCAGCGACGAGCAGCTGAAGAG
       CGGCACCGCCAGCGTGGTGTGCCTGCTGAACAACTTCTACCCCAGGGAGGCCAAGGTGCAGTG
       GAAGGTGGACAACGCCCTGCAGAGCGGCAACAGCCAGGAGAGCGTGACCGAGCAGGACAGCA
       AGGACAGCACCTACAGCCTGAGCAGCACCCTGACCCTGAGCAAGGCCGACTACGAGAAGCACA
       AGGTGTACGCCTGCGAGGTGACCCACCAGGGCCTGAGCAGCCCCGTGACCAAGAGCTTCAACA
       GGGGCGAGTGC

69    QVQLQESGPGLVKPSETLSLTCTVSGGSVSSGDYYWTWIRQSPGKGLEWIGHIYYSGN
       TNYNPSLKSRLTISIDTSKTQFSLKLSSVTAADTAIYYCVRDRVTGAFDIWGQGTMVTVSS
       (Anti-EGFR VH AA Seq)

70    DIQMTQSPSSLSASVGDRVTITCQASQDISNYLNWYQQKPGKAPKLLIYDASNLETGVP
       SRFSGSGSGTDFTFTISSLQPEDIATYFCQHFDHLPLAFGGGTKVEIK
       (Anti-EGFR VL AA Seq)

71    SGDYYWT
       (Anti-EGFR VH CDR1 AA Seq)

72    HIYYSGNTNYNPSLK
       (Anti-EGFR VH CDR2 AA Seq)

73    RVTGAFDI
       (Anti-EGFR VH CDR3 AA Seq)

74    QASQDISNYL
       (Anti-EGFR VL CDR1 AA Seq)

75    ASNLET
       (Anti-EGFR VL CDR2 AA Seq)

76    QHFDHLPLA
       (Anti-EGFR VL CDR3 AA Seq)

77    EVQLLESGGGLVQPGGSLRLSCAASGFTFSSYAMSWVRQAPGKGLEWVSQISPAGGYTN
       YADSVKGRFTISRDNSKNTLYLQMNSLRAEDTAVYYCARGELPYFRMSKVMDVWGQGTL
       VTVSS
       (Anti-NRP1 VH AA Seq)

78    EIVLTQSPGTLSLSPGERATLSCRASQFLSSYLAWYQQKPGQAPRLLIYGASARASG
       IPDRFSGSdGSGTDFTLTISRLEPEDFAVYYCQQYLASPATFGQGTKVEIK
       (Anti-NRP1 VL AA Seq)

79    FTFSSYAM
       (Anti-NRP1 VH CDR1 AA Seq)

80    QISPAGGYTNYADSVK
       (Anti-NRP1 VH CDR2 AA Seq)

81    GELPYFRMSKVMDV
       (Anti-NRP1 VH CDR3 AA Seq)

82    GELPYHRMSKVMDV
       (Anti-NRP1 VH CDR3 AA Seq)

83    GELPYYQMSKVMDV
       (Anti-NRP1 VH CDR3 AA Seq)

84    GELPFFRMSQVMDV
       (Anti-NRP1 VH CDR3 AA Seq)

85    RASQFLSSYLA
       (Anti-NRP1 VL CDR1 AA Seq)

86    RASQYFSSYLA
       (Anti-NRP1 VL CDR1 AA Seq)

87    RASQFLSSFLA
       (Anti-NRP1 VL CDR1 AA Seq)

-continued

---

SEQUENCE LISTING SUMMARY

---

SEQ
ID
NO:  Sequence

---

88    GASARAS
      (Anti-NRP1 VL CDR2 AA Seq)

89    QQYLASPAT
      (Anti-NRP1 VL CDR3 AA Seq)

---

SEQUENCE LISTING

Sequence total quantity: 89
SEQ ID NO: 1              moltype = AA   length = 474
FEATURE                  Location/Qualifiers
REGION                   1..474
                         note = Synthetic
source                   1..474
                         mol_type = protein
                         organism = synthetic construct
SEQUENCE: 1
QVQLQESGPG LVKPSETLSL TCTVSGGSVS SGDYYWTWIR QSPGKGLEWI GHIYYSGNTN  60
YNPSLKSRLT ISIDTSKTQF SLKLSSVTAA DTAIYYCVRD RVTGAFDIWG QGTMVTVSSA  120
STKGPSVFPL APCSRSTSES TAALGCLVKD YFPEPVTVSW NSGALTSGVH TFPAVLQSSG  180
LYSLSSVVTV PSSNFGTQTY TCNVDHKPSN TKVDKTVERK CCVECPPCPA PPVAGPSVFL  240
FPPKPKDTLM ISRTPEVTCV VVDVSHEDPE VQFNWYVDGV EVHNAKTKPR EEQFNSTFRV  300
VSVLTVVHQD WLNGKEYKCK VSNKGLPAPI EKTISKTKGQ PREPQVYTLP PSREEMTKNQ  360
VSLTCLVKGF YPSDIAVEWE SNGQPENNYK TTPPMLDSDG SFFLYSKLTV DKSRWQQGNV  420
FSCSVMHEAL HNHYTQKSLS LSPGKGGGGS GGGGSGGGGS HTPGNSKPTR TPRR        474

SEQ ID NO: 2              moltype = AA   length = 705
FEATURE                  Location/Qualifiers
REGION                   1..705
                         note = Synthetic
source                   1..705
                         mol_type = protein
                         organism = synthetic construct
SEQUENCE: 2
QVQLQESGPG LVKPSETLSL TCTVSGGSVS SGDYYWTWIR QSPGKGLEWI GHIYYSGNTN  60
YNPSLKSRLT ISIDTSKTQF SLKLSSVTAA DTAIYYCVRD RVTGAFDIWG QGTMVTVSSA  120
STKGPSVFPL APCSRSTSES TAALGCLVKD YFPEPVTVSW NSGALTSGVH TFPAVLQSSG  180
LYSLSSVVTV PSSNFGTQTY TCNVDHKPSN TKVDKTVERK CCVECPPCPA PPVAGPSVFL  240
FPPKPKDTLM ISRTPEVTCV VVDVSHEDPE VQFNWYVDGV EVHNAKTKPR EEQFNSTFRV  300
VSVLTVVHQD WLNGKEYKCK VSNKGLPAPI EKTISKTKGQ PREPQVYTLP PSREEMTKNQ  360
VSLTCLVKGF YPSDIAVEWE SNGQPENNYK TTPPMLDSDG SFFLYSKLTV DKSRWQQGNV  420
FSCSVMHEAL HNHYTQKSLS LSPGKGGGGS GGGGSGGGGS EVQLVESGGG LVQPGGSLRL  480
SCAASGFTFS SYAMSWVRQA PGKGLEWVSQ ISPAGGYTNY ADSVKGRFTI SADTSKNTAY  540
LQMNSLRAED TAVYYCARGE LPYYRMSKVM DVWGQGTLVT VSSGGGGSGG GGSGGGGSDI  600
QMTQSPSSLS ASVGDRVTIT CRASQYFSSY LAWYQQKPGK APKLLIYGAS SRASGVPSRF  660
SGSGSGTDFT LTISSLQPED FATYYCQQYL GSPPTFGQGT KVEIK                 705

SEQ ID NO: 3              moltype = AA   length = 705
FEATURE                  Location/Qualifiers
REGION                   1..705
                         note = Synthetic
source                   1..705
                         mol_type = protein
                         organism = synthetic construct
SEQUENCE: 3
QVQLQESGPG LVKPSETLSL TCTVSGGSVS SGDYYWTWIR QSPGKGLEWI GHIYYSGNTN  60
YNPSLKSRLT ISIDTSKTQF SLKLSSVTAA DTAIYYCVRD RVTGAFDIWG QGTMVTVSSA  120
STKGPSVFPL APCSRSTSES TAALGCLVKD YFPEPVTVSW NSGALTSGVH TFPAVLQSSG  180
LYSLSSVVTV PSSNFGTQTY TCNVDHKPSN TKVDKTVERK CCVECPPCPA PPVAGPSVFL  240
FPPKPKDTLM ISRTPEVTCV VVDVSHEDPE VQFNWYVDGV EVHNAKTKPR EEQFNSTFRV  300
VSVLTVVHQD WLNGKEYKCK VSNKGLPAPI EKTISKTKGQ PREPQVYTLP PSREEMTKNQ  360
VSLTCLVKGF YPSDIAVEWE SNGQPENNYK TTPPMLDSDG SFFLYSKLTV DKSRWQQGNV  420
FSCSVMHEAL HNHYTQKSLS LSPGKGGGGS GGGGSGGGGS EVQLVESGGG LVQPGGSLRL  480
SCAASGFTFS SYAMSWVRQA PGKGLEWVSQ ISPAGGYTNY ADSVKGRFTI SADTSKNTAY  540
LQMNSLRAED TAVYYCARGE LPYFRMSKVM DVWGQGTLVT VSSGGGGSGG GGSGGGGSDI  600
QMTQSPSSLS ASVGDRVTIT CRASQFLSSY LAWYQQKPGK APKLLIYGAS ARASGVPSRF  660
SGSGSGTDFT LTISSLQPED FATYYCQQYL ASPATFGQGT KVEIK                 705

```
SEQ ID NO: 4          moltype = AA   length = 705
FEATURE               Location/Qualifiers
REGION                1..705
                      note = Synthetic
source                1..705
                      mol_type = protein
                      organism = synthetic construct
SEQUENCE: 4
QVQLQESGPG LVKPSETLSL TCTVSGGSVS SGDYYWTWIR QSPGKGLEWI GHIYYSGNTN   60
YNPSLKSRLT ISIDTSKTQF SLKLSSVTAA DTAIYYCVRD RVTGAFDIWG QGTMVTVSSA  120
STKGPSVFPL APCSRSTSES TAALGCLVKD YFPEPVTVSW NSGALTSGVH TFPAVLQSSG  180
LYSLSSVVTV PSSNFGTQTY TCNVDHKPSN TKVDKTVERK CCVECPPCPA PPVAGPSVFL  240
FPPKPKDTLM ISRTPEVTCV VVDVSHEDPE VQFNWYVDGV EVHNAKTKPR EEQFNSTFRV  300
VSVLTVVHQD WLNGKEYKCK VSNKGLPAPI EKTISKTKGQ PREPQVYTLP PSREEMTKNQ  360
VSLTCLVKGF YPSDIAVEWE SNGQPENNYK TTPPMLDSDG SFFLYSKLTV DKSRWQQGNV  420
FSCSVMHEAL HNHYTQKSLS LSPGKGGGGS GGGGSGGGGS EVQLVESGGG LVQPGGSLRL  480
SCAASGFTFS SYAMSWVRQA PGKGLEWVSQ ISPAGGYTNY ADSVKGRFTI SADTSKNTAY  540
LQMNSLRAED TAVYYCARGE LPYYQMSKVM DVWGQGTLVT VSSGGGGSGG GGSGGGGSDI  600
QMTQSPSSLS ASVGDRVTIT CRASQYFSSY LAWYQQKPGK APKLLIYGAS ARASGVPSRF  660
SGSGSGTDFT LTISSLQPED FATYYCQQYL ASPATFGQGT KVEIK             705

SEQ ID NO: 5          moltype = AA   length = 705
FEATURE               Location/Qualifiers
REGION                1..705
                      note = Synthetic
source                1..705
                      mol_type = protein
                      organism = synthetic construct
SEQUENCE: 5
QVQLQESGPG LVKPSETLSL TCTVSGGSVS SGDYYWTWIR QSPGKGLEWI GHIYYSGNTN   60
YNPSLKSRLT ISIDTSKTQF SLKLSSVTAA DTAIYYCVRD RVTGAFDIWG QGTMVTVSSA  120
STKGPSVFPL APCSRSTSES TAALGCLVKD YFPEPVTVSW NSGALTSGVH TFPAVLQSSG  180
LYSLSSVVTV PSSNFGTQTY TCNVDHKPSN TKVDKTVERK CCVECPPCPA PPVAGPSVFL  240
FPPKPKDTLM ISRTPEVTCV VVDVSHEDPE VQFNWYVDGV EVHNAKTKPR EEQFNSTFRV  300
VSVLTVVHQD WLNGKEYKCK VSNKGLPAPI EKTISKTKGQ PREPQVYTLP PSREEMTKNQ  360
VSLTCLVKGF YPSDIAVEWE SNGQPENNYK TTPPMLDSDG SFFLYSKLTV DKSRWQQGNV  420
FSCSVMHEAL HNHYTQKSLS LSPGKGGGGS GGGGSGGGGS EVQLVESGGG LVQPGGSLRL  480
SCAASGFTFS SYAMSWVRQA PGKGLEWVSQ ISPAGGYTNY ADSVKGRFTI SADTSKNTAY  540
LQMNSLRAED TAVYYCARGE LPFFRMSQVM DVWGQGTLVT VSSGGGGSGG GGSGGGGSDI  600
QMTQSPSSLS ASVGDRVTIT CRASQFLSSY LAWYQQKPGK APKLLIYGAS ARASGVPSRF  660
SGSGSGTDFT LTISSLQPED FATYYCQQYL ASPATFGQGT KVEIK             705

SEQ ID NO: 6          moltype = AA   length = 705
FEATURE               Location/Qualifiers
REGION                1..705
                      note = Synthetic
source                1..705
                      mol_type = protein
                      organism = synthetic construct
SEQUENCE: 6
QVQLQESGPG LVKPSETLSL TCTVSGGSVS SGDYYWTWIR QSPGKGLEWI GHIYYSGNTN   60
YNPSLKSRLT ISIDTSKTQF SLKLSSVTAA DTAIYYCVRD RVTGAFDIWG QGTMVTVSSA  120
STKGPSVFPL APCSRSTSES TAALGCLVKD YFPEPVTVSW NSGALTSGVH TFPAVLQSSG  180
LYSLSSVVTV PSSNFGTQTY TCNVDHKPSN TKVDKTVERK CCVECPPCPA PPVAGPSVFL  240
FPPKPKDTLM ISRTPEVTCV VVDVSHEDPE VQFNWYVDGV EVHNAKTKPR EEQFNSTFRV  300
VSVLTVVHQD WLNGKEYKCK VSNKGLPAPI EKTISKTKGQ PREPQVYTLP PSREEMTKNQ  360
VSLTCLVKGF YPSDIAVEWE SNGQPENNYK TTPPMLDSDG SFFLYSKLTV DKSRWQQGNV  420
FSCSVMHEAL HNHYTQKSLS LSPGKGGGGS GGGGSGGGGS EVQLVESGGG LVQPGGSLRL  480
SCAASGFTFS SYAMSWVRQA PGKGLEWVSQ ISPAGGYTNY ADSVKGRFTI SADTSKNTAY  540
LQMNSLRAED TAVYYCARGE LPYFRMSKVM DVWGQGTLVT VSSGGGGSGG GGSGGGGSDI  600
QMTQSPSSLS ASVGDRVTIT CRASQFLSSF LAWYQQKPGK APKLLIYGAS ARASGVPSRF  660
SGSGSGTDFT LTISSLQPED FATYYCQQYL ASPATFGQGT KVEIK             705

SEQ ID NO: 7          moltype = AA   length = 709
FEATURE               Location/Qualifiers
REGION                1..709
                      note = Synthetic
source                1..709
                      mol_type = protein
                      organism = synthetic construct
SEQUENCE: 7
QVQLQESGPG LVKPSETLSL TCTVSGGSVS SGDYYWTWIR QSPGKGLEWI GHIYYSGNTN   60
YNPSLKSRLT ISIDTSKTQF SLKLSSVTAA DTAIYYCVRD RVTGAFDIWG QGTMVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSRDEL  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGKG GGSGGGGSG GGGSEVQLVE SGGGLVQPGG  480
```

-continued

```
SLRLSCAASG FTFSSYAMSW VRQAPGKGLE WVSQISPAGG YTNYADSVKG RFTISADTSK   540
NTAYLQMNSL RAEDTAVYYC ARGELPYFRM SKVMDVWGQG TLVTVSSGGG GSGGGGSGGG   600
GSDIQMTQSP SSLSASVGDR VTITCRASQF LSSYLAWYQQ KPGKAPKLLI YGASARASGV   660
PSRFSGSGSG TDFTLTISSL QPEDFATYYC QQYLASPATF GQGTKVEIK               709

SEQ ID NO: 8              moltype = AA  length = 705
FEATURE                   Location/Qualifiers
REGION                    1..705
                          note = Synthetic
source                    1..705
                          mol_type = protein
                          organism = synthetic construct
SEQUENCE: 8
QVQLQESGPG LVKPSETLSL TCTVSGGSVS SGDYYWTWIR QSPGKGLEWI GHIYYSGNTN   60
YNPSLKSRLT ISIDTSKTQF SLKLSSVTAA DTAIYYCVRD RVTGAFDIWG QGTMVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKKVEPK SCDKTHTCPP CPAPELLGGP   240
SVFLFPPKPK DTLMISRTPE VTCVVVDVSH EDPEVKFNWY VDGVEVHNAK TKPREEQYNS   300
TYRVVSVLTV LHQDWLNGKE YKCKVSNKAL PAPIEKTISK AKGQPREPQV YTLPPSRDEL   360
TKNQVSLTCL VKGFYPSDIA VEWESNGQPE NNYKTTPPVL DSDGSFFLYS KLTVDKSRWQ   420
QGNVFSCSVM HEALHNHYTQ KSLSLSPGKG GGGSGGGGSG GGGSEVQLVE SGGGLVQPGG   480
SLRLSCAASG FTFSSYAMSW VRQAPGKGLE WVSQISPAGG YTNYADSVKG RFTISADTSK   540
NTAYLQMNSL RAEDTAVYYC ARGELPYFRM SKVMDVWGQG TLVTVSSDGG SSGGGGASDI   600
QMTQSPSSLS ASVGDRVTIT CRASQFLSSY LAWYQQKPGK APKLLIYGAS ARASGVPSRF   660
SGSGSGTDFT LTISSLQPED FATYYCQQYL ASPATFGQGT KVEIK                  705

SEQ ID NO: 9              moltype = AA  length = 714
FEATURE                   Location/Qualifiers
REGION                    1..714
                          note = Synthetic
source                    1..714
                          mol_type = protein
                          organism = synthetic construct
SEQUENCE: 9
QVQLQESGPG LVKPSETLSL TCTVSGGSVS SGDYYWTWIR QSPGKGLEWI GHIYYSGNTN   60
YNPSLKSRLT ISIDTSKTQF SLKLSSVTAA DTAIYYCVRD RVTGAFDIWG QGTMVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKKVEPK SCDKTHTCPP CPAPELLGGP   240
SVFLFPPKPK DTLMISRTPE VTCVVVDVSH EDPEVKFNWY VDGVEVHNAK TKPREEQYNS   300
TYRVVSVLTV LHQDWLNGKE YKCKVSNKAL PAPIEKTISK AKGQPREPQV YTLPPSRDEL   360
TKNQVSLTCL VKGFYPSDIA VEWESNGQPE NNYKTTPPVL DSDGSFFLYS KLTVDKSRWQ   420
QGNVFSCSVM HEALHNHYTQ KSLSLSPGKG GGGSGGGGSG GGGSEVQLVE SGGGLVQPGG   480
SLRLSCAASG FTFSSYAMSW VRQAPGKGLE WVSQISPAGG YTNYADSVKG RFTISADTSK   540
NTAYLQMNSL RAEDTAVYYC ARGELPYFRM SKVMDVWGQG TLVTVSSGGG GSGGGGSGGG   600
GSGGGGSDIQ MTQSPSSLSA SVGDRVTITC RASQFLSSYL AWYQQKPGKA PKLLIYGASA   660
RASGVPSRFS GSGSGTDFTL TISSLQPEDF ATYYCQQYLA SPATFGQGTK VEIK        714

SEQ ID NO: 10             moltype = AA  length = 709
FEATURE                   Location/Qualifiers
REGION                    1..709
                          note = Synthetic
source                    1..709
                          mol_type = protein
                          organism = synthetic construct
SEQUENCE: 10
QVQLQESGPG LVKPSETLSL TCTVSGGSVS SGDYYWTWIR QSPGKGLEWI GHIYYSGNTN   60
YNPSLKSRLT ISIDTSKTQF SLKLSSVTAA DTAIYYCVRD RVTGAFDIWG QGTMVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKKVEPK SCDKTHTCPP CPAPELLGGP   240
SVFLFPPKPK DTLMISRTPE VTCVVVDVSH EDPEVKFNWY VDGVEVHNAK TKPREEQYNS   300
TYRVVSVLTV LHQDWLNGKE YKCKVSNKAL PAPIEKTISK AKGQPREPQV YTLPPSRDEL   360
TKNQVSLTCL VKGFYPSDIA VEWESNGQPE NNYKTTPPVL DSDGSFFLYS KLTVDKSRWQ   420
QGNVFSCSVM HEALHNHYTQ KSLSLSPGKG GGGSGGGGSG GGSDIQMTQ SPSSLSASVG   480
DRVTITCRAS QFLSSYLAWY QQKPGKAPKL LIYGASARAS GVPSRFSGSG SGTDFTLTIS   540
SLQPEDFATY YCQQYLASPA TFGQGTKVEI KGGGGSGGGG SGGGGSEVQL VESGGGLVQP   600
GGSLRLSCAA SGFTFSSYAM SWVRQAPGKG LEWVSQISPA GGYTNYADSV KGRFTISADT   660
SKNTAYLQMN SLRAEDTAVY YCARGELPYF RMSKVMDVWG QGTLVTVSS             709

SEQ ID NO: 11             moltype = AA  length = 709
FEATURE                   Location/Qualifiers
REGION                    1..709
                          note = Synthetic
source                    1..709
                          mol_type = protein
                          organism = synthetic construct
SEQUENCE: 11
QVQLQESGPG LVKPSETLSL TCTVSGGSVS SGDYYWTWIR QSPGKGLEWI GHIYYSGNTN   60
YNPSLKSRLT ISIDTSKTQF SLKLSSVTAA DTAIYYCVRD RVTGAFDIWG QGTMVTVSSA   120
STKGPSVFPL APSSKSTSGG TAALGCLVKD YFPEPVTVSW NSGALTSGVH TFPAVLQSSG   180
```

```
LYSLSSVVTV PSSSLGTQTY ICNVNHKPSN TKVDKKVEPK SCDKTHTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSRDEL  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGKG GGGSGGGGSG GGGSEVQLLE SGGGLVQPGG  480
SLRLSCAASG FTFSSYAMSW VRQAPGKGLE WVSQISPAGG YTNYADSVKG RFTISRDNSK  540
NTLYLQMNSL RAEDTAVYYC ARGELPYFRM SKVMDVWGQG TLVTVSSGGG GSGGGGSGGG  600
GSEIVLTQSP GTLSLSPGER ATLSCRASQF LSSYLAWYQQ KPGQAPRLLI YGASARASGI  660
PDRFSGSGSG TDFTLTISRL EPEDFAVYYC QQYLASPATF GQGTKVEIK           709

SEQ ID NO: 12          moltype = AA   length = 214
FEATURE                Location/Qualifiers
REGION                 1..214
                       note = Synthetic
source                 1..214
                       mol_type = protein
                       organism = synthetic construct
SEQUENCE: 12
DIQMTQSPSS LSASVGDRVT ITCQASQDIS NYLNWYQQKP GKAPKLLIYD ASNLETGVPS  60
RFSGSGSGTD FTFTISSLQP EDIATYFCQH FDHLPLAFGG GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                            214

SEQ ID NO: 13          moltype = AA   length = 5
FEATURE                Location/Qualifiers
REGION                 1..5
                       note = Synthetic
source                 1..5
                       mol_type = protein
                       organism = synthetic construct
SEQUENCE: 13
GGGGS                                                            5

SEQ ID NO: 14          moltype = DNA   length = 1422
FEATURE                Location/Qualifiers
misc_feature           1..1422
                       note = Synthetic
source                 1..1422
                       mol_type = other DNA
                       organism = synthetic construct
SEQUENCE: 14
caagtgcagc tgcaggaatc cggccccggg cttgtgaagc ctagcgaaac actctcgctc  60
acctgtactg tcagcggtgg atcagtgtcc tccggcgatt actactggac ctggattcgg  120
cagagccctg aaaagggact ggagtggatc ggacacatct actactccgg gaacactaac  180
tacaacccgt cgttgaagtc cagactgacg atcagtatcg atacctccaa gacccagttc  240
agcctgaagc tgagctcagt gacagccgcc gacactgcaa tctactactg cgtgcgggac  300
agagtgaccg gagccttcga catctggggc cagggaacca tggtcactgt gtcgtctgcg  360
tcaaccaagg gtccgtccgt gtttcccctg gccccgtgct cgcggagcac ctccgagtcc  420
actgccgcct tgggctgcct ggtcaaagac tacttccctg aacccgtgac tgtcagctgg  480
aactccggag ctctgacctc gggagtgcac accttcccgg ccgtgctgca atcgagcggc  540
ctctactccc tgtcctccgt cgtgaccgtg ccatcatcaa gttcggaac ccaaacttat  600
acgtgcaacg tcgaccacaa gccctccaat accaaagtcg acaagaccgt ggagaggaaa  660
tgctgcgtgg agtgtccgcc ttgccccgcg ccgccggtgg ccggacctag cgtgttcctg  720
ttcccgccga agccaaagga cactctcatg atctcccgca cccctgaagt cacttgcgtc  780
gtggtggacg tttcccacga ggatcccgaa gtgcagttca attggtacgt ggacgggggtg  840
gaagtacata acgccaagac caagcccagg gaagaacagt ttaactccac cttccgggtg  900
gtgtcggtgc tcactgtggt gcatcaggat tggctcaatg gaaaggagta caagtgcaaa  960
gtgtcgaaca agggtctgcc cgctcctatt gaaaagacca tttccaaaac caagggacag  1020
cccagagagc ctcaggtcta caccctgcct ccgagccgcg aggaaatgac caagaaccaa  1080
gtgtctctga cttgcctcgt gaagggattc tacccctccg atatcgcggt ggagtgggag  1140
agcaacgggc agccagagaa caactataag accacacccgc ctatgctgga ctccgatggc  1200
tccttcttct tgtactcgaa gctgaccgtg gacaagtccc gctggcaaca gggaaacgtg  1260
ttcagctgta gcgtgatgca cgaagccctg cacaaccact acacccagaa gtccctgtcg  1320
ctttcccccg ggaagggcgg tggcggatcc ggcggcgggg gcagcggggg cggcggttcc  1380
catacccccgg ggaactcaaa gcccaccgg actccacggc gc                    1422

SEQ ID NO: 15          moltype = DNA   length = 2121
FEATURE                Location/Qualifiers
misc_feature           1..2121
                       note = Synthetic
source                 1..2121
                       mol_type = other DNA
                       organism = synthetic construct
SEQUENCE: 15
caggttcagc tgcaagagtc tggccctggc ctggtcaagc cttccgaaac actgtctctg  60
acctgcaccg tgtctggcgg ctctgtgtcc tctggcgatt actactggac ctggatccgg  120
cagtctcctg gcaaggcct ggaatggatc ggccacatct actactccgg caacaccaac  180
tacaacccca gcctgaagtc ccggctgacc atctccatcg acaccagcaa gacccagttc  240
tccctgaagc tgtcctctgt gaccgccgct gataccgcca tctactattg cgtgcgggac  300
```

```
agagtgaccg gcgcctttga tatttggggc cagggcacca tggtcaccgt gtccagtgct    360
tctaccaagg gacccagcgt gttccctctg gctccttgct ccagatccac ctccgagtct    420
acagctgctc tgggctgtct ggtcaaggac tacttccctg agcctgtgac cgtgtcctgg    480
aattctggcg ctctgacatc tggcgtgcac acctttccag ctgtgctgca gtctagcggc    540
ctgtactctc tgtcctccgt cgtgaccgtg ccttcctcta actttggcac ccagacctac    600
acctgtaatg tggaccacaa gccatccaac accaaggtgg acaagaccgt ggaacggaag    660
tgctgcgtgg aatgccctcc ttgtcctgct cctcctgtgg ctggcccttc cgtgtttctg    720
ttccctccaa agcctaagga caccctgatg atctctcgga cccctgaagt gacctgcgtg    780
gtggtggatg tgtctcacga ggatcccgag gtgcagttca attggtacgt ggacggcgtg    840
gaagtgcaca acgccaagac caagcctaga gaggaacagt tcaactccac cttcagagtg    900
gtgtccgtgc tgaccgtggt gcatcaggat tggctgaacg gcaaagagta caagtgcaag    960
gtgtccaaca agggcctgcc tgctcctatc gaaaagacca tctctaagac caaggggcag   1020
ccccgggaac ctcaggttta cacactgcct ccaagccggg aagagatgac caagaaccag   1080
gtgtccctga cctgtctcgt gaagggcttc tacccctccg atatcgccgt ggaatgggag   1140
tctaatggcc agcctgagaa caactacaag accacacctc ctatgctgga ctccgacggc   1200
tcattcttcc tgtactccaa gctgacagtg gacaagtcca gatggcagca gggcaacgtg   1260
ttctcctgct ccgtgatgca cgaggccctg cacaatcact acacccagaa gtccctgtct   1320
ctgtcccctg gaaaaggcgg cggaggatct ggcggaggcg gtagcggtgg tggcggatct   1380
gaagttcagc tggttgaatc tggcggcgga ctggttcaac caggcggatc tctgagactg   1440
tcttgtgccg cctccggctt caccttctcc tcttacgcta tgtcctgggt ccgacaggcc   1500
ccaggcaaag gattggagtg ggtgtcccag atctctcccg ctggcggcta caccaattac   1560
gccgactctg tgaagggcag attcaccatc tctgccgaca cctccaagaa caccgcctac   1620
ctgcagatga actccctgag agccgaggac accgccgtgt actattgtgc tagaggcgag   1680
ctgccctact accggatgtc caaagtgatg gacgtgtggg gacagggaac cctcgtgaca   1740
gtttctagcg gtggcggagg tagcggaggc ggtggaagcg gcggaggcgg aagtgatatt   1800
cagatgaccc agtctccttc cagcctgtcc gcttctgtgg gcgatagagt gaccatcacc   1860
tgtcgggcct ctcagtactt ctcctcctac ctggcttggt atcagcagaa gcctggcaag   1920
gcccctaagc tgctgatcta cggcgcctcc tctagagcta gcggcgtgcc ctctagattc   1980
tccgatctg gctctggcac cgactttacc ctgacaatct ccagcctgca gcctgaggac    2040
ttcgccacct actactgcca gcagtacctg ggctctcctc caacctttgg ccagggaaca   2100
aaggtcgaga tcaagcgctg a                                             2121
```

```
SEQ ID NO: 16          moltype = DNA  length = 2121
FEATURE                Location/Qualifiers
misc_feature           1..2121
                       note = Synthetic
source                 1..2121
                       mol_type = other DNA
                       organism = synthetic construct
SEQUENCE: 16
caggttcagc tgcaagagtc tggccctggc ctggtcaagc cttccgaaac actgtctctg     60
acctgcaccg tgtctggcgg ctctgtgtcc tctggcgatt actactggac ctggatccgg    120
cagtctcctg gcaaaggcct ggaatggatc ggccacatct actactccgg caacaccaac    180
tacaacccca gcctgaagtc ccggctgacc atctccatcg acaccagcaa gacccagttc    240
tccctgaagc tgtcctctgt gaccgccgct gataccgcca tctactattg cgtgcgggac    300
agagtgaccg gcgcctttga tatttggggc cagggcacca tggtcaccgt gtccagtgct    360
tctaccaagg gacccagcgt gttccctctg gctccttgct ccagatccac ctccgagtct    420
acagctgctc tgggctgtct ggtcaaggac tacttccctg agcctgtgac cgtgtcctgg    480
aattctggcg ctctgacatc tggcgtgcac acctttccag ctgtgctgca gtctagcggc    540
ctgtactctc tgtcctccgt cgtgaccgtg ccttcctcta actttggcac ccagacctac    600
acctgtaatg tggaccacaa gccatccaac accaaggtgg acaagaccgt ggaacggaag    660
tgctgcgtgg aatgccctcc ttgtcctgct cctcctgtgg ctggcccttc cgtgtttctg    720
ttccctccaa agcctaagga caccctgatg atctctcgga cccctgaagt gacctgcgtg    780
gtggtggatg tgtctcacga ggatcccgag gtgcagttca attggtacgt ggacggcgtg    840
gaagtgcaca acgccaagac caagcctaga gaggaacagt tcaactccac cttcagagtg    900
gtgtccgtgc tgaccgtggt gcatcaggat tggctgaacg gcaaagagta caagtgcaag    960
gtgtccaaca agggcctgcc tgctcctatc gaaaagacca tctctaagac caaggggcag   1020
ccccgggaac ctcaggttta cacactgcct ccaagccggg aagagatgac caagaaccag   1080
gtgtccctga cctgtctcgt gaagggcttc tacccctccg atatcgccgt ggaatgggag   1140
tctaatggcc agcctgagaa caactacaag accacacctc ctatgctgga ctccgacggc   1200
tcattcttcc tgtactccaa gctgacagtg gacaagtcca gatggcagca gggcaacgtg   1260
ttctcctgct ccgtgatgca cgaggccctg cacaatcact acacccagaa gtccctgtct   1320
ctgtcccctg gaaaaggcgg cggaggatct ggcggaggcg gtagcggtgg tggcggatct   1380
gaagttcagc tggttgaatc tggcggcgga ctggttcaac caggcggatc tctgagactg   1440
tcttgtgccg cctccggctt caccttctcc tcttacgcta tgtcctgggt ccgacaggcc   1500
ccaggcaaag gattggagtg ggtgtcccag atctctcccg ctggcggcta caccaattac   1560
gccgactctg tgaagggcag attcaccatc tctgccgaca cctccaagaa caccgcctac   1620
ctgcagatga actccctgag agccgaggac accgccgtgt actattgtgc tagaggcgag   1680
ctgccctact ccggatgtc caaagtgatg gacgtgtggg gacagggaac cctcgtgaca   1740
gtttctagcg gtggcggagg tagcggaggc ggtggaagcg gcggaggcgg aagtgatatt   1800
cagatgaccc agtctccttc cagcctgtcc gcttctgtgg gcgatagagt gaccatcacc   1860
tgtcgggcct ctcagttcct gtcctcctac ctggcttggt atcagcagaa gcctggcaag   1920
gcccctaagc tgctgatcta cggcgcttct gctagagctt ccggcgtgcc ctccagattt   1980
tctggctctg gatctggcac cgactttacc ctgacaatct ccagcctgca gcctgaggac   2040
ttcgccacct actactgcca gcagtacctg gcctctcctc ccacatttgg ccagggaaca   2100
aaggtcgaga tcaagcgctg a                                             2121
```

```
SEQ ID NO: 17          moltype = DNA  length = 2121
FEATURE                Location/Qualifiers
```

```
misc_feature          1..2121
                      note = Synthetic
source                1..2121
                      mol_type = other DNA
                      organism = synthetic construct
SEQUENCE: 17
caggttcagc tgcaagagtc tggccctggc ctggtcaagc cttccgaaac actgtctctg   60
acctgcaccg tgtctggcgg ctctgtgtcc tctggcgatt actactggac ctggatccgg   120
cagtctcctg gcaaaggcct ggaatggatc ggccacatct actactccgg caacaccaac   180
tacaacccca gcctgaagtc ccggctgacc atctccatcg acaccagcaa gacccagttc   240
tccctgaagc tgtcctctgt gaccgccgct gataccgcca tctactattg cgtgcgggac   300
agagtgaccg gcgcctttga tatttggggc cagggcacca tggtcaccgt gtccagtgct   360
tctaccaagg gacccagcgt gttccctctg gctccttgct ccagatccac ctccgagtct   420
acagctgctc tgggctgtct ggtcaaggac tacttccctg agcctgtgac cgtgtcctgg   480
aattctggcg ctctgacatc tggcgtgcac acctttccag ctgtgctgca gtctagcggc   540
ctgtactctc tgtcctccgt cgtgaccgtg ccttcctcta actttggcac ccagacctac   600
acctgtaatg tggaccacaa gccatccaac accaaggtgg acaagaccgt ggaacggaag   660
tgctgcgtgg aatgccctcc ttgtcctgct cctcctgtgg ctggcccttc cgtgtttctg   720
ttccctccaa agcctaagga caccctgatg atctctcgga ccccctgaagt gacctgcgtg   780
gtggtggatg tgtctcacga ggatcccgag gtgcagttca attggtacgt ggacggcgtg   840
gaagtgcaca acgccaagac caagcctaga gaggaacagt tcaactccac cttcagagtg   900
gtgtccgtgc tgaccgtggt gcatcaggat tggctgaacg gcaaagagta caagtgcaag   960
gtgtccaaca agggcctgcc tgctcctatc gaaaagacca tctctaagac caagggggcag   1020
ccccgggaac ctcaggttta cacactgcct ccaagccggg aagagatgac caagaaccag   1080
gtgtccctga cctgtctcgt gaagggcttc tacccctccg atatcgccgt ggaatgggag   1140
tctaatggcc agcctgagaa caactacaag accacacctc ctatgctgga ctccgacggc   1200
tcattcttcc tgtactccaa gctgacagtg gacaagtcca gatggcagca gggcaacgtg   1260
ttctcctgct ccgtgatgca cgaggccctg cacaatcact acacccagaa gtccctgtct   1320
ctgtcccctg gaaaaggcgg cggaggatct ggcggaggcg gtagcggtgg tggcggatct   1380
gaagttcagc tggttgaatc tggcggcgga ctggttcaac caggcggatc tctgagactg   1440
tcttgtgccg cctccggctt caccttctcc tcttacgcta tgtcctgggt ccgacaggcc   1500
ccaggcaaag gattggagtg ggtgtcccag atctctcccg ctggcggcta caccaattac   1560
gccgactctg tgaagggcag attcaccatc tctgccgaca cctccaagaa caccgcctac   1620
ctgcagatga actccctgag agccgaggac accgccgtgt actattgtgc tagaggcgag   1680
ctgcccctact accagatgtc caaagtgatg gacgtgtggg gacagggaac cctcgtgaca   1740
gtttctagcg gtggcggagg tagcggaggc ggtggaagcg gcggaggcgg aagtgatatt   1800
cagatgaccc agtctccttc cagcctgtcc gcttctgtgg gcgatagagt gaccatcacc   1860
tgtcgggcct ctcagtactt ctcttcctat ctggcatggt atcagcagaa gcctggcaag   1920
gcccctaagc tgctgatcta cggcgccttct gctagagctt ccggcgtgcc ctccagattt   1980
tctggctctg gatctggcac cgactttacc ctgacaatct ccagcctgca gcctgaggac   2040
ttcgccacct actactgcca gcagtacctg gcctctcctg ccacatttgg ccagggaaca   2100
aaggtcgaga tcaagcgctg a                                             2121
```

```
SEQ ID NO: 18         moltype = DNA   length = 2121
FEATURE               Location/Qualifiers
misc_feature          1..2121
                      note = Synthetic
source                1..2121
                      mol_type = other DNA
                      organism = synthetic construct
SEQUENCE: 18
caggttcagc tgcaagagtc tggccctggc ctggtcaagc cttccgaaac actgtctctg   60
acctgcaccg tgtctggcgg ctctgtgtcc tctggcgatt actactggac ctggatccgg   120
cagtctcctg gcaaaggcct ggaatggatc ggccacatct actactccgg caacaccaac   180
tacaacccca gcctgaagtc ccggctgacc atctccatcg acaccagcaa gacccagttc   240
tccctgaagc tgtcctctgt gaccgccgct gataccgcca tctactattg cgtgcgggac   300
agagtgaccg gcgcctttga tatttggggc cagggcacca tggtcaccgt gtccagtgct   360
tctaccaagg gacccagcgt gttccctctg gctccttgct ccagatccac ctccgagtct   420
acagctgctc tgggctgtct ggtcaaggac tacttccctg agcctgtgac cgtgtcctgg   480
aattctggcg ctctgacatc tggcgtgcac acctttccag ctgtgctgca gtctagcggc   540
ctgtactctc tgtcctccgt cgtgaccgtg ccttcctcta actttggcac ccagacctac   600
acctgtaatg tggaccacaa gccatccaac accaaggtgg acaagaccgt ggaacggaag   660
tgctgcgtgg aatgccctcc ttgtcctgct cctcctgtgg ctggcccttc cgtgtttctg   720
ttccctccaa agcctaagga caccctgatg atctctcgga ccccctgaagt gacctgcgtg   780
gtggtggatg tgtctcacga ggatcccgag gtgcagttca attggtacgt ggacggcgtg   840
gaagtgcaca acgccaagac caagcctaga gaggaacagt tcaactccac cttcagagtg   900
gtgtccgtgc tgaccgtggt gcatcaggat tggctgaacg gcaaagagta caagtgcaag   960
gtgtccaaca agggcctgcc tgctcctatc gaaaagacca tctctaagac caagggggcag   1020
ccccgggaac ctcaggttta cacactgcct ccaagccggg aagagatgac caagaaccag   1080
gtgtccctga cctgtctcgt gaagggcttc tacccctccg atatcgccgt ggaatgggag   1140
tctaatggcc agcctgagaa caactacaag accacacctc ctatgctgga ctccgacggc   1200
tcattcttcc tgtactccaa gctgacagtg gacaagtcca gatggcagca gggcaacgtg   1260
ttctcctgct ccgtgatgca cgaggccctg cacaatcact acacccagaa gtccctgtct   1320
ctgtcccctg gaaaaggcgg cggaggatct ggcggaggcg gtagcggtgg tggcggatct   1380
gaagttcagc tggttgaatc tggcggcgga ctggttcaac caggcggatc tctgagactg   1440
tcttgtgccg cctccggctt caccttctcc tcttacgcta tgtcctgggt ccgacaggcc   1500
ccaggcaaag gattggagtg ggtgtcccag atctctcccg ctggcggcta caccaattac   1560
gccgactctg tgaagggcag attcaccatc tctgccgaca cctccaagaa caccgcctac   1620
ctgcagatga actccctgag agccgaggac accgccgtgt actattgtgc tagaggcgag   1680
```

```
ctgccattct tccggatgtc ccaagtgatg gacgtgtggg gacagggaac cctcgtgaca   1740
gtttctagcg gtggcggagg tagcggaggc ggtggaagcg gcggaggcgg aagtgatatt   1800
cagatgaccc agtctccttc cagcctgtcc gcttctgtgg gcgatagagt gaccatcacc   1860
tgtcgggcct ctcagttcct gtctagttat ctggcatggt atcagcagaa gcccggcaag   1920
gctcccaagc tgttgatcta cggcgcctct gctagagctt ccggcgtgcc atctagattc   1980
tccggctctg gctctggcac cgactttacc ctgacaatct ccagcctgca gcctgaggac   2040
ttcgccacct actactgcca gcagtacctg gcctctcctg ccacatttgg ccagggaaca   2100
aaggtcgaga tcaagcgctg a                                             2121
```

```
SEQ ID NO: 19        moltype = DNA   length = 2121
FEATURE              Location/Qualifiers
misc_feature         1..2121
                     note = Synthetic
source               1..2121
                     mol_type = other DNA
                     organism = synthetic construct
SEQUENCE: 19
caggttcagc tgcaagagtc tggccctggc ctggtcaagc cttccgaaac actgtctctg   60
acctgcaccg tgtctggcgg ctctgtgtcc tctggcgatt actactggac ctggatccgg   120
cagtctcctg gcaaaggcct ggaatggatc ggccacatct actactccgg caacaccaac   180
tacaacccca gcctgaagtc ccggctgacc atctccatcg acaccagcaa gacccagttc   240
tccctgaagc tgtcctctgt gaccgccgct gataccgcca tctactattg cgtgcgggac   300
agagtgaccg gcgcctttga tatttggggc cagggcacca tggtcaccgt gtccagtgct   360
tctaccaagg gacccagcgt gttccctctg gctccttgct ccagatccac ctccgagtct   420
acagctgctc tgggctgtct ggtcaaggac tacttccctg agcctgtgac cgtgtcctgg   480
aattctggcg ctctgacatc tggcgtgcac acctttccag ctgtgctgca gtctgctggc   540
ctgtactctc tgtcctccgt cgtgaccgtg ccttcctcta ctttggcac ccagacctac   600
acctgtaatg tggaccacaa gccatccaac accaaggtgg acaagaccgt ggaacggaag   660
tgctgcgtg aatgccctcc ttgtcctgct cctcctgtgg ctggcccttc cgtgtttctg   720
ttccctccaa agcctaagga caccctgatg atctctcgga cccctgaagt gacctgcgtg   780
gtggtggatg tgtctcacga ggatcccgag gtgcagttca attggtacgt ggacggcgtg   840
gaagtgcaca cgccaagac caagcctaga gaggaacagt tcaactccac cttcagagtg   900
gtgtccgtgc tgaccgtggt gcatcaggat tggctgaacg gcaaagagta caagtgcaag   960
gtgtccaaca agggcctgcc tgctcctatc gaaaagacca tctctaagc caaggggcag   1020
ccccgggaac ctcaggttta cacactgcct ccaagccggg aagagatgac caagaaccag   1080
gtgtccctga cctgtctcgt gaagggcttc taccctccg atatcgccgt ggaatgggag   1140
tctaatggcc agcctgagaa caactacaag accacacctc ctatgctgga ctccgacggc   1200
tcattcttcc tgtactccaa gctgacagtg gacaagtcca gatggcagca gggcaacgtg   1260
ttctcctgct ccgtgatgca cgaggccctg cacaatcact acacccagaa gtccctgtct   1320
ctgtcccctg aaaaggcgg cggaggatct ggcggaggcg gtagcggtgg tggcggatct   1380
gaagttcagc tggttgaatc tggcggcgga ctggttcaac caggcggatc tctgagactg   1440
tcttgtgccg cctccggctt caccttctcc tcttacgcta tgtcctgggt ccgacaggcc   1500
ccaggcaaag gattggagtg ggtgtcccag atctctccag ctggcggcta caccaattac   1560
gccgactctg tgaagggcag attcaccatc tctgccgaca cctccaagaa caccgcctac   1620
ctgcagatga actccctgag agccgaggac accgccgtgt actattgtgc tagaggcgag   1680
ctgccctact tccagatgtc caaagtgatg gacgtgtggg gacagggaac cctcgtgaca   1740
gtttctagcg gtggcggagg tagcggaggc ggtggaagcg gcggaggcgg aagtgatatt   1800
cagatgaccc agtctccttc cagcctgtcc gcttctgtgg gcgatagagt gaccatcacc   1860
tgtcgggcct ctcagtactt ctactcctat ctggcttggt atcagcagaa gcctggcaag   1920
gcccctaagc tgctgatcta cggcgcttct gctagagctt ccggcgtgcc ctccagattt   1980
tctggctctg gatctggcac cgactttacc ctgacaatct ccagcctgca gcctgaggac   2040
ttcgccacct actactgcca gcagtacctg gcctctcctg ccacatttgg ccagggaaca   2100
aaggtcgaga tcaagcgctg a                                             2121
```

```
SEQ ID NO: 20        moltype = DNA   length = 2133
FEATURE              Location/Qualifiers
misc_feature         1..2133
                     note = Synthetic
source               1..2133
                     mol_type = other DNA
                     organism = synthetic construct
SEQUENCE: 20
caggttcagc tgcaagagtc tggccctggc ctggtcaagc cttccgaaac actgtctctg   60
acctgcaccg tgtctggcgg ctctgtgtcc tctggcgatt actactggac ctggatccgg   120
cagtctcctg gcaaaggcct ggaatggatc ggccacatct actactccgg caacaccaac   180
tacaacccca gcctgaagtc ccggctgacc atctccatcg acaccagcaa gacccagttc   240
tccctgaagc tgtcctctgt gaccgccgct gataccgcca tctactattg cgtgcgggac   300
agagtgaccg gcgcctttga tatttggggc cagggcacca tggtcaccgt gtccagtgct   360
tctaccaagg gacccagcgt gttccctctg gctccttgct ccagtctcac ctctggcgga   420
acagctgctc tgggctgtct ggtcaaggac tacttccctg agcctgtgac cgtgtcctgg   480
aattctggcg ctctgacatc tggcgtgcac acctttccag ctgtgctgca gtctagcggc   540
ctgtactctc tgtcctccgt cgtgaccgtg ccttctagct ctctgggcac ccagacctac   600
atctgcaatg tgaaccacaa gccatccaac accaaggtgg acaagaaggt ggaacccaag   660
tcctgcgaca gacccacac ctgtcctcca tgtcctgctc cagaactgct cggcggacct   720
tccgtgttcc tgtttcctcc aaagcctaag gacaccctga tgatctctcg gacccctgaa   780
gtgacctgcg tggtggtgga tgtgtctcac gaggatcccg aagtgaagtt caattggtac   840
gtggacggcg tggaagtgca caacgccaag accaagccta gagaggaaca gtacaactcc   900
acctacagag tggtgtccgt gctgaccgtg ctgcaccagg attggctgaa cggcaaagag   960
tacaagtgca aggtgtccaa caaggccctg cctgctccta tcgaaaagac catcagcaag   1020
```

```
gctaagggcc agcctcggga accccaggtt tacacattgc ctccatctcg ggacgagctg   1080
accaagaacc aggtgtccct gacctgtctc gtgaagggct tctacccctc cgatatcgcc   1140
gtggaatggg agtccaatgg ccagcctgag aacaactaca agacaacccc tcctgtgctg   1200
gactccgacg gctcattctt cctgtactcc aagctgacag tggacaagtc cagatggcag   1260
cagggcaacg tgttctcctg ctccgtgatg cacgaggccc tgcacaatca ctacacccag   1320
aagtccctgt ctctgtcccc tggaaaaggc ggcggaggat ctggcggagg tggaagcgga   1380
ggcggtggat ctgaagtgca gctggttgaa agtggcggcg gattggttca gcctggcgga   1440
tctctgagac tgtcttgtgc cgcctccggc tttaccttct cctcctacgc tatgtcctgg   1500
gtccgacagg ctcccggaaa aggacttgaa tgggtgtccc agatctcccc tgctggcggc   1560
tacaccaatt acgccgactc tgtgaagggc agattcacca tctctgccga cacctccaag   1620
aacaccgcct acctgcagat gaactccctg agagccgagg acaccgccgt gtactattgt   1680
gctagaggcg agctgcccta cttccggatg tccaaagtga tggacgtgtg gggacaggga   1740
accctcgtga cagtttctag tggtggcgga ggaagcggcg gaggcggttc tggcggtggt   1800
ggatctgata tccagatgac ccagtctcct agcagcctgt ctgcctctgt gggcgataga   1860
gtgaccatca cctgtcgggc ctctcagttc ctgtccagct acctggcttg gtatcagcag   1920
aagcctggca aggcccctaa gctgctgatc tacggcgctt ctgctagagc ttccggcgtg   1980
ccctccagat tttctggctc tggatctggc accgacttta ccctgacaat ctccagcctg   2040
cagcctgagg acttcgccac ctactactgc cagcagtacc tggcctctcc tgccacattt   2100
ggccagggaa caaaggtcga gatcaagcgc tga                                  2133

SEQ ID NO: 21          moltype = DNA  length = 2118
FEATURE                Location/Qualifiers
misc_feature           1..2118
                       note = Synthetic
source                 1..2118
                       mol_type = other DNA
                       organism = synthetic construct
SEQUENCE: 21
caggttcagc tgcaagagtc tggccctggc ctggtcaagc cttccgaaac actgtctctg   60
acctgcaccg tgtctggcgg ctctgtgtcc tctggcgatt actactggac ctggatccgg   120
cagtctcctg gcaaaggcct ggaatggatc ggccacatct actactccgg caacaccaac   180
tacaacccca gcctgaagtc ccggctgacc atctccatcg acaccagcaa gacccagttc   240
tccctgaagc tgtcctctgt gaccgccgct gataccgcca tctactattg cgtgcgggac   300
agagtgaccg gcgcctttga tatttggggc cagggcacca tggtcaccgt gtccagtgct   360
tctaccaagg gacccagcgt gttccctctg gctccttcca gcaagtctac ctctggcgga   420
acagctgctc tgggctgtct ggtcaaggac tacttccctg agcctgtgac cgtgtcctgg   480
aattctggcg ctctgacatc tggcgtgcac acctttccag ctgtgctgca gtctagcggc   540
ctgtactctc tgtcctccgt cgtgaccgtg ccttctagct ctctgggcac ccagacctac   600
atctgcaatg tgaaccacaa gccatccaac accaaggtgg acaagaaggt ggaacccaag   660
tcctgcgaca gaacccacac ctgtcctcca tgtcctgctc cagaactgct cggcggacct   720
tccgtgttcc tgtttcctcc aaagcctaag gacaccctga tgatctctcg gacccctgaa   780
gtgacctgcg tggtggtgga tgtgtctcac gaggatcccg aagtgaagtt caattggtac   840
gtggacggcg tggaagtgca caacgccaag accaagccta gagaggaaca gtacaactcc   900
acctacagag tggtgtccgt gctgaccgtg ctgcaccagg attggctgaa cggcaaagag   960
tacaagtgca aggtgtccaa caaggccctg cctgctccta tcgaaaagac catcagcaag   1020
gctaaggccc agcctcggga accccaggtt tacacattgc ctccatctcg ggacgagctg   1080
accaagaacc aggtgtccct gacctgtctc gtgaagggct tctacccctc cgatatcgcc   1140
gtggaatggg agtccaatgg ccagcctgag aacaactaca agacaacccc tcctgtgctg   1200
gactccgacg gctcattctt cctgtactcc aagctgacag tggacaagtc cagatggcag   1260
cagggcaacg tgttctcctg ctccgtgatg cacgaggccc tgcacaatca ctacacccag   1320
aagtccctgt ctctgtcccc tggaaaaggc ggcggaggat ctggcggagg tggaagcgga   1380
ggcggtggat ctgaagtgca gctggttgaa agtggcggcg gattggttca gcctggcgga   1440
tctctgagac tgtcttgtgc cgcctccggc tttaccttct cctcctacgc tatgtcctgg   1500
gtccgacagg ctcccggaaa aggacttgaa tgggtgtccc agatctcccc tgctggcggc   1560
tacaccaatt acgccgactc tgtgaagggc agattcacca tctctgccga cacctccaag   1620
aacaccgcct acctgcagat gaactccctg agagccgagg acaccgccgt gtactattgt   1680
gctagaggcg agctgcccta cttccggatg tccaaagtga tggacgtgtg gggacaggga   1740
accctcgtga cagtgtctag cggagatgga tctagtggtg cgcggaggcgc ttccgacatc   1800
cagatgacac agtctccctc cagcctgtct gcctctgtgg gcgatagagt gaccatcacc   1860
tgtcgggcct ctcagttcct gtccagctac ctggcttggt atcagcagaa gcctggcaag   1920
gcccctaagc tgctgatcta cggcgcttct gctagagctt ccggcgtgcc ctccagattt   1980
tctggctctg gatctggcac cgactttacc ctgacaatca gcagcctgca gcctgaggac   2040
ttcgccacct actactgcca gcagtacctg gcctctcctg ccacatttgg ccagggaaca   2100
aaggtcgaga tcaagtga                                                   2118

SEQ ID NO: 22          moltype = DNA  length = 2145
FEATURE                Location/Qualifiers
misc_feature           1..2145
                       note = Synthetic
source                 1..2145
                       mol_type = other DNA
                       organism = synthetic construct
SEQUENCE: 22
caggttcagc tgcaagagtc tggccctggc ctggtcaagc cttccgaaac actgtctctg   60
acctgcaccg tgtctggcgg ctctgtgtcc tctggcgatt actactggac ctggatccgg   120
cagtctcctg gcaaaggcct ggaatggatc ggccacatct actactccgg caacaccaac   180
tacaacccca gcctgaagtc ccggctgacc atctccatcg acaccagcaa gacccagttc   240
tccctgaagc tgtcctctgt gaccgccgct gataccgcca tctactattg cgtgcgggac   300
agagtgaccg gcgcctttga tatttggggc cagggcacca tggtcaccgt gtccagtgct   360
```

```
tctaccaagg gacccagcgt gttccctctg gctccttcca gcaagtctac ctctggcgga    420
acagctgctc tgggctgtct ggtcaaggac tacttccctg agcctgtgac cgtgtcctgg    480
aattctggcg ctctgacatc tggcgtgcac acctttccag ctgtgctgca gtctagcggc    540
ctgtactctc tgtcctccgt cgtgaccgtg ccttctagct ctctgggcac ccagacctac    600
atctgcaatg tgaaccacaa gccatccaac accaaggtgg acaagaaggt ggaacccaag    660
tcctgcgaca gacccacac ctgtcctcca tgtcctgctc cagaactgct cggcggacct    720
tccgtgttcc tgtttcctcc aaagcctaag gacaccctga tgatctctcg gacccctgaa    780
gtgacctgcg tggtggtgga tgtgtctcac gaggatcccg aagtgaagtt caattggtac    840
gtggacggcg tggaagtgca caacgccaag accaagccta gagaggaaca gtacaactcc    900
acctacagag tggtgtccgt gctgaccgtg ctgcaccagg attggctgaa cggcaaagag    960
tacaagtgca aggtgtccaa caaggccctg cctgctccta tcgaaaagac catcagcaag   1020
gctaagggcc agcctcggga accccaggtt tacacattgc ctccatctcg ggacgagctg   1080
accaagaacc aggtgtccct gacctgtctc gtgaagggct ctacccctc cgatatcgcc   1140
gtggaatggg agtccaatgg ccagcctgag aacaactaca agacaacccc tcctgtgctg   1200
gactccgacg gctcattctt cctgtactcc aagctgacag tggacaagtc cagatggcag   1260
cagggcaacg tgttctcctg ctccgtgatg cacgaggccc tgcacaatca ctacacccag   1320
aagtccctgt ctctgtcccc tggaaaaggc ggcggaggat ctggcggagg tggaagcgga   1380
ggcggtggat ctgaagtgca gctggttgaa agtggcggcg gattggttca gcctggcgga   1440
tctctgagac tgtcttgtgc cgcctccggc tttaccttct cctcctacgc tatgtcctgg   1500
gtccgacagg ctcccggaaa aggacttgaa tgggtgtccc agatctcccc tgctggcggc   1560
tacaccaatt acgccgactc tgtgaagggc agattcacca tctctgccga cacctccaag   1620
aacaccgcct acctgcagat gaactccctg agagccgagg acaccgccgt gtactattgt   1680
gctagaggcg agctgcccta cttccggatg tccaaagtga tggacgtgtg gggacaggga   1740
accctcgtga cagtttctag tggtggcgga ggaagcggcg gaggcggttc tggcggtggt   1800
ggctctggcg tgtgcggatc tgatatccag atgacccagt ctcctagcag cctgtctgcc   1860
tctgtgggcg atagagtgac catcacctgt cgggcctctc agttcctgtc cagctacctg   1920
gcttggtatc agcagaagcc tggcaaggcc cctaagctgc tgatctacgg cgcttctgct   1980
agagcttccg gcgtgccctc cagattctct ggctctggat ctggcaccga ctttaccctg   2040
acaatctcca gcctgcagcc tgaggacttc gccacctact actgccagca gtacctggcc   2100
tctcctgcca catttggcca gggaacaaag gtcgagatca agtga                   2145
```

```
SEQ ID NO: 23              moltype = DNA  length = 2130
FEATURE                    Location/Qualifiers
misc_feature               1..2130
                           note = Synthetic
source                     1..2130
                           mol_type = other DNA
                           organism = synthetic construct
SEQUENCE: 23
caggttcagc tgcaagagtc tggccctggc ctggtcaagc cttccgaaac actgtctctg     60
acctgcaccg tgtctggcgg ctctgtgtcc tctggcgatt actactggac ctggatccgg    120
cagtctcctg gcaaaggcct ggaatggatc ggccacatct actactccgg caacaccaac    180
tacaacccca gcctgaagtc ccggctgacc atctccatcg acacccagca gacccagttc    240
tccctgaagc tgtcctctgt gaccgccgct gataccgcca tctactattg cgtgtcgggac    300
agagtgaccg cgcgcctttga tatttggggc caggccacca tggtcaccgt gtccagtgct    360
tctaccaagg gacccagcgt gttccctctg gctccttcca gcaagtctac ctctggcgga    420
acagctgctc tgggctgtct ggtcaaggac tacttccctg agcctgtgac cgtgtcctgg    480
aattctggcg ctctgacatc tggcgtgcac acctttccag ctgtgctgca gtctagcggc    540
ctgtactctc tgtcctccgt cgtgaccgtg ccttctagct ctctgggcac ccagacctac    600
atctgcaatg tgaaccacaa gccatccaac accaaggtgg acaagaaggt ggaacccaag    660
tcctgcgaca gacccacac ctgtcctcca tgtcctgctc cagaactgct cggcggacct    720
tccgtgttcc tgtttcctcc aaagcctaag gacaccctga tgatctctcg gacccctgaa    780
gtgacctgcg tggtggtgga tgtgtctcac gaggatcccg aagtgaagtt caattggtac    840
gtggacggcg tggaagtgca caacgccaag accaagccta gagaggaaca gtacaactcc    900
acctacagag tggtgtccgt gctgaccgtg ctgcaccagg attggctgaa cggcaaagag    960
tacaagtgca aggtgtccaa caaggccctg cctgctccta tcgaaaagac catcagcaag   1020
gctaagggcc agcctcggga accccaggtt tacacattgc ctccatctcg ggacgagctg   1080
accaagaacc aggtgtccct gacctgtctc gtgaagggct ctacccctc cgatatcgcc   1140
gtggaatggg agtccaatgg ccagcctgag aacaactaca agacaacccc tcctgtgctg   1200
gactccgacg gctcattctt cctgtactcc aagctgacag tggacaagtc cagatggcag   1260
cagggcaacg tgttctcctg ctccgtgatg cacgaggccc tgcacaatca ctacacccag   1320
aagtccctgt ctctgtcccc tggaaaaggc ggcggaggat ctggcggagg tggaagcgga   1380
ggcggtggat ctgatatcca gatgacccag tctcctagca gcctgtctgc ctctgtgggc   1440
gatagagtga ccatcacctg tcgggcctct cagttcctgtc cagctacct ggcttggcct   1500
cagcagaagc ctggcaaggc ccctaagctg ctgatctacg gcgcttctgc tagagcttcc   1560
ggcgtgccct ccagattttc tggctctgga tctggcaccg actttaccct gacaatctcc   1620
agcctgcagc ctgaggactt cgccacctac tactgccagc agtacctggc ctctcctgcc   1680
acatttggcc agggaacaaa ggtggaaatc aaaggtggcg gcggtagtgg tggcggagga   1740
agcggcggag gcggctctga agttcagctt gttgaatctg gcggcggact ggttcagcct   1800
ggcggatctc tgagactgtc ttgtgccgcc agcggcttca ccttctcctc ttacgctatg   1860
tcctgggtcc gacaggcccc aggcaaagga ttggagtggg tgtcccagat ctctcctgct   1920
ggcggctaca ccaattacgc cgactctgtg aagggcagat tcaccatctc tgccgacacc   1980
tccaagaaca ccgcctacct gcagatgaac tccctgagag ccgaggacac cgccgtgtac   2040
tattgtgcta gaggcgagct gccctacttc cggatgtcca agtgatgga cgtgtgggga   2100
cagggaaccc tcgtgacagt gtcctcttga                                    2130
```

```
SEQ ID NO: 24              moltype = DNA  length = 2130
FEATURE                    Location/Qualifiers
misc_feature               1..2130
```

```
                            note = Synthetic
source                      1..2130
                            mol_type = other DNA
                            organism = synthetic construct
SEQUENCE: 24
caggttcagc tgcaagagtc tggccctggc ctggtcaagc cttccgaaac actgtctctg   60
acctgcaccg tgtctggcgg ctctgtgtcc tctggcgatt actactggac ctggatccgg  120
cagtctcctg gcaaaggcct ggaatggatc ggccacatct actactccgg caacaccaac  180
tacaacccca gcctgaagtc ccggctgacc atctccatcg acaccagcaa gacccagttc  240
tccctgaagc tgtcctctgt gaccgccgct gataccgcca tctactattg cgtgcgggac  300
agagtgaccg gcgcctttga tatttggggc cagggcacca tggtcaccgt gtccagtgct  360
tctaccaagg gacccagcgt gttccctctg gctccttcca gcaagtctac ctctggcgga  420
acagctgctc tgggctgtct ggtcaaggac tacttccctg agcctgtgac cgtgtcctgg  480
aattctggcg ctctgacatc tggcgtgcac acctttccag ctgtgctgca gtctagcggc  540
ctgtactctc tgtcctccgt cgtgaccgtg ccttctagct ctctgggcac ccagacctac  600
atctgcaatg tgaaccacaa gccatccaac accaaggtgg acaagaaggt ggaacccaag  660
tcctgcgaca gacccacac ctgtcctcca tgtcctgctc cagaactgct cggcggacct  720
tccgtgttcc tgtttcctcc aaagcctaag gacaccctga tgatctctcg gacccctgaa  780
gtgacctgcg tggtggtgga tgtgtctcac gaggatcccg aagtgaagtt caattggtac  840
gtggacggcg tggaagtgca caacgccaag accaagccta gagaggaaca gtacaactcc  900
acctacagag tggtgtccgt gctgaccgtg ctgcaccagg attggctgaa cggcaaagag  960
tacaagtgca aggtgtccaa caaggccctg cctgctccta tcgaaaagac catcagcaag 1020
gctaagggcc agcctcggga accccaggtt tacacattgc ctccatctcg ggacgagctg 1080
accaagaacc aggtgtccct gacctgtctg gtgaagggct tctaccctc cgatatcgcc 1140
gtggaatggg agtccaatgg ccagcctgag aacaactaca agacaacccc tcctgtgctg 1200
gactccgacg gctcattctt cctgtactcc aagctgacag tggacaagtc cagatggcag 1260
cagggcaacg tgttcctg ctccgtgatg cacgaggccc tgcacaatca ctacacccag 1320
aagtccctgt ctctgtcccc tggaaaaggc ggcggaggat ctggcggagg tggaagcgga 1380
ggcggtggat ctgaagtgca gctgttggaa agtggcggcg gattggttca gcctggcgga 1440
tctctgagac tgtcttgtgc cgcctccggc tttaccttct cctcctacgc tatgtcctgg 1500
gtccgacagg ctcccggaaa aggacttgaa tgggtgtccc agatctcccc tgctggcggc 1560
tacaccaatt acgccgactc tgtgaaggc agattcacca tctctcggga caactccaag 1620
aacaccctgt acctgcagat gaactccctg agagccgagg acaccgccgt gtactattgt 1680
gctagaggcg agctgccta cttccggatg tccaaagtga tggacgtgtg gggacaggga 1740
accctcgtga cagtttctag tggtggcgga ggaagcggcg gaggcggttc tggcggtggc 1800
ggatctgaaa ttgtgctgac ccagtctcca ggcacactca gtttgagccc tggcgagaga 1860
gctaccctga ctgtagagc ctctcagttc ctgtccagct acctggcttg gtatcagcag 1920
aagccaggac aggcccctcg gctgttgatc tatggcgctt ctgctagagc cagcggcatc 1980
cctgatagat tctccggctc tggctctggc accgacttca ccctgacaat ctcccggctg 2040
gaacctgagg acttcgctgt gtactactgc cagcagtacc tggcctctcc tgccacattt 2100
ggccagggaa caaaggtcga gatcaagtga                                    2130

SEQ ID NO: 25            moltype = DNA  length = 642
FEATURE                  Location/Qualifiers
misc_feature             1..642
                         note = Synthetic
source                   1..642
                         mol_type = other DNA
                         organism = synthetic construct
SEQUENCE: 25
gacatccaga tgacccagtc tccatcatcc ctgtcggcct cagtgggcga cagagtgacc   60
atcacttgtc aagcctccca agacattagc aactacctga ctggtaccga gcagaagccc  120
ggaaaggccc cgaagctgct catctatgac gcttccaacc ttgagactgg agtgccttcg  180
cgcttctccg gctccgggag cggtaccgat ttcaccttca ccatctcctc cctgcaaccc  240
gaggacattg cgacttactt ctgccaacat ttcgatcaac tccctctcgc gttcggcggc  300
ggaactaagg tcgagattaa gcggaccgtg gctgccccgt ccgtgttcat cttcccgccg  360
tccgatgaac agctgaagtc cggtaccgca tcagtcgtgt gcttgctgaa caacttctac  420
ccccgggaag ccaaggtcca gtggaaagtg gacaatgcgc tgcagtcggg aaaactcgcag  480
gaatccgtga ccgaacagga ttcgaaggac agcacataca gcctgtcatc caccctcacg  540
ctgtcgaagg ccgactacga gaagcacaaa gtgtacgcct gcgaagtgac ccaccaaggg  600
cttagcagcc ctgtgaccaa gtccttcaac cgcggagagt gc                      642

SEQ ID NO: 26            moltype = DNA  length = 15
FEATURE                  Location/Qualifiers
misc_feature             1..15
                         note = Synthetic
source                   1..15
                         mol_type = other DNA
                         organism = synthetic construct
SEQUENCE: 26
ggcggtggcg gatcc                                                     15

SEQ ID NO: 27            moltype = DNA  length = 15
FEATURE                  Location/Qualifiers
misc_feature             1..15
                         note = Synthetic
source                   1..15
                         mol_type = other DNA
                         organism = synthetic construct
```

```
SEQUENCE: 27
ggcggcgggg gcagc                                                     15

SEQ ID NO: 28          moltype = DNA   length = 15
FEATURE                Location/Qualifiers
misc_feature           1..15
                       note = Synthetic
source                 1..15
                       mol_type = other DNA
                       organism = synthetic construct
SEQUENCE: 28
ggcggcggag gatct                                                     15

SEQ ID NO: 29          moltype = DNA   length = 15
FEATURE                Location/Qualifiers
misc_feature           1..15
                       note = Synthetic
source                 1..15
                       mol_type = other DNA
                       organism = synthetic construct
SEQUENCE: 29
ggcggaggcg gtagc                                                     15

SEQ ID NO: 30          moltype = DNA   length = 15
FEATURE                Location/Qualifiers
misc_feature           1..15
                       note = Synthetic
source                 1..15
                       mol_type = other DNA
                       organism = synthetic construct
SEQUENCE: 30
ggtggtggcg gatct                                                     15

SEQ ID NO: 31          moltype = DNA   length = 15
FEATURE                Location/Qualifiers
misc_feature           1..15
                       note = Synthetic
source                 1..15
                       mol_type = other DNA
                       organism = synthetic construct
SEQUENCE: 31
ggcggcggag gatct                                                     15

SEQ ID NO: 32          moltype = DNA   length = 15
FEATURE                Location/Qualifiers
misc_feature           1..15
                       note = Synthetic
source                 1..15
                       mol_type = other DNA
                       organism = synthetic construct
SEQUENCE: 32
ggcggaggtg gaagc                                                     15

SEQ ID NO: 33          moltype = DNA   length = 15
FEATURE                Location/Qualifiers
misc_feature           1..15
                       note = Synthetic
source                 1..15
                       mol_type = other DNA
                       organism = synthetic construct
SEQUENCE: 33
ggaggcggtg gatct                                                     15

SEQ ID NO: 34          moltype = DNA   length = 15
FEATURE                Location/Qualifiers
misc_feature           1..15
                       note = Synthetic
source                 1..15
                       mol_type = other DNA
                       organism = synthetic construct
SEQUENCE: 34
ggtggcggag gaagc                                                     15

SEQ ID NO: 35          moltype = DNA   length = 15
FEATURE                Location/Qualifiers
misc_feature           1..15
                       note = Synthetic
source                 1..15
                       mol_type = other DNA
```

```
                          organism = synthetic construct
SEQUENCE: 35
ggcggaggcg gttct                                                            15

SEQ ID NO: 36             moltype = DNA   length = 15
FEATURE                   Location/Qualifiers
misc_feature              1..15
                          note = Synthetic
source                    1..15
                          mol_type = other DNA
                          organism = synthetic construct
SEQUENCE: 36
ggcggtggcg gatct                                                            15

SEQ ID NO: 37             moltype = DNA   length = 15
FEATURE                   Location/Qualifiers
misc_feature              1..15
                          note = Synthetic
source                    1..15
                          mol_type = other DNA
                          organism = synthetic construct
SEQUENCE: 37
ggcggtggcg gatcc                                                            15

SEQ ID NO: 38             moltype = DNA   length = 15
FEATURE                   Location/Qualifiers
misc_feature              1..15
                          note = Synthetic
source                    1..15
                          mol_type = other DNA
                          organism = synthetic construct
SEQUENCE: 38
ggcggcgggg gcagc                                                            15

SEQ ID NO: 39             moltype = AA   length = 709
FEATURE                   Location/Qualifiers
REGION                    1..709
                          note = Synthetic
source                    1..709
                          mol_type = protein
                          organism = synthetic construct
SEQUENCE: 39
QVQLQESGPG LVKPSETLSL TCTVSGGSVS SGDYYWTWIR QSPGKGLEWI GHIYYSGNTN    60
YNPSLKSRLT ISIDTSKTQF SLKLSSVTAA DTAIYYCVRD RVTGAFDIWG QGTMVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKKVEPK SCDKTHTCPP CPAPELLGGP   240
SVFLFPPKPK DTLMISRTPE VTCVVVDVSH EDPEVKFNWY VDGVEVHNAK TKPREEQYNS   300
TYRVVSVLTV LHQDWLNGKE YKCKVSNKAL PAPIEKTISK AKGQPREPQV YTLPPSRDEL   360
TKNQVSLTCL VKGFYPSDIA VEWESNGQPE NNYKTTPPVL DSDGSFFLYS KLTVDKSRWQ   420
QGNVFSCSVM HEALHNHYTQ KSLSLSPGKG GGGSGGGGSG GGGSEVQLLE SGGGLVQPGG   480
SLRLSCAASG FTFSSYAMSW VRQAPGKGLE WVSQISPAGG YTNYADSVKG RFTISRDNSK   540
NTLYLQMNSL RAEDTAVYYC ARGELPYHRM SKVMDVWGQG TLVTVSSGGG GSGGGGSGGG   600
GSEIVLTQSP GTLSLSPGER ATLSCRASQF LSSYLAWYQQ KPGQAPRLLI YGASARASGI   660
PDRFSGSGSG TDFTLTISRL EPEDFAVYYC QQYLASPATF GQGTKVEIK             709

SEQ ID NO: 40             moltype = DNA   length = 2127
FEATURE                   Location/Qualifiers
misc_feature              1..2127
                          note = Synthetic
source                    1..2127
                          mol_type = other DNA
                          organism = synthetic construct
SEQUENCE: 40
caggttcagc tgcaagagtc tggccctggc ctggtcaagc cttccgaaac actgtctctg    60
acctgcaccg tgtctggcgg ctctgtgtcc tctggcgatt actactggac ctggatccgg   120
cagtctcctg gcaaaggcct ggaatggatc ggccacatct actactccgg caacaccaac   180
tacaacccca gcctgaagtc ccggctgacc atctccatcg acaccagcaa gacccagttc   240
tccctgaagc tgtcctctgt gaccgccgct gataccgcca tctactattg cgtgcgggac   300
agagtgaccg gcgcctttga tatttgtggc cagggcacca tggtcaccgt gtccagtgct   360
tctaccaagg gccccagcgt gttccctctg gctcctcca gcaagtctac ctctggcgga    420
acagctgctc tgggctgtct ggtcaaggac tacttccctg agcctgtgac cgtgtcctgg   480
aattctggcg ctctgacatc tggcgtgcac acctttccag ctgtgctgca gtctagcggc   540
ctgtactctc tgtcctccgt cgtgaccgtg ccttctagct ctctgggcac ccagacctac   600
atctgcaatg tgaaccacaa gccatccaac accaaggtgg acaagaaggt ggaacccaag   660
tcctgcgaca gaacccacac ctgtcctcca tgtcctgctc cagaactgct cggcggacct   720
tccgtgttcc tgtttcctcc aaagcctaag gacaccctga tgatctctcg gacccctgaa   780
gtgacctgcg tggtggtgga tgtgtctcac gaggatcccg aagtgaagtt caattggtac   840
gtggacggcg tggaagtgca caacgccaag accaagccta gagaggaaca gtacaactcc   900
acctacagag tggtgtccgt gctgaccgtg ctgcaccagg attggctgaa cggcaaagag   960
```

-continued

```
tacaagtgca aggtgtccaa caaggccctg cctgctccta tcgaaaagac catcagcaag  1020
gctaagggcc agcctcggga accccaggtt tacacattgc ctccatctcg ggacgagctg  1080
accaagaacc aggtgtccct gacctgtctc gtgaagggct tctacccctc cgatatcgcc  1140
gtggaatggg agtccaatgg ccagcctgag aacaactaca agacaacccc tcctgtgctg  1200
gactccgacg gctcattctt cctgtactcc aagctgacag tggacaagtc cagatggcag  1260
cagggcaacg tgttctcctg ctccgtgatg cacgaggccc tgcacaatca ctacacccag  1320
aagtccctgt ctctgtcccc tggaaaaggc ggcggaggat ctggcggagg tggaagcgga  1380
ggcggtggat ctgaagtgca gctgttggaa agtggcggcg gattggttca gcctggcgga  1440
tctctgagac tgtcttgtgc cgcctccggc tttaccttct cctcctacgc tatgtcctgg  1500
gtccgacagg ctcccggaaa aggacttgaa tgggtgtccc agatctcccc tgctggcggc  1560
tacaccaatt acgccgactc tgtgaagggc agattcacca tctctcggga caactccaag  1620
aacaccctgt acctgcagat gaactccctg agagccgagg acaccgccgt gtactattgt  1680
gctagaggcg agctgcccta ccaccggatg tccaaagtga tggatgtgtg gggacaggga  1740
accctcgtga cagtctctag tggtggcgga ggaagcggcg gaggcggttc tggcggtggc  1800
ggatctgaaa ttgtgctgac ccagtctcca ggcacactca gtttgagccc tggcgagaga  1860
gctaccctga ctgtagagc ctctcagttc ctgtccagct acctggcttg gtatcagcag  1920
aagccaggac aggcccctcg gctgttgatc tatggcgctt ctgctagagc cagcggcatc  1980
cctgatagat tctccggctc tggctctggc accgacttca ccctgacaat ctcccggctg  2040
gaacctgagg acttcgctgt gtactactgc cagcagtacc tggcctctcc tgccacattt  2100
ggccagggaa caaaggtcga gatcaag                                      2127
```

```
SEQ ID NO: 41            moltype = AA  length = 453
FEATURE                  Location/Qualifiers
REGION                   1..453
                         note = Synthetic
source                   1..453
                         mol_type = protein
                         organism = synthetic construct
SEQUENCE: 41
EVQLVESGGG LVQPGGSLRL SCAASGFTFS SYAMSWVRQA PGKGLEWVSQ ISPAGGYTNY  60
ADSVKGRFTI SADTSKNTAY LQMNSLRAED TAVYYCARGE LPYFRMSKVM DVWGQGTLVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEL  240
LGGPSVFLFP PKPKDTLMIS RTPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
REEMTKNQVS LTCLVKGFYP SDIAVEWESN GQPENNYKTT PPVLDSDGSF FLYSKLTVDK  420
SRWQQGNVFS CSVMHEALHN HYTQKSLSLS PGK                               453
```

```
SEQ ID NO: 42            moltype = AA  length = 453
FEATURE                  Location/Qualifiers
REGION                   1..453
                         note = Synthetic
source                   1..453
                         mol_type = protein
                         organism = synthetic construct
SEQUENCE: 42
EVQLVESGGG LVQPGGSLRL SCAASGFTFS SYAMSWVRQA PGKGLEWVSQ ISPAGGYTNY  60
ADSVKGRFTI SADTSKNTAY LQMNSLRAED TAVYYCARGE LPYYQMSKVM DVWGQGTLVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEL  240
LGGPSVFLFP PKPKDTLMIS RTPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
REEMTKNQVS LTCLVKGFYP SDIAVEWESN GQPENNYKTT PPVLDSDGSF FLYSKLTVDK  420
SRWQQGNVFS CSVMHEALHN HYTQKSLSLS PGK                               453
```

```
SEQ ID NO: 43            moltype = AA  length = 453
FEATURE                  Location/Qualifiers
REGION                   1..453
                         note = Synthetic
source                   1..453
                         mol_type = protein
                         organism = synthetic construct
SEQUENCE: 43
EVQLVESGGG LVQPGGSLRL SCAASGFTFS SYAMSWVRQA PGKGLEWVSQ ISPAGGYTNY  60
ADSVKGRFTI SADTSKNTAY LQMNSLRAED TAVYYCARGE LPFFRMSQVM DVWGQGTLVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEL  240
LGGPSVFLFP PKPKDTLMIS RTPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
REEMTKNQVS LTCLVKGFYP SDIAVEWESN GQPENNYKTT PPVLDSDGSF FLYSKLTVDK  420
SRWQQGNVFS CSVMHEALHN HYTQKSLSLS PGK                               453
```

```
SEQ ID NO: 44            moltype = AA  length = 453
FEATURE                  Location/Qualifiers
REGION                   1..453
                         note = Synthetic
source                   1..453
                         mol_type = protein
                         organism = synthetic construct
```

```
SEQUENCE: 44
EVQLVESGGG LVQPGGSLRL SCAASGFTFS SYAMSWVRQA PGKGLEWVSQ ISPAGGYTNY    60
ADSVKGRFTI SADTSKNTAY LQMNSLRAED TAVYYCARGE LPYFRMSKVM DVWGQGTLVT   120
VSSASTKGPS VFPLAPSSKS TSGGTAALGC LVKDYFPEPV TVSWNSGALT SGVHTFPAVL   180
QSSGLYSLSS VVTVPSSSLG TQTYICNVNH KPSNTKVDKK VEPKSCDKTH TCPPCPAPEL   240
LGGPSVFLFP PKPKDTLMIS RTPEVTCVVV DVSHEDPEVK FNWYVDGVEV HNAKTKPREE   300
QYNSTYRVVS VLTVLHQDWL NGKEYKCKVS NKALPAPIEK TISKAKGQPR EPQVYTLPPS   360
REEMTKNQVS LTCLVKGFYP SDIAVEWESN GQPENNYKTT PPVLDSDGSF FLYSKLTVDK   420
SRWQQGNVFS CSVMHEALHN HYTQKSLSLS PGK                                453

SEQ ID NO: 45            moltype = AA   length = 453
FEATURE                  Location/Qualifiers
REGION                   1..453
                         note = Synthetic
source                   1..453
                         mol_type = protein
                         organism = synthetic construct
SEQUENCE: 45
EVQLLESGGG LVQPGGSLRL SCAASGFTFS SYAMSWVRQA PGKGLEWVSQ ISPAGGYTNY    60
ADSVKGRFTI SRDNSKNTLY LQMNSLRAED TAVYYCARGE LPYFRMSKVM DVWGQGTLVT   120
VSSASTKGPS VFPLAPSSKS TSGGTAALGC LVKDYFPEPV TVSWNSGALT SGVHTFPAVL   180
QSSGLYSLSS VVTVPSSSLG TQTYICNVNH KPSNTKVDKK VEPKSCDKTH TCPPCPAPEL   240
LGGPSVFLFP PKPKDTLMIS RTPEVTCVVV DVSHEDPEVK FNWYVDGVEV HNAKTKPREE   300
QYNSTYRVVS VLTVLHQDWL NGKEYKCKVS NKALPAPIEK TISKAKGQPR EPQVYTLPPS   360
REEMTKNQVS LTCLVKGFYP SDIAVEWESN GQPENNYKTT PPVLDSDGSF FLYSKLTVDK   420
SRWQQGNVFS CSVMHEALHN HYTQKSLSLS PGK                                453

SEQ ID NO: 46            moltype = AA   length = 453
FEATURE                  Location/Qualifiers
REGION                   1..453
                         note = Synthetic
source                   1..453
                         mol_type = protein
                         organism = synthetic construct
SEQUENCE: 46
EVQLLESGGG LVQPGGSLRL SCAASGFTFS SYAMSWVRQA PGKGLEWVSQ ISPAGGYTNY    60
ADSVKGRFTI SRDNSKNTLY LQMNSLRAED TAVYYCARGE LPYYQMSKVM DVWGQGTLVT   120
VSSASTKGPS VFPLAPSSKS TSGGTAALGC LVKDYFPEPV TVSWNSGALT SGVHTFPAVL   180
QSSGLYSLSS VVTVPSSSLG TQTYICNVNH KPSNTKVDKK VEPKSCDKTH TCPPCPAPEL   240
LGGPSVFLFP PKPKDTLMIS RTPEVTCVVV DVSHEDPEVK FNWYVDGVEV HNAKTKPREE   300
QYNSTYRVVS VLTVLHQDWL NGKEYKCKVS NKALPAPIEK TISKAKGQPR EPQVYTLPPS   360
REEMTKNQVS LTCLVKGFYP SDIAVEWESN GQPENNYKTT PPVLDSDGSF FLYSKLTVDK   420
SRWQQGNVFS CSVMHEALHN HYTQKSLSLS PGK                                453

SEQ ID NO: 47            moltype = AA   length = 453
FEATURE                  Location/Qualifiers
REGION                   1..453
                         note = Synthetic
source                   1..453
                         mol_type = protein
                         organism = synthetic construct
SEQUENCE: 47
EVQLLESGGG LVQPGGSLRL SCAASGFTFS SYAMSWVRQA PGKGLEWVSQ ISPAGGYTNY    60
ADSVKGRFTI SRDNSKNTLY LQMNSLRAED TAVYYCARGE LPFFRMSQVM DVWGQGTLVT   120
VSSASTKGPS VFPLAPSSKS TSGGTAALGC LVKDYFPEPV TVSWNSGALT SGVHTFPAVL   180
QSSGLYSLSS VVTVPSSSLG TQTYICNVNH KPSNTKVDKK VEPKSCDKTH TCPPCPAPEL   240
LGGPSVFLFP PKPKDTLMIS RTPEVTCVVV DVSHEDPEVK FNWYVDGVEV HNAKTKPREE   300
QYNSTYRVVS VLTVLHQDWL NGKEYKCKVS NKALPAPIEK TISKAKGQPR EPQVYTLPPS   360
REEMTKNQVS LTCLVKGFYP SDIAVEWESN GQPENNYKTT PPVLDSDGSF FLYSKLTVDK   420
SRWQQGNVFS CSVMHEALHN HYTQKSLSLS PGK                                453

SEQ ID NO: 48            moltype = AA   length = 214
FEATURE                  Location/Qualifiers
REGION                   1..214
                         note = Synthetic
source                   1..214
                         mol_type = protein
                         organism = synthetic construct
SEQUENCE: 48
DIQMTQSPSS LSASVGDRVT ITCRASQFLS SYLAWYQQKP GKAPKLLIYG ASARASGVPS    60
RFSGSGSGTD FTLTISSLQP EDFATYYCQQ YLASPATFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 49            moltype = AA   length = 214
FEATURE                  Location/Qualifiers
REGION                   1..214
                         note = Synthetic
source                   1..214
```

-continued

```
                              mol_type = protein
                              organism = synthetic construct
SEQUENCE: 49
DIQMTQSPSS LSASVGDRVT ITCRASQYFS SYLAWYQQKP GKAPKLLIYG ASARASGVPS    60
RFSGSGSGTD FTLTISSLQP EDFATYYCQQ YLASPATFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 50           moltype = AA  length = 214
FEATURE                 Location/Qualifiers
REGION                  1..214
                        note = Synthetic
source                  1..214
                        mol_type = protein
                        organism = synthetic construct
SEQUENCE: 50
DIQMTQSPSS LSASVGDRVT ITCRASQFLS SYLAWYQQKP GKAPKLLIYG ASARASGVPS    60
RFSGSGSGTD FTLTISSLQP EDFATYYCQQ YLASPATFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 51           moltype = AA  length = 214
FEATURE                 Location/Qualifiers
REGION                  1..214
                        note = Synthetic
source                  1..214
                        mol_type = protein
                        organism = synthetic construct
SEQUENCE: 51
DIQMTQSPSS LSASVGDRVT ITCRASQFLS SFLAWYQQKP GKAPKLLIYG ASARASGVPS    60
RFSGSGSGTD FTLTISSLQP EDFATYYCQQ YLASPATFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 52           moltype = AA  length = 214
FEATURE                 Location/Qualifiers
REGION                  1..214
                        note = Synthetic
source                  1..214
                        mol_type = protein
                        organism = synthetic construct
SEQUENCE: 52
EIVLTQSPGT LSLSPGERAT LSCRASQFLS SYLAWYQQKP GQAPRLLIYG ASARASGIPD    60
RFSGSGSGTD FTLTISRLEP EDFAVYYCQQ YLASPATFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 53           moltype = AA  length = 214
FEATURE                 Location/Qualifiers
REGION                  1..214
                        note = Synthetic
source                  1..214
                        mol_type = protein
                        organism = synthetic construct
SEQUENCE: 53
EIVLTQSPGT LSLSPGERAT LSCRASQFLS SYLAWYQQKP GQAPRLLIYG ASARASGIPD    60
RFSGSGSGTD FTLTISRLEP EDFAVYYCQQ YLASPATFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 54           moltype = AA  length = 214
FEATURE                 Location/Qualifiers
REGION                  1..214
                        note = Synthetic
source                  1..214
                        mol_type = protein
                        organism = synthetic construct
SEQUENCE: 54
EIVLTQSPGT LSLSPGERAT LSCRASQFLS SYLAWYQQKP GQAPRLLIYG ASARASGIPD    60
RFSGSGSGTD FTLTISRLEP EDFAVYYCQQ YLASPATFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 55           moltype = DNA  length = 1359
FEATURE                 Location/Qualifiers
misc_feature            1..1359
                        note = Synthetic
source                  1..1359
                        mol_type = other DNA
```

```
                            organism = synthetic construct
SEQUENCE: 55
gaggtgcagc tggtggagag cggcggcggc ctggtgcagc ccggcggcag cctgaggctg    60
agctgcgccg ccagcggctt caccttcagc agctacgcca tgagctgggt gaggcaggcc   120
cccggcaagg gcctggagtg ggtgagccag atcagccccg ccggcggcta caccaactac   180
gccgacagcg tgaagggcag gttcaccatc agcgccgaca ccagcaagaa caccgcctac   240
ctgcagatga acagcctgag ggccgaggac accgccgtgt actactgcgc caggggcgag   300
ctgccctact tcaggatgag caaggtgatg gacgtgtggg gccagggcac cctggtgacc   360
gtgagcagcg ccagcaccaa gggccccagc gtgttccccc tggcccccag cagcaagagc   420
accagcggcg gcaccgccgc cctgggctgc ctggtgaagg actacttccc cgagcccgtg   480
accgtgagct ggaacagcgg cgccctgacc agcggcgtgc acaccttccc cgccgtgctg   540
cagagcagcg gcctgtacag cctgagcagc gtggtgaccg tgcccagcag cagcctgggc   600
acccagacct acatctgcaa cgtgaaccac aagcccagca acaccaaggt ggacaagaag   660
gtggagccca agagctgcga caagacccac acctgccccc cctgccccgc ccccgagctg   720
ctgggcggcc ccagcgtgtt cctgttcccc cccaagccca aggacaccct gatgatcagc   780
aggacccccg aggtgacctg cgtggtggtg gacgtgagcc acgaggaccc cgaggtgaag   840
ttcaactggt acgtggacgg cgtggaggtg cacaacgcca agaccaagcc cagggaggag   900
cagtacaaca gcacctacag ggtggtgagc gtgctgaccg tgctgcacca ggactggctg   960
aacggcaagg agtacaagtg caaggtgagc aacaaggccc tgcccgcccc catcgagaag  1020
accatcagca aggccaaggg ccagcccagg gagccccagg tgtacaccct gcccccagc    1080
agggaggaga tgaccaagaa ccaggtgagc ctgacctgcc tggtgaaggg cttctacccc  1140
agcgacatcg ccgtggagtg ggagagcaac ggccagcccg agaacaacta caagaccacc  1200
cccccgtgc tggacagcga cggcagcttc ttcctgtaca gcaagctgac cgtggacaag    1260
agcaggtggc agcagggcaa cgtgttcagc tgcagcgtga tgcacgaggc cctgcacaac  1320
cactacaccc agaagagcct gagcctgagc cccggcaag                          1359

SEQ ID NO: 56                  moltype = DNA  length = 1359
FEATURE                        Location/Qualifiers
misc_feature                   1..1359
                               note = Synthetic
source                         1..1359
                               mol_type = other DNA
                               organism = synthetic construct
SEQUENCE: 56
gaggtgcagc tggtggagag cggcggcggc ctggtgcagc ccggcggcag cctgaggctg    60
agctgcgccg ccagcggctt caccttcagc agctacgcca tgagctgggt gaggcaggcc   120
cccggcaagg gcctggagtg ggtgagccag atcagccccg ccggcggcta caccaactac   180
gccgacagcg tgaagggcag gttcaccatc agcgccgaca ccagcaagaa caccgcctac   240
ctgcagatga acagcctgag ggccgaggac accgccgtgt actactgcgc caggggcgag   300
ctgccctact accagatgag caaggtgatg gacgtgtggg gccagggcac cctggtgacc   360
gtgagcagcg ccagcaccaa gggccccagc gtgttccccc tggcccccag cagcaagagc   420
accagcggcg gcaccgccgc cctgggctgc ctggtgaagg actacttccc cgagcccgtg   480
accgtgagct ggaacagcgg cgccctgacc agcggcgtgc acaccttccc cgccgtgctg   540
cagagcagcg gcctgtacag cctgagcagc gtggtgaccg tgcccagcag cagcctgggc   600
acccagacct acatctgcaa cgtgaaccac aagcccagca acaccaaggt ggacaagaag   660
gtggagccca agagctgcga caagacccac acctgccccc cctgccccgc ccccgagctg   720
ctgggcggcc ccagcgtgtt cctgttcccc cccaagccca aggacaccct gatgatcagc   780
aggacccccg aggtgacctg cgtggtggtg gacgtgagcc acgaggaccc cgaggtgaag   840
ttcaactggt acgtggacgg cgtggaggtg cacaacgcca agaccaagcc cagggaggag   900
cagtacaaca gcacctacag ggtggtgagc gtgctgaccg tgctgcacca ggactggctg   960
aacggcaagg agtacaagtg caaggtgagc aacaaggccc tgcccgcccc catcgagaag  1020
accatcagca aggccaaggg ccagcccagg gagccccagg tgtacaccct gcccccagc    1080
agggaggaga tgaccaagaa ccaggtgagc ctgacctgcc tggtgaaggg cttctacccc  1140
agcgacatcg ccgtggagtg ggagagcaac ggccagcccg agaacaacta caagaccacc  1200
cccccgtgc tggacagcga cggcagcttc ttcctgtaca gcaagctgac cgtggacaag    1260
agcaggtggc agcagggcaa cgtgttcagc tgcagcgtga tgcacgaggc cctgcacaac  1320
cactacaccc agaagagcct gagcctgagc cccggcaag                          1359

SEQ ID NO: 57                  moltype = DNA  length = 1359
FEATURE                        Location/Qualifiers
misc_feature                   1..1359
                               note = Synthetic
source                         1..1359
                               mol_type = other DNA
                               organism = synthetic construct
SEQUENCE: 57
gaggtgcagc tggtggagag cggcggcggc ctggtgcagc ccggcggcag cctgaggctg    60
agctgcgccg ccagcggctt caccttcagc agctacgcca tgagctgggt gaggcaggcc   120
cccggcaagg gcctggagtg ggtgagccag atcagccccg ccggcggcta caccaactac   180
gccgacagcg tgaagggcag gttcaccatc agcgccgaca ccagcaagaa caccgcctac   240
ctgcagatga acagcctgag ggccgaggac accgccgtgt actactgcgc caggggcgag   300
ctgcccttct tcaggatgag ccaggtgatg gacgtgtggg gccagggcac cctggtgacc   360
gtgagcagcg ccagcaccaa gggccccagc gtgttccccc tggcccccag cagcaagagc   420
accagcggcg gcaccgccgc cctgggctgc ctggtgaagg actacttccc cgagcccgtg   480
accgtgagct ggaacagcgg cgccctgacc agcggcgtgc acaccttccc cgccgtgctg   540
cagagcagcg gcctgtacag cctgagcagc gtggtgaccg tgcccagcag cagcctgggc   600
acccagacct acatctgcaa cgtgaaccac aagcccagca acaccaaggt ggacaagaag   660
gtggagccca agagctgcga caagacccac acctgccccc cctgccccgc ccccgagctg   720
ctgggcggcc ccagcgtgtt cctgttcccc cccaagccca aggacaccct gatgatcagc   780
```

-continued

```
aggacccccg aggtgacctg cgtggtggtg gacgtgagcc acgaggaccc cgaggtgaag   840
ttcaactggt acgtggacgg cgtggaggtg cacaacgcca agaccaagcc cagggaggag   900
cagtacaaca gcacctacag ggtggtgagc gtgctgaccg tgctgcacca ggactggctg   960
aacggcaagg agtacaagtg caaggtgagc aacaaggccc tgcccgcccc catcgagaag  1020
accatcagca aggccaaggg ccagcccagg gagccccagg tgtacaccct gcccccagc   1080
agggaggaga tgaccaagaa ccaggtgagc ctgacctgcc tggtgaaggg cttctacccc  1140
agcgacatcg ccgtggagtg ggagagcaac ggccagcccg agaacaacta caagaccacc  1200
cccccgtgc tggacagcga cggcagcttc ttcctgtaca gcaagctgac cgtggacaag  1260
agcaggtggc agcagggcaa cgtgttcagc tgcagcgtga tgcacgaggc cctgcacaac  1320
cactacaccc agaagagcct gagcctgagc cccggcaag                         1359
```

```
SEQ ID NO: 58          moltype = DNA   length = 1359
FEATURE                Location/Qualifiers
misc_feature           1..1359
                       note = Synthetic
source                 1..1359
                       mol_type = other DNA
                       organism = synthetic construct
SEQUENCE: 58
gaggtgcagc tggtggagag cggcggcggc ctggtgcagc ccggcggcag cctgaggctg   60
agctgcgccg ccagcggctt caccttcagc agctacgcca tgagctgggt gaggcaggcc  120
cccggcaagg gcctggagtg ggtgagccag atcagccccg ccggcggcta caccaactac  180
gccgacagcg tgaagggcag gttcaccatc agcgccgaca ccagcaagaa caccgcctac  240
ctgcagatga acagcctgag ggccgaggac accgccgtgt actactgcgc caggggcgag  300
ctgccctact tcaggatgag caaggtgatg gacgtgtggg gccagggcac cctggtgacc  360
gtgagcagcg ccagcaccaa gggccccagc gtgttccccc tggcccccag cagcaagagc  420
accagcggcg gcaccgccgc cctgggctgc ctggtgaagg actacttccc cgagcccgtg  480
accgtgagct ggaacagcgg cgccctgacc agcggcgtgc acaccttccc cgccgtgctg  540
cagagcagcg gcctgtacag cctgagcagc gtggtgaccg tgcccagcag cagcctgggc  600
acccagacct acatctgcaa cgtgaaccac aagcccagca acaccaaggt ggacaagagc  660
gtggagccca gagctgcga caagacccac acctgccccc cctgcccgc ccccgagctg   720
ctgggcggcc ccagcgtgtt cctgttcccc cccaagccca aggacaccct gatgatcagc  780
aggacccccg aggtgacctg cgtggtggtg gacgtgagcc acgaggaccc cgaggtgaag   840
ttcaactggt acgtggacgg cgtggaggtg cacaacgcca agaccaagcc cagggaggag   900
cagtacaaca gcacctacag ggtggtgagc gtgctgaccg tgctgcacca ggactggctg   960
aacggcaagg agtacaagtg caaggtgagc aacaaggccc tgcccgcccc catcgagaag  1020
accatcagca aggccaaggg ccagcccagg gagccccagg tgtacaccct gcccccagc   1080
agggaggaga tgaccaagaa ccaggtgagc ctgacctgcc tggtgaaggg cttctacccc  1140
agcgacatcg ccgtggagtg ggagagcaac ggccagcccg agaacaacta caagaccacc  1200
cccccgtgc tggacagcga cggcagcttc ttcctgtaca gcaagctgac cgtggacaag  1260
agcaggtggc agcagggcaa cgtgttcagc tgcagcgtga tgcacgaggc cctgcacaac  1320
cactacaccc agaagagcct gagcctgagc cccggcaag                         1359
```

```
SEQ ID NO: 59          moltype = DNA   length = 1359
FEATURE                Location/Qualifiers
misc_feature           1..1359
                       note = Synthetic
source                 1..1359
                       mol_type = other DNA
                       organism = synthetic construct
SEQUENCE: 59
gaggtgcagc tgctggagag cggcggcggc ctggtgcagc ccggcggcag cctgaggctg   60
agctgcgccg ccagcggctt caccttcagc agctacgcca tgagctgggt gaggcaggcc  120
cccggcaagg gcctggagtg ggtgagccag atcagccccg ccggcggcta caccaactac  180
gccgacagcg tgaagggcag gttcaccatc agcagggaca acagcaagaa caccctgtac  240
ctgcagatga acagcctgag ggccgaggac accgccgtgt actactgcgc caggggcgag  300
ctgccctact tcaggatgag caaggtgatg gacgtgtggg gccagggcac cctggtgacc  360
gtgagcagcg ccagcaccaa gggccccagc gtgttccccc tggcccccag cagcaagagc  420
accagcggcg gcaccgccgc cctgggctgc ctggtgaagg actacttccc cgagcccgtg  480
accgtgagct ggaacagcgg cgccctgacc agcggcgtgc acaccttccc cgccgtgctg  540
cagagcagcg gcctgtacag cctgagcagc gtggtgaccg tgcccagcag cagcctgggc  600
acccagacct acatctgcaa cgtgaaccac aagcccagca acaccaaggt ggacaagaag  660
gtggagccca gagctgcga caagacccac acctgccccc cctgcccgc ccccgagctg   720
ctgggcggcc ccagcgtgtt cctgttcccc cccaagccca aggacaccct gatgatcagc  780
aggacccccg aggtgacctg cgtggtggtg gacgtgagcc acgaggaccc cgaggtgaag   840
ttcaactggt acgtggacgg cgtggaggtg cacaacgcca agaccaagcc cagggaggag   900
cagtacaaca gcacctacag ggtggtgagc gtgctgaccg tgctgcacca ggactggctg   960
aacggcaagg agtacaagtg caaggtgagc aacaaggccc tgcccgcccc catcgagaag  1020
accatcagca aggccaaggg ccagcccagg gagccccagg tgtacaccct gcccccagc   1080
agggaggaga tgaccaagaa ccaggtgagc ctgacctgcc tggtgaaggg cttctacccc  1140
agcgacatcg ccgtggagtg ggagagcaac ggccagcccg agaacaacta caagaccacc  1200
cccccgtgc tggacagcga cggcagcttc ttcctgtaca gcaagctgac cgtggacaag  1260
agcaggtggc agcagggcaa cgtgttcagc tgcagcgtga tgcacgaggc cctgcacaac  1320
cactacaccc agaagagcct gagcctgagc cccggcaag                         1359
```

```
SEQ ID NO: 60          moltype = DNA   length = 1359
FEATURE                Location/Qualifiers
misc_feature           1..1359
                       note = Synthetic
```

103

104

-continued

```
source                   1..1359
                         mol_type = other DNA
                         organism = synthetic construct
SEQUENCE: 60
gaggtgcagc tgctggagag cggcggcggc ctggtgcagc ccggcggcag cctgaggctg   60
agctgcgccg ccagcggctt caccttcagc agctacgcca tgagctgggt gaggcaggcc  120
cccggcaagg gcctggagtg ggtgagccag atcagccccg ccggcggcta caccaactac  180
gccgacagcg tgaagggcag gttcaccatc agcagggaca acagcaagaa caccctgtac  240
ctgcagatga acagcctgag ggccgaggac accgccgtgt actactgcgc cagggggcgag  300
ctgccctact accagatgag caaggtgatg gacgtgtggg gccagggcac cctggtgacc  360
gtgagcagcg ccagcaccaa gggccccagc gtgttccccc tggcccccag cagcaagagc  420
accagcggcg gcaccgccgc cctgggctgc ctggtgaagg actacttccc cgagcccgtg  480
accgtgagct ggaacagcgg cgccctgacc agcggcgtgc acaccttccc cgccgtgctg  540
cagagcagcg gcctgtacag cctgagcagc gtggtgaccg tgcccagcag cagcctgggc  600
acccagacct acatctgcaa cgtgaaccac aagcccagca acaccaaggt ggacaagaag  660
gtggagccca gagctgcga caagacccac acctgcccccc cctgccccgc ccccgagctg  720
ctgggcggcc ccagcgtgtt cctgttcccc cccaagccca aggacaccct gatgatcagc  780
aggacccccg aggtgacctg cgtggtggtg gacgtgagcc acgaggaccc cgaggtgaag  840
ttcaactggt acgtggacgg cgtggaggtg cacaacgcca agaccaagcc cagggaggag  900
cagtacaaca gcacctacag ggtggtgagc gtgctgaccg tgctgcacca ggactggctg  960
aacggcaagg agtacaagtg caaggtgagc aacaaggccc tgcccgcccc catcgagaag 1020
accatcagca aggccaaggg ccagcccagg gagccccagg tgtacaccct gccccccagc 1080
agggaggaga tgaccaagaa ccaggtgagc ctgacctgcc tggtgaaggg cttctacccc 1140
agcgacatcg ccgtggagtg gggagagcaac ggccagcccg agaacaacta caagaccacc 1200
cccccgtgc tggacagcga cggcagcttc ttcctgtaca gcaagctgac cgtggacaag 1260
agcaggtggc agcagggcaa cgtgttcagc tgcagcgtga tgcacgaggc cctgcacaac 1320
cactacaccc agaagagcct gagcctgagc cccggcaag                          1359

SEQ ID NO: 61              moltype = DNA   length = 1359
FEATURE                    Location/Qualifiers
misc_feature               1..1359
                           note = Synthetic
source                     1..1359
                           mol_type = other DNA
                           organism = synthetic construct
SEQUENCE: 61
gaggtgcagc tgctggagag cggcggcggc ctggtgcagc ccggcggcag cctgaggctg   60
agctgcgccg ccagcggctt caccttcagc agctacgcca tgagctgggt gaggcaggcc  120
cccggcaagg gcctggagtg ggtgagccag atcagccccg ccggcggcta caccaactac  180
gccgacagcg tgaagggcag gttcaccatc agcagggaca acagcaagaa caccctgtac  240
ctgcagatga acagcctgag ggccgaggac accgccgtgt actactgcgc cagggggcgag  300
ctgcccttct tcaggatgag ccaggtgatg gacgtgtggg gccagggcac cctggtgacc  360
gtgagcagcg ccagcaccaa gggccccagc gtgttccccc tggcccccag cagcaagagc  420
accagcggcg gcaccgccgc cctgggctgc ctggtgaagg actacttccc cgagcccgtg  480
accgtgagct ggaacagcgg cgccctgacc agcggcgtgc acaccttccc cgccgtgctg  540
cagagcagcg gcctgtacag cctgagcagc gtggtgaccg tgcccagcag cagcctgggc  600
acccagacct acatctgcaa cgtgaaccac aagcccagca acaccaaggt ggacaagaag  660
gtggagccca gagctgcga caagacccac acctgcccccc cctgccccgc ccccgagctg  720
ctgggcggcc ccagcgtgtt cctgttcccc cccaagccca aggacaccct gatgatcagc  780
aggacccccg aggtgacctg cgtggtggtg gacgtgagcc acgaggaccc cgaggtgaag  840
ttcaactggt acgtggacgg cgtggaggtg cacaacgcca agaccaagcc cagggaggag  900
cagtacaaca gcacctacag ggtggtgagc gtgctgaccg tgctgcacca ggactggctg  960
aacggcaagg agtacaagtg caaggtgagc aacaaggccc tgcccgcccc catcgagaag 1020
accatcagca aggccaaggg ccagcccagg gagccccagg tgtacaccct gccccccagc 1080
agggaggaga tgaccaagaa ccaggtgagc ctgacctgcc tggtgaaggg cttctacccc 1140
agcgacatcg ccgtggagtg gggagagcaac ggccagcccg agaacaacta caagaccacc 1200
cccccgtgc tggacagcga cggcagcttc ttcctgtaca gcaagctgac cgtggacaag 1260
agcaggtggc agcagggcaa cgtgttcagc tgcagcgtga tgcacgaggc cctgcacaac 1320
cactacaccc agaagagcct gagcctgagc cccggcaag                          1359

SEQ ID NO: 62              moltype = DNA   length = 642
FEATURE                    Location/Qualifiers
misc_feature               1..642
                           note = Synthetic
source                     1..642
                           mol_type = other DNA
                           organism = synthetic construct
SEQUENCE: 62
gacatccaga tgacccagag cccccagcagc ctgagcgcca gcgtgggcga cagggtgacc   60
atcacctgca gggccagcca gttcctgagc agctacctgg cctggtacca gcagaagccc  120
ggcaaggccc ccaagctgct gatctacggc gccagccgcca gggccagcgg cgtgcccagc  180
aggttcagcg gcagcggcag cggcaccgac ttcaccctga ccatcagcag cctgcagccc  240
gaggacttcg ccacctacta ctgccagcag tacctgccag ccccgccac cttcggccag  300
ggcaccaagg tggagatcaa gaggaccgtg gccgccccca gcgtgttcat cttccccccc  360
agcgacgagc agctgaagag cggcaccgcc agcgtggtgt gcctgctgaa caacttctac  420
cccagggagg ccaaggtgca gtggaaggtg gacaacgccc tgcagagcgg caacagccag  480
gagagcgtga ccgagcagga cagcaaggac agcacctaca gcctgagcag caccctgacc  540
ctgagcaagg ccgactacga gaagcacaag gtgtacgcct gcgaggtgac ccaccagggc  600
ctgagcagcc ccgtgaccaa gagcttcaac aggggcgagt gc                       642
```

```
SEQ ID NO: 63          moltype = DNA  length = 642
FEATURE                Location/Qualifiers
misc_feature           1..642
                       note = Synthetic
source                 1..642
                       mol_type = other DNA
                       organism = synthetic construct
SEQUENCE: 63
gacatccaga tgacccagag ccccagcagc ctgagcgcca gcgtgggcga cagggtgacc   60
atcacctgca gggccagcca gtacttcagc agctacctgg cctggtacca gcagaagccc  120
ggcaaggccc ccaagctgct gatctacggc gccagcgcca gggccagcgg cgtgcccagc  180
aggttcagcg gcagcggcag cggcaccgac ttcaccctga ccatcagcag cctgcagccc  240
gaggacttcg ccacctacta ctgccagcag tacctggcca gccccgccac cttcggccag  300
ggcaccaagg tggagatcaa gaggaccgtg gccgccccca gcgtgttcat cttcccccc   360
agcgacgagc agctgaagag cggcaccgcc agcgtggtgt gcctgctgaa caacttctac  420
cccagggagg ccaaggtgca gtggaaggtg gacaacgccc tgcagagcgg caacagccag  480
gagagcgtga ccgagcagga cagcaaggac agcacctaca gcctgagcag caccctgacc  540
ctgagcaagg ccgactacga gaagcacaag gtgtacgcct gcgaggtgac ccaccagggc  600
ctgagcagcc ccgtgaccaa gagcttcaac aggggcgagt gc                     642

SEQ ID NO: 64          moltype = DNA  length = 642
FEATURE                Location/Qualifiers
misc_feature           1..642
                       note = Synthetic
source                 1..642
                       mol_type = other DNA
                       organism = synthetic construct
SEQUENCE: 64
gacatccaga tgacccagag ccccagcagc ctgagcgcca gcgtgggcga cagggtgacc   60
atcacctgca gggccagcca gttcctgagc agctacctgg cctggtacca gcagaagccc  120
ggcaaggccc ccaagctgct gatctacggc gccagcgcca gggccagcgg cgtgcccagc  180
aggttcagcg gcagcggcag cggcaccgac ttcaccctga ccatcagcag cctgcagccc  240
gaggacttcg ccacctacta ctgccagcag tacctggcca gccccgccac cttcggccag  300
ggcaccaagg tggagatcaa gaggaccgtg gccgccccca gcgtgttcat cttcccccc   360
agcgacgagc agctgaagag cggcaccgcc agcgtggtgt gcctgctgaa caacttctac  420
cccagggagg ccaaggtgca gtggaaggtg gacaacgccc tgcagagcgg caacagccag  480
gagagcgtga ccgagcagga cagcaaggac agcacctaca gcctgagcag caccctgacc  540
ctgagcaagg ccgactacga gaagcacaag gtgtacgcct gcgaggtgac ccaccagggc  600
ctgagcagcc ccgtgaccaa gagcttcaac aggggcgagt gc                     642

SEQ ID NO: 65          moltype = DNA  length = 642
FEATURE                Location/Qualifiers
misc_feature           1..642
                       note = Synthetic
source                 1..642
                       mol_type = other DNA
                       organism = synthetic construct
SEQUENCE: 65
gacatccaga tgacccagag ccccagcagc ctgagcgcca gcgtgggcga cagggtgacc   60
atcacctgca gggccagcca gttcctgagc agcttcctgg cctggtacca gcagaagccc  120
ggcaaggccc ccaagctgct gatctacggc gccagcgcca gggccagcgg cgtgcccagc  180
aggttcagcg gcagcggcag cggcaccgac ttcaccctga ccatcagcag cctgcagccc  240
gaggacttcg ccacctacta ctgccagcag tacctggcca gccccgccac cttcggccag  300
ggcaccaagg tggagatcaa gaggaccgtg gccgccccca gcgtgttcat cttcccccc   360
agcgacgagc agctgaagag cggcaccgcc agcgtggtgt gcctgctgaa caacttctac  420
cccagggagg ccaaggtgca gtggaaggtg gacaacgccc tgcagagcgg caacagccag  480
gagagcgtga ccgagcagga cagcaaggac agcacctaca gcctgagcag caccctgacc  540
ctgagcaagg ccgactacga gaagcacaag gtgtacgcct gcgaggtgac ccaccagggc  600
ctgagcagcc ccgtgaccaa gagcttcaac aggggcgagt gc                     642

SEQ ID NO: 66          moltype = DNA  length = 642
FEATURE                Location/Qualifiers
misc_feature           1..642
                       note = Synthetic
source                 1..642
                       mol_type = other DNA
                       organism = synthetic construct
SEQUENCE: 66
gagatcgtgc tgacccagag ccccggcacc ctgagcctga gccccggcga gagggccacc   60
ctgagctgca gggccagcca gttcctgagc agctacctgg cctggtacca gcagaagccc  120
ggccaggccc ccaggctgct gatctacggc gccagcgcca gggccagcgg catccccgac  180
aggttcagcg gcagcggcag cggcaccgac ttcaccctga ccatcagcag gctggagccc  240
gaggacttcg ccgtgtacta ctgccagcag tacctggcca gccccgccac cttcggccag  300
ggcaccaagg tggagatcaa gaggaccgtg gccgccccca gcgtgttcat cttcccccc   360
agcgacgagc agctgaagag cggcaccgcc agcgtggtgt gcctgctgaa caacttctac  420
cccagggagg ccaaggtgca gtggaaggtg gacaacgccc tgcagagcgg caacagccag  480
gagagcgtga ccgagcagga cagcaaggac agcacctaca gcctgagcag caccctgacc  540
ctgagcaagg ccgactacga gaagcacaag gtgtacgcct gcgaggtgac ccaccagggc  600
```

```
ctgagcagcc ccgtgaccaa gagcttcaac aggggcgagt gc                                642

SEQ ID NO: 67              moltype = DNA   length = 642
FEATURE                    Location/Qualifiers
misc_feature               1..642
                           note = Synthetic
source                     1..642
                           mol_type = other DNA
                           organism = synthetic construct
SEQUENCE: 67
gagatcgtgc tgacccagag ccccggcacc ctgagcctga gccccggcga gagggccacc    60
ctgagctgca gggccagcca gttcctgagc agctacctgg cctggtacca gcagaagccc   120
ggccaggccc ccaggctgct gatctacggc gccagcgcca gggccagcgg catccccgac   180
aggttcagcg gcagcggcag cggcaccgac ttcaccctga ccatcagcag gctggagccc   240
gaggacttcg ccgtgtacta ctgccagcag tacctggcca gccccgccac cttcggccag   300
ggcaccaagg tggagatcaa gaggaccgtg gccgcccca gcgtgttcat cttccccccc   360
agcgacgagc agctgaagag cggcaccgcc agcgtggtgt gcctgctgaa caacttctac   420
cccagggagg ccaaggtgca gtggaaggtg gacaacgccc tgcagagcgg caacagccag   480
gagagcgtga ccgagcagga cagcaaggac agcacctaca gcctgagcag caccctgacc   540
ctgagcaagg ccgactacga gaagcacaag gtgtacgcct gcgaggtgac ccaccagggc   600
ctgagcagcc ccgtgaccaa gagcttcaac aggggcgagt gc                        642

SEQ ID NO: 68              moltype = DNA   length = 642
FEATURE                    Location/Qualifiers
misc_feature               1..642
                           note = Synthetic
source                     1..642
                           mol_type = other DNA
                           organism = synthetic construct
SEQUENCE: 68
gagatcgtgc tgacccagag ccccggcacc ctgagcctga gccccggcga gagggccacc    60
ctgagctgca gggccagcca gttcctgagc agctacctgg cctggtacca gcagaagccc   120
ggccaggccc ccaggctgct gatctacggc gccagcgcca gggccagcgg catccccgac   180
aggttcagcg gcagcggcag cggcaccgac ttcaccctga ccatcagcag gctggagccc   240
gaggacttcg ccgtgtacta ctgccagcag tacctggcca gccccgccac cttcggccag   300
ggcaccaagg tggagatcaa gaggaccgtg gccgcccca gcgtgttcat cttccccccc   360
agcgacgagc agctgaagag cggcaccgcc agcgtggtgt gcctgctgaa caacttctac   420
cccagggagg ccaaggtgca gtggaaggtg gacaacgccc tgcagagcgg caacagccag   480
gagagcgtga ccgagcagga cagcaaggac agcacctaca gcctgagcag caccctgacc   540
ctgagcaagg ccgactacga gaagcacaag gtgtacgcct gcgaggtgac ccaccagggc   600
ctgagcagcc ccgtgaccaa gagcttcaac aggggcgagt gc                        642

SEQ ID NO: 69              moltype = AA   length = 119
FEATURE                    Location/Qualifiers
REGION                     1..119
                           note = Synthetic
source                     1..119
                           mol_type = protein
                           organism = synthetic construct
SEQUENCE: 69
QVQLQESGPG LVKPSETLSL TCTVSGGSVS SGDYYWTWIR QSPGKGLEWI GHIYYSGNTN    60
YNPSLKSRLT ISIDTSKTQF SLKLSSVTAA DTAIYYCVRD RVTGAFDIWG QGTMVTVSS    119

SEQ ID NO: 70              moltype = AA   length = 107
FEATURE                    Location/Qualifiers
REGION                     1..107
                           note = Synthetic
source                     1..107
                           mol_type = protein
                           organism = synthetic construct
SEQUENCE: 70
DIQMTQSPSS LSASVGDRVT ITCQASQDIS NYLNWYQQKP GKAPKLLIYD ASNLETGVPS    60
RFSGSGSGTD FTFTISSLQP EDIATYFCQH FDHLPLAFGG GTKVEIK                  107

SEQ ID NO: 71              moltype = AA   length = 7
FEATURE                    Location/Qualifiers
REGION                     1..7
                           note = Synthetic
source                     1..7
                           mol_type = protein
                           organism = synthetic construct
SEQUENCE: 71
SGDYYWT                                                                 7

SEQ ID NO: 72              moltype = AA   length = 15
FEATURE                    Location/Qualifiers
REGION                     1..15
                           note = Synthetic
source                     1..15
```

```
                        mol_type = protein
                        organism = synthetic construct
SEQUENCE: 72
HIYYSGNTNY NPSLK                                              15

SEQ ID NO: 73          moltype = AA   length = 8
FEATURE                Location/Qualifiers
REGION                 1..8
                       note = Synthetic
source                 1..8
                       mol_type = protein
                       organism = synthetic construct
SEQUENCE: 73
RVTGAFDI                                                      8

SEQ ID NO: 74          moltype = AA   length = 10
FEATURE                Location/Qualifiers
REGION                 1..10
                       note = Synthetic
source                 1..10
                       mol_type = protein
                       organism = synthetic construct
SEQUENCE: 74
QASQDISNYL                                                    10

SEQ ID NO: 75          moltype = AA   length = 6
FEATURE                Location/Qualifiers
REGION                 1..6
                       note = Synthetic
source                 1..6
                       mol_type = protein
                       organism = synthetic construct
SEQUENCE: 75
ASNLET                                                        6

SEQ ID NO: 76          moltype = AA   length = 9
FEATURE                Location/Qualifiers
REGION                 1..9
                       note = Synthetic
source                 1..9
                       mol_type = protein
                       organism = synthetic construct
SEQUENCE: 76
QHFDHLPLA                                                     9

SEQ ID NO: 77          moltype = AA   length = 123
FEATURE                Location/Qualifiers
REGION                 1..123
                       note = Synthetic
source                 1..123
                       mol_type = protein
                       organism = synthetic construct
SEQUENCE: 77
EVQLLESGGG LVQPGGSLRL SCAASGFTFS SYAMSWVRQA PGKGLEWVSQ ISPAGGYTNY   60
ADSVKGRFTI SRDNSKNTLY LQMNSLRAED TAVYYCARGE LPYFRMSKVM DVWGQGTLVT  120
VSS                                                              123

SEQ ID NO: 78          moltype = AA   length = 108
FEATURE                Location/Qualifiers
REGION                 1..108
                       note = Synthetic
source                 1..108
                       mol_type = protein
                       organism = synthetic construct
SEQUENCE: 78
EIVLTQSPGT LSLSPGERAT LSCRASQFLS SYLAWYQQKP GQAPRLLIYG ASARASGIPD   60
RFSGSDGSGT DFTLTISRLE PEDFAVYYCQ QYLASPATFG QGTKVEIK              108

SEQ ID NO: 79          moltype = AA   length = 8
FEATURE                Location/Qualifiers
REGION                 1..8
                       note = Synthetic
source                 1..8
                       mol_type = protein
                       organism = synthetic construct
SEQUENCE: 79
FTFSSYAM                                                      8

SEQ ID NO: 80          moltype = AA   length = 16
```

-continued

```
FEATURE              Location/Qualifiers
REGION               1..16
                     note = Synthetic
source               1..16
                     mol_type = protein
                     organism = synthetic construct
SEQUENCE: 80
QISPAGGYTN YADSVK                                              16

SEQ ID NO: 81        moltype = AA   length = 14
FEATURE              Location/Qualifiers
REGION               1..14
                     note = Synthetic
source               1..14
                     mol_type = protein
                     organism = synthetic construct
SEQUENCE: 81
GELPYFRMSK VMDV                                                14

SEQ ID NO: 82        moltype = AA   length = 14
FEATURE              Location/Qualifiers
REGION               1..14
                     note = Synthetic
source               1..14
                     mol_type = protein
                     organism = synthetic construct
SEQUENCE: 82
GELPYHRMSK VMDV                                                14

SEQ ID NO: 83        moltype = AA   length = 14
FEATURE              Location/Qualifiers
REGION               1..14
                     note = Synthetic
source               1..14
                     mol_type = protein
                     organism = synthetic construct
SEQUENCE: 83
GELPYYQMSK VMDV                                                14

SEQ ID NO: 84        moltype = AA   length = 14
FEATURE              Location/Qualifiers
REGION               1..14
                     note = Synthetic
source               1..14
                     mol_type = protein
                     organism = synthetic construct
SEQUENCE: 84
GELPFFRMSQ VMDV                                                14

SEQ ID NO: 85        moltype = AA   length = 11
FEATURE              Location/Qualifiers
REGION               1..11
                     note = Synthetic
source               1..11
                     mol_type = protein
                     organism = synthetic construct
SEQUENCE: 85
RASQFLSSYL A                                                   11

SEQ ID NO: 86        moltype = AA   length = 11
FEATURE              Location/Qualifiers
REGION               1..11
                     note = Synthetic
source               1..11
                     mol_type = protein
                     organism = synthetic construct
SEQUENCE: 86
RASQYFSSYL A                                                   11

SEQ ID NO: 87        moltype = AA   length = 11
FEATURE              Location/Qualifiers
REGION               1..11
                     note = Synthetic
source               1..11
                     mol_type = protein
                     organism = synthetic construct
SEQUENCE: 87
RASQFLSSFL A                                                   11
```

-continued

```
SEQ ID NO: 88         moltype = AA  length = 7
FEATURE               Location/Qualifiers
REGION                1..7
                      note = Synthetic
source                1..7
                      mol_type = protein
                      organism = synthetic construct
SEQUENCE: 88
GASARAS                                                    7

SEQ ID NO: 89         moltype = AA  length = 9
FEATURE               Location/Qualifiers
REGION                1..9
                      note = Synthetic
source                1..9
                      mol_type = protein
                      organism = synthetic construct
SEQUENCE: 89
QQYLASPAT                                                  9
```

The invention claimed is:

1. A bispecific antibody comprising a first binding domain that binds to human neuropilin-1 receptor (NRP1) and a second binding domain that binds to epidermal growth factor receptor (EGFR), wherein the first binding domain comprises:

(i) an antibody heavy chain variable (VH) domain comprising CDR1, CDR2 and CDR3 regions (HCDR1, HCDR2 and HCDR3, respectively), wherein HCDR1 consists of the sequence shown in SEQ ID NO: 79, HCDR2 consists of the sequence shown in SEQ ID NO: 80, and HCDR3 consists of the sequence shown in SEQ ID NO: 81s; and (ii) an antibody light chain variable (VL) domain comprising CDR1, CDR2 and CDR3 regions (LCDR1, LCDR2 and LCDR3, respectively), wherein LCDR1 consists of the sequence shown in SEQ ID NO: 85, LCDR2 consists of the sequence shown in SEQ ID NO: 88, and LCDR3 consists of the sequence shown in SEQ ID NO: 89; and wherein the second binding domain comprises:

(i) an antibody heavy chain variable (VH) domain comprising CDR1, CDR2 and CDR3 regions (HCDR1, HCDR2 and HCDR3, respectively), wherein HCDR1 consists of the sequence shown in SEQ ID NO: 71, HCDR2 consists of the sequence shown in SEQ ID NO: 72, and HCDR3 consists of the sequence shown in SEQ ID NO: 73; and (ii) an antibody light chain variable (VL) domain comprising CDR1, CDR2 and CDR3 regions (LCDR1, LCDR2 and LCDR3, respectively), wherein LCDR1 consists of the sequence shown in SEQ ID NO: 74, LCDR2 consists of the sequence shown in SEQ ID NO: 75, and LCDR3 consists of the sequence shown in SEQ ID NO: 76.

2. The bispecific antibody of claim 1, wherein the second binding domain is comprised of an N-terminal EGFR-binding heavy chain variable domain (VH) and a heavy chain constant 1 domain (CH1), and the first binding domain is comprised of a C-terminal NRP1-binding single chain variable fragment (scFv), wherein the N-terminal variable heavy chain (VH) and the C-terminal scFv binding domains are at opposite ends of a contiguous sequence.

3. The bispecific antibody of claim 2, wherein the second binding domain further comprises a heavy chain constant 2 domain (CH2) and a heavy chain constant 3 domain (CH3).

4. The bispecific antibody of claim 3, wherein the C-terminal NRP1-binding scFv comprises a light chain variable domain (VL) connected to a heavy chain variable domain (VH) by a flexible linker peptide.

5. The bispecific antibody of claim 4, which further comprises a corresponding EGFR binding light chain variable domain (VL) and light chain constant domain (CL), wherein the bispecific antibody is comprised of two polypeptides.

6. A bispecific antibody, comprising:

a first binding domain that binds to human neuropilin-1 receptor (NRP1); and a second binding domain that binds to epidermal growth factor receptor (EGFR), wherein the first binding domain that binds human NRP1 comprises a VH domain comprising the sequence shown in SEQ ID NO: 77 and a VL domain comprising the sequence shown in SEQ ID NO: 78, and the second binding domain that binds EGFR comprises a VH domain comprising the sequence shown in SEQ ID NO: 69 and a VL domain comprising the sequence shown in SEQ ID NO: 70.

7. The bispecific antibody of claim 1, wherein the first binding domain comprises a VH domain comprising the sequence shown in SEQ ID NO: 77 and a VL domain comprising the sequence shown in SEQ ID NO: 78; and the second binding domain comprises a VH domain comprising the sequence shown in SEQ ID NO: 69 and a VL domain comprising the sequence shown in SEQ ID NO: 70.

8. The bispecific antibody of claim 1, wherein the first binding domain and the second binding domain comprise a heavy chain comprising the amino acid sequence shown in SEQ ID NO: 11.

9. The bispecific antibody of claim 8, wherein the heavy chain is paired with a light chain comprising the amino acid sequence shown SEQ ID NO: 12.

10. A pharmaceutical composition comprising the bispecific antibody of claim 1.

11. A polynucleotide encoding the bispecific antibody of claim 1.

12. The polynucleotide of claim 11, wherein the bispecific antibody comprises a heavy chain polypeptide encoded by the polynucleotide sequence set forth in SEQ ID NO: 24.

13. The polynucleotide of claim 12, wherein the polynucleotide sequence is inserted into a vector for protein expression.

* * * * *